US012545920B2

(12) United States Patent
Bauer et al.

(10) Patent No.: US 12,545,920 B2
(45) Date of Patent: Feb. 10, 2026

(54) INCREASING GENE EDITING AND SITE-DIRECTED INTEGRATION EVENTS UTILIZING MEIOTIC AND GERMLINE PROMOTERS

(71) Applicant: Monsanto Technology LLC, St. Louis, MO (US)

(72) Inventors: Matthew J. Bauer, Manchester, MO (US); Lisa Kanizay, Chesterfield, MO (US); Jonathan Lamb, Wildwood, MO (US); Matthew S. Marengo, Wildwood, MO (US); Brent O'Brien, St. Charles, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 18/624,980

(22) Filed: Apr. 2, 2024

(65) Prior Publication Data

US 2024/0368610 A1 Nov. 7, 2024

Related U.S. Application Data

(62) Division of application No. 17/470,784, filed on Sep. 9, 2021, now Pat. No. 11,981,900.

(60) Provisional application No. 63/076,705, filed on Sep. 10, 2020.

(51) Int. Cl.

| | |
|---|---|
| ***C12N 15/82*** | (2006.01) |
| ***C12N 9/22*** | (2006.01) |
| ***C12N 15/11*** | (2006.01) |

(52) U.S. Cl.

CPC ........... *C12N 15/8213* (2013.01); *C12N 9/22* (2013.01); *C12N 15/11* (2013.01); *C12N 2310/20* (2017.05)

(58) Field of Classification Search

None

See application file for complete search history.

(56) References Cited

U.S. PATENT DOCUMENTS

| | | | |
|---|---|---|---|
| 4,897,355 | A | 1/1990 | Eppstein et al. |
| 4,946,787 | A | 8/1990 | Eppstein et al. |
| 5,049,386 | A | 9/1991 | Eppstein et al. |
| 5,106,739 | A | 4/1992 | Comai et al. |
| 5,159,135 | A | 10/1992 | Umbeck et al. |
| 5,188,958 | A | 2/1993 | Moloney et al. |

(Continued)

FOREIGN PATENT DOCUMENTS

| | | | |
|---|---|---|---|
| CA | 2401858 | A1 | 9/2001 |
| CA | 3036234 | A1 | 3/2018 |

(Continued)

OTHER PUBLICATIONS

Wang et al. ("Egg cell-specific promoter-controlled CRISPR/Cas9 efficiently generates homozygous mutants for multiple target genes in *Arabidopsis* in a single generation" 2015 Genome Biology 16:144). (Year: 2015).*

(Continued)

*Primary Examiner* — Matthew R Keogh
*Assistant Examiner* — Rebecca Stephens
(74) *Attorney, Agent, or Firm* — Morrison & Foerster LLP

(57) ABSTRACT

This disclosure provides methods and compositions for increasing genome editing and site-directed integration events utilizing guided endonucleases and meiotic cell-preferred, egg cell-preferred or embryo tissue-preferred promoters.

5 Claims, 5 Drawing Sheets

Figure 1:
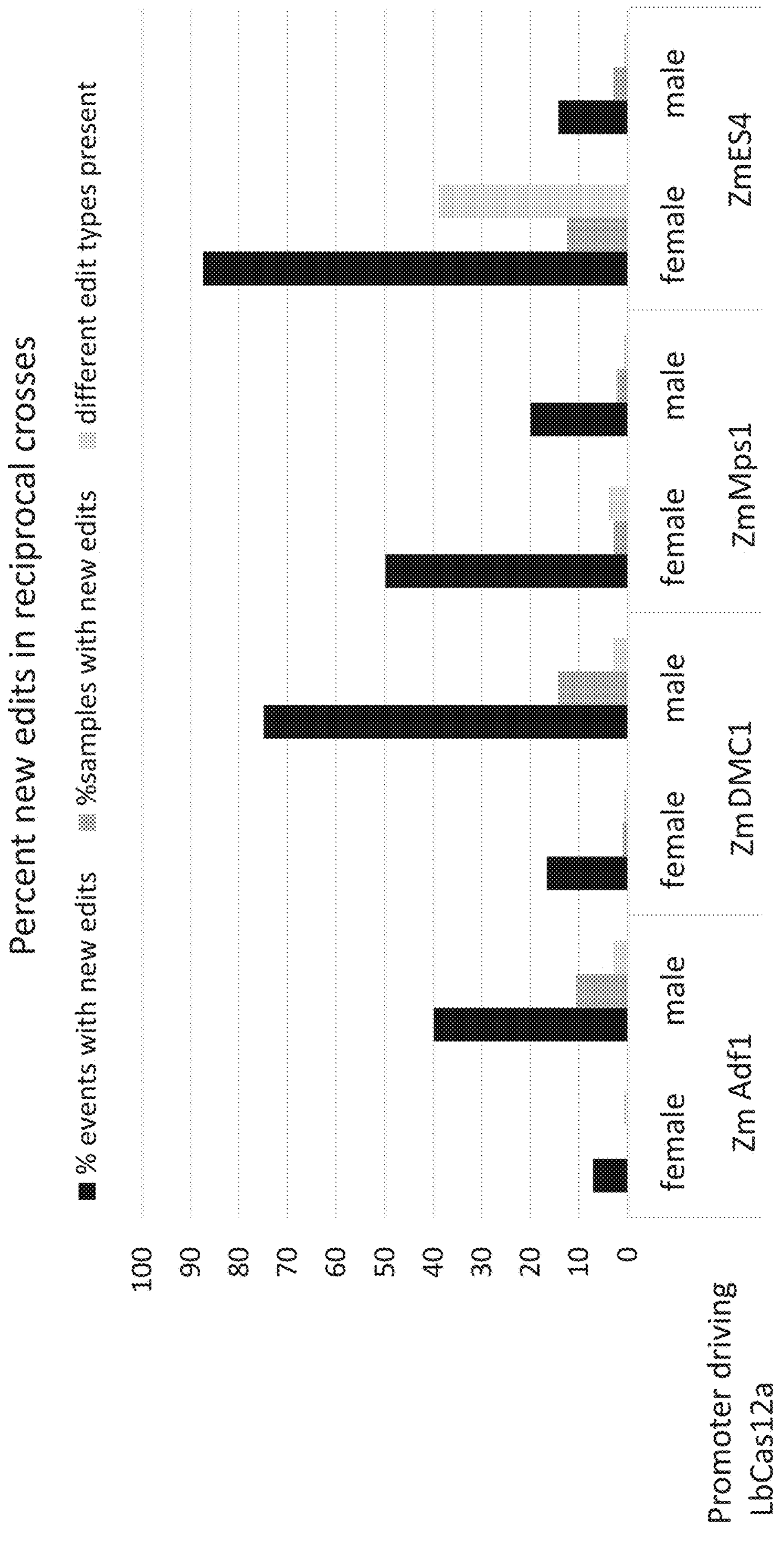

Specification includes a Sequence Listing.

(56) References Cited

U.S. PATENT DOCUMENTS

| | | | |
|---|---|---|---|
| 5,322,938 | A | 6/1994 | Mcpherson et al. |
| 5,352,605 | A | 10/1994 | Fraley et al. |
| 5,359,142 | A | 10/1994 | Mcpherson et al. |
| 5,378,619 | A | 1/1995 | Rogers |
| 5,463,174 | A | 10/1995 | Moloney et al. |
| 5,530,196 | A | 6/1996 | Fraley et al. |
| 5,538,880 | A | 7/1996 | Lundquist et al. |
| 5,550,318 | A | 8/1996 | Adams et al. |
| 5,591,616 | A | 1/1997 | Hiei et al. |
| 5,641,876 | A | 6/1997 | Mcelroy et al. |
| 5,750,871 | A | 5/1998 | Moloney et al. |
| 5,824,877 | A | 10/1998 | Hinchee et al. |
| 5,837,848 | A | 11/1998 | Ely et al. |
| 5,850,019 | A | 12/1998 | Maiti et al. |
| 6,051,753 | A | 4/2000 | Comai et al. |
| 6,096,950 | A | 8/2000 | John |
| 6,140,078 | A | 10/2000 | Sanders et al. |
| 6,153,812 | A | 11/2000 | Fry et al. |
| 6,160,208 | A | 12/2000 | Lundquist et al. |
| 6,175,060 | B1 | 1/2001 | Lefebvre et al. |
| 6,177,611 | B1 | 1/2001 | Rice |
| 6,194,636 | B1 | 2/2001 | Mcelroy et al. |
| 6,232,526 | B1 | 5/2001 | Mcelroy et al. |
| 6,252,138 | B1 | 6/2001 | Karimi et al. |
| 6,294,714 | B1 | 9/2001 | Matsunaga et al. |
| 6,384,301 | B1 | 5/2002 | Martinell et al. |
| 6,399,861 | B1 | 6/2002 | Anderson et al. |
| 6,426,446 | B1 | 7/2002 | Mcelroy et al. |
| 6,429,357 | B1 | 8/2002 | Mcelroy et al. |
| 6,429,362 | B1 | 8/2002 | Crane |
| 6,433,252 | B1 | 8/2002 | Kriz et al. |
| 6,437,217 | B1 | 8/2002 | Mcelroy et al. |
| 6,635,806 | B1 | 10/2003 | Kriz et al. |
| 7,151,204 | B2 | 12/2006 | Houmard et al. |
| 10,995,327 | B2 | 5/2021 | Chittoor et al. |
| 11,447,786 | B2 | 9/2022 | Fox |
| 2004/0216189 | A1 | 10/2004 | Houmard et al. |
| 2007/0050869 | A1 | 3/2007 | Dresselhaus |
| 2007/0130645 | A1 | 6/2007 | Wu |
| 2013/0274129 | A1* | 10/2013 | Katzen .............. C12N 15/1082 506/14 |
| 2015/0267205 | A1 | 9/2015 | Froelich et al. |
| 2018/0092316 | A1 | 4/2018 | Chintamanani |
| 2019/0136250 | A1 | 5/2019 | Que |
| 2019/0169596 | A1 | 6/2019 | Armstrong et al. |
| 2019/0376074 | A1 | 12/2019 | Li |
| 2019/0376075 | A1 | 12/2019 | Que et al. |
| 2020/0080096 | A1 | 3/2020 | Flasinski et al. |
| 2020/0299717 | A1 | 9/2020 | Pennell et al. |

FOREIGN PATENT DOCUMENTS

| | | | |
|---|---|---|---|
| CA | 3043774 | A1 | 5/2018 |
| CN | 105916989 | A | 8/2016 |
| CN | 107338265 | A | 11/2017 |
| CN | 108738326 | A | 11/2018 |
| CN | 109982560 | A | 7/2019 |
| CN | 111465321 | A | 7/2020 |
| WO | 199116024 | A1 | 10/1991 |
| WO | 199117424 | A1 | 11/1991 |
| WO | 0011200 | A2 | 3/2000 |
| WO | 0164924 | A1 | 9/2001 |
| WO | 03104464 | A1 | 12/2003 |
| WO | 2006128707 | A1 | 12/2006 |
| WO | 2014025858 | A1 | 2/2014 |
| WO | 2014093622 | A2 | 6/2014 |
| WO | 2016106338 | A2 | 6/2016 |
| WO | 2018052919 | A1 | 3/2018 |
| WO | 2018102816 | A1 | 6/2018 |
| WO | 2019084148 | A1 | 5/2019 |
| WO | 2019113000 | A1 | 6/2019 |
| WO | 2020131788 | A1 | 6/2020 |
| WO | 2020214986 | A1 | 10/2020 |

OTHER PUBLICATIONS

Zheng et al. ("CRISPR/Cas9-Based Gene Editing Using Egg Cell-Specific Promoters in *Arabidopsis* and Soybean" Jun. 16, 2020 Frontiers Plant Science 11:800, 15 total pages). (Year: 2020).*

Amien et al. ("Defensin-Like ZmES4 Mediates Pollen Tube Burst in Maize via Opening of the Potassium Channel KZM1" 2010 PLoS Biology 8(6): e1000388, 13 total pages; doi:10.1371/journal.pbio.1000388). (Year: 2010).*

Liu et al. ("Synthetic TAL effectors for targeted enhancement of transgene expression in plants" 2014 Plant Biotech. J. 12:436-446). (Year: 2014).*

Altschul, S.F. et al. (1990). "Basic Local Alignment Search Tool," J. Mol. Biol. 215: 403-410.

Bevan, M. e al. (1983). "Structure and Transcription of the Nopaline Synthase Gene Region of T-DNA," Nucleic Acids Research 11(2):369-385.

Campbell, W. H. et al. (1990). "Codon Usage in Higher Plants, Green Algae, and Cyanobacteria," Plant Physiol. 92:1-11.

Chandler, V. L. et al. (Dec. 1989). "Two Regulatory Genes of the Maize Anthocyanin Pathway Are Homologous: Isolation of B Utilizing R Genomic Sequences," The Plant Cell 1:1175-1183.

Chenna, R. et al. (Jul. 1, 2003). "Multiple Sequence Alignment with the Clustal Series of Programs," Nucleic Acids Research 31(13):3497-3500.

Cordts, S. et al. (Jan. 2001). "ZmES Genes Encode Peptides with Structural Homology to Defensins and are Specifically Expressed in the Female Gametophyte of Maize," Plant J. 25(1):103-114.

Depicker, A. et al. (1982). "Nopaline Synthase: Transcript Mapping and DNA Sequence," Journal of Molecular and Applied Genetics 1(6):561-573.

Ebert, P. R. et al. (Aug. 1987). "Identification of an Essential Upstream Element in the Nopaline Synthase Promoter by Stable and Transient Assays," Proc. Natl. Acad. Sci. USA 84:5745-5749.

Feng, C. et al. (Nov. 2018). "High-efficiency Genome Editing Using a dmc1 Promoter-controlled CRISPR/Cas9 System in Maize," Plant Biotech. J. 16:1848-1857.

Fraley, R. T. et al. (Aug. 1983). "Expression of Bacterial Genes in Plant Cells," Proc. Natl. Acad. Sci. USA 80: 4803-4807.

GenBank Accession No. AC232233, created on Sep. 13, 2014, located at https://www.ncbi.nlm.nih.gov/nuccore/AC232233, last visited on Jan. 11, 2022.

GenBank Accession No. JN185196, created on Aug. 1, 2011, located at https://www.ncbi.nlm.nih.gov/nuccore/JN185196, last visited on Jan. 11, 2022, 1 page.

GenBank Accession No. V00087, created on Mar. 18, 1996, located at <http://www.ncbi.nlm.nih.gov>, last visited on Jun. 20, 2022, 2 pages.

Gilles, L. M. et al. (Oct. 23, 2017). "Haploid Induction in Plants," Current Biology 27(20):R1095- R1097.

Kam, N. W. S. et al. (Jun. 9, 2004). "Nanotube Molecular Transporters: Internalization of Carbon Nanotube-Protein Conjugates into Manunalian Cells," J. Am. Chem. Soc. 126(22):6850-6851.

Khodakovskaya, M. et al. (Oct. 27, 2009). "Carbon Nanotubes are Able to Penetrate Plant Seed Coat and Dramatically Affect Seed Germination and Plant Growth," ACS Nano 3(10):3221-3227.

Larkin, M. A. et al. (e-pub Sep. 10, 2007, Nov. 1, 2007). "Clustal W and Clustal X Version 2.0," Bioinformatics 23(21): 2947-2948.

Lawton, M. A. et al. (1987). "Expression of a Soybean Beta-Conclycinin Gene Under the Control of the Cauliflower Mosaic Virus 35S and 19S promoters in Transformed Petunia Tissues," Plant Molecular Biology 9:315-324.

Liu, Q. et al. (2009). "Carbon Nanotubes as Molecular Transporters for Walled Plant Cells," Nano Letters 9(3):1007-1010.

Mao, Y. et al. (Feb. 2016). "Development of Germ-line-specific CRISPR-Cas9 Systems to Improve the Production of Heritable Gene Modifications in *Arabidopsis*", Plant Biotechnology Journal 14:519-532.

Murray, E. E. et al. (1989). "Codon Usage in Plant Genes," Nucleic Acids Res. 17(2):477-498.

(56) References Cited

OTHER PUBLICATIONS

Nakamura, Y. et al. (2000). "Codon Usage Tabulated From The International DNA Sequence Databases: Status For The Year 2000," Nucl. Acids Res. 28(1):292, 1 page.
Odell, J. T. et al. (Feb. 28, 1985). "Identification of DNA Sequences Required for Activity of the Cauliflower Mosaic Virus 35S Promoter," Nature 313:810-812.
Schmidt, C. et al. (May 2019). "Efficient Induction of Heritable Inversions in Plant Genomes Using the CRISPR/Cas System," The Plant Journal 98:577-589.
Smith, T. F. et al. (1981). "Comparison of Biosequences," Advances in Applied Mathematics 2:482-489.
Streatfield, S. J. et al. (Aug. 2004). "Analysis of the Maize Polyubiquitin-1 Promoter Heat Shock Elements andGeneration of Promoter Variants with Modified Expression Characteristics," Transgenic Res. 13:299-312.
Thompson, J.D. (Nov. 11, 1994). "Clustal W: Improving the Sensitivity of Progressive Multiple Sequence Alignment Through Sequence Weighting, Position-Specific Gap Penalties and Weight Matrix Choice," Nucleic Acids Res. 22(22):4673-4680.
U.S. Appl. No. 09/757,089, filed Jan. 9, 2001, for Nancy Houmard et al. (U.S. Patent Application is not submitted herewith pursuant to the waiver of 37 C.F.R. §1.98(a)(2)(iii) issued by the Office on Sep. 21, 2004.).
Wang, M. et al. (Aug. 2018). "Multiplex Gene Editing in Rice with Simplified CRISPR-Cpfl and CRISPR-Cas9 Systems," Journal of Integrative Plant Biology, 60(8):626-631.
Yang, N. S. et al. (Jun. 1990). "Maize sucrose Synthase-1 Promoter Directs Phloem Cell-Specific Expression of Gus Gene in Transgenic Tobacco Plants," Proc. Natl. Acad. Sci. USA 87:4144-4148.
Zhang, J. et al. (1997). "PowerBLAST: A New Network BLAST Application for Interactive or Automated Sequence Analysis and Annotation," Genome Methods 7:649-656.
International Search Report and Written Opinion, mailed Feb. 9, 2022, for PCT Application No. PCT/US2021/49680, filed on Sep. 9, 2021, 16 pages.
Eid, A. et al. (Jul. 2016, e-pub. May 28, 2016). "High Efficiency of Targeted Mutagenesis in *Arabidopsis* via Meiotic Promoter-Driven Expression of Cas9 Endonuclease," Plant Cell Rep. 35(7):1555-1558.
Wang, Z. P. et al. (Jul. 21, 2015). "Egg Cell-Specific Promoter-Controlled CRISPR/Cas9 Efficiently Generates Homozygous Mutants for Multiple Target Genes in Arabidopsis in a Single Generation," Genome Biology 16:144, 12 pages.
Zheng, N. et al. (Jun. 16, 2020). "CRISPR/Cas9-Based Gene Editing Using Egg Cell-Specific Promoters in Arabidopsis and Soybean," Front Plant Sci. 11:800, 15 pages.

* cited by examiner

Robust expression of LbCas12a in Egg/Embryo/Meiocytes

SEQUENCE LISTING

```
Sequence total quantity: 102
SEQ ID NO: 1            moltype = DNA  length = 1568
FEATURE                 Location/Qualifiers
regulatory              1..1568
                        note = promoter - Promoter from ZmDSUL1
                        regulatory_class = promoter
source                  1..1568
                        mol_type = unassigned DNA
                        organism = Zea mays
SEQUENCE: 1
tttgctcaca ggtgactcag tagatgacga tcatgatgcg ctttaggtca tatatttgaa  60
gttcatcact gacctcatca aggaacatgt ttctagtgac cttggtgtta gggtgttctt  120
atggggtcgt aggtcatgct accatcactg tcgatcgagg cattgtagga atcgttcagt  180
caagtcattg accgcccttc actcaatcag tcattgaccg cccatcactc aaccaggtca  240
cgagtacctg acttatgcat gggacaatac ttcctttact aggtgcgata aggcactata  300
tggcaatggt tgtcttcatg ggggtaggct cgatgtcact ctgaagtcac aaccctaggc  360
gtgataccat actttttttg tgcaatagat agagcaactc gtaggtcatg gatcttagag  420
ttccaagggc ccttaagggg ggtctaggcg atcaagagga ctcaaggaga atgagagcgt  480
cttggagtgt cctaggggcc ttgagtgccc tctgtttcac ttgttctaac aaatggttgt  540
ggctgggata gtcttacatg tctacggagg cccgagacca gatcctctga tatgttaggc  600
ttgtatctta gctagagtcg aggttagtcg cggatcagac aattccttct atcgaggttc  660
tttgaaaggc atcctatcaa ctcattaggg tatgatctac tcccgttgtt aataaacgta  720
ttttataaca caacactcac atcatgaatt gtatttaaac tcaaccagaa cttcagcatc  780
tcctcaccag tatgaatcat cacatattca tcaacgatgt tttcagagtc catgcctcta  840
aataaattta ttataaaaaa tattctataa ctaatctaat aatacttatt ttatattaaa  900
aaattagtac ttatataact ttagtcaaag ttcaaactgt ttgaggaagc caacattata  960
ctttttatgg atggttgaag tatacagttt tctataaact ttgtcaaatt atgtatggta  1020
acttaactta gaaaataaca agaaataatg gagagatatc acatttggaa acggcgtagt  1080
attccacttg gaacactttt attttaagat gcaaaaaaaa atggctggtg gagctaaaat  1140
attttttatt tgagccgaga cattcttttt ttgtgaacta cttcatctgc gcagcggcag  1200
acttcgcgtg cgtattaatg tttatactgt gttgaacttt agatacataa accgataaac  1260
gcatgcaaat taaaagttgt tcttgctgcc acgcctatcg gttgagttgc atgactttca  1320
ggccaacaca ctgcaagcaa aatggaattg gagatttact acgagagcga gtggtcaagt  1380
attcatgact agccggctgc ctcgtcttct tctcgaatgg aatggctccc acttgctgca  1440
aacggcccgc cggagacgct tcgttacccc actaatccct ggaaaggagt ttacatggac  1500
agtgggagcc tatataagca cgttcatggc gagacactac atccgagaag gacgatcagg  1560
cttcaggc                                                           1568

SEQ ID NO: 2            moltype = DNA  length = 2000
FEATURE                 Location/Qualifiers
regulatory              1..2000
                        note = promoter - Promoter from ZmEA1
                        regulatory_class = promoter
source                  1..2000
                        mol_type = unassigned DNA
                        organism = Zea mays
SEQUENCE: 2
cacgtccacg tgcaccaagg aggagaggac actactgtcg ccacttttat tttactagta  60
gtcttccaga gaccgcccag gcgcgcgccc aaccatgcgc cccttcgact gcgaccctac  120
cctagagcta gccagcaaac atacgaacag cagctaatcc gccgtctttg tggaggactg  180
caaagtaaag ctgcgggttc gcaaggaacg ccgcgcggga tataacctgc ccggcgacgc  240
cgggtgcaac cattgtcacc aagggacaaa cagatgacac agctggaccc accacgaagg  300
acactatggc cgccgccacc gccaccgccg ccaccgccag tagtgagaac actgctccca  360
tgatcttgaa ggagagtgat gaatcaaaca agtcgtcaag cgcgctcgct ctctggtata  420
gggttggtac tattgataga caccgcgtgg aatttctgcg acagagaagt catctatttg  480
taggtcggcc agaggcggct gctggccttc tatgggggtg cgttgcatgc gtgcgtaatt  540
gctgccgtct cacgtacggc gaagtgcgcg tgctggggaa aacgaatcgg cctgggaact  600
ccaagaggcg ttgctccgcc tccgactctg agtgcatagc caagtactgc agctactgcc  660
cgctccgccc gatgcgccga tcaacaccca tttcgcaaag tgtagccggc cccatcaaat  720
gcagaagtcg actcgtcgat tcggagtgag aacgatcatt ttccgacaat actaatccaa  780
aggcaggctc atggtggtac atgtccaagt ccaatcttct aatgggtata gttaggttat  840
ttaaaataat accctgagtt ctgtcacttt cttcattttt aatactaatc caagctgcca  900
cgacggattg gtgggtagtg gacgagtagt atcggcaaaa aaaaaaatac tacttttgcc  960
ggtgaaattt aattactact ctacataatt agcaaatgaa attaatcacc tcttatgcac  1020
gtatgtgttt taatttccat cagttcactt ttagggctga tttggtggtc agtgatcccg  1080
agaggatcca tgagaggaat cccccttgata ttcaaaattg aattgtaagg ggatttctct  1140
```

```
cccatgaatc atcttggaat ctctgatcac caaatcagcc cttaaaatga aaaagaaatt  1200
tatattatcc ggaagctttg gaaaatatac tcataatttc gtatataaac caaaagcatt  1260
attaaacctt gagtcaaatg catgtaacct tgaggggtta cctaatccta gtgtgccaaa  1320
gcatgtaacc ttgaggggtc ggttccttag gaaggcgccg taaggcaagg gtaaaaccaa  1380
cgttctaccc gaggtaaaac cacacgccct tgtgagcccc agattcacct ggatgtcttg  1440
tatttacggc accgggctgc gggggccaat gcaccatcat ttaagctatg tcgaccgctg  1500
gcctttatag catggcctcg aggtgactcg tagttaatga aattaattta attactactc  1560
tacataatta gcagatgaaa ttaattacct cttatgcacg ttctcactac taccaagcaa  1620
caattcagct tctgcatttc gctaccgttc tcttcaactt caatgcgctc gactgatcgc  1680
gcacattgcg aagctgtctc ttcgtcgtcg cctcccatcg tgatttgaga ctggggagca  1740
aatgcgcacg gcatgcatcg caatgcacgc gatgaagctg agcagccgcc tggccaacct  1800
cgatccggcg ctgcagccta ctacaaatag atgttcaatt aacacaacac gcagcgaccg  1860
ctgtccagtg tccattcatt ccaaacccag ccgatcgctc tcctccaatt aagcagcaag  1920
ggcagaagca acaccggcgt gccacccgga cgacgctgaa tcctgcatgt caacctgccc  1980
ggccatcgtc attcgtcaac                                                2000

SEQ ID NO: 3           moltype = DNA  length = 2000
FEATURE                Location/Qualifiers
regulatory             1..2000
                       note = promoter - Promoter from ZmES4
                       regulatory_class = promoter
source                 1..2000
                       mol_type = unassigned DNA
                       organism = Zea mays
SEQUENCE: 3
tttccttaat ctcctgggtc acttagaccc cgcaaggacc accacacact taggtgtctc  60
ttgcttcgat tacaaatcac ttgagaaaag aaatgggaaa ggaagaaggc aatccaagag  120
gcaagagctc aaaagaacac aaaatctctc tctcacaagt cactaagtgc ttgagttgaa  180
tttgggactt ggagaggctt tgatcttttg aattgtgtct acgagtgaat gctagagctc  240
ttgtaatgaa tgtgatactc agaaatcttg gatgcttgga gtggtggtgg ttggggggta  300
tttatagccc tcaaccacca aacaaccgtt ggggagggcc gctgtcgatg ggcgcaccgg  360
acagtctggt acgccaccgg acactgtccg gtgcgccagc cacgtcacgc aaccgttagg  420
gtttgggagc tgtcgaccgt tggaggcttt gtcctctagt ggcaccggac agtccggtgc  480
cgcaccggat agccactgtt cagtgtccgg tatgctctaa ctctaggctc tgactcagcc  540
gcgtattgtt gtgcgctgta gcgctcgtca ggagccgttg cagtcgacca ttgcgctgga  600
ttgtcgttac tccgctggtg caccggacag tccggtggca caccggatag tccggtgaat  660
tgtagcggag agcgccagaa gaaacccgag agtggccgtt tggactctgt acggtcctgg  720
tgcaccagac actgtccggt ggcacaccgg aaagtccggt gcgtgaaaga gaaatatggt  780
ttaacttttt cctataaatg attttggtgg ttgaatgccc aacacaaata attgtactaa  840
ctagtttgct ccagattata tattctatag gtgcataaaa ggttcaacac aaaccaataa  900
aagatcaaag ttagggttta aaaagaaagg aacaaagaaa ccaaagtgtg ccctggtctg  960
gcacaccgga ctgttcggtg tgccacgtcg atgtttgcac agctcgcccg aggccactct  1020
tgggcgggag accccagggt agcctcgcgt gagccatgac tgtgcctccc gtccgagtgt  1080
ggcctcagac gacagacata gaaccatgat gtactgtaga tatatatcta tgtttatagt  1140
acatcaacag attctgaagt ctatttcagg ttgaattagg tttgtactcg gacgagtgat  1200
atttatcgtt ccatatctat gttttatata aattttttac tctcgtcgta acatataggc  1260
acatacctgt tcaaatatat gtgcgattgt gctcatatgg gtagaagaag gaactggatg  1320
tgaagacatg tatatataga ccaaaaatgt atcttagccg atttcaaact gcctagcgaa  1380
aagatgaagc tgctccgtgt ttgggtgact gcagcattat gtatcttatt aatcgatttc  1440
acagaagact tgtctctcat ggaacaaacg aacctattag cagtctgtat ataaagaagt  1500
gacttccaga ctgccaagtt tagtgattag ggctgctgtg actgaccatt taccttgcaa  1560
acaatctttc gatctactgc tctgtcatgc atggtttttg catcgtccat tatgtttatt  1620
tcccattgtt gcagcttacg atatcgtgta tacctggcac ctatgtttat gacaatgaaa  1680
ctcaccatct ttattctatt ggcattcatt ttcattcaaa ttacataacg tatgctagaa  1740
cgaccgaata caaattactg ctaataaaca tcctgcgtac gcgcaatggt gcaccattta  1800
ccaattaata gctgtaacgg tactgcaagt aatggtcgaa gcgttatgtt ttctctcctc  1860
tcttcccacc gtacaggatc atatattcat atatatatac acatgcctct ggaacggcta  1920
attcgatagt tccaccacgt tacttccata tatttccctt ggattggatc gtcggcgccc  1980
aaacgaatac taatccggca                                                2000

SEQ ID NO: 4           moltype = DNA  length = 2999
FEATURE                Location/Qualifiers
regulatory             1..2999
                       note = promoter - Promoter from ZmDMC1
                       regulatory_class = promoter
source                 1..2999
                       mol_type = unassigned DNA
                       organism = Zea mays
SEQUENCE: 4
acctaacctg gctgagccaa cacctgaggc cctcccctaa accagggagt ccctgatgat  60
ccctactcaa aggtgataag ggtgaaaacc cttcattata cacattttga aaagcatttt  120
cttttgatcc cggctgggtg gccataataa cttgtctcaa aatcatatca tgcataaaat  180
aacaggctga gggttgtggt tgaaaaatca taggtaattt atgcatcaaa gggatccagt  240
gagtttgtcg tgcttatccg acgaaggggg aagaggagct cgcggaactg tcttctagct  300
ccactgcctg gcgtagactt gcagatctgg cctccacgag acgacatgaa cgctccgata  360
actatgcaac atgaataagc aaacatacaa accaacaagt ataccaacaa atatttagta  420
tagtggtcag aatagcgata tatggatggg tagagtcgtg agtagaatct gtgtcatgtg  480
gtgttgagat actactagtg gtggagcgga ggtgcttacc aggagggtgg actggaggcg  540
aagcgacact atgcgtgtag ccggcagagc ggagtaacta agtgagtggg gtgtttgcct  600
```

```
tggctgaggg tgttgagtgt gtgtggagag ggagagggta gctgggtgta tttatagctg  660
ggtgtatgtg gtgtagcaca atgaagttca ttgttggtga gaatagtgac atatgaatcg  720
tctgacttag tatgaacagg agagttatat gcagaatatg ggacaagagt attttgggag  780
ttttctggaa tatgaaccat acttaagtga tgacatggtt ggatagggaa taatttgata  840
agaatttaga aacaagaatt attggaatcg gagtttggaa gcctggttcg aaggaatctc  900
aaagttaagc gtgctcaact tagagaaacc tgggatgggt gaccagatgg gaagttccct  960
actggaagga aaatcacagt caccggagtt cgtatgactg aaatatgggt ctggctggtc  1020
ttaggtggac tggatagcat gatggatgag tagttgaaat ttagggtgat cggatgatcg  1080
atgaatagtg tcttggaatg agaaggaaga aagcacgatt gcaaaagcta agcgacaaga  1140
gcgacaaata acacacagat cactctctct ctcaagtcac taatcactaa tgatcacttg  1200
tcttaattgt ggaacttgga gagattggaa gctttgattg tgtcttggaa tggattgcta  1260
gctcttgtat tgaatgtgaa ggattggaat gcttgggtgt catgaatgga ggtggttggg  1320
gttgtattta tagccctcaa ccacttccta gccgttgctc cttttctacc gaccgcggac  1380
ggtccgcgcc cctggtccgg acagtccgcc cctgcacatc aacggctgaa atcgcaacga  1440
tcagcagtaa cggctatatc aacggctata tagcatttaa tgtgtcgtca gatgtcagat  1500
aaaagcagtc gcagacggtc cggtcatgca ccccggacgg tccgcgagga tgctataatt  1560
cattttaccg aacccgtcac cttcgggttt ttcggttctt caccgacctg atggtccgcg  1620
cctgaggccg gatggtccgc gcttggtctc ggacggtgct tggctttcca tcggacggtc  1680
cgtagtgtag acttgtgttt ttgtattggt tctgtcctag gctcacccta gtttcgcgga  1740
cggtccgccg caagggccca gacggtccgc gcttatgtga ttttccaaaa agcttctcct  1800
gtccagaata atctacggta ttccggacag tcgactttag aatagttgta gatgaactta  1860
tgcacctgtg gaatgatcaa ttagacaaac cggttagtcc acaaggtttg tgatggtcgt  1920
caaacaccaa aaccgattat agggaatatt gaaactattt ccctttcaat tatatttgtt  1980
tagttgaggt tctaaatttt ttatagcaag gcccgtttgg ttagagagac taattttagt  2040
ccctgacttt tagtctcatt tagtctctat tttgccaaac ggaaggacta aagtagggac  2100
taattggttt tagggcatgt ttggttcgtt acctcaattg ccacattttg cctaactttt  2160
ctgcctaagg ttagttattc aattcgaata actaacctta ggcaaagtgg ggcacagtta  2220
gccacaaacc aaacaagccc ttagtcttta gtcccttaca tagatgctaa aagggactaa  2280
aggggaatat ttactctaat taccettgcc tagaaaacta gtgtgaaaca aaaaaaagag  2340
tattttgatc tttatgtatt acatttaatg tatttaaaat ctgtttagcc cctacaacta  2400
aacaatatag agactaaagt ttagtttagg gactaaactt tagtcctaag actaatggag  2460
ccaaacgggg cccaaatctc gtttaaaaat ttgaagcaaa cacatcctta acggaccgtg  2520
ggcaatgagc tgagtctccc ctgactctgg gccgcaaagt cctggtacac ttgatcatgt  2580
tggtccatcc tatggctgac cgcgacttcc ctagactgaa atcaacccat tcctaggctc  2640
ctagcccagc ccaacggccg agcacacgat ccgttcgaga gcgagaaggt cctccggcct  2700
cagcaccctc aagtacacag tacaccctcg caccggtacc gcggtccgcg gcacacgaca  2760
cccccactcg tctgtcgact cacgtctgat cgtctctccc caacaatctc tcgagtcttg  2820
ccattcgcct cagcttgccc ctcctccaag cgtccaagcc ccacccggcc attgcctcct  2880
cctcctgccg caggtaagct agctgctcca gcttctcttg ccatcgcgtg tcctgcactc  2940
accgccctcg cgcgtgtaac tcctcctccg tcccccgatc gggctactag tgcaggcac   2999
```

```
SEQ ID NO: 5            moltype = DNA  length = 1979
FEATURE                 Location/Qualifiers
regulatory              1..1979
                        note = promoter - Promoter from ZmMps1
                        regulatory_class = promoter
source                  1..1979
                        mol_type = unassigned DNA
                        organism = Zea mays
SEQUENCE: 5
tgatatggtt tggttgcact tgagaaatga ttagtttcct aatttgcacc attctaaatt  60
aatgcctcgt gttgctggtc cttttaaggt gctaacaaag attaatgata atgcttatat  120
ccttgacctg tctgtagaat ttggtgttta cactagtttt aatgttccag atttgaaacc  180
atacatgggc gaggatgacg agttaccgtt gaggatgact tcacttcaag aaggggagga  240
tgatgaggat atcaactgca acacgagtac gatacaccag cagcaccacc acctcaggcg  300
ccacatccct cctcagctag gccaacttca ccttaggcac cacttccttc attagttggg  360
caaatcactc ggacccgtgc aagagatctt aacttcgtca tgctactgaa taatgaggga  420
ccagaagaat agacgaccgg cccaattacg acccaaggtg gaggacctag gatgggccgc  480
ccctagggtt gcgtttttcc accttggccg ccaccagggg ctgtgcccct ctctctattt  540
atctagtagc tgcacctcct tttgttcctt gagttttgtt ttacattagc cttagctatt  600
cccaaacacg cacatattag cgctgtcttc gtgtattcag aactccacca tcgagtaata  660
gactagattg ctcgtatctt tttcttgttc gttcttcgat tgcgtgcagg aaatgatctt  720
tgtgatcagg ctgatcttgc accagcaagg tcggtaacca tagggagttg gttcagcgat  780
tgcattggcg cctcgagctt gctcgtcgta gtcggaccgt gagggtcatc ttcgccagat  840
cgaaattatc tccactcacc gaaagatcgg gcacttcagc cttatcaggg agtggctgcg  900
gcatgggtcc cttcggtcag ctagtgatga ggtcggtgca gtgatttggt ttgggccgag  960
gagaagattc agcccaggtc taggtatgct tctcttcttt atattttgtg ccttctttct  1020
tgaatttaga ttctatattc aactccaaat tatttttgag tttcaaacta taaatataca  1080
aacaataatg caacaatatt ttattattct atttatttat tattctagag aagcaattgc  1140
ttctagctat gtaattcaca cataaatagt ttattttaga gaaataattt ctattgtata  1200
gctatcaaga tatgatttaa ctcaaatttc tttaaagagt tatagatcaa caaagggata  1260
acttaattat cttttcattt gatcttttat tagaaaaagt tattcatttt gtgagaaaat  1320
ccttattaaa aagatatgtt ggttcaaatc cttttggaga agcttttata ggtgctagaa  1380
taggattttg gggttagagt gttgctctag ctaattaaaa tagtagaata gccgtttgta  1440
gtcgcggtcc tagaataggc gggtttatgt taaattcgtt gatcacggat cacggtccac  1500
atattcttgg gtgggcctct cctctcgttt gcctgcgccg ccgcgatcgc caatcggcgc  1560
tcttcccaaa ccccgcccgc caacgccgac ggcgtcagcg gccacgggca cctcctcgtc  1620
gcgaatagac tcgccatcgc taaaggccgc gctcgcaatg gctctcatcc actacaaccg  1680
cctccctggc aaagccaacg ccaccgcggg cacatcaccc ccgtctctcc tccactggaa  1740
```

```
gcgcaaggtc ccattcccct agcagcaaca accctcggat tcaaacccta cctccgcctc  1800
tgacattaga tctccttctc ccgcccaggc caaggaccgg aagcgcgaaa tcctccgcct  1860
ccgcgaggag ctcaaggtcc tccaaggtat gtaaggccat gccaatctat ccgcgctatt  1920
gttcgtctgg ccgaattcca ttgcaggcgt cgtggaaatt gagtttgtta tcggagcag   1979

SEQ ID NO: 6           moltype = DNA  length = 1824
FEATURE                Location/Qualifiers
regulatory             1..1824
                       note = promoter - Promoter from ZmAdf1
                       regulatory_class = promoter
source                 1..1824
                       mol_type = unassigned DNA
                       organism = Zea mays
SEQUENCE: 6
agaccaacac gagaatttg tgcgtacttt gtcctcactc atacgcacca gagaatactt  60
ttcgatcgat cactcatcct aaggttgctt taggccaaac acgtttaacc taaaggttct  120
ttcgcagcag gcttccgaaa aaaagataca ccttgttgat atggatattc tattaatttt  180
attaagtctt agcgaggatg tcacaatcca accaggctag gatatcacaa tcctccctct  240
tagaagaccg acgtcctcat cggtcaaccc caagccaaaa acctccctct tacccgtgac  300
tgtatgtcta gtgtcgtcat attccatgcc atttgaccac tctgagccta catacgtcgt  360
gcaacatata cccaaaaccc tagcctacac acgtccgtga aaccacgagg gtcgtctctg  420
ataccatttg taacatctca tccactgtcg gaccagtgat acttactcct gacaaccctc  480
tagaaccata aaccatcctt acaaaccaac acgagtcttt tgtgcgcact ttatcctcac  540
tcatacgaac tagggaggat ttgtcggtcg ggcacacatc ctaagattgc tctagaccaa  600
gcacacttaa cctagatggt tcttttaaga catacttcat aatgtagtta tttgttttga  660
tttatttcta ttattccaac aaattatgta acatttacat ccttgcagtg accataacta  720
tagatgcaat acaatgaact atggagttca atgtatctat aggtgttgtt ctgctagtgc  780
taaactctag ggaggttgcg ctgtgtccaa tgtcgctggc catgtcgcgt gacgtgcctc  840
gcgacaggct actggtagtt ctgcgccgaa cattggttga tccacgccta agaccacgca  900
ctaagccggt ctatccgtgt tcaacatcgt agttctgcac ctctgggata cacaaccgcc  960
ttgtccaacg ccatgcccca agccaccgca tacgtcgggg ctatcagtgt ctcctttctc  1020
agcgtgctaa catgatacat gttacaatcg aagacgagct cgcatcgtgg caacaaattt  1080
tggtgctcca aagctttgga aaggttatcc tcaacattgt tgggatccat ggcggtctag  1140
aatcaaccat atgaaacact agcggctagg gttcggagga gatcattagg gaggagaagg  1200
agaggtcaag tctaagttgg gctaggtgag aacgatcatg ggtagatgga tggcagtacc  1260
gggtaatttt catcaactta cgattaatag tgggtctttt attaaaaata agctgatata  1320
agcatctttt gagaagctta tagggttatc ataatctcaa gtactagatt atataatttt  1380
atcacataag ttgcttcata cttagtttgt ctatcactag cttatttaca tagaatttag  1440
attatataat accaaaccct aaatgacctg aaccaaagat acccagattg cttcacatca  1500
tttgtgtggc actgtggcta catgaggacg tgggaatggg cgaatggcgc ggaacgaccc  1560
ccgataggtt tccgatattg ccctccccac gcgcacgatt taaccgatcc gcccccgttt  1620
ctttcttttt ctccacgaga acgagattac gagacaagag acaagtagac aacccagctc  1680
tccagcggtc cagcggtcca gcctctccta gccgaggcca aaacccccat accaacacac  1740
acttcgcttc tcgctgcctc cgcggcggcg cgccgctccg ctccgagccc tcttcctcct  1800
cctcctctgc ccgttcggtc gaga                                         1824

SEQ ID NO: 7           moltype = DNA  length = 3681
FEATURE                Location/Qualifiers
misc_feature           1..3681
                       note = Synthetic sequence
source                 1..3681
                       mol_type = other DNA
                       organism = synthetic construct
SEQUENCE: 7
tcgaagctcg agaagttcac caactgctac tcgctgagca agacgctgcg gttcaaggcg  60
atccccgtcg ggaagaccca ggagaacatc gacaacaagc ggctcctggt cgaggacgag  120
aagcgcgccg aggactacaa gggcgtcaag aagctgctgg accggtacta cctctccttc  180
atcaacgacg tcctgcactc gatcaagctc aagaacctga acaactacat ctcgctgttc  240
cgcaagaaga cacggaccga gaaggagaac aaggagctcg agaacctcga gatcaacctg  300
cgcaaggaga tcgcgaaggc gttcaagggc aacgaggggt acaagagcct gttcaagaaa  360
gacatcatcg agaccatcct gccggagttc ctggacgaca aggacgagat cgcgctggtg  420
aactcgttca acgggttcac cacggccttc accgggtttt tcgacaaccg ggagaacatg  480
ttcagcgagg aggccaagtc gaccagcatc gccttccggt gcatcaacga gaacctcacc  540
cgctacatca gcaacatgga catcttcgag aaggtggacg ccatcttcga caagcacgag  600
gtccaggaga tcaaggaaaa gatcctgaac tcggactacg acgtggaaga cttctttgag  660
ggcgagttct tcaacttcgt cctcacccag gagggcatcg acgtctacaa cgccatcatc  720
ggcggcttcg tgacggagag cggcgagaag atcaagggcc tcaacgagta catcaacctc  780
tacaaccaga agactaagca gaagctcccg aagttcaagc cgctgtacaa gcaagtcctg  840
agcgaccggg agtccctctc gttctacggc gagggctaca cgagcgacga ggaggtgctg  900
gaggtgttcc gcaacacgct gaacaagaac agcgagatct tcagctcgat caagaaactc  960
gagaagctgt tcaagaactt cgacgagtac agcagcgccg gcatcttcgt caagaacggg  1020
cccgcgatca gcaccatcag caaggacatc ttcggggagt ggaacgtgat ccgcgacaag  1080
tggaacgccg agtacgacga catccacctc aagaaaaagg cggtggtcac ggagaagtac  1140
gaggacgacc gccggaagtc cttcaagaaa atcgggagct tcagcctcga gcagctccag  1200
gagtacgcgg acgccgacct gagcgtggtg gagaagctca aggagatcat catccagaag  1260
gtcgacgaga tctacaaggt ctacggctcg agcgagaagc tgttcgacgc ggacttcgtg  1320
ctggagaagt ccctcaagaa gaacgacgcc gtggtggcca tcatgaagga tctgctcgac  1380
agcgtgaagt cgttcgagaa ctacatcaag gcattctttg ggagagggcaa ggagacgaac  1440
cgggacgagt ccttctacgg ggacttcgtg ctcgcgtacg acatcctcct gaaggtcgac  1500
```

```
cacatctacg acgcgatccg gaactacgtc acgcagaagc cctacagcaa ggacaagttc  1560
aagctctact tccagaaccc gcagttcatg ggcgggtggg acaaggacaa ggagaccgac  1620
taccgggcca cgatcctgcg gtacgggtcc aagtactacc tcgccatcat ggacaagaag  1680
tacgccaagt gcctccagaa gattgacaag gacgacgtga acgggaacta cgagaagatc  1740
aactacaagc tcctcccggg gcccaacaag atgctgccga aggtgttctt cagcaagaag  1800
tggatggcct actacaaccc ctcggaggac atccagaaga tatacaagaa cggcacgttc  1860
aaaaaggggg acatgttcaa cctgaacgac tgccacaagc tgatcgactt tttcaaggac  1920
agcatcagcc gctacccgaa gtggtcgaac gcctacgact tcaacttctc ggagacggag  1980
aagtacaagg acattgcggg cttctaccgg gaggtggagg agcagggcta caaggtctcc  2040
ttcgagagcg cctccaagaa agaggtggac aagctcgtgg aggagggcaa gctgtacatg  2100
ttccagatct acaacaagga cttctcggac aagtcgcacg gcaccccgaa cctccacacg  2160
atgtacttca agctgctgtt cgacgagaac aaccacgggc agatccgcct cagcggcggg  2220
gcggagctgt tcatgcgccg cgcgtccctc aagaaggagg agctggtcgt gcaccccgcc  2280
aactccccga tcgcgaacaa gaaccccgac aaccccaaga agacaaccac cctctcgtac  2340
gacgtctaca aggacaagcg gttctcggag gaccagtacg agctgcacat cccgatcgcc  2400
atcaacaagt gccccaagaa catcttcaag atcaacaccg aggtgcgggt gctgctcaag  2460
cacgacgaca acccctacgt catcgggatc gaccgcggcg agcggaacct gctctacatc  2520
gtggtcgtgg acgggaaggg gaacatcgtg gagcagtaca gcctgaacga gatcatcaac  2580
aacttcaacg gcatccgcat caagacggac taccacagcc tcctggacaa gaaggagaag  2640
gagcggttcg aggcgcggca gaactggacc tccatcgaga acatcaagga gctgaaggcc  2700
ggctacatca gccaggtcgt gcacaagatc tgcgagctcg tggagaagta cgacgcggtg  2760
atcgcgctgg aggacttgaa cagcgggttc aagaactccc gggtcaaggt cgagaagcag  2820
gtctaccaga agttcgagaa gatgctgatc gacaagctca actacatggt ggacaagaag  2880
tccaacccct gcgccaccgg cggcgccctc aagggctacc agatcaccaa caagttcgag  2940
tccttcaagt cgatgtctac gcagaacggg ttcatttttct acatcccggc gtggctcacc  3000
agcaagatcg acccgagcac gggcttcgtc aacctcctga agaccaagta caccagcatc  3060
gcggacagca agaagttcat ctcctcgttc gaccgcatca tgtacgtccc cgaggaagac  3120
ctgttcgagt tcgccctcga ctacaagaac ttctcccgga cggacgccga ctacatcaaa  3180
aagtggaagc tctacagcta cggcaaccgg atccgcatct tccgcaaccc caagaagaac  3240
aatgtgttcg actgggagga ggtgtgcctg acgagcgcct acaaggagct cttcaacaag  3300
tacggcatca actaccagca aggggacatc cgcgcgctgc tctgcgagca gtccgacaag  3360
gcgttctact cgtcgttcat ggccctgatg agcctcatgc tccagatgcg caacagcatc  3420
accggccgga cggacgtgga cttcctgatc agcccggtca agaacagcga cggcattttc  3480
tacgacagcc ggaactacga ggcccaggag aacgccatcc tccccaagaa cgccgacgcg  3540
aacggcgcct acaacatcgc gcggaaggtg ctgtgggcca tcggccagtt taaaaaggcg  3600
gaggacgaga agctggacaa ggtcaagatc gccatcagca acaaggagtg gctcgagtac  3660
gcgcagacga gcgtgaagca c                                            3681
```

```
SEQ ID NO: 8            moltype = DNA  length = 36
FEATURE                 Location/Qualifiers
misc_structure          1..36
                        note = NLS1-Monopartite Nuclear Localization Signal (NLS)
                         from the tomato heat stress transcription factor HSFA1
source                  1..36
                        mol_type = unassigned DNA
                        organism = Lycopersicum esculentum
SEQUENCE: 8
atggcgggat ctaagaagag aagaattaaa caagat                            36

SEQ ID NO: 9            moltype = DNA  length = 33
FEATURE                 Location/Qualifiers
misc_feature            1..33
                        note = NLS2-Monopartite Nuclear Localization Signal (NLS)
                         from the tomato heat stress transcription factor HSFA1
source                  1..33
                        mol_type = unassigned DNA
                        organism = Lycopersicum esculentum
SEQUENCE: 9
ggatctaaga agagaagaat taaacaagat tga                               33

SEQ ID NO: 10           moltype = DNA  length = 200
FEATURE                 Location/Qualifiers
regulatory              1..200
                        note = promoter - Promoter from ZmU6
                        regulatory_class = promoter
source                  1..200
                        mol_type = unassigned DNA
                        organism = Zea mays
SEQUENCE: 10
cggcgtatgt gccaaaaact tcgtcacaga gagggccata agaaacatgg cccacggccc  60
aatacgaagc accgcgacga agcccaaaca gcagtccgta ggtggagcaa agcgctgggt  120
aatacgcaaa cgttttgtcc caccttgact aatcacaaga gtggagcgta ccttataaac  180
cgagccgcaa gcaccgaatt                                              200

SEQ ID NO: 11           moltype = DNA  length = 2008
FEATURE                 Location/Qualifiers
regulatory              1..2008
                        note = promoter - Promoter, 5' UTR and intron from ZmUbqM1
                        regulatory_class = promoter
```

```
source                  1..2008
                        mol_type = unassigned DNA
                        organism = Zea mays
SEQUENCE: 11
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttaa aactaaaact  420
ctattttagt tttttattta ataatttaga tataaaatga aataaaataa attgactaca  480
aataaaacaa ataccctta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct tttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc tttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtc                                     2008

SEQ ID NO: 12           moltype = DNA  length = 927
FEATURE                 Location/Qualifiers
misc_feature            1..927
                        note = synthetic sequence
source                  1..927
                        mol_type = other DNA
                        organism = synthetic construct
SEQUENCE: 12
tgcccggtct ccattattcg caagaccctt cctctatata aggaagttca tttcatttgg  60
agaggacacg ctgaaatcac cagtctctct ctacaaatct atctctctct attttccgga  120
ccgaccgtct tcggtacgcg ctcactccgc cctctgcctt tgttactgcc acgtttctct  180
gaatgctctc ttgtgtggtg attgctgaga gtggtttagc tggatctaga attacactct  240
gaaatcgtgt tctgcctgtg ctgattactt gccgtccttt gtagcagcaa aatataggga  300
catggtagta cgaaacgaag atagaaccta cacagcaata cgagaaatgt gtaatttggt  360
gcttagcggt atttatttaa gcacatgttg gtgttatagg gcacttggat tcagaagttt  420
gctgttaatt taggcacagg cttcatacta catgggtcaa tagtataggg attcatatta  480
taggcgatac tataataatt tgttcgtctg cagagcttat tatttgccaa aattagatat  540
tcctattctg tttttgtttg tgtgctgtta aattgttaac gcctgaagga ataaatataa  600
atgacgaaat tttgatgttt atctctgctc ctttattgtg accataagtc aagatcagat  660
gcacttgttt taaatattgt tgtctgaaga aataagtact gacagtattt tgatgcattg  720
atctgcttgt ttgttgtaac aaaatttaaa aataaagagt ttcctttttg ttgctctcct  780
tacctcctga tggtatctag tatctaccaa ctgacactat attgcttctc tttacatacg  840
tatcttgctc gatgccttct ccctagtgtt gaccagtgtt actcacatag tctttgctca  900
tttcattgta atgcagatac caagcgg                                      927

SEQ ID NO: 13           moltype = DNA  length = 987
FEATURE                 Location/Qualifiers
misc_feature            1..987
                        note = synthetic sequence
source                  1..987
                        mol_type = other DNA
                        organism = synthetic construct
SEQUENCE: 13
tgcccggtct ccattatttt gcttcttgta tgcccggtct ccattattcc tctcattata  60
tgcccggtct ccattattcg caagaccctt cctctatata aggaagttca tttcatttgg  120
agaggacacg ctgaaatcac cagtctctct ctacaaatct atctctctct attttccgga  180
ccgaccgtct tcggtacgcg ctcactccgc cctctgcctt tgttactgcc acgtttctct  240
gaatgctctc ttgtgtggtg attgctgaga gtggtttagc tggatctaga attacactct  300
gaaatcgtgt tctgcctgtg ctgattactt gccgtccttt gtagcagcaa aatataggga  360
catggtagta cgaaacgaag atagaaccta cacagcaata cgagaaatgt gtaatttggt  420
```

```
gcttagcggt atttatttaa gcacatgttg gtgttatagg gcacttggat tcagaagttt  480
gctgttaatt taggcacagg cttcatacta catgggtcaa tagtataggg attcatatta  540
taggcgatac tataataatt tgttcgtctg cagagcttat tatttgccaa aattagatat  600
tcctattctg tttttgtttg tgtgctgtta aattgttaac gcctgaagga ataaatataa  660
atgacgaaat tttgatgttt atctctgctc ctttattgtg accataagtc aagatcagat  720
gcacttgttt taaatattgt tgtctgaaga aataagtact gacagtattt tgatgcattg  780
atctgcttgt ttgttgtaac aaaatttaaa aataaagagt ttccttttttg ttgctctcct  840
tacctcctga tggtatctag tatctaccaa ctgacactat attgcttctc tttacatacg  900
tatcttgctc gatgccttct ccctagtgtt gaccagtgtt actcacatag tctttgctca  960
tttcattgta atgcagatac caagcgg                                      987

SEQ ID NO: 14          moltype = DNA  length = 1077
FEATURE                Location/Qualifiers
misc_feature           1..1077
                       note = synthetic sequence
source                 1..1077
                       mol_type = other DNA
                       organism = synthetic construct
SEQUENCE: 14
tgcccggtct ccattattct gacgactata tgcccggtct ccattatttc ctgctaatta  60
tgcccggtct ccattattat cctcaccata tgcccggtct ccattatttt gcttcttgta  120
tgcccggtct ccattattcc tctcattata tgcccggtct ccattattcg caagaccctt  180
cctctatata aggaagttca tttcatttgg agaggacacg ctgaaatcac cagtctctct  240
ctacaaatct atctctctct attttccgga ccgaccgtct tcggtacgcg ctcactccgc  300
cctctgcctt tgttactgcc acgtttctct gaatgctctc ttgtgtggtg attgctgaga  360
gtggtttagc tggatctaga attacactct gaaatcgtgt tctgcctgtg ctgattactt  420
gccgtccttt gtagcagcaa aatataggga catggtagta cgaaacgaag atagaaccta  480
cacagcaata cgagaaatgt gtaatttggt gcttagcggt atttatttaa gcacatgttg  540
gtgttatagg gcacttggat tcagaagttt gctgttaatt taggcacagg cttcatacta  600
catgggtcaa tagtataggg attcatatta taggcgatac tataataatt tgttcgtctg  660
cagagcttat tatttgccaa aattagatat tcctattctg tttttgtttg tgtgctgtta  720
aattgttaac gcctgaagga ataaatataa atgacgaaat tttgatgttt atctctgctc  780
ctttattgtg accataagtc aagatcagat gcacttgttt taaatattgt tgtctgaaga  840
aataagtact gacagtattt tgatgcattg atctgcttgt ttgttgtaac aaaatttaaa  900
aataaagagt ttcctttttg ttgctctcct tacctcctga tggtatctag tatctaccaa  960
ctgacactat attgcttctc tttacatacg tatcttgctc gatgccttct ccctagtgtt  1020
gaccagtgtt actcacatag tctttgctca tttcattgta atgcagatac caagcgg     1077

SEQ ID NO: 15          moltype = DNA  length = 18
FEATURE                Location/Qualifiers
misc_feature           1..18
                       note = synthetic sequence
source                 1..18
                       mol_type = other DNA
                       organism = synthetic construct
SEQUENCE: 15
tgcccggtct ccattatt                                                18

SEQ ID NO: 16          moltype = DNA  length = 2973
FEATURE                Location/Qualifiers
misc_feature           1..2973
                       note = synthetic sequence
source                 1..2973
                       mol_type = other DNA
                       organism = synthetic construct
SEQUENCE: 16
cctgcagctc aggtggacct ccgcaccctt ggctactctc agcaacagca agagaagatc  60
aagccaaagg tgcggtcaac agtcgcacag caccatgagg cactggtggg ccacgggttc  120
acccacgctc atattgtcgc actcagccag catcctgcag cacttggcac cgttgcagtg  180
acgtaccagc acatcattac agccctccca gaggcgaccc atgaggacat cgtcggcgtt  240
gggaagcagt ggagcggcgc aagagctctc gaggctctgc tcaccgatgc aggcgagctt  300
agggggcctc ctctgcagct cgacacaggc caactggtga agatcgcaaa gagaggcggg  360
gtcaccgcga tggaggctgt tcacgcaagc cggaacgctc tcaccggtgc accgcttaat  420
ctcactccag ctcaggtcgt ggctatcgcg tccaacaatg gcggcaagca ggcgctcgag  480
actgtccaga ggctcctccc cgttctgtgc caggaccacg ggctcacccc agatcaggtg  540
gtcgctatcg cgtcccatga cggcgggaag caggccctgg agaccgtgca gcgcctcctg  600
ccggtcctct gccaggacca cggcctgacg ccagatcagg ttgtggctat tgccagccac  660
gatggcggga agcaggcgct cgagacagtt cagaggctcc tgccagtgct gtgccaggat  720
cacggcctga ctcctgatca ggtcgttgcg atcgcttcgc acgatggggg gaagcaggct  780
ctggagaccg tccagcggct cctgccggtt ctgtgccagg atcatgggct cacgccagat  840
caggtggtcg ccattgcgtc taacaatggc gggaagcagg cgctcgaaac agtgcagcgc  900
ctcctgccag tcctctgcca ggaccatggg ctcactcctg atcaggttgt ggctatcgcc  960
tcaaacaatg gcgggaagca ggccctggaa accgttcaga ggctcctgcc ggtgctgtgc  1020
caggaccatg ggctgacccc agatcaggtc gttgcgattg cttccaatgg cgggggcaag  1080
caggcgctcg aaaccgtgca gcggctcctg ccagttctgt gccaggatca cgggctgact  1140
cctgaccagg tcgtcgctat cgcgagccat gacgggggca agcaggccct ggagactgtc  1200
cagcgcctcc tgccggtctt atgccaggat catgggctga ctccggacca ggtcgtggct  1260
attgcctcga acgggggggg gaagcaggcg ctcgaaactg tgcagaggct cctgccagtc  1320
ctgtgccagg accatggcct caccccggac caggtggttg cgatcgcttc tcacgacggc  1380
```

```
gggaagcagg ccctggaaac agtgcagcgg ctcctgccgg tcctgtgcca ggaccacggg  1440
ctgaccccgg accaggtcgt ggccattgcg tcacatgacg gggggaagca ggcgctcgaa  1500
acggtccagc gcctcctgcc agtcttatgc caggaccatg gcctgacccc ggaccaggtg  1560
gtggctatcg cctccaacat cggggggaag caggccctgg aaactgtcca gaggctcctg  1620
ccggtcttgt gtcaggatca tgggctgaca ccggaccagg tcgttgcgat cgcctccaat  1680
ggcggcggca agcaggcgct cgaaacagta cagcggctcc tgccagtctt gtgtcaggac  1740
catgggctga cacctgacca ggttgtcgct atcgcgtcga acgggggtgg gaagcaggcc  1800
ctggaaacgg ttcagcgcct cctgccggtc ctatgccagg atcatggcct caccccggat  1860
caggtcgtcg ctatcgccag caatataggt gggaagcagg ccctcgagac agtccagagg  1920
ctcctgccag tcttatgtca ggatcatggc ctcactccgg accaggttgt tgcgatcgct  1980
tccaacggcg gcggcaagca ggccctcgag actgtccagc ggctcctgcc ggtgctctgc  2040
caggatcatg gcctcactcc agaccaggtt gtggcgattg cctctaatgg gggggggaag  2100
caggctctcg agtctattgt ggcgcagctc tcaagaaggg acccggcgct agcggctctg  2160
actaatgacc atctcgtggc tctggcttgc ctgggggggc ggcctgctct ggacgctgtg  2220
aagaaggggc tcccacacgc tccagagttc atccgcaggg tgaacaggag gattgctgag  2280
cggacaagcc acagggtcgc tgactacgct catgtggtcc gcgttctgga gttcttccag  2340
tgccactcgc atccggctca cgccttcgat gaggccatga cccagttcgg catgtctcgg  2400
catgggctgg tccagctctt caggcgggtt ggcgtgactg agttcgaggc tcgctacggg  2460
accctgccac cagcgtccca gcgctgggac aggatcctcc aggcgagcgg catgaagagg  2520
gctaagccaa gccctacctc ggctcagacg ccagaccaga catctctcca cgcgttcgct  2580
gattcactgg agagggacct cgatgctcca tccccaatgc atgagggcga ccagaccagg  2640
gcgtccagcc gcaagaggtc acggtccgat agggctgtga cggggccatc ggctcagcag  2700
gctgtcgagg ttagggtgcc tgagcagagg gacgctctcc acctgccact ctcctggagg  2760
gtcaagcgcc ctaggacgag gatctggggc gggctgccag accctggcac accgattgcc  2820
gcggatctcg ctgcctcgtc tactgttatg tgggagcagg acgctgctcc attcgctggc  2880
gctgctgacg atttcccagc cttcaatgag gaggagctgg cttggctgat ggagctgctg  2940
cctcagtcgg ggtcggttgg cgggacaatc tga                               2973
```

```
SEQ ID NO: 17          moltype = AA  length = 990
FEATURE                Location/Qualifiers
REGION                 1..990
                       note = synthetic sequence
source                 1..990
                       mol_type = protein
                       organism = synthetic construct
SEQUENCE: 17
PAAQVDLRTL GYSQQQQEKI KPKVRSTVAQ HHEALVGHGF THAHIVALSQ HPAALGTVAV  60
TYQHIITALP EATHEDIVGV GKQWSGARAL EALLTDAGEL RGPPLQLDTG QLVKIAKRGG  120
VTAMEAVHAS RNALTGAPLN LTPAQVVAIA SNNGGKQALE TVQRLLPVLC QDHGLTPDQV  180
VAIASHDGGK QALETVQRLL PVLCQDHGLT PDQVVAIASH DGGKQALETV QRLLPVLCQD  240
HGLTPDQVVA IASHDGGKQA LETVQRLLPV LCQDHGLTPD QVVAIASNNG GKQALETVQR  300
LLPVLCQDHG LTPDQVVAIA SNNGGKQALE TVQRLLPVLC QDHGLTPDQV VAIASNGGGK  360
QALETVQRLL PVLCQDHGLT PDQVVAIASH DGGKQALETV QRLLPVLCQD HGLTPDQVVA  420
IASNGGGKQA LETVQRLLPV LCQDHGLTPD QVVAIASHDG GKQALETVQR LLPVLCQDHG  480
LTPDQVVAIA SHDGGKQALE TVQRLLPVLC QDHGLTPDQV VAIASNIGGK QALETVQRLL  540
PVLCQDHGLT PDQVVAIASN GGGKQALETV QRLLPVLCQD HGLTPDQVVA IASNGGGKQA  600
LETVQRLLPV LCQDHGLTPD QVVAIASNIG GKQALETVQR LLPVLCQDHG LTPDQVVAIA  660
SNGGGKQALE TVQRLLPVLC QDHGLTPDQV VAIASNGGGK QALESIVAQL SRRDPALAAL  720
TNDHLVALAC LGGRPALDAV KKGLPHAPEF IRRVNRRIAE RTSHRVADYA HVVRVLEFFQ  780
CHSHPAHAFD EAMTQFGMSR HGLVQLFRRV GVTEFEARYG TLPPASQRWD RILQASGMKR  840
AKPSPTSAQT PDQTSLHAFA DSLERDLDAP SPMHEGDQTR ASSRKRSRSD RAVTGPSAQQ  900
AVEVRVPEQR DALHLPLSWR VKRPRTRIWG GLPDPGTPIA ADLAASSTVM WEQDAAPFAG  960
AADDFPAFNE EELAWLMELL PQSGSVGGTI                                   990
```

```
SEQ ID NO: 18          moltype = DNA  length = 612
FEATURE                Location/Qualifiers
regulatory             1..612
                       note = promoter - 35S promoter
                       regulatory_class = promoter
source                 1..612
                       mol_type = unassigned DNA
                       organism = Cauliflower mosaic virus
SEQUENCE: 18
ggtccgattg agacttttca acaaagggta atatccggaa acctcctcgg attccattgc  60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga gg                                                      612
```

```
SEQ ID NO: 19          moltype = DNA  length = 501
FEATURE                Location/Qualifiers
source                 1..501
                       mol_type = unassigned DNA
```

```
                         organism = Citrus yellow mosaic virus
SEQUENCE: 19
ctggtggccc tccaccagca caaactcgct tacatcagaa gcaaagctac aagggacaac  60
gcatatgccg ataggctacc cacatgcaat cgggaccacg agcaactgtg tgaagtggtc  120
gagctattag aaggaatctc ggaaagaatc agcgatacag ctgtctagga cagctggctt  180
caattatgga gcgtgatgga cccccccgca ataatccaaa gtttggtgtg cttttagtag  240
tgcgtcttta tggaccacta ctttattgta ataatcgatg ctttttgtag tgcgctcttc  300
gtgcgctcta ctttatgctt ttgcttttgt aagtgcgctg taagtgcgcc tgtctttctt  360
cagatgctta tcctttaagc atcttttgct ttttgcgtgg catcctttag ttcacaattt  420
aaagaatgac gatggggccc aagatgtgca cccggttctc taaattgcct atataaggat  480
atcccatagc cttgtttttg c                                          501

SEQ ID NO: 20          moltype = DNA  length = 560
FEATURE                Location/Qualifiers
source                 1..560
                       mol_type = unassigned DNA
                       organism = Sorghum bicolor
SEQUENCE: 20
agaagtaaaa aaaaagttcg tttcagaatc ataaaggtaa gttaaaaaaa gaccatacaa  60
aaaagaggta tttaatgata aactataatc cagaatttgt taggatagta tataagaata  120
agaccttgtt tagtttcaaa aaaatttgca aaattttcca gattcctcgt cacatcaaat  180
ctttagaggt atgcatggag tattaaatat agacaagacc taaataagaa aacatgaaat  240
gttcacgaaa aaaatcaagc caatgcatga tcgaagcaaa cggtatagta acggtgttaa  300
cctgatccat tgatctttgt aatctttaac ggccacctac cgcgggcagc aaacggcgtc  360
cccctcctcg atatctccgc ggcggcctct ggctttttcc gcggaattgc gcggtgggga  420
cggattccac gagaccgcaa cgcaaccgcc tctcgccgct gggccccaca ccgctcggtg  480
ccgtagcccg tagcctcacg ggattctttc tccctcctcc cccgtgtata aattggcttc  540
atcccctccc tgcctcatcc                                            560

SEQ ID NO: 21          moltype = DNA  length = 1998
FEATURE                Location/Qualifiers
source                 1..1998
                       mol_type = unassigned DNA
                       organism = Zea mays
SEQUENCE: 21
tgcccgggtc ggggccggaa gtcgcgcgtg gggcctgtcc atcgaacaaa agcgagagaa  60
aacgtgcatc ggccggtggt ggcccgtacg gtgggctggg ctcgaatcaa cagcagatga  120
attggtagac aagacagcgc gatgcatgaa tagtgcgtga ttgggcttct cgagatagac  180
gcggttaatt gggccggatt gcacacgcaa aaacaaaaaa aaaaaactgt cggcgtttgc  240
agttgcagtt gggcagtgtg cacacacgtt aacaacagca gaagcagcaa atgacacggc  300
tcggctcatc aattagctgc tgccacaaac aagggtttac ctgtcggctc atcaattagc  360
tactactaat aatcagcagc gctcggcact ctggcagcac aagcgcagga cccaccagta  420
ctgtgtgcgt gacagcgtga gtactgagtt gggaagccac accccacacc acacggcgta  480
ttggctgtca accgacccgg atcgatcgac tagttgcggt tgccgtcggt tgctcggaca  540
ctcagccctg tcaaggtagc agtactcctc ccggccttat cactccggtg cagtgcagtg  600
gaaacaaaag gcagaaatcc ctaccacggc ggcgcattga tgaatccccg ctgctgtgac  660
tcagagcctg acgagggggt gctatgctac ggcctactcc gggctagggt gtggagcgag  720
tgtctgggac tgggagaatc cagcgtcgtg tactgtccac gcgtacgcgg gttctcggca  780
aggccaagtg ggcaacatgg cagggtggca agacggtact gtatgtacct accggcacta  840
cgcttcgacg cctccttttt tccaaaacct tccaagcccc gcgttcaaac tgtgcctagg  900
cgacggatcc tcggtgctag tagatcacac acacacacac acacacgggc gaaatgtcgg  960
cgagttaatg acggtggtta aagtgaaacc tggatccagc accagcagca gtctttcagg  1020
tttcaagaac actcaggtcc tgcgttactg tggactgtgg taaaagtgcc ggaagttcag  1080
ttcgacgggg gaagaaaaga agggccgcac ctgcacacag cacacctact acactagtac  1140
actgctgcaa tgtactacct gggccgtgct ccaaaagtcg taaccactcg gagacttccc  1200
tctgtcctat ctccgatcac tgatacatct cacaccctca ccacaccgtg acataatttg  1260
ccagtagggt ttacggtgcg gtatcgataa taaccacact acttgcacaa cagctcactt  1320
cttcgttatt tttttttgt caagtggggt cgatctggcg ctgcctatga ttcaagtgtg  1380
agaattcagc aacagccagc cagctcctgt ttccgtgtac atacgctttc taaaagctgg  1440
accaggccgg cccaatgctc cagttgcccg tgcgcgctgc ttcgcccccct accccaggcc  1500
tagccgcacg gaaatgaatg cgggcccact gcccggacga cttgcaacta gtctccaccc  1560
tgttcaatta aatccacaga cgctgggaaa acaattcttt ttgaaaggta gaaataaata  1620
aaagattgtg ggctgttgaa gtgcaatcta accccttttct cagactatct tctaaataac  1680
tacttttcgc agaatcaggc gtgtcatctc tagacgatga gattacacca gtcagctaca  1740
gatgacgaat ctgattaaaa aaaatttggt gctagtatac tctaatcgtt ttacgctaga  1800
tatgttgtca ttaattaatt gataaaaaaa aaacaatatt tgtaactgat gccatgcatg  1860
cagcaggctg cacggcacgg tcgtccggaa ctccggatga tgatataaga ccagcgtcac  1920
ccccgcgcgc gcagcctgct gtgatgcgcc caagtcgatc aatcatcgtc cgctctcatc  1980
atctcatcgc aaagccaa                                              1998

SEQ ID NO: 22          moltype = DNA  length = 1992
FEATURE                Location/Qualifiers
source                 1..1992
                       mol_type = unassigned DNA
                       organism = Zea mays
SEQUENCE: 22
atctctcctc tcctctcctc tcctcccgtt ggtgtgactg tagtagatcc tttgcccgtg  60
tcagaacaag ctgctcctcg gaccgggtaa tgttaaacat cggaggagcc tttgcctagg  120
atccgtaacg gggaggaaag agaaaaaaaa ctaaggatga ttatggatac cgtgtaataa  180
```

```
ctgctaacta cagttagccc atctcagcgg actctctgcc ctatattgta tgtcactttc  240
tattataaac tacactatac aacctatgat gtaaaataat gttttgcacg ttcatatata  300
aatcagtcga agaaagggtg cctcactaca gggaatggtt tctattggac accttagcat  360
tcaatcagtc atgtcccccc cccccccaa aaaaaaaatg cacccatcca gtcgattttt  420
gtcatatttg aattcggtgg tgctccatgc acgcgtacct gctttgacca atttatacga  480
tcaatatata acttacgttc ttacggttct tagactttat gagactttgc aagtatgttt  540
ggatacaaat cacactaatg tgcatctttg taaactaaat tcttttgatt aaatttgtaa  600
ttttaaggtt taacctgttt ttgttgtgta gacgacgtta ggcaccgatc gtcgcttcgc  660
tatatatctt tgttgtagac gacgttagac tcctagatta aataagcgaa aaccgatcgt  720
cgcttcgcta tctttgttta tttgtttgtg gctgctctac gctgaagagc ccacaggcca  780
cagccccaca cgacacgtta ggcacccca cccaccatcc gcgcataata taagctactg  840
caaaatatat gccggcggag cccgagcgag ctttgtactt gctccgccgt ggcctggctc  900
caggatgctt tggatttcgt gcggcgccgt acgtccaggc aaacagacaa gtggagctgc  960
atgtcctaaa agcccggcaa tcaaacacgc tctagcagca gcatggatca cagatatcag  1020
tcatggggtg gcgctggcgc gggtgggtgg ccaggtggag gtgggtgcat gtcgtcgtcg  1080
tcgtcccata cagaaattgg ctcacgtatg tatacgctgc gtacaggcag tagtacacaa  1140
ttactagcac caatgcaatc caacggatgg atcttcgcac acccgccacc cggttaaatt  1200
aagctactcc tacctctccc agtctccctt ggcctgcctc tatatttttg ggcagcctcc  1260
accagccggg cggatggggt tggatcgtcg tatctgaggc ggcgtggtcg tccaaggcga  1320
aagcaacggc gcagggctgg gaccctagta ggtgcatgag gtcgtgcatg gcgcgcgaga  1380
tgcatggttt gggttaggcc taggaggttc tctctccatg gcatgggtag ctcgcgccgc  1440
ttggctgccg ttctcgtgta tgcgcatgca ccaggcattt gcaccgcgcc gtgtatattt  1500
ctggcgtggg ggccggcgcc gcattggagc tgcagccccg tttcggcacg gacacgggac  1560
acctcccgtt agggtaagcc cggggcagtg ggtaactgcc cagcgccact actccgaatt  1620
taccctcctt ttatttttaa agcttgggag aggggagaat ggatggatgg atggatgtag  1680
acgcgtgaaa aagatgcgcg agaccggcag cgtgtgctac aggggcagcc aggcacacac  1740
acacacagtg accctgcccc ttttcccggc cgtctcgctc tccaccgata ttccgctcct  1800
cctgtccagt cctcctcccc cgagccggct cattatatcg tccgtcgcgc agcacaacgc  1860
aagtttgcta gcggccggat cagcagccac aaaacgagga gagcaaccac gctgcacaca  1920
gagacgcccg tgtgtgagat atagagcaag ctcgatcgaa ggaaggaggg aagctagaga  1980
tcgtacgtcg cc                                                     1992
```

```
SEQ ID NO: 23          moltype = DNA  length = 1998
FEATURE                Location/Qualifiers
source                 1..1998
                       mol_type = unassigned DNA
                       organism = Zea mays
SEQUENCE: 23
atagaaaatt cctcaaggaa ctgcacgagg aaatgatcca gcaagacata tgcaaaatca  60
atccagcaca cagaaccatt ccacgtgagg actgcggaac gcagtggaaa ctccaagtta  120
gaagttagaa cagttgtgtt tttgaaggaa cagagaggcc ctttgtctgg aaacgcatga  180
gcatgcatgc atgtctcatg catctgtgca ggatgtccta attattatcc attaccctgg  240
agcagcagat caagtttttt ttggtgccct ttagttcaca aaatataacg taaataataa  300
taataatggt ttacattcga gtactggtgg taataataag tttgaataga ccgatatcaa  360
tttttagtat gatatctgat tatggttgaa tttaagcaaa cataatttaa cgttatcagt  420
tacccaatta attacaaata taaaaatcaa acggcaccta gggtacgcag atgtacacag  480
gagtcaggag gcgctgaacg atctccatgg tcagttctta ataacatcca tgcatgcacc  540
taagtcaaat catacaataa taccgaccct gcagttgttg gatgaggccc agcattacgt  600
acacacacga aaattttttt gataatggaa ataagtgttc cggcttttcg catcatcaga  660
tacgtacaac cattacatgt caattattga ttcaatggac agttatttag ttctttattt  720
gaaaaatgaa actaactcga caaaaccaaa taacatagct atggaaaata aacactaggc  780
acacataagt cttgcatttg atcgccatcg atgaatcgca aagatttcca tcaccatcac  840
ttctaaagct tgtcacatat cgagaatttc ttgttgtact tcctccttct gtaggagtct  900
ctaaaacctg agccagtggg tacctctgaa aatgacctac acaattgatg atattggttt  960
ttgattaaaa gtcacctcgt ttcgaataag ccaaatagac caaaataaag ttgatattac  1020
agtaagtagt aactttttta tactagacca caattacttg tccaagacct gataatatga  1080
ttaatgttga ctgtcgtttc tatttctaga gcaagataaa ttatcatcca aatatttttg  1140
gcaatatagc aatcgaaaaa gagttaagta cacacacgaa ctgatatagg caaacagtat  1200
tttggccgct agctagtctt cctcatccct gttgcttcaa ctcgatttta cacggttcca  1260
tgtaaatatg ctgctggtaa aacaagtaac gatgcatgtg tgcgtatgca tgcatatcga  1320
tctgaaagaa gatttcagca tcggtctatc cattattcat gtgagcctgc agtgactgtg  1380
aggtcggtat atcgtcgagt ttcacaggcc tgtttagtgg atgtgggtaa tgccggtgat  1440
gatgagaaac aaaaggttac atgtgtatga tgtctataga tagtctcata gaacatttgg  1500
actgtgtata tgtatgtggg catgcagcag gcacagtgtg aacatgatag accaagcagg  1560
gcctcgcgct tgtgcgaatg gaccaacctt ttcctagcta actctgagga ctgtatgcag  1620
ccttgacagc aagaggagtc cgccgtttga aactcaagac catggaaaac attttcaagg  1680
tccattcggg gtagtagtcc cttaatttcc tttttattaa ttttttttaa aaggaaaagg  1740
accgggctac ttttcaacgc ttagcttgtc gacccagcag ctagctagct ggccgataga  1800
acgagctagc ggggcaagcg ctctctctgg attctataaa tccagcattt tgctcacatt  1860
ctgctctcgc cacctttgaa cgatagcctt tctcactccg acacttgaaa cacgttcatc  1920
aggagctcgt cctcaggctt gctagtagct tatattacct acctagctag ctagctagtc  1980
aagactcaag atccatcc                                               1998
```

```
SEQ ID NO: 24          moltype = DNA  length = 1898
FEATURE                Location/Qualifiers
source                 1..1898
                       mol_type = unassigned DNA
                       organism = Zea mays
SEQUENCE: 24
```

```
cgacgagaac tgttttcggt ctgatatcca cggctctgag ccagacctgt gtgcctcctg  60
gaaaaacctc gttacatcca gtaggtttat tttgtccccc taggtctact tttgatatgt  120
ttctatcaca gatgagtggg tgcgctggta cccttttatt ttgtcgatat gagacaatct  180
ttactgtttt gttatgcaaa taatagaaac ggatcctacc gtcgtaaaaa atgaccaaag  240
tccataatgg atcgatgaat tagttgttgt ttttgccatc aaacatgata tacgttaaaa  300
aaactatatg gacaaaagaa gcaaacatac tgctaagtct tttccttacc gaatcgaagc  360
catgtgtgtc ttgctgaatg tggattccct tgatgggcag ggcattagga aagagtgggg  420
tcaggtgatg tctccagctc agtgtcaggg ctcactggtt cgccaagctc accaactgcc  480
acggacgagt cacatcatcg tgatgagcga tattaggctt gccgggctgg ctggcgttgc  540
gatgacgatg agcggggcgg gcgacatcac atacctagaa cgggcagtgg tggtaatatc  600
gagaacgggg catcgaggtg gactgactag agcagcgtca ggaataatag gattgaatgg  660
atagatgcga ggactaatcc aaaaaaggag gataggagtc aagaggactg gactgatctt  720
acgaggaggc caagataaaa cgattttagc ccactaaaaa actttaattt tttctatact  780
taaccctaaa tgaacactag gtataagagg ttataaaaat taagggccca ctttgcaccc  840
cctgaatcag ccgctagtaa gtgtccactc tccaatctcc atggcggcaa gcgacagacg  900
acaggtctat ttggttgtat aactaagatg cctaaatttg acacatattt tctgccacac  960
ttgactgagg ttaggtattc aaattcttcg tcacatctta gcatactaag acaactttgc  1020
tgtactttta caagtcattg acgagttaga cctctgtata ggagaaaaat tttgtcataa  1080
ctatggctac aaaccaaaca cgtgactaag ctagtcaaat atgtctaacc ttaaacttgg  1140
taacagagac aacaaaccaa acatgccccc catgttttcc tcattttctt tttccacttt  1200
tgtttcaatt tttcttgggt aatatacagt gagtatatta ttttcttctt ctttttctca  1260
tggccaaaat ccacaatgga tcgatgaatt agctgtcgtt gttgccaaca aaagaacaaa  1320
atcatgtgac gcacgagcac aatgcaagta gccaaactga gcttccgggc accgacgaac  1380
ggttgcacgc catcggcggg aaggaacagg ccgggctgtc aatggacaaa cgggccgcca  1440
agctggaggg agtgtcatgg gctttgagaa ccatcgtcag ggcctagttt tttcttttgt  1500
ttttatcaaa ggcggtaaac tcggggaacg aatatactag gaaaaacact agccagtcag  1560
agtcagtcaa agtggactga gttaaaattg caacgataca tacacacgca gcagtcaggg  1620
cgtcgggaat gaacaatgga tgaatttatt atagtctgaa gaaaacgaag ggacacagcc  1680
acaacgaaca ctggggagtg aatgaatgca tgcattccac tggactgttc cagcgcttcg  1740
tgtgcatcgc tagatgcgct gaacactcga acgccatgga cctcgctccg ctctctatat  1800
atagagggaa ggccttcagt ctacttctcg ggatatacca ctgaacgtca ccaagaagag  1860
tactgatcga tcagcaactc gatcgttctc agagagag                          1898

SEQ ID NO: 25          moltype = DNA  length = 1118
FEATURE                Location/Qualifiers
source                 1..1118
                       mol_type = unassigned DNA
                       organism = Zea mays
SEQUENCE: 25
agtcacactt gaacatgatt aatacttatt ctgcaaatat gtcaaataac atttgaagta  60
gtattttttt aatgtacata actaggaaaa ggtatacctt tttgacataa gtatccacgt  120
gcaactgctt gcaattgagc tatgttatgc ccataatatt tgttcaattt tcttcaaaac  180
tatagatgtg catacagata gttaaaatgt taaactcatc attgttttcc ttccacatgt  240
ttccatagaa aaaatctaag gaaaaccatt acaattttcc ttgaatgcct tgtttctaat  300
aaaaagcggg aacaaaacgg ggcagtttga tctcaattaa gaagggtctc ttccttccat  360
tctttaattg tcgtgatcct actttcttat acttaagggg atattctatt tcaatatgca  420
ttttttgagt tgatggtggt cgttaataaa ttcttctaag aaaataatct ttagtgacta  480
tatgatgttt tcttagtatt aactactaag ttgtgtagtt gttccataat tctacaagat  540
taggtacaat aatacaagtt gttaccacat tattatattg ttaagatttt gaactgattt  600
gatacttgcg atatttggac tttatgtggt caaatattgc tcatattgtt taatatattt  660
aatttagtaa gctaaggatt ttatgtggtt gtaatatttg gattttatgt ggttcaaata  720
tatgagttag gctacggctt gttttagtgc cgcactagtt ttgtatactt taggctggca  780
caatgccatc aaaaaaaaaa ttagttctac ttaactcgaa ctattttaat acgaagcaaa  840
gtccggccag cactactgcc tgccacggca cactactggc ctctgtagct cacgacacgg  900
tctccaagaa gaagctgttt cccaatgtta tcatggagtc catggatcag taaattagtt  960
cggggacagc gtggaatacg aaggcatttt gcataaatca agggacttat catacaggta  1020
atataaatac cccctctgat cgctagtagt agttcactat cacactaacc ttgcatcaaa  1080
taaaccatta ctacttcacc ttgccaggcc gcctgggc                          1118

SEQ ID NO: 26          moltype = DNA  length = 1898
FEATURE                Location/Qualifiers
source                 1..1898
                       mol_type = unassigned DNA
                       organism = Zea mays
SEQUENCE: 26
ccgaaggttc tcaaagaaaa tgagcgaact cctagatgtc accgccgttg acgtggtgag  60
tgcattcacc tacgacacca ccaacgagtc gtccacgagc ttggacaggg gtgacaaaag  120
atggccaccg acctcttcga catagcggtc gctgacgagg aagacgtggt gggggcaatt  180
ttccgcaaga gaaaaaactc gcgtgatgcc gacgagccca gcggcgaaac gagggatcaa  240
cgagagcacc ctggtagacg tcagataaac cactgcccca cacgaaccga ggaaggagaa  300
gacactgtcg cggaccggtc gctaggggtg ggcgttcggg ttacccgaaa ttttcgggtc  360
gggtaattcg ggtttttaaa atttcgggtt ttgagaattg atacccgaaa ttacaatggg  420
ttttgcaata cccgaaaatt cgggtacccg gaatttcggg ttcgggttcg ggtattcccg  480
aactacccga actattatgt tggcttcata aaaacacata taccctatta aattagtata  540
aaaacatagt ttgaataatg atatacatgg acatataaaa cataagctat ctacaatcac  600
aagttatgca cacttacaca taattataga tgtacaaatt aataattaat catgacatga  660
gtatatgaca catgaaagtt cgggtaattc gggtacccga attttccgaa ataaattcgg  720
gttttgtaag ttgctacccg aaattctcga acaaaattcg ggtatttcga gttcaggttc  780
gggtattccg gattcgggtt tcgggttacg ggttttttgc tcagccttac cggccgccca  840
```

```
cacaactggc gaagaacgac aacgaccact tatagagtgg aaatacctat agagtggaaa  900
tttttgacac gaggcggtgg ctgtatggac aggaccggag gaggatgcgc ggtacgtagg  960
ccgattgtgc cagcctatta gggcatgtac agtgggtgtt ttaagttgtg tcttacaacg  1020
tgtctagagg ggtgaatgta aaaaaactta agacacgtat cttgacgaag acacagtgtc  1080
ttagctctat gttcgagaca gaagactagc tgattggtca ttttaattta ttgaatgctc  1140
tgattggtac aatgaatatc gtaagacaca tgttttagat atgaccactg tattatgttg  1200
tgttttagtt gtatcttgta cttggagtac cgtgcagcag tatctgggtt gtacgtgccc  1260
ttatgtaggg gaagggagta gaaatacgat caatgcgaac gcacgttgat gacggtgaaa  1320
acggtagaaa ccggtggaag tagagattac agcaaacatg gagggacggc tttcgtccac  1380
ccaccggtcc ttggcgcgcg cgcggcgagc ctacgatcca aaagccgcga ccgcttggtg  1440
ttttggctga cgcttgggaa cctgccgcag ctgcatttct tgctttggga gccatgtacg  1500
gcgaactcat acttttgacg tcggttcttt ttcgaaaaaa cttttgacgg tcagttttcc  1560
ccactcccgc tatatttaaa accccccacc actcccccaa tatttatgac ttgacaacaa  1620
ttcccacatc gattcattgt cacttgccag aagtcgggcg gccatcgatc ccactcccac  1680
cgcttacagc cggcccagtc ctcgtcggcg ccggacgggg cgaaggtaac ccccaagctt  1740
ccagattctc tgtcaacttc agttatgcgt ttttctttta agatgaacct gaaacatttt  1800
agctttagat caccggagtc attttttttt ttcattaggc gattggagtt aaaacaggcc  1860
gagtgggaga atttcctgga tcttatctgt tctccatc                         1898

SEQ ID NO: 27          moltype = DNA  length = 2000
FEATURE                Location/Qualifiers
source                 1..2000
                       mol_type = unassigned DNA
                       organism = Zea mays
SEQUENCE: 27
ccgacaacat cggcatacgg cggaaatact ggcagatgct gctcgtctcg tcgctcgcta  60
tcttttattt acgacgatca cttgctcaca gtcacagcta gcgctagcta gcgatcgaac  120
aggcagcgaa cgtggcagcg gcagctgccg cgccggccgt gcggaggatg gtaaaataca  180
actgcgggtt ggcctcgaac accgcgcggc agatgaccca acctgcggcg ccgggcgcct  240
tcatcatcat ccccgccgaa gcggggccca ccacgggcca caggaaatag atgccgaaga  300
cgcccatggc ggcaaacgcc accgccgctc ccatagcgcc tatgccctcg tcgtccttca  360
tgttgacgaa tgacgatggc cgggcaggtt gacatgcagg attcagcgtc gtccgggtgg  420
cacgccggtg ttgcttctgc ccttgctgct taattggagg agagcgatcg gctgggtttg  480
gaatgaatgg acactggaca gcggtcgctg cgtgttgtgt taattgaaca tctatttgta  540
gtaggctgca gcgccggatc gaggttggcc aggcggctgc tcagcttcat cgcgtgcatt  600
gcgatgcatg ccgtgcgcat ttgctcccca gtctcaaatc acgatgggag gcgacgacga  660
agagacagct tcgcaatgtg cgcgatcagt cgagcgcatt gaagttgaag agaacggtag  720
cgaaatgcag aagctgaatt gttgcttggt agtagtgaga acgtgcataa gaggtaatta  780
atttcatctg ctaattatgt agagtagtaa ttaaattaat ttcattaact acgagtcacc  840
tcgaggccat gctataaagg ccagcggtcg acatagctta aatgatggtg cattggcccc  900
cgcagcccgg tgccgtaaat acaagacatc caggtgaatc tggggctcac aagggcgtgt  960
ggttttacct cgggtagaac gttggtttta cccttgcctt acggcgcctt cctaaggaac  1020
cgacccctca aggttacatg ctttggcaca ctaggattag gtaacccctc aaggttacat  1080
gcatttgact caaggtttaa taatgctttt ggtttatata cgaaattatg agtatatttt  1140
ccaaagcttc cggataatat aaatttcttt ttcattttaa gggctgattt ggtgatcaga  1200
gattccaaga tgattcatgg gagagaaatc cccttacaat tcaattttga atatcaaggg  1260
gattcctctc atggatcctc tcgggatcac tgaccaccaa atcagcccta aaagtgaact  1320
gatggaaatt aaaacacata cgtgcataag aggtgattaa tttcatttgc taattatgta  1380
gagtagtaat taaatttcac cggcaaaagt agtatttttt tttttgccga tactactcgt  1440
ccactaccca ccaatccgtc gtggcagctt ggattagtat taaaaatgaa gaaagtgaca  1500
gaactcaggg tattatttta aataacctaa ctatacccat tagaagattg gacttggaca  1560
tgtaccacca tgagcctgcc tttggattag tattgtcgga aaatgatcgt tctcactccg  1620
aatcgacgag tcgacttctg catttgatgg ggccggctac actttgcgaa atgggtgttg  1680
atcggcgcat cgggcggagc gggcagtagc tgcagtactt ggctatgcac tcagagtcgg  1740
aggcggagca acgcctcttg gagttcccag gccgattcgt tttccccagc acgcgcactt  1800
cgccgtacgt gagacggcag caattacgca cgcatgcaac gcacccccat agaaggccag  1860
cagccgcctc tggccgacct acaaatagat gacttctctg tcgcagaaat tccacgcggt  1920
gtctatcaat agtaccaacc ctataccaga gagcgagcgc gcttgacgac ttgtttgatt  1980
catcactctc cttcaagatc                                             2000

SEQ ID NO: 28          moltype = DNA  length = 2000
FEATURE                Location/Qualifiers
source                 1..2000
                       mol_type = unassigned DNA
                       organism = Zea mays
SEQUENCE: 28
tttccttaat ctcctgggtc acttagaccc cgcaaggacc accacacact taggtgtctc  60
ttgcttcgat tacaaatcac ttgagaaaag aaatgggaaa ggaagaaggc aatccaagag  120
gcaagagctc aaaagaacac aaaatctctc tctcacaagt cactaagtgc ttgagttgaa  180
tttgggactt ggagaggctt tgatcttttg aattgtgtct acgagtgaat gctagagctc  240
ttgtaatgaa tgtgatactc agaaatcttg gatgcttgga gtggtggtgg ttggggggta  300
tttatagccc tcaaccacca aacaaccgtt ggggagggcc gctgtcgatg ggcgcaccgg  360
acagtctggt acgccaccgg acactgtccg gtgcgccagc cacgtcacgc aaccgttagg  420
gtttgggagc tgtcgaccgt tggaggcttt gtcctctagt ggcaccggac agtccggtgc  480
cgcaccggat agccactgtt cagtgtccgg tatgctctaa ctctaggctc tgactcagcc  540
gcgtattgtt gtgcgctgta gcgctcgtca ggagccgttg cagtcgacca ttgcgctgga  600
ttgtcgttac tccgctggtg caccggacag tccggtggca caccggatag tccggtgaat  660
tgtagcggag agcgccagaa gaaacccgag agtggccgtt tggactctgt acggtcctgg  720
tgcaccagac actgtccggt ggcacaccgg aaagtccggt gcgtgaaaga gaaatatggt  780
```

```
ttaacttttt cctataaatg attttggtgg ttgaatgccc aacacaaata attgtactaa  840
ctagtttgct ccagattata tattctatag gtgcataaaa ggttcaacac aaaccaataa  900
aagatcaaag ttagggttta aaaagaaagg aacaaagaaa ccaaagtgtg ccctggtctg  960
gcacaccgga ctgttcggtg tgccacgtcg atgtttgcac agctcgcccg aggccactct  1020
tgggcgggag accccagggt agcctcgcgt gagccatgac tgtgcctccc gtccgagtgt  1080
ggcctcagac gacagacata gaaccatgat gtactgtaga tatatatcta tgtttatagt  1140
acatcaacag attctgaagt ctatttcagg ttgaattagg tttgtactcg gacgagtgat  1200
atttatcgtt ccatatctat gttttatata aattttttac tctcgtcgta acatataggc  1260
acatacctgt tcaaatatat gtgcgattgt gctcatatgg gtagaagaag gaactggatg  1320
tgaagacatg tatatataga ccaaaaatgt atcttagccg atttcaaact gcctagcgaa  1380
aagatgaagc tgctccgtgt ttgggtgact gcagcattat gtatcttatt aatcgatttc  1440
acagaagact tgtctctcat ggaacaaacg aacctattag cagtctgtat ataaagaagt  1500
gacttccaga ctgccaagtt tagtgattag ggctgctgtg actgaccatt taccttgcaa  1560
acaatctttc gatctactgc tctgtcatgc atggtttttg catcgtccat tatgtttatt  1620
tcccattgtt gcagcttacg atatcgtgta tacctggcac ctatgtttat gacaatgaaa  1680
ctcaccatct ttattctatt ggcattcatt ttcattcaaa ttacataacg tatgctagaa  1740
cgaccgaata caaattactg ctaataaaca tcctgcgtac gcgcaatggt gcaccattta  1800
ccaattaata gctgtaacgg tactgcaagt aatggtcgaa gcgttatgtt ttctctcctc  1860
tcttcccacc gtacaggatc atatattcat atatatatac acatgcctct ggaacggcta  1920
attcgatagt tccaccacgt tacttccata tatttccctt ggattggatc gtcggcgccc  1980
aaacgaatac taatccggca                                              2000
```

```
SEQ ID NO: 29          moltype = DNA  length = 2000
FEATURE                Location/Qualifiers
source                 1..2000
                       mol_type = unassigned DNA
                       organism = Zea mays
SEQUENCE: 29
ccttaccggc gatgtgtgcg catgccggag agcaaggagg agtgcaaggc ctcacgacgc  60
ggcgccaggt gagggctact catgtgcgtc acccattgct ggtaagtcct cattgctcct  120
cccttctcaa gtctctgcta cgcgtgtgca ttagttgtag ggaatacatg atgttaagta  180
tgtactgatt ttctgatgca acctcaatag atttgtaagt tttggctatc ttctaagagg  240
tacatagaat tagtgacagg atggactact tcctatctga tgtctcatgt aagctgggac  300
ctgggagcat gaaaatgttg gtgcatgata ccagcaatgt cttttttttt tgcttatgtc  360
atcttgtttg aaccaaaaca aaatacatta ggtaacacga tcctatgatg tcgggtcatg  420
ctcaagagaa tggtgctgtc gctgaaattt tgcattaatt tatcatgttc agctccttgt  480
gcctagatac gagagatggt taactgaaac tagatatttt accatgttca tctcctgatg  540
tctggataca aggtggttaa ctgaaacaag atggaatgtg tttgcaaggg acaccaacaa  600
ggttactgtc atgtacatac atattgatta acgagcatga cacgaacctc tttgttgaat  660
gtgattttga cgtaagaact tttagttcat gtggtttcaa acctatttat atgatatata  720
acaattgtag caaaacacgg acaactagct agtatatatt tataacattt gacactttaa  780
tatccccttc ctgtcacttc tatagcattt gtctagtgtt gctcattcaa aacttctcgg  840
tcgacttcat ggtcttattt tttgttctgg taaaattccg ataaaaatca gtaaattccg  900
attaaaatcg gtaaccgaac aaaacgatcg taaaaatgat acactgattt cgatactgat  960
ttcgtttcct aataatattg ttacccgtga atccgatcga gaaaaatcga aaacggtttt  1020
cgaaattcta agaaattccg aaactgtttt catcatacct ttgcctgtct ctccaatgga  1080
ttctggagtg gcggcatcgc ctatcagagt agaatttctt ccccaagaac aaccaaccgc  1140
tgaaccaaca gcagaatgag ggcttttccc ttccaaaggt gaacatgttt cggagttacc  1200
ctagctgtcg cagagaagat ggagtacgaa accagagatg atgacttggg ggacttccag  1260
gctgctcaat tgatataccg tgtatcttgt acataccgaa tgttactgag acgacatttt  1320
catttttggt ctatcttcta gcggctctca ggtactatga ttttttagat caaatggtgt  1380
ttgagaacac atacaagatc gaactctgaa ttttaaacta ttgttttgcc aataccacgg  1440
tattttgggg ttaaaaaatc tttggtctag accaaagttt ttttgtttgc gcgcagctat  1500
atcatgatat acattaaact gcggtattat aagatgttgt tttaagaaat aaagttccta  1560
aataggccct cagtgttcct gtaagcctcc tcttctcata ttctatatac agtacgtact  1620
agtactacaa cacactagct agctagtcag tcaaagtcga ttgcacggat gcacacgcag  1680
tcacggtcac gggcttgaga atgaacgatg gatgacctta gcaggcagca gctgttactc  1740
tcatgttatt aattatctgt gtgaggaaaa cgaagggaca cagccaccca ccgcaacaca  1800
ggggaatgaa tggatgcatt ccacttgacc gttcgttcca atccagcgct tgacagtttg  1860
acactaggta gaacgccatc gaccacgctc cgcactctat aaatagaggg aaggcctcca  1920
ctctcctctg cgggagatac cagtaaacgg cgacgaagac aattctctac caagaagagg  1980
actgatcgag tgggagagat                                              2000
```

```
SEQ ID NO: 30          moltype = DNA  length = 2000
FEATURE                Location/Qualifiers
source                 1..2000
                       mol_type = unassigned DNA
                       organism = Zea mays
SEQUENCE: 30
cctgccgacc ccaagacgac ccaaggatct tacccctccc gaggggcaag atgacttcgt  60
ctacttcact taagatttct tcctcgaatt gatctcttaa ttcctaggcg actctacgtc  120
gtctggggac gccctaggtg acttgctgac ccggagcacc ctaaggtctc ttccctaggg  180
ggcgagatct aggtcctatg aggagaagaa gacgaccatg cgccatccca gaccgtccag  240
cccagagcgc agatcgtccg tacagcgtgc agggaagaag ccgcttctgt cgccaggtcg  300
cggaccatcc aacctagagc cacgggcagt ccgcgcaatc gcagcaagca ccgccaggca  360
acccagcgac gcgtcgcgga ccgccgcgcc atccacctcg cacaaccgaa cccaaggtat  420
tgctcatcac gagaagaccc tagggttcgt tactgtttgg tcccacatag gtggtggcca  480
tcatagaggt ggtattacac cttcatgata accatcttag gtacatcaag tgataatccc  540
cttgtctata aggattcctt tgaagaccac attcaagata atgttatttg tcttacatct  600
```

```
tatttgttat ctccctcccc atggtctcga cccaccgtgg gcaaaaccta gggatcatcc  660
ccaaggtccg aactcactac gaggacgacc taggaatcat gtcacttttg tagcatttgt  720
ctagcgttgc tcattcaaaa cttccccgtc ggattcatgg gtttttttatt ctggtaaaat  780
ttcgataaaa acgagaaatt tcaattaaaa tcggtaactg aacaaaacag tcgtaaaaat  840
ggtacaccga ttttgatacc gattatgttt cctaataata ttgttaccgg tgaatctgat  900
cgagaaaaac taaaatgatt ttcaaaattc taaaaaattc tgaaatcgtt ttcatcccta  960
ccttcacctg tctctccaac ggattctgga atggcagcgt cgcctatcag agtataattt  1020
cttccccaag agcaactggc cactgaaccc aacagcagaa cgagggcttt cccttccaaa  1080
ggtgaacctg tttcggagca actagctacc gcaaagaagt tggagcaaaa aaacggggat  1140
gacgacttag gggacttcca ggctgcttag gtgatatacc gtgtatcatg tacatacaga  1200
atgttactta gaccacattt tcatttttgg tctatcttct tgcgacactc agggtctgta  1260
tgggaacaca atattttctt agttataata ccgtagcatt tgcgcatact atagtatttt  1320
agatcaaatg tagtttgata ggacatacag aactttgtat ttttaaacta ttgtttgcta  1380
ataccacact atttttgggg ggttaaaaaa tctttggtct tgaccaaagt tttttgtttg  1440
catgcagcta cagttttctt ttctcttaca ttacaactaa aatactatgt ctctaaacag  1500
gtgttgaatt ggactgacgt aaaatataca tagttatatc acgatataca ttaaactgcg  1560
cggtattata agctgcggtt ttaagaaaca aagttactaa ataggcccac agtgttcctg  1620
taagcttcct tttcatgacc tacaacacac tatctagcta gtcagtcaaa gtcgattgca  1680
cagattcaca cgatcacggg cttgggaatg aacaatggat gaatttagcc gccgctgtta  1740
ctctcgtgtt attaattatc tgtgtgaaga aaacgaaggg acacagccac caaccgtggc  1800
aacacagggg aatcaatgaa tgcatgcact ccactggacc gttcgttcca ttccagcgct  1860
tgacactggc tagaacgcca tcgaccacgc tccgcactct atatatagag ggaaggcctc  1920
cactctcctt tgcgggagat accagtaaac ggcgacgaag gcaatcctct attaagaaga  1980
ggactgatcg agtgagagag                                              2000

SEQ ID NO: 31          moltype = DNA  length = 2000
FEATURE                Location/Qualifiers
source                 1..2000
                       mol_type = unassigned DNA
                       organism = Zea mays
SEQUENCE: 31
ttcactgctc ctcactcgca accttgccgg cgaccttacc ggcgaagtgt gcgcgtgccg  60
gagagcaagg aggagtgcaa ggcctcacga cgcgccgcca ggtgagggct actcatgtgc  120
gtcacccatt gctggtaagt cctcattgct cctcccttct caagtctctg ctacgcgtgt  180
gcattagttg tagggaatac atgatgttaa gtatgtactg attttctgat gcaacctcga  240
tagatttgta agttttggct atcttctaag aggtacatag aattagtgac aggatggact  300
acttcctatc tgatgtctca tgtaagctgg gacctgggag catgaaaatg ttggtgcatg  360
ataccagcaa tgtctttttt tgcttatgtc gtcttgtttg aaccaaaaca aaatacatta  420
ggtaacacga tcctatgatg tcaggtcatg ctcaagagaa tggtggtgtc gctgaaattt  480
tgcattaatt tatcctgttc agctccttgt gcctagatac gagagatggt taactgaaac  540
tagatatttt atcatgttca tctcctgatg tctggataca aggtggttaa ctgaaacaag  600
atggaatgtg tttgcaaggg acgccaacaa agttactgtc atgtacatac atattgatta  660
acgagcatga cccgaacctc tttgttgaat gtgattttga ggtaagaact tttagttcat  720
gtagtttcaa acctatttat atgatatata acaattgtag caaaacacgg acaactagct  780
agtatatatt tataacattt gacactttaa tatccccttc ctgtcacttc tatagcattt  840
gtctagtgtt gctcattcaa aacttctcgg tcgacttcat ggtcttattt tttgttctgg  900
taaaattccg ataaaaaatc agtaaattcc gattaaaatc ggtaaccgaa caaaacggtc  960
gtaaaaatga tacactgatt tcgatactga ttctgtttcc taataatatt gttactcatg  1020
aatccgatcg agaaaaatcg aaaacggttt tcgaaattct aagaaattcc gaaactgttt  1080
tcatcctacc tttgcatgtc tctccaatgg attctggagt gacggcgtcg cctatcagag  1140
tagaatttct tccccaagaa caaccaaccg ctgaaaccaa cagcagaatg agggcttttc  1200
ccttccaaag gtgaacatgt tttggagtta ccctagctgt cgcagagaag atggagtagg  1260
aaaccagaga tgatgacttg ggggacttcc aggctcctca attgatatac cgtgtatctt  1320
gtacataccg aatgttactg agaagacatt ttcatttttt gtctatcttc tagcggctct  1380
caggtactat gatattttag atcaaatggt gtttgagaac acatacaaga tcgaactctg  1440
aattttaaac tattgttttg ccaataccac ggtattttgg ggttaaaaaa tctttggtct  1500
agaccaaagt tttttgtttg cgcgcagcta tatcatgaca tacattaaac tgtggtatta  1560
taagatgtgg ttttaagaaa taaagttcct aaataggccc ttcctgtaag cttcctcttc  1620
tcataaccta tatacgtact acaacacact agctagctaa tcagtcaaag tcgattgcac  1680
ggatgcacac acagtcacgg tcacgggctt gggaatgaac aatggatgaa tttagccgct  1740
gttactctcg tgttattaat tatctgtgtg aggaaaacga aggggcacag ccacccacaa  1800
ccacagcaca ggggaatgaa tgcatgcact ccactggacc gttcgttcca tttcagcgct  1860
tgacactagc tagaacgcca tcgaccacgc tccgcactct atatatagag ggaaggcctc  1920
cactctccac tgcgggagat accagcaaac ggcgacgaag acaatcctct accaagaaga  1980
ggactgatcg attgagacag                                              2000

SEQ ID NO: 32          moltype = DNA  length = 2000
FEATURE                Location/Qualifiers
source                 1..2000
                       mol_type = unassigned DNA
                       organism = Zea mays
SEQUENCE: 32
gtagcaaaat ggttcgtgcc agatgcacga gggacagtgg acaatgttta caggttcggg  60
ccgcttagag atgcgtaaca ccctacgtcc tggtgagtat gcttggtgaa tgaggttaca  120
agagagctct ctgaattgag aatgcagaga attgaggtgg gtggctgagt aatagggtcg  180
atcgttctga aggggtgccc cctaggcctt atatactcga ccgtggggca atacacgtgg  240
atatgataac aatgtgtaag aaaaagatag tgaactgttt gagtttatct ccctatagtt  300
ttgccgacct atcctcgcat ggctccgttg cttgggggct ccagcgcggg aaagtcggat  360
ctctgttgtg gtcgctcgct cgatgttgtg ggccgtccgg gcttgcacca atccggcctc  420
```

```
atgtcaatct gctttgctga ttgtccctcc caggcccacg aaagaatgac cttacgattt  480
attggaccct tgggcctttc gtgaggtctt ttacttcttc tagtggaccc aagggatatc  540
tgtcccccac accaccatac tagttcctaa ggtaagcatt aatatatgtc atgaacctcc  600
atgttgtaga catgttgtcc acacatgata ggctagcggt gttgttcacc ctacttcatt  660
gcacctccta gtacattgtg cacacattac aaggatccca agatgctata tgtctgtctt  720
agagccccca gagtgctttg tagactaggt tgtgcgttca tgcacacttt gtaatgccat  780
ttatcttgca ttaaatgtgt tgtatcgtat aattatatac taagctattg ttttatacca  840
ctcttcgaga tttcactcgg acgaggccca catattggtt gtatacgccc ctaacaagcc  900
cctagtgttc gtatggtcct tgctgggcct gagctatttg ttaaacatat ggccgagaca  960
cgtgtgagtc taaggaaata tcacgcgagg gatgccgggg cgaggggccc tgggacttga  1020
gggactttaa ggtctcatct attatgcatc gcgaggtgcg agacgaccta gggccttagt  1080
caataggtgc cttagggcac gaggcatctc gaggtcttga tcattaagcg ccctagggca  1140
tgatggacct caagtcttta ttcaataggt gcctcaaggc acgagggacc taggggcttt  1200
atttgttaag tgtcctaaca tgtgatgggt cccatggtcc tatatgttag gtgttcaggg  1260
tgcgaggtgt tctgtggttt tatttatttg gtgtctcgat gcgtgagggg tccgaggcct  1320
tatccattag acatcttgag ataagaagag ctctaaaggc ttatttagtg aatgttccaa  1380
gacatacgaa gcctcgatcc agctcgataa ttgaccagag atgtgtgagt ccttgtgtta  1440
aggatccttg agcacgttac aatactatcg aggagggcta tgtgctttcc tagatactaa  1500
catatggtgg agggctatgt cctttctcag atgctaacat atgatgcgca aagaaaagtg  1560
ttgtgtactt tgtacctaaa cttaggggct gtttggtttg tgcctaacta tgccacattt  1620
tgtttaaggt tagtcgttcg aattgaaaaa ctaatcttaa acagaaaagt tagacaaaat  1680
atgacaagtt agggagagaa ccaaacatac ccttaatgta gggcattggt tacggtatag  1740
cggtcaattt aattggcctg tttgttacgc tgtagaaaac cttaagtaat aacgaccgtt  1800
gggggtacat aatgcgtttt ttttgcatgt tatacgcatc gttttccaat aaatgatgtc  1860
cataactcca tcagttagca cctctggacg taacagtgca aaagaagagt cactgcatat  1920
ttatatggag agagaggtag aagacgtgaa gttggggatt cacagccttc tccttctccc  1980
tcgctcgcgt gttagaaata                                             2000

SEQ ID NO: 33          moltype = DNA  length = 1595
FEATURE                Location/Qualifiers
source                 1..1595
                       mol_type = unassigned DNA
                       organism = Zea mays
SEQUENCE: 33
tgagtacttc gatgaatcag cttgattcgt atattcatgt cttgcactcc acatttattc  60
cagcacattg ctagagcatt gcaagcacca aaagcctagt gaggagatta gagaatcata  120
atccgcgttt gttcctcatt agcgctagcg agagccacct agagcacaca ccacttgcat  180
taggcttctc ttggtcaagc gaaagtctac gacttgttac tcttggtgat cggcatcacc  240
tagacggctt ggtggcgttg ggagctcggt gatcaccgtg aagatcttgt tggtgacccg  300
actcaagttt gtaagcggtc tcgagggatc caccgcgccg gagtggcaaa ggatcatctc  360
gtagtgagca cttggttctt gcgaggacca agggggagcg ataccccttgc gcgggtgctc  420
caacgaggac taatggagag tgccgactct tcggtacctc gggaaaaatt ggaggagtct  480
tctaaacttt gctttacatt ccgcacttaa ttcaagcact ttacattgtg tatttgttta  540
gcaagtattt gaagtattgt cttagcattg ttgcatttct agtattatat tcttagtgct  600
agttgttggg gtgaagttgg gctcttgctt agtctttaat tagtgttgat ttttagaaaa  660
gcccaattca ccccccctat tgggcatcgt gatcctttca aggttctttg caatgccaga  720
taaaaatttt cccagcacac aaattcctta gtagatgatc tgggaaggat ttgcggccta  780
ttttagagag ggcaataaaa ttgagaccat gttttttggt cagatccgaa acgtatctaa  840
gttttttaaa tccttgaact cattgttgtt ctaaaagatt ccttttattg ggaaacagtt  900
aattaataat caagcccggc ctctttttag aacacaacga accgtaatcc gtaactatat  960
ggttttgtac atactgactt aatcagtcca tcaatgccat ctgtctcttc atgtataata  1020
tccgcacaca aatgatttaa aataaaataa tcaaactctt cgtcctctag tactcccttt  1080
cccataaaat cagataaatc agccttgttc ttacctatat taatctctaa tttttttaac  1140
tggccaatag aggaagcaac tgaactagga ttagaacccg ctaaaatatc aatattttta  1200
aaagaatcaa aaatataatt atcaggtaaa ccaataaaaa acattattac ctttagtcgg  1260
ctgaactagt atgaattggc atcggtagga aatgcagttc acacgactag gaaggataaa  1320
atcgcagccc taaactgtaa attctctttg tgtaaactgg aaaacgagaa gtttctgaag  1380
taaattagct tcaatgcccg actcttcgtg cgaactggaa agacgctttt gtcgtttcgt  1440
tttctgatct gtgacctgtc agactccagg gcgattcagc gcatgctgca cgcaccagcc  1500
accaggtatt ttaaggggtc acacttgctt gtttcatgta ctagcacaag aagaaaccgt  1560
accacttcat caggccaaat cgccagcaat ccacc                             1595

SEQ ID NO: 34          moltype = DNA  length = 970
FEATURE                Location/Qualifiers
source                 1..970
                       mol_type = unassigned DNA
                       organism = Zea mays
SEQUENCE: 34
agtgtacaaa gtctaatcca cagctgtgac cctgtgagct gggggttggg cctgcctcgg  60
aggggatcgt gtcttttctg tttgtgcaat tatcagtgcc taaagaacat gtgttataac  120
agttatacac ggtcaattat tcaatccatc ttttaacgtg tgtttggttg tacgtataag  180
aagggatcaa agagggcggc cacattttct ataacatttg gatgagagtc acacgagaac  240
gagatgaaca ccgaagtaat tttttatgac agcatgatcc aaaaaaatcg agagaacggt  300
gttatccccg tctcatccta ttttgatctc aaaccaaaca cataattagt caatgagcac  360
tgacttgatg tagaagaact tggtacatat accaggaaat gactctgact tgctgagatg  420
ccttgtagtc cctcggtccc gtaaattata cagtagtatt taaacttcct cgcacaaagg  480
aaaactattt gtttttgcat gccttgtaaa ttagctatca agtttttttt taaaaaaaac  540
gacctttgaa aaccagtaag gaggactcgt tcggtattca gttttaaagt tcaaggttaa  600
aaatcgaact gacgtgcaaa acaccctggg ggttaaaatc aaaacacaca aatttggaaa  660
```

```
atgagcaggc atgacttatg ttgtgtccgt tgaagtgccg tggctccatg gcacggtgga  720
actttacatt agtgcggtag tgtcactgtg gcagtaaagc ccacttattt tccattagag  780
agagggagat taaaaacgtg gctttacaca ttctgaaact aattgtgagt ttgtgactct  840
tggcttgcct gcagtgtccg cctgcacctt ctataagtac agtcgcgagc ctcagctata  900
caaaccaact agcgcatagt atctcctgag ctccattcat catcccaagt cttcactggt  960
cttagatcac                                                         970

SEQ ID NO: 35          moltype = DNA  length = 1995
FEATURE                Location/Qualifiers
source                 1..1995
                       mol_type = unassigned DNA
                       organism = Zea mays
SEQUENCE: 35
tctggagtcc caccggacca caaaagcaac cacttgtttg cgcatgtcaa gtaggccagg  60
gcaagcagat tgtttgttgc aggtgaccta atccagcgga aatgtcttct gatggcgact  120
gcaggagatg gtgccagacc acaattcatg tgtcatgagt aattcagctc aggacatgcc  180
aacagagaca gtggcctcca gcgaggggca tccaacccaa taaaacaacg ttcaagttcc  240
taatccgaga cacacatcgg taaaagtagg gggtgttgaa gatctatcca gttacagtgc  300
tcacgtatgc gtaaagcaag cccaagtgct aacattcaag acaaagcaag gccagtgccc  360
tctgtacatt cttacatcac acatcagttg tgaccaatgg gccataacct cttctccaca  420
ggataataca acaacaatta aagacagaaa tgtcagtgcg caatcataaa tgaactgcga  480
caatgaagaa caggtagcaa gccttatttc tagcaaacag tcagctcagc gctaagaaac  540
taactactat actagatcat gtaattctaa gaaaagggca tgattctgaa tacacaagtt  600
ttacttagca ttctgggact caattttaga tgaatctaat ttccgtcaac catatttccg  660
agagaaagct ggaatcttcc agttcaagca actgccaagc taaatgctat ggtgcagtga  720
attgcgacta cagtaacgaa gcgagcaaga atcatggaag ggagggaaca tgggtacgcg  780
tgttacccac ccgggagcag ccgagttttg gaggcccatt ttgcgcttac ggatatctgt  840
taagaggagg tccaaaagaa tccgtaaacc aatctcaaaa caaatattag tagagaatag  900
tgatcttctt tgctccaaac agctccccta ttctcctctc caaaatttcg tatccctcat  960
ctacctcctt cgctcccgta tatttttgca tgattgatgg ctccacacgc gctggcgttt  1020
ttgtttctcg cacatagact tgtttcgatg gagacatcaa ccaggaagct gtttggaggt  1080
tacgaaggcc tacatttcca aatattgcga agggcccata tacatgtgca aagtgggctg  1140
ccaggagggc gttttatttt aaatttgagt ccagtttttt ggtttttcag ttttgactgt  1200
tggagtagac acaatatttc acccctaaaa aattttaggc ccctttgaaa tgcatgattg  1260
ataaaatgca ggaatagaaa aaaaaaaacg taggaatgga gttgtactac aactacaatc  1320
atacaagaat taaaaatact tgaaaacatc aaatagagtg tttagatgca gcgtataaag  1380
aacaaatgag ttagaggaga gagatacaca caaaggaacg tttttcgagg ttggacctct  1440
tgttataaat cctccaaaat tttactacaa tgaataattt tatagggatt tttatagaatt  1500
tgtaggaact taatccttta ttctaaaagg ctatatagga aaatttccta tatgattcca  1560
atcctctaaa atcccactac ttttcatttg ttctaaagga ggccctagcc ctattccgat  1620
aacatctttt ctttgaaaca ttttaggttt tttttttgga gttgctctaa atggagctag  1680
gcaaaaagag cgatactcct ctcaatttgg aacttgggac gtatttattg catgcatgcg  1740
gaccggggag gagttgaaca gacaggccgg cgtcggggag ggaaacgatg caattgaaat  1800
tgaatgaata gaatataatg caaatgaaat tgaaccgaaa cgacagccaa tccgatccgc  1860
ttgccttcct gcgcgcctct accacttcca ccaactgagt gaatagtata cagtatacat  1920
accgctaggc gctagcttct ccaaatctct accacaccaa cctgcctcgc tctccaacaa  1980
acatagcagc cagcc                                                   1995

SEQ ID NO: 36          moltype = DNA  length = 7579
FEATURE                Location/Qualifiers
misc_difference        686..785
                       note = n is a, c, g, or t
misc_difference        1937..2036
                       note = n is a, c, g, or t
misc_difference        7521..7579
                       note = n is a, c, g, or t
source                 1..7579
                       mol_type = unassigned DNA
                       organism = Zea mays
SEQUENCE: 36
gcaagtgatg cacatattca gggggagttg tgctacaact tgaccctttg agactaaccg  60
tttgcttgag tttgcttgat ttagtctcaa aggaagtttg aaagggaaaa ggtggacttg  120
gaccatgaaa gacttccact acactccgat gagagggtaa cttattccaa gttcatctca  180
tgtactctta ttgcctttgt attcttattt gaagattttg gtgaggcaat ggggttattg  240
ggccaagatt ggtcccgttt tggtgcttga tgccaaaggg ggagaaaata aaggccaaag  300
caataaatgg atcagatacc acttgagagt ttttttgaaa atagtagaat agagcttttt  360
gtttgtcaaa aagcttttat tgtctctctt gtcaaaagtt ggcttcttgt ggggagaagt  420
gttgattatg ggaaaaaggg ggagtttttg aaatcttgaa tcaatttctc ttggaatgac  480
tctctttatg tcttaacaag tatgtttgac ttagagatag aaatttgagt ttgatttgca  540
aaaataaacc aagtggtggc aaagagtgat ccatatatgc caaatatgaa tcaaaacaat  600
tttgagttct catttgcatc cctcttcccc ttgttctagt tgctttatgt tgtgtggcat  660
aaatcaacga attccaaagg tctagnnnnn nnnnnnnnnn nnnnnnnnnn nnnnnnnnnn  720
nnnnnnnnnn nnnnnnnnnn nnnnnnnnnn nnnnnnnnnn nnnnnnnnnn nnnnnnnnnn  780
nnnnnttaag gttgttgttg ggcataaaat cacccaaaaa ggggggagga attgaaaggg  840
gccatttcta agtattttgg ggattgaatg caacacaagt gctttgtgta atctatgcaa  900
agtggtggac aaagtgcaaa tcatgtcaaa ggtatgtttc tggacttagt acattgtttt  960
attgactaat gtattgtatc taagtgctgg aaacaggaaa aattgaattg gaaatgagat  1020
ggctacgttc agcctaagtc agctcggtct gggtgcaccg gacagtgtcc ggtggtgcac  1080
cggacagtgt ctggtgcgcc aggctggctc tagcgaacag gctgctctcg ggacttcgac  1140
```

```
gacggcgtac ggctaaaatt caccggactg cccggtggtg caccggactg tccggtgagc  1200
caacggtctg ccggggcaac agtcggccga ggattccgcg cgtgacgcgt ggccgagcca  1260
acgatcacat tggagcaccg gactgtccgg tgtgcaccgg acagtgtccg gtgcgccaac  1320
ggctcccagg cgccaacggt cggcttcgct aaataaggaa agagatccgc accggacagt  1380
gtacggtggt gcaccggact gtccggtgcg ccaggcggca gaaggcaaga tcagccttcc  1440
tggaatgctc tcaacggctc ctagctgcat tggggctata aaagggaccc taggcacatg  1500
gaggagatac ccaagcatac tcaaagcatt cctaagcacc aagacttctt ttccacgcat  1560
ttgtttcttc gtgatagcat ctagagctct tgttgagttg tgaactcgtc gggttgtgtt  1620
gcgagctctt gttgccactt gtgtgcgtgt tgacattctg acttcgtgtc ttgtgtgcgt  1680
tgatcatccc tcccttactc cgtgcttctt tgtgaacttt aagtgtaagg gcgagagact  1740
ccaagttgtg gagattcctc gcggaaggga ttaagaaaag caaagcaaaa caccgtggta  1800
ttcaagtggg tctttggacc gcttgagagg ggttgattgc aaccctcgtc catttggacg  1860
ccacaacgtg gagtaggcaa gtgttggtat tggccgaacc cacgggataa ccaccgtgcc  1920
cacataaaaa gaaggannnn nnnnnnnnnn nnnnnnnnnn nnnnnnnnnn nnnnnnnnnn  1980
nnnnnnnnnn nnnnnnnnnn nnnnnnnnnn nnnnnnnnnn nnnnnnnnnn nnnnnnctaa  2040
ggattcaagc tttgaattcg ttgctacaag cagaaatggt aagttgaact gagttagaag  2100
aggactgatt atataatcag cgtggataaa tattgtttct aaccaagctt tctatcctat  2160
atttgcatgt tcttcaaagg gatgtatatg gaccttccaa atacactaga cttttgcaag  2220
caaccaaaga tactctcaga gaagaaggtt tgccttgcct tgaatacttc ttgacttatg  2280
tcatattgag catttgagct attgagaaac atactaatac agacattgtt gatcttgcac  2340
ttgcatgcct ctatgtaata ggctaaacta agcagcattg tataggatac tggtactttt  2400
gcacttgcat tatctcttct tgctaggtag agtcctaccc catagtctgg aactagaaga  2460
attctgattt tccttttagg aatcaatgtc tatttgagct ttgtttggtc agaaatgcat  2520
tgtagaaaaa tttagatggt gagattttta tctttgttct catttttatt cattgtagta  2580
taattttttt cagaggttgt tctcatttat ctataacttt ttattttttt tacgaaaagc  2640
cggtgcatgc tgattatgca ccaagaaaca tagttacagg cagatacttg ttgtagtgct  2700
ctctttacaa tttatgtgta ctatatgctg tattctcagg tagtctggct gaacggctgc  2760
cccagtggaa gagatgaccg cgcagtgcag tgcagcactg cgttggtgga tgatcgatcg  2820
tccagttgta tgtgactaaa acgccatgcc ctgtgcatta gagaagatag agaatcgcca  2880
tgccctgtac aggacagtga gccaaattct tgttcttttt gcactatgat acagattgat  2940
tcattaggcc ctaggttgga ggttgtgact gatgagttgg gaagggatta cttgattggt  3000
ggtgtacaat tcttggacag gatacaggtt ccagtttttg gtccattagt tcaggaattg  3060
tttcatttac atgtatattc agtacactcg tataatggaa acagacaaaa tctctatctc  3120
attctttagt tatcgtgtta ttatatggtt ccgttgcaac gcacgggcac ccacctagta  3180
atatattgtg catgttgcga ttgtaaaata cctatggtac cgcagttaag taaaatacct  3240
atggccgacg gagtgcttca tttgagaact ggaaggtctg gtagtaattt cacattgatt  3300
caaactcacg tgtgtttcta aaatacggca gttcaaacga acacgcggct ctcgacttcc  3360
gttgcattgc caatgccaat gcggctgcat tgcatgtggt gttggttcac attcgctcat  3420
caatatacgg cccggccaga gctggttgct tggcaaagca accgttcaat ctccctctcc  3480
ctctcctctg tagtatatat agtagtatac aactagcagt attcaagaag tcacatctct  3540
gagctctatg gcaactcgtt gtcagtctgc tggtttcatc gaattcaagc tcgacttcgc  3600
agcatccaac caccttgccg tcggcgacat cgtccgctcc gacgatttct cggcaggcgg  3660
gcacttatgg agagtaattt gctacccaaa gggagacgag gttggtaatg gcaattacct  3720
ctctctctac ctacggctcg tcagcgactc caagtccgag aaaatcaagg ccatcatcga  3780
cgctttccta ctcggcagaa acggcgcacc gtcatcatct tcgcatggaa agcgttgggt  3840
gcatgtgtat tcttcacccg atggctcgcg atcacgtggg tttccagagt tcgtgaaacg  3900
gagcgtccta gatcagtctg actgcgtcac ggacggcttc gtcacattca tggttgtagt  3960
catagttctt agggatagcc ccatggccat acccgtacca tcttctgaca tcgccgacca  4020
tcttggccgc ctcctggatc acgctaatga cggttccacc gacgtgacct tcactgtcgg  4080
caccgagacg ttccacgcgc acagggccgt gctcgctgcc cggtcgccgg tgttcaaagc  4140
gcagctcttc ggctctatgg cggacgccaa gatcacgctg caaggcatcc gtccggaggt  4200
gttccggatc ctgctgcggt tcatgtacac cgatgcgttt ccgggcgacg acagcgacaa  4260
cgacaacgat gacgctgaag attcgttgcc gagagacgac gacgatgaag acgagcagga  4320
gggttattcc gacatcgacc tgttccagga tttgctcgcg gcagctgaca tgtaccacct  4380
ggaccggctg aagctcatgt gcgcccgcaa gctgtgggac cgcgtatcgg gagagactgt  4440
agccaagctt cttgtctgcg ctgaactgcg tgactgctcg gagctcaaga gcgcctgcct  4500
cgacttcttt cttgtcgaga aaaatttcaa ggtggctgta ctaacagatg ggtatttgca  4560
gcttatgcag agctttccat ccgtcatcgc cgagataaaa gcgcgggttc gtcagatcta  4620
aataagacat agcgtgcgtg cgagctatat tatatagttt gcagtttctt taatatttag  4680
gccagaatga tgctttcgtc agatctgaat aaagacatat atatgatgcg tccgatctac  4740
aatattataa tggtatgctg tttctcagaa tctgtaagac cgaatgttgc tttatcagag  4800
tacattatat attatgtgtc gaggaaacat gaaattatgc ctacctcata aaaaatgacc  4860
ataaatccta aacactaaac aagacaatct aaatctctac tacatattaa gacaataaag  4920
gtagtctgtc tcccctcgtt tttccgtttt gccgtccatc gatctggacc gtccgtatcc  4980
tatcgttcgt ctgcgtctcc cacgctccat ccccctccac cgcacgaccg cacccaatcc  5040
ctaacctttc cccgcacgtt cctctcctct caatgccacg ttgcctgccc cctgcccctg  5100
ccgcgataga tgcctcgcgg cccccgacaa cgacaaccgc gccaccatga cctcccatcg  5160
cctccatgaa agagaaatgt gcccttgggc catttctaag tattttggtg atttagtgtc  5220
caacacaagt gcttaagtga taaacaagtg cttaagtgat aaactatgtc aaatgatgga  5280
taaaggtgca aatcaataca aagatatgat tctagactta gtacattggt ttttgtgtgc  5340
taacatgttt gtctaagtgt tagaatcaga gaaaatgcaa ttgaaaaaga gtggcttgaa  5400
gcagccaaga gtctgctcag tctgggtgca ccggaccgtc cggtggtgta ccggacagtg  5460
tccggtgcgc caggttggct ctggcgaact ggctgctctc aggacttcga cggcggcata  5520
cgactataaa tcaccagact gtccggtggt gcaccgggta gaatccgcgc gcgacgcgtg  5580
gcaagtgcca acggtcagat ggggcaccgg actgtccggt gcgccaacgg ctccaaagcg  5640
ccaacggtcg gcttcgccaa agaaggaaag aaatccgcac cggacagtgt ccggtgcgcc  5700
aggcgacaga aggcaagaat tgccttcctg gaatgcactc aacggctcct agctgcctta  5760
gggctataaa agggacccct aggcgcatgg aggaggaacc caaacattct ctaagcattc  5820
ctaagcacca agacttcgat tccgcgcatt tgattctttg tgatagcaac tagagctcca  5880
```

```
ttttagttgt gaacttgtcg ggttgtgttg tgagatcttg ttgtgacttg tgtgcatgtt  5940
ggttctctga tttcgtgtct tgtgtgcgtt gctcatccct tccttactcc gtgcttcttt  6000
gtgaacatca aagtgtaagg gcgagaggct ccaagttgtg gagattcctc gcaaacggga  6060
tatagtaaag caaagcaaaa caccgtggta ttcaagtggt ctttagaccg cttgagaggg  6120
gttgattgca accctcgtcc gttgggacgc cacaacgtgg agtaggcaag tgttgaactt  6180
ggccgaacca cgggataaac cactgtgtct atctgtgatt gatcttcttg tggttatcgt  6240
gtcttgcaaa gactcttatc tagccacttg gctttattgt gctaactcct aaccaagttt  6300
tgtggcatta aagtttaagt tttacaggat cacctattca ccccccctcta ggtgctctca  6360
attggtatcg gagccgttct cttcaagaaa gggactaatc gcccgaagag atggatccta  6420
agggcaaggg gatggtggtc aacgataagg agaaggagtc ctttgtcaat gatccaaagg  6480
aggacaagcc tactgactcg ggctcgagcc acaaaagaaa agatgggagg aagaagaaaa  6540
caaggcgcat caaagagata gtctactacg acagcgacga atcctcttct tcccaaaagg  6600
acgacgacaa cgactatgag aaaaagaaga cggttaattc aaacttctct tttgattatt  6660
ctcgtattcc tcaaagtacc aatgctcatt tactttccat tccacttggt aaacctcctc  6720
attttgatgg agagtactag ggattttgga gtcacaaaat gcgtagtcac ttgttctctc  6780
tccatcctag tatatgggag atagtagaga gtggaatgaa atttgatagc tcggatagtc  6840
ctttgtttat caatgaacag attcataaaa atgcacaagc tactactgtg ttgttagcct  6900
cattgtgcag ggacgagtac cataagttga gcggcttgga caatgccaag cagatctggg  6960
acaccctcaa gatctcacat gaggggaacg acgtcaccat gctcaccaag atggagttgg  7020
tggaaggcga actcgggaga ttcgcgatga taagagggga ggagccaacc catacataca  7080
acaggctcaa gactctcgtc aacaagataa ggagctatgg aagcacgcga tggacggacc  7140
acgacgtcgt ccgcctaatg ctaaggtcct ttactgtact tgatccacat ctggtgaaca  7200
atatttgtga aaatcctagg tacaccaaga tgtcgcccga agaaattctt gggaaatttg  7260
taaccgggcg gatgatgatc aaggaggcga gatacgtgga tgatgcattg aatggcccaa  7320
tccacgagcc tcaaaccgtt gctctcaagg cgacaaggag caaggaggca ctacctagca  7380
aggtggcgca agttgaggcg gtcgggctta atgaggaaga aatggccctt atcatcaagc  7440
ggttcaagat ggcgctaaag ggtcgcaagg agcaccccaa caagaacaag acgaagggaa  7500
gacgaatctt tagatttccc nnnnnnnnnn nnnnnnnnnn nnnnnnnnnn nnnnnnnnnn  7560
nnnnnnnnnn nnnnnnnnn                                               7579
```

```
SEQ ID NO: 37          moltype = DNA  length = 2000
FEATURE                Location/Qualifiers
source                 1..2000
                       mol_type = unassigned DNA
                       organism = Zea mays
SEQUENCE: 37
ttgcaatcgt gtgtgtgtat atatatatat atatatatat atatatatat atatatatat  60
ataatctgct tttgtatttc acatttactt cacatctagt ctttctaaga taatgttcat  120
tgtgtatata ctaaattgat tcatttcagc tactaactcc tactgctata tattgtttaa  180
tcacactgct atgctatgct actagcattg aactatataa ttgtgtaacc atataaacta  240
aaatgtgtgt caattggtat tacttgcagt gtgttaagtg gaagcaacac atgaagcgga  300
catggagaag gaagctggca tgacactaaa acgcataaag ttgacatgtg acgttcatgt  360
tttagatgtc ttattctact gccaaacttc ataatactcc atttttatac tatattgtct  420
atctgtacgt gtgaatggag atgatgatat tatgtgatgt gatgatggat ggattagctt  480
cgttgaatat tagatgatat tatgtgatga tgatattaaa cgggcattgc agtattgata  540
catgcttcat atttctggat ttttagtgat gttttattgt ttatgagttt tctaaatatt  600
ccttattttt gtttgatttt ttctaaattt ttgatgtatt ttttgctcaa gaggggtatt  660
tagccccttt cttcccaaac aacgccagga aaatatatcc gggaggggag attctctccg  720
ggaaataagg tgacatctaa aatcccctcc agggttagtt tccaagggat atttttctct  780
tcactgccaa actagccctc agcgtccttc tcgatctccg tggattggta agtggctgct  840
ggcatttcat ccccaatatc aacatactca tccacctgct cagccactgt agtactcttc  900
acaggttcct cgctctcctg caaaaaataat aaataaacaa actagcatca gcgcccaatt  960
catatgtcca ctagctgcaa ccaaaaacaa acgtgctgct cttattgtca ttaccgcatc  1020
gtcgttgtca accaatgtag gcacatcgcc cacaggtgca gtgtcatcct cagccacagc  1080
agtactggtt acatcagcaa cgccaccatt gatcatcgca gcacgctggg acttcttgag  1140
cgccttgttg aagttagtaa cgaaacgatc aagctcccac tgtgtctcaa catccatcac  1200
atcaatatca agctcgatct catccccaag catctccggg ttgttgttcc tcttgcgcac  1260
aatctgaagc acattgtgca tcttctcttc gggcaggctc accagcccca gcctgagcat  1320
gttcttctcc tctaggctca tctccctctt gttaggctcc ctcgccttag ggcttccgca  1380
tcctcacatt ccctgctctc gtcttagcct tcgcctcgac aggctcaact gccggcggag  1440
gtggcagctc agccgccact ggcctcggcg gctcaaggcg cttgtgctct tcatcgaaac  1500
aagcgtaaca tactgttatg catttattaa gtgaaattta aattatagac gcatcggtca  1560
cctcagcctt aaattccacc taggcgaccc ttcgtcttct gcacctatgc atcgcactcg  1620
cagctcaagc gtcaataaaa tgcaggcggc agcgaaatca tactcacacc acagacccgc  1680
tcgcggcctc accaacgttt tcgtatggct aatgtttcac aggccgtagc tatgccgtcc  1740
tcctcccgcc gccacggtgg tcgccacaga gcagaacctc ctcgcattca ccagcgccca  1800
gcgagccgag ggactggacg gcgctgcctc aggacatcct gataaccgtc ttccttaagc  1860
ttgggccccg cgagatcatg ctgggcgcag agttcgtgtg cacgacgtgg cggcgtgtag  1920
ccgtcggcga ggctctgctg tggcgccgca tcgacatggg catagacaaa atttcggttt  1980
ttcaccccgc taggcgcgcg                                              2000
```

```
SEQ ID NO: 38          moltype = DNA  length = 1799
FEATURE                Location/Qualifiers
source                 1..1799
                       mol_type = unassigned DNA
                       organism = Zea mays
SEQUENCE: 38
tttctccggg tgcccccctga gaacttgccg tggggtgggg ttccctggtg ccccgggaca  60
gtccggttgt cccacgggac agtccgtgct ccacgcacag acagtctgta ggcaacacac  120
```

```
ttggactttc ttagatcttt ttattgtctt cttttgaggg tgttgctttc ctcaattcct  180
tagtccaaag ttaatcttag catcctgtga actacaaaca caaacacaaa cactagaaaa  240
cttattagtt cacgaattgt gttgatcatc aaacaccaaa actcaattag ccaaatggcc  300
cggggtccat tttccttaca ccccacaaat gcggtttgat ggcagtgcaa aagtgtttca  360
aagcctcatg tgccgtagat tcaccagtgc gtatgtattc gtcaacggca tccgcaggaa  420
cacggtatgc aaggatacga acaacagcaa caactttctg cagagcagat agacctagct  480
caccggcaca gtttggtcgt tgaacgaagt agggatcgac ttgttgcaca tcatgaacca  540
ggtgctcaaa cacatggcga cgcatgcgaa acctataatg gaaaatacag tgagtacaag  600
tgtgaagcac gtattatgga cgtaagaata gatgggcgta cgaaaaaaga tacctccttg  660
ggaattgagc atccatgtac accggttggg cgcaaaagta gttcgctcgg attcttgcat  720
cgccactcat atggtcacga tggattcgaa catgaccggg aattgaacca gcataccgac  780
gctcgttgcg tgcacgacgc ctaagatgtt ggtacgtcgc aacctccaac tcatgttctt  840
catcttccat gtcttgcgtc atcctaagaa aaatattgca atctacgtac cggttcattg  900
ttgtggagca ctctaagtga agtgttgaag cgtgagtgat tatttataga acggataggc  960
ttcggagaca agccatcctc ttgttgtgca gacgaagcta gtcgatggct tgttcaagaa  1020
gtgtcatggc ttacggtaga agcatgtgaa tttgcaaaca tattttgata ctaataaaat  1080
actatgcgac attttatcga caacaattac acactaaata acatcgaatg ttaattaatt  1140
tttacaattc gaaattatta atcaagcatt gttttggaga ttattatttc gaaaattagt  1200
aaatacatta ttttgtgcat cctttgtata gcgtgaaatg ggaagaaaac aaagaaaata  1260
gaaaatgaaa tggaaaaaag aaatctgtta acactgtagc tttagatgac cgaatttaga  1320
ggacgttact ggagaataag aagatataga ggacataatc ttttagagtg tgctgtaaag  1380
aacagataat aatcttttag gggatggaat ttaggggacg ctactggaga caaccttatt  1440
ctctggttcc tgaactctat tccatttaac aagattagtt tagtctttgc agtacacaga  1500
attggtggca ctcaattaat attctttcta acgttgggac tgccctttgg acagcgttaa  1560
ttcgttgctg caatgaaatt tctctctatt tgttcttgcg tgcgttagct caaccgacgt  1620
tctcgagaaa cccatttcag tttagctcca cccatgaata ctgatcaatg ataatgaatg  1680
ctgctgtagt acttagtaac tcccaatcct agctgttgta tataacaggc acgacacgta  1740
cggccatacg cagcatctgc acacagacaa gtctcgaatc ttccaatccc aacacggca   1799

SEQ ID NO: 39          moltype = DNA  length = 2000
FEATURE                Location/Qualifiers
source                 1..2000
                       mol_type = unassigned DNA
                       organism = Zea mays
SEQUENCE: 39
cattcgtaat cttctctgtg ttcgtcttct ccatagcctc gtaaaaccta gctagtgcag  60
ggtcaacaac cttcttctct ttaaccatat agtaagaact tgtgcgaatg ccgaagctcg  120
caaatcaaac aaaagctggc agagcaagaa aatccaagct tgaaaaatgg cacaagtggt  180
tgagatggca catcaaatgc tatcaatgcg ggttcctatt tatatgccca gcgtatcaca  240
acttggtggc ctccacatgt cattgacttt cactattcta gcgaaggaaa ggtgtttttt  300
aaaccttcga ctaaaggcct ttgttcacgt cgtagtccaa atttgttaat acaaaaacaa  360
attaatactg tgatgggcta ctgttggggg ccttcctctt ccgaaggccc tcaaaacgta  420
actaatgtgt ttttcggtat aacatagact gttacaggag gcttcggctt tgagatgaag  480
gtgtgcgtga tatgaaggta cggtctgaag gaagggtgaa cgagcgccga agctgtggct  540
gaaggacctt cggtttagta tgacgacgaa ggtggaagat gaaaccgacc taaaagggga  600
tagactactt agcccttgat agctcgccct acgattacca gtaaatgtca gggatataaa  660
tgtaattttg tctgggctgt gtcctgtgcc tataaataga tgaacagtaa caccgtacaa  720
ttcacgctgc attgtaattg ctcccgcgtc attcactttc tcaccttttg tcaagccgaa  780
ggtatcaatg aaatataaat attgtgaaca tctattcatg tttatgaaat aaaataagaa  840
tgtaaacaat tcattgctat attgttatca tttacattct tcttctgtat ttcatttcgt  900
gtttcctcat ttatatttat ttacttacca agatgatgaa gatacgtctt tcattacctt  960
cgtctaaaga ttattatata caaaagaaaa taatgtttcg gaggacgaag atctttaatc  1020
attaaataat cgtgttgctt tgttttttgt gtataacatt cgagaacaag gaacatcaat  1080
agtccaagcc actttcctg ccatctggcg cacattagtg atcggtccat catttcctct  1140
gaaaatgtaa attatttcat gttttccata aattgtgtaa tttcatttgc ttaattatgt  1200
aattggatag atttttattt tcataaatta tgtgtttcat gtcaattaac agtctataaa  1260
atgaaactaa cgtaatggtg agatagctgc aaactagcgc taaaggttgt acactaaaac  1320
gttaggtaga taaagataga caaaaatcaa tagtacactt aataattaat aatacagtca  1380
atagctaagg ccaaatataa ccctaaaata tcagttcggt ttttttaagt ataaaagatg  1440
gttaaaagat tatatgatac aaccttaaga ctatgaatca taaatgtagc tgaaagataa  1500
cgtgtacgga aaattatgaa cagatgttct attcacgaaa agtatgtccc ttatgttttc  1560
tcacttagct ctttagagac cactcaagac agggtttaca catgccctaa tgtgccacga  1620
tcggatggta aacataaaca tagaacatct gaatttcgag catcctttta gctagccgaa  1680
ctgtgatgag ttctcgcagt cggtcaaaat tgtcatgaaa aaccgtgaag gcgttagtat  1740
gaccacaatt tcccacaaaa aattaattac cgcctcgctc aaaatgacga cgagtcgacg  1800
actcttcggg attgcgcttt gacgctccga gttatcagac actaatcact cagacggatc  1860
agctcgtgca tgcgcagcac atttcacact agttatcacc agtatataaa tacgagagct  1920
caatagcatg gtagtcttat tcttcacaaa gaagtagcct gctcttgtta gttcttacta  1980
gcagtccaac agcagccaca                                              2000

SEQ ID NO: 40          moltype = DNA  length = 2000
FEATURE                Location/Qualifiers
source                 1..2000
                       mol_type = unassigned DNA
                       organism = Zea mays
SEQUENCE: 40
tatcttatat aatacactag gtgagtgccc gtgcgtcaca ggcccgagtt tctcttcgat  60
gtcatctcgg acagctcgta tatgtcatcc tttatctcat aactatataa cacatatgtg  120
catatataag ttatcgagat attatatatc cccgttgcaa cgcacgggta ctgacctagt  180
```

```
taaataaaga gagagagtgg tgctatctat aagcctagag taagcctaaa cacataaatc  240
gagatggtgc agagagtgaa ttaagtatta aaaacagcta tagatttttt tttgattatg  300
gaaacaagag ttccggcttt agcatacaaa tgcgtacagc cattacataa cgattattgg  360
accatagagc agttgcttga ataattaaac taactcaaag aaaacaaaat gccatgacta  420
tagaaaacac tagccatctt caattcttgc attcgagcgc catccatgca ttgcaaaaac  480
ttccatcgcc accacctcca aagctcgaca ggcatcgaga atttgttggt gtttttcctc  540
cttctgtaga agtctccaaa atctgaacca gtgagtaacc ctgaaaataa cctacacaat  600
tgatggtatt ggtttatgat taaacaccac ctcatttcga cagagccaga tggaccaaaa  660
taaagctgat attccagtca gtaataatgt tttgtatgcc agagcattat tagattccca  720
agacccaata atatgattaa tgctaatggg catgtctatt tttaaagcaa agtaaatgat  780
tctccatata cttttggcaa tgtaacagtc aaaaaagaga tgatgtatac tctcattgtt  840
gttgcaaaag ctacaggtca agctaccatt ccaacgcctt ctagctaaat tatctttagt  900
gaggatcgct ccccgacata aattccacag taaaactttt atttttagag ggagcttaag  960
tctccaaagc atcttactcc gattgctgtt aggattattc atcaaaagat ggtacatcaa  1020
ttggacagag aaaatttcat tcttatgacc atcccaaaca aaattgtccc tagtcggatt  1080
cagagtaacc gtagttagca agtttaacaa gttatgtcat tccaccattt taattcccct  1140
aattgttcgg cgaaaagata aattaagatt tgaatctgaa aagacgtcta caaccaaggc  1200
cgatttgtta cgcactatat taaaggttcg ggaattgctc actgagaggt cgactggtta  1260
accatatatc cttccagaat ctggtagcat gaccattcct cacttgaaag tgacctcatt  1320
taagaaattg atccttaata ttcattagac ctgaccaaaa gtgtgaattg tccggtcttc  1380
tagatatttg agtaagagat ttatgtccta agtatttgtt tttaagtagc tgttgtcacc  1440
tcccctcttc attgagtaat ttaaatagtc atttgctgag taagctaata ttttttaaag  1500
ccagattaga gacacctaag cctcctaacg ctttgggttg acaaacaata tagatagcat  1560
agatgttata gatatctact gtagatacat cattgcaaag atttactata gtatagtagt  1620
atatagatgg catagatgtt attagagatg tgatatatct atatacctgt ctcttcgatt  1680
ttcgttctgt aaaaaacgaa atggttactc ccgtctataa tctcttcgat ctccgctctg  1740
tctcttttac taacaaatta atcctgccaa gcaagtccca ataacaacac atcgtctctg  1800
gttttgttcc ggagacgacg gtccatctcc tccgttactt caatcgtcgt tcttcgctgc  1860
tcggagctac atgcgtcgtt gacgtacacc cagttctcga atggccgtag tatacactag  1920
tatgtgctag gtgtctctat ttatatctac cattatattc tagtatctcg tccagcaagc  1980
actccagcta ctgtgtagac                                             2000

SEQ ID NO: 41          moltype = DNA  length = 2000
FEATURE                Location/Qualifiers
source                 1..2000
                       mol_type = unassigned DNA
                       organism = Zea mays
SEQUENCE: 41
tttttaagta catgttttta gctttctaat tttttaaatg agtgaaacaa agaaatattc  60
cacatttgtt ttaatagaga taaagacaaa gatttacact tgtttgaatc aaacaagttt  120
tagcattctc ataacttaca cctacaacaa ctttttatag cttatagtta tagtttttct  180
ttcaccgcca cgacttaaca aaatagccct tatacaatga gcagacaaag tgctaacgcc  240
aaactcatct caacccaatc actatatata aatatttgat atatttttag aataaataga  300
caaatagagc acgcttgacc agagcatggt aacatagatt ttccaacttt gtcaaatgca  360
agattagatt gctttgcaac tattttggat cctagaaaaa aacttgatgg gttacaaact  420
gctttagaag gaattggcga cttgctagat atggactatt catatgcttt caatcatgtg  480
aaagatgaat tatttcgtgt ttttggcttt tattataaca aatatggtga aagtgatgtt  540
gcaggaacaa cgactgaaca tgacatagaa cattcagata gttctttgac agctcactta  600
tggaagagat ctaaggggaa agaatctgct aactctacaa caaatcaaag gtggaatcct  660
aatgctgaat tgaatcatta tctatctact aactttgcag cgactgatcg caccttgaag  720
ggtgataagg taaaattact tgatggtgga gggaacacaa gtatagtttt ccagtattat  780
ctcattttgc tagagatatt cttcttgttc ctgtttcgac ggtttcctct gaagcaacat  840
ttagcacagt gggtagaatt attgaagaaa ggaggtcctc tctttcacct gagacagtgg  900
aggccattac ctgccttaag gattggaaaa gagcatatga tagaaagcaa catcaacttg  960
aagatcctga ggttgaacaa gcttttgctg atttcagcca tgattagtgt tacttttatc  1020
tagttcatgt ggactgttat tgtaatatgg actggacatt aaaatttttt ccgatctgta  1080
ctcttttcct tacagaggga gccccacact gggttgtaag gtttttaacg aggcagatcg  1140
aggaataaaa aacattttcc ctctaaaatt tgtttgtgtt gtctaattta ttgtaactgt  1200
ttatttaaat aaatgacttg tttatgtatt ttaactgttt ttaattggac tgttgtttat  1260
gttgcctgag aggtttggac ttgtttctgt atctgaccta gtcatatgat gattaattgc  1320
gggccgggtc tgggccagca cagcccaatg taagcccgtc gtgctttaga gccgtgttga  1380
gcctacgttt taggaggtca gcacgttttg gcccggctcg aaagaaattt atgctagcac  1440
gacccaaagt atttaagcct aaagcacgat ggcccggccc ggcctaactt gcaggactag  1500
ctggacggat tgagtcaacg agttgtttcc tccgtagatc cctactgagt gctagttggc  1560
gtcgttactc ttatgaacaa aaaaagtagg aacaattgga tctataccat taaaagatcc  1620
aaactttaga tatataccat ggaccccaca tgtcattgac tcatgtggac ccacatgtaa  1680
gtgagatagt aatggtatgg attcaaagtg gtgatctttt aatggtatgg atccaaattt  1740
cccaaaaagt aataataata aacatatgta atgaagaaaa ataagttaca tgcacgtaac  1800
ttcatcaact aatggattta atttatgaga cacagaaggt tgaattataa ctcatgccgc  1860
tagaaataaa caccattaat gactatagct ccgttacaga tatgtagctg gaattaacta  1920
cactttctca tataaagcta gaccacccat gactgaagca ccaacacaat ttctaccctc  1980
aaaactgttt tggagaaaca                                             2000

SEQ ID NO: 42          moltype = DNA  length = 2000
FEATURE                Location/Qualifiers
source                 1..2000
                       mol_type = unassigned DNA
                       organism = Zea mays
SEQUENCE: 42
```

```
ttgcgtgccg tgttagaatt ttgaaggcag gaattgacta gccatgcttc ggatcgcaca  60
aagtttctgc aacttgggag cggtgcagag tcgataatgg aggaacggcg gtggagagga  120
gaatattccg gcgatactgc cgatcgggtc caatattcct tccagctgat gatcggaggt  180
ctggccactg ccgatcggat cgaccacgca ggcagccgtg tggtgtggtg tggtgtgggt  240
ggcctgcgac ggaacgtcga cggagcatgt gaccgtgacc tctgcctctg cctgctgtgt  300
caggtcaggg gctccgttgc ctctactgta ccggggcgcc agaaaaagac aggccttgac  360
tgtgtcgcgt cgcgtgtgtc catcgtccat gcttggatct gtactgtacg aacgagatgc  420
catgtgaacg tactgtatgc gtgagaggcg gatgcataga ctggccagat ggtaactttt  480
ttaaaaaaaa aaaatcgctt catatcactc gttataaaaa aaatacactc tccgctcaat  540
ttataattta tttaactttt ttttaccaaa tttgaataac acgtcttatt caaaaaaaac  600
ataattatta ttaagttcta ctatgttacc gtttagtata taatatattt taaataaagc  660
tttgaatttt tcgttttctc gcaaatattt gaattagacg agccgtttga taaagaaagt  720
taaacgaatt ataaaattaa gatagagcga gtaaaaattt actcgtcttt cattgacgtg  780
cccttaatcc tcgatgctcc tcttccgata cgctggtgcc aaaagcaacc gcgtccccca  840
tcggagccat atccacgact ccacgagcgc cgtcctcact agcgagctct gcctcacacc  900
tcatctcgtg cgcttaacga gaggaccaca cctatgctcg tgccaacgca tggttgtgca  960
tgtgcctaca ccacgccagc acgcgggggc cactccatgc gcctccatag aggtcacgtc  1020
cctctagagc ttgttcggtt gccgggagat tgaaggggat taaatcctct cctattcaat  1080
tttgaatagg agggaattta atccccttca atccccgtca aaccactaat aaccgaacat  1140
gaccctaggc gtttctgagc acagggctat tctaagcggc gcagcgcagt agccaagggg  1200
gcgggtaggg gccttggccc ctctcgcgta aatatatata gacaaataga gaacatataa  1260
attgtatagt ttttgttgat taaaataaac aaattgttta aataagtcgt catgttttct  1320
aaaatattaa attcgccgct aataataaaa ttcatgaatt ttaaataaag ttgtcatcag  1380
atagttgttg tgtatacgac gaatttgaca tgtacgtgcg caaattgacg aattttcagg  1440
gatcctcgag gctaattaga tttttgaatt ctcttaaaaa attgttagct gcctcgtgca  1500
tactagagtc attatataaa aagttaaatc tcatcataat agtaaataac atccacgcac  1560
gtgccatata tgttagttta tttggccatg ccatgcatct gcagaccatc gtgcaaaaaa  1620
gttttctgaa tagttattat ttgatagctg agagaaatgc atagaaaaga tatgcacgtt  1680
ttttatgcaa ctccatcaaa taactcctaa gttattaacc tttttctgtc gattaaactc  1740
ctaaggttat ttggccaaat taacagggtt tattaactag ctagagcgta actcctgtca  1800
taaatagaat cctcattaat taaacaaatc cgctaataac gccaccgcag tttcataaat  1860
agaatcttta ttattttata tgaaatattt ccacctataa aaaccaggtg ttccttcctc  1920
gtcctagacc agtgcaagtc gttccatcca ctacaccttc ttacacaacg cacgaccatc  1980
accaagccgt gaagaacgaa                                              2000

SEQ ID NO: 43          moltype = DNA  length = 2000
FEATURE                Location/Qualifiers
source                 1..2000
                       mol_type = unassigned DNA
                       organism = Zea mays
SEQUENCE: 43
ggaccttcgt cgggaacttc tagggcacct acaagctcca tggaagctcc tggaccttaa  60
gaggtgcacc caaaagagca gtgagagcct tcgggactac atccgaaggt tctcaaagaa  120
aatgagcgaa ctcctagatg tcaccgccgt tgacgtggtg agtgcattca cctacgacac  180
caccaacgag tcgtccacga gcttggacag gggtgacaaa agatggccac cgacctcttc  240
gacatagcgg tcgctgacga ggaagacgtg gtgggggcaa ttttccgcaa gagaaaaaac  300
tcgcgtgatg ccgacgagcc cagcggcgaa acgagggatc aacgagagca ccctggtaga  360
cgtcagataa accactgccc cacacgaacc gaggaaggag aagacactgt cgcggaccgg  420
tcgctagggg tgggcgttcg ggttacccga aattttcggg tcgggtaatt cgggttttta  480
aaatttcggg ttttgagaat tgatacccga aattacaatg ggttttgcaa tacccgaaaa  540
ttcgggtacc cggaatttcg ggttcgggtt cgggtattcc cgaactaccc gaactattat  600
gttggcttca taaaaacaca tataccctat taaattagta taaaaacata gtttgaataa  660
tgatatacat ggacatataa aacataagct atctacaatc acaagttatg cacacttaca  720
cataattata gatgtacaaa ttaataatta atcatgacat gagtatatga cacatgaaag  780
ttcgggtaat tcgggtaccc gaattttccg aaataaattc gggttttgta agttgctacc  840
cgaaattctc gaacaaaatt cggtatttc gagttcaggt tcgggtattc cggattcggg  900
tttcgggtta cgggtttttt gctcagcctt accggccgcc cacacaactg gcgaagaacg  960
acaacgacca cttatagagt ggaaatacct atagagtgga aatttttgac acgaggcggt  1020
ggctgtatgg acaggaccgg aggaggatgc gcggtacgta ggccgattgt gccagcctat  1080
tagggcatgt acagtgggtg ttttaagttg tgtcttacaa cgtgtctaga ggggtgaatg  1140
taaaaaaact taagacacgt atcttgacga agacacagtg tcttagctct atgttcgaga  1200
cagaagacta gctgattggt cattttaatt tattgaatgc tctgattggt acaatgaata  1260
tcgtaagaca catgttttag atatgaccac tgtattatgt tgtgttttag ttgtatcttg  1320
tacttggagt accgtgcagc agtatctggg ttgtacgtgc ccttatgtag gggaagggag  1380
tagaaatacg atcaatgcga acgcacgttg atgacggtga aaacggtaga aaccggtgga  1440
agtagagatt acagcaaaca tggagggacg gctttcgtcc acccaccggt ccttggcgcg  1500
cgcgcggcga gcctacgatc caaaagccgc gaccgcttgg tgttttggct gacgcttggg  1560
aacctgccgc agctgcattt cttgctttgg gagccatgta cggcgaactc atacttttga  1620
cgtcggttct ttttcgaaaa aacttttgac ggtcagtttt ccccactccc gctatattta  1680
aaaccccccca ccactccccc aatatttatg acttgacaac aattcccaca tcgattcatt  1740
gtcacttgcc agaagtcggg cggccatcga tcccactccc accgcttaca gccggcccag  1800
tcctcgtcgg cgccggacgg ggcgaaggta acccccaagc ttccagattc tctgtcaact  1860
tcagttatgc gtttttcttt taagatgaac ctgaaacatt ttagctttag atcaccggag  1920
tcattttttt ttttcattag gcgattggag ttaaaacagg ccgagtggga gaatttcctg  1980
gatcttatct gttctccatc                                              2000

SEQ ID NO: 44          moltype = DNA  length = 2000
FEATURE                Location/Qualifiers
source                 1..2000
```

mol_type = unassigned DNA
organism = Zea mays
SEQUENCE: 44
agtcatgact tgagctcgaa acacaacaca cggagttcgc aactcaaatg gagctcaaat 60
cactagcaca gagaatcaaa tgtgtggagt cggagtctgg gagttttaaa atgtttcttg 120
aaagcttggt gtactcctcc attcgcctag gggtcccttt tatagcccca aggcagctag 180
gagccattgg agacaatctt ggaaggcaat tcctgccttc tatcgagtgg tgcaccagac 240
agtccggtgc accaccggac aaccactttt catgtccggt gcacgatctc cttccaaatc 300
aggtgcatcc tccgggccca ttggcgcacc ggacactgtc cggtgcacac cagacagtcc 360
ggtgtgccca accgaccgtt ggagcgagac acgcgtcgcc cgcagattgc gcggctgacc 420
gttggcgctg gcgaccgttg gctcaccgga cagtccggtg aattatagcc acatcgtctt 480
ttccgtttcc cgagagcggc gagttcgtcg cagacgactc accggacagt ctggtgcacc 540
accggacagt ccggtgaatt atagtcgtac aactccatcg attcccgaga ccggctactt 600
caccgttgac cagcctggcg caccggacac tgtccggtgt gccaggcccg agcagatact 660
tggctgttca cagccaagcc ttttccaatg cgtttcttct tttgttggcc ctgtttctag 720
cacttaggca aacacattag tgtacaaaat aatatactaa gtctagaaac ataccttgta 780
cattgatttg cacttttcac ccatttagca cataagtgct caattagtgt gttgtgcatc 840
taatcaccaa aatacttata gaaattgccc aggggcacat ttccctttca gctgcttctg 900
accgtctacg gactgtccga ccattatagc cggaccgtct gcttctgtct cggaccgttc 960
ggccttagta cccggaccgt ccggcgtacg caggacaagt gaccgtgatc gggtgtccga 1020
tcgtgcttgc ccccggtgcc ttcggtcttt cttttgtctg gagctttctg agtaactatt 1080
ctgcgtgaca tatttggtgt gcggggatca ccaatgacga tatttttatc tttgctttta 1140
tcggccgcac aaggccgaat tatggccttt ttgctcgttg gcaaaaaatgt ggtgacaggg 1200
acatatggcc catcaatttt cacctctttt taaacctcaa tgggtcttcg tttatagcca 1260
attgtatttg ccgacggaag acgacacaat cattggtgtt atggggaaag gagccatgtc 1320
atttgcatta tacgcgccat ttgcaatata cacaatctta gttgactaaa aattgctagt 1380
gaaattagca agttaacaaa tagctatcta actattagtt aatttactaa aaataggtaa 1440
tagctaaagt attagttgta ctgtttggat gtctcgacta attttagtaa ctaactatta 1500
gttttattgt attcaagcac cacttgagta gttaagatag ctgccataac aagtgattca 1560
cgggctcttg ccctgatggg cttggagggc cgatttatgg gcctatgttg gctgaaagcc 1620
tgttatggat agtatcacgg actagttttt tttttttttg ataaaaaagt attgatttaa 1680
cagtatgaat tggcgtcggt aggaaatgca gttcacacga ctaggaagga taaaatcgca 1740
gccctaaact gtaaattctc cttgtgtaaa ctggaaaacg agaagtttct gaagtaaatt 1800
agcttcaatg cccgactctt cgtgcgaact ggaagaggct tttgtcgttt cgttttctga 1860
attgtgacct gtcagattcc agggcgattc agcgcatgct gcacgcacca gatattttaa 1920
gggtcacact tgcttgtttc atgtactagc acaagaagta accgtaccac ttcttcaagc 1980
caaatcgcca gcaatccacc 2000

SEQ ID NO: 45 moltype = DNA length = 2000
FEATURE Location/Qualifiers
source 1..2000
mol_type = unassigned DNA
organism = Zea mays
SEQUENCE: 45
gaggtctttt atctctttag tggacccagg ggatatctat cccccactgc acgtgaagga 60
gaagaagatc aaaatatgaa tgagttccgt gattggatcg caaactggtt gtttgcaaga 120
gcctggagta catgttttgt aataaaaagt atttggacta tatgtacttt ggtatttgaa 180
ctacatgtac tttggcatgg tatgaacatg tgtgtacaca attctgtgcg tttgtttcct 240
gtgaacctgg caccaagttt ctgcgtgtcc aaaattgttg tgtttggtgc caagcatgtg 300
tacctggaat ccaaattgtt ggcgccaaga gcacccactt tattattacg ggtaatgcaa 360
tctttatgca ttgtaattag tgcacttcag tgaaatttag tcaatagaac taaacatggt 420
attttagtga ttaaacttta gtcattaaat tttaatcggg tgagtaaatg aatcaaatga 480
agttttaata ataaagtcaa tcgctagcta taagactgtc ttcagcggtt accctaaatt 540
tctcccccta tattccactc acgtgccacg tcagcgttct cttcccctat atctccaccc 600
tgtatagcgg ttcccctaaa tccttcctct ataccccact acaaccataa aatatcattt 660
tctataccta cttttcacct cctatcaatt tttcatctac taataattgg aagtgggccc 720
acgtgaacag tgttagaggg ggagagagac gcacgccaga acgagggaga gagagaagct 780
tgctagggga acctctgcgt agggcgcccg ctagagtgaa acgttgagcg tatgtcgtgt 840
gtactgtagc cgttgtattt ggcgtgtggg agcgatagcg agaaccgttg aagacggtct 900
aaggatcctt atagccacct atttaaccca tctatatatc agtttacctt ttaatattaa 960
tgcaagacct cacatgtctc tctcacaaag cttcttaggc cccgtttggt ttgagggact 1020
aaaaattagt tcctctgttt tagtccctaa attactaaac ggtagggcta aaacaagaat 1080
taaactgttt tagtatctag ttgctcaaga ggtgactaaa agagactaaa tcatataaaa 1140
tttatttttt tgtcatcctt tatttcagtt gtactaatga caaaagaatg ttaagagatg 1200
ttttaatcat cttatgattt atttaatgtg ttttgaatag ttttagtcgt tataatcaat 1260
attataatca acatggtaga gactaaactt taatttaatg actaaacttt agtcaagcct 1320
tagggcctgt ttggttcgtg gctaactgtg ccacactttg cctaaggtta gtcgttcgaa 1380
ttgaagaact aaccttaggc agaaaagtta ggcaaagggg ccgtaataaa tagcaacaat 1440
acacaaagat taaaatgaag caagaaatat ccggctacca ataataaatg cccttcgcga 1500
cgtattctac tttatctatt ctatttattt attatcacta aatttataaa aaatattata 1560
aatatttata tctctaaata aaattactac cgataattaa tttattaata atatttaata 1620
tctactgtga atattaatat ttttatatat gtggtacaag ttaaacacgt ggcactggta 1680
attatgggac gggaggtagt acgtcggaag ccggaacgaa ccgcctacta gcctagtccc 1740
agtgccagcc taggctgcga gttcaagcag cgccgctgcg acttcctatg cacagcactc 1800
gcacagctcc cggagcgcgc tgctcgcccc ttcgccttcc caggtctcag cggctgcact 1860
cctcgggagt cgggcctcgc catataaaca tgcctgggct aaaacatctc acacgtcgcc 1920
gactcgcgtc aagaaccagc agccacacta caacgccacc acatagttcc cagttcccac 1980
cattgtttgc acttggcaac 2000

```
SEQ ID NO: 46          moltype = DNA  length = 501
FEATURE                Location/Qualifiers
source                 1..501
                       mol_type = unassigned DNA
                       organism = Zea mays
SEQUENCE: 46
atccatctag ctagactgct gctgctactt cacaagcttg ggacgatgtg tgatgatgca  60
tgcttggact gtcatcagtc tctatgtagc ttctgaataa aataaaatgt aacgatgctc  120
gattgggttt cacttgctcg cttgttccag ccaagttatt atatatatca tcaggctcgt  180
acgccagcta tatatatatg catgcaggtg catggattgt gcaacgcgaa cgcgtgattg  240
tgctaatccg ttagttgatg cgttctgttg ctttgatatg taatccggcc actcattaag  300
catgtcaagg tgcaatgatc agaagtcaat atgtagttac tagttagtag tctctgaaca  360
agcagtacgg ccagcccttt taattaaaca accctccaga ccaagaggag tcaaagaacg  420
tactagcatt ttttagtatc aagatcttcc acgagctaga tgaaatgaag tgtttgaaag  480
attagatatc atatttttgc t                                            501

SEQ ID NO: 47          moltype = DNA  length = 501
FEATURE                Location/Qualifiers
source                 1..501
                       mol_type = unassigned DNA
                       organism = Zea mays
SEQUENCE: 47
gtatagctag caggtgttgt gtaccggcgt cgtgtcttgc aggcaccgtc ttatttcctc  60
acccgctgtt ggtaaataaa agtacggagt cgtagcgtag tagctagcag ctcactagtt  120
cagtaaggat ttggctttgt tgggaagtca agacgatagt tgtatgagat gggcgttaga  180
ctttgtttgg gaaagcttct aagtgctctc taaatccatc aaaataacta tatacctttt  240
ttccccaagc acttctctat cgaagaatct ggattcttga aaaattcagg tctaaggcca  300
catccatgga ttttatagag tattgctccg aaaacacaag ttttgtactt ctgataaggt  360
cttgttatcc gtatcgaatg ggattgaaag gaaatgaatc ccattctatt tctatttaat  420
tttaactagg aagggctcgt tttggtagag ttctgctcca tgattctcta gtttcgagag  480
ctctaataga gtgatttcga g                                            501

SEQ ID NO: 48          moltype = DNA  length = 501
FEATURE                Location/Qualifiers
source                 1..501
                       mol_type = unassigned DNA
                       organism = Zea mays
SEQUENCE: 48
gctcgcgatg atggttttcg ttgacagtct tagtattact actatcttcc tcatgcatgt  60
aacgagttgc ttcgtttctc gtattatggt tatggtttcc cttggatgca tgatgaacta  120
gtgcttgcag ttgattttcc ccttattagt ttgagctgct taattcttag tagccctttt  180
ttttttcttg tgcttgtcat gcacgtatgc acacacacat gagacgggca gctagcattt  240
tctgtggttc tatctcctct cggttttgtg cctgtcattt ggggcttaaa tgtatcagtt  300
gtcttttctc gtgcttggca tgcatagtat atatatgccc acatgagcaa actgctgctg  360
cttcagttcc aagtagtaca aaagattcaa attaaaattc catcgtattt aaccctagat  420
tttaattgaa tatattagat ccgcatagtt ataccaacat gactgattac acatgatacg  480
tgccctttag ttttatatca a                                            501

SEQ ID NO: 49          moltype = DNA  length = 500
FEATURE                Location/Qualifiers
source                 1..500
                       mol_type = unassigned DNA
                       organism = Zea mays
SEQUENCE: 49
atccatcgag ctagactgct agcaagctag ctgcttgttg catggcaatc tagcgtggga  60
tttgtgatcc tgaatgaatg tatggaccgt cgtcagtctc cgtagcctct aaataaaatg  120
ttaagctgct cgatcgtttc tgggtatcat ttgctcgcat gtttacgata gaagtttatt  180
atatgtcatt aggcaggctc gtacgtcatc agctatttac ccgatatatt tcgatatatc  240
ctgttatatc catatatatc ccaatatttg cacttttgga gaatcctagg gataaatctc  300
ttatctcgct atttaaaaca atggttcgat tgagttagtt ccagaaaaaa aaatcttacc  360
gccattgttt tcttatctga taattcagct actagaagct cattgagttg ggttagtgga  420
tggcctagtg catgtacata tgtctcgttt gctcagttaa tcagtttatt gatgagaaac  480
cagtgtagga gaacatgcaa                                              500

SEQ ID NO: 50          moltype = DNA  length = 500
FEATURE                Location/Qualifiers
source                 1..500
                       mol_type = unassigned DNA
                       organism = Zea mays
SEQUENCE: 50
atctatcgag ctagatgcta gctagctagc tgcttgttgc atggcaagct agcatgggat  60
ttgtgatcct gaatgaatgt atggatcgtc gtcagtcttc ttagcctcta aataaaatgt  120
taagctgatt gatcgtttct gggtatcatt tgctcgcatg tttatcgata caagtttatt  180
atatatcatt atcaggccat ttaaaacact tttggagaag cctaaggata aatctcttat  240
cctgctattt aaaacactgg ttcattgagt tagtgccaga aaaaaaatct taccgccatt  300
gttttcttgc ttgataattc agctactagg agctcattga gttgggttat tggatggtct  360
agtgcttgta catatgtctc gtgtgctctg ttaatcagtt tagtgatgag aaaccagtgt  420
aggagactag cacacctgca agaatgttga gatctgttcc attaggcaga gatcaaaaaa  480
gctctcattg accacatttt                                              500
```

```
SEQ ID NO: 51          moltype = DNA  length = 500
FEATURE                Location/Qualifiers
source                 1..500
                       mol_type = unassigned DNA
                       organism = Zea mays
SEQUENCE: 51
ataaatcttg ctagacttgt tagcaagcta gctgcttgtt gcatgacaag ctagcgtggg  60
atttgtgatc ctgaatgaat gtatgggccg tcatcagtct ccgtagcctc taaataaaat  120
gttaagctgc ttgatcgttt ttggacatca tttgctcaga tgtttacgag ataagattat  180
tatatatcat caggtaggct cgtacgtcat cagctaaata tatatagtat gggtctttta  240
aattggtgct cttagacctt agttttggtg gtgtgctcac ctatacgatg tagcgcttgt  300
gtggtcaacc aacgcaaatg aatgattgtg ttaatccgtt agtagcttga tgctagcatg  360
ctgcttgtct ttttcatata taacctgtct accttgtgag agaagtagga atttctttga  420
gcacgagacg gtggtggcaa tgacaagcta gcagcttcag ttctgctgtt gacaagaggt  480
tcgtgttcac cgattaatga                                              500

SEQ ID NO: 52          moltype = DNA  length = 500
FEATURE                Location/Qualifiers
source                 1..500
                       mol_type = unassigned DNA
                       organism = Zea mays
SEQUENCE: 52
tgaacgtgtc catgcgttgt ttcgatcgga caaaaaataaa cagccagcgt tatggtacag  60
tgaagaaatt ttacatgtat tttttatatt ttacttaaaa gggtgcaggt gcagtgcagt  120
ggtgcacaca gcaaagcaag caaggtatgc tggctagcta gtcatgctgc tgctgggatt  180
ttcacttgcc attgccatgt atgagagtta tgattcttac ctgatcttgt gttcatcctt  240
gtcatgctat caattcatct tttttgccgt ctggttcacg aaacgtaacg aaacgtaacg  300
taaatggtaa tagtaatgat tcacactcga ttaccagtag ttacaagttt gaatataaca  360
ttttatcagt ttctagtgca gcacctgatt atggttgaac ttaaccagac atggtttaac  420
gttatcggtt atcatttacg ttacaaatat gtgaatcaaa caacacctta tatttgtgat  480
atgtatggtt tgaagtgtgc                                              500

SEQ ID NO: 53          moltype = DNA  length = 500
FEATURE                Location/Qualifiers
source                 1..500
                       mol_type = unassigned DNA
                       organism = Zea mays
SEQUENCE: 53
tagtcgtcgt tgttgcttta ctctataatt agccccaata ataacaatct atgtctgtgt  60
tttcctgctg aatttgtaag ttatcatttt ggccactggt acttggtaac tactataaca  120
gttcgagcat ataataaact agtgcatcag gcgcgcccat gcgcgcgtac caagcagctg  180
tcaattattt tttatattta gttttagtaa ggtaatataa tggtatattc tatatacact  240
tgtagcagtt attttaacat aagtataaga gcaaatttaa actggtagta gtgattacat  300
aaggtgcacc gagtttataa ttgtagtgat tacaatctat attagactga aagaaccaca  360
catattacat tgtgtttcag caatgtgttg catgagtgac agattacata gagcataggt  420
taaactgaca aggtttcatc agctttgttt tatgtacgca aaagcatttg agcttcacgt  480
cacatggtca gtggcggagc                                              500

SEQ ID NO: 54          moltype = DNA  length = 500
FEATURE                Location/Qualifiers
source                 1..500
                       mol_type = unassigned DNA
                       organism = Zea mays
SEQUENCE: 54
ctatggatca ggatgtggat gtgttcgttc gatcgtttcc acgtccaatc tcgctgaata  60
aattgtctcg agaaagtttg gctttgccga gataaataat agtgataatt cttactcctg  120
ctacaaactg ttttccttga agcaactatg agcatcttcc atagattcgc gacacgattt  180
aaattttaaa aataacattt ttaaaaaaat gtgtcacggt tacacaactt tttttttaac  240
actagttgcg ccccgcgtcc aagcttactc cctgaaattg cattcaaact ctcgattcat  300
gtctgccctt ctcaccttct gtgtgcctgt gtgggctcga cgtctagtcg tcttcggctc  360
ttcgcctaca tcagtcacct cctcacacga cgtgtctgcg acacaggccg cggcatagag  420
cacgggcatg tagttttgaa caagtgcatg ttgctacctc gactatgatc atgcaaaata  480
ttttttttat tatttataga                                              500

SEQ ID NO: 55          moltype = DNA  length = 500
FEATURE                Location/Qualifiers
source                 1..500
                       mol_type = unassigned DNA
                       organism = Zea mays
SEQUENCE: 55
ggtctgcatg ttgtgtcccg cccagagtgc agtacaaaaa cctgatattt atttgcattt  60
cctatcagct gggctctccg aacattatta ctaccaagtt tcttttttgt ttgtatggtc  120
gttgcccaat ttggttttga gtagcaggga ggttttgaat tgggaacgag aatacttctt  180
ctgtggtgcg tagcggcaga ctttaacgct gtttttgtgg cggttggttt tgatgatgct  240
agtatctgtt agacgatata acttttgttg aaatttggat gtggcacaaa aattccggcg  300
gagaagtgca aaagtgtata acttgtgttc atctaattaa cctggatata tgaatcgtcg  360
ggctgcagat tctgtctagc ttaattccgt aatgggacac aatccggccc aaccccactc  420
caatcctata agtttaaaaa gtcaacccag cctacttaaa tccaaattga tttggtacag  480
```

```
ttcaatccaa tccgtttttt                                          500

SEQ ID NO: 56          moltype = DNA  length = 500
FEATURE                Location/Qualifiers
source                 1..500
                       mol_type = unassigned DNA
                       organism = Zea mays
SEQUENCE: 56
ataagacata gcgtgcgtgc gagctatatt atatagtttg cagtttcttt aatatttagg  60
ccagaatgat gctttcgtca gatctgaata aagacatata tatgatgcgt ccgatctaca  120
atattataat ggtatgctgt ttctcagaat ctgtaagacc gaatgttgct ttatcagagt  180
acattatata ttatgtgtcg aggaaacatg aaattatgcc tacctcataa aaaatgacca  240
taaatcctaa acactaaaca agacaatcta aatctctact acatattaag acaataaagg  300
tagtctgtct cccctcgttt ttccgttttg ccgtccatcg atctggaccg tccgtatcct  360
atcgttcgtc tgcgtctccc acgctccatc cccctccacc gcacgaccgc acccaatccc  420
taacctttcc ccgcacgttc ctctcctctc aatgccacgt tgcctgcccc ctgcccctgc  480
cgcgatagat gcctcgcggc                                          500

SEQ ID NO: 57          moltype = DNA  length = 500
FEATURE                Location/Qualifiers
source                 1..500
                       mol_type = unassigned DNA
                       organism = Zea mays
SEQUENCE: 57
agaattgatc atggtggaag agatggcctt gattataata gctgggagat tccttgcaac  60
taaatggctg tgccatctgt catcaagttt tatatacatg aacttgccac tacttgggat  120
gatcttaaat gcactgtatc cttttgcaaa tgtatgtcgt cagttatgca tggatgttaa  180
tgctagattt aagtattttc actttttcag tgtggtgcta gatgtattta tatgggttca  240
aatcttgttg ccacaattaa catccacagc gcaagtgctt aagccgccat tgcacctgca  300
cggctgtttt cgtgcctgac agcaccattg cgttttggcg caattttgct ggcgcgtaat  360
ggctgtttcc cgtcctgccc tcagccaata tgcagacttg ctgatctgca tctgctccac  420
tctcatgctc ggctgtgtat cttagtatcg taataaaacg actcatcatt cccctaccta  480
caagttgccc accctgatta                                          500

SEQ ID NO: 58          moltype = DNA  length = 500
FEATURE                Location/Qualifiers
source                 1..500
                       mol_type = unassigned DNA
                       organism = Zea mays
SEQUENCE: 58
attgcatgct ggaacgtctt caaccccgtg ctcgtcggat tgttcgtcat ctggcgatta  60
tcttagcatt gtcgtctgct tgcagtggct agcgcccctg tttatcttat ccaaattaga  120
taattaaata aatgtatcga actacctttt aatataatta tttaaatttc gtctagtagc  180
agataaaaac taattctgat attagatata tggcgtacag tcattctctt gctttccact  240
gttatcgtct tgctaatatt atgtacagct ggttgttcta ctgctgtacc aagagtcgta  300
gtggccttat tattatttat taccggtagc tcattttgct agtaaccatc atgaaattga  360
tctccgtatt ggagtcaccg agcattccgt tagattttgg aaagcacact tttgatcttg  420
atttatcttt caaacttcca tgttattcat tgaagagaga ctctagaaag taagcttgtg  480
acattgagtc agctactagt                                          500

SEQ ID NO: 59          moltype = DNA  length = 500
FEATURE                Location/Qualifiers
source                 1..500
                       mol_type = unassigned DNA
                       organism = Zea mays
SEQUENCE: 59
aggtcaggtc agcagcatgt atataatgca tgctagtcaa tggatgtagt actagtacca  60
gctttattca tggtattttg ataagttcga caaatgatat ctgatgaagt ctattggaaa  120
gtgttttgag ttttctgttt tcaagtgtcc tactattatc ttattactat catgattttt  180
ttttctgttg gtatttcgaa ttcttggctc cataaaaaaa tgctatttta tcactctcag  240
cgtgggctat ctgttattat gtctccctat gtctatgact tgtgggacca ttgtgtctat  300
gatttgtaag tccgatggtc aaatagagaa gcgcataact gagagtgaca aaatagcaaa  360
tgcccaaaaa aaagtgatgc aaaacatgtt aatagtggcc catagagcag gtgtcggcgg  420
ttcatgtgca cagacgccat tccagggggt gctgagcttg gggactcct accgagatgt  480
tgaagagcat ttgttggttg                                          500

SEQ ID NO: 60          moltype = DNA  length = 500
FEATURE                Location/Qualifiers
source                 1..500
                       mol_type = unassigned DNA
                       organism = Zea mays
SEQUENCE: 60
acagacactc ttttatcata tagttttgac agcgacgacg aacacggccg ggtgtgtcca  60
gcatatatga actggtgctg tatttgttat atgctgcgtc aaccatgtaa gctagcgttc  120
aaataaatgt cgagcacacg accacacgtg atcattcaac atcaacaaaa tgggactcag  180
tattgttgtc taaaagttag acaactgtgc aggattggat ttaatttaca gatataaata  240
atgagataag agattgagag tacaaccgtc tcgactctcg tgaacccgat tcacatacac  300
gcgcatgaga ttttaagatt atactgtcgg gcaccggctc ttgcgcatct ccccttccgc  360
ctatggtttc ctttactacg ggaatccggc attttggtga atgttcaacg ctttgtcgag  420
```

```
tatattttgt cggacactcg acaaagcagt ctttatatta ctgtccggca ccggctcttg  480
cgcatctccc cttccgccta                                              500

SEQ ID NO: 61          moltype = DNA  length = 500
FEATURE                Location/Qualifiers
source                 1..500
                       mol_type = unassigned DNA
                       organism = Zea mays
SEQUENCE: 61
ctaagcgaca catctcgtgg ccaagtgtag tcaggcaacg gtgttgtcgg gaccataatt  60
aggggtaccc tcaagacgcc taattctcag ctggtaaccc ccatcagcat aaagctgcaa  120
aggcctgatg ggtacgatta agtcagggat cagtccacac gagtgactcg atcacgcttc  180
acccgagcct agcctcggcc aagggcagcc gacctcgaga gacttccgtc tcgcccgagg  240
cccccctttt tacggcggac acacctccgg ctcgcccgag gccttggctt cgctcagaag  300
caaccctgac taaatcgcca caccgactga ccaagttgca ggagcattta acgcaaaggt  360
ggcctgacac ctttatcctg acacgcgccc cccggcagag ccgaagtgac cgccgtcact  420
ccaccgctcc actgaccagt ctgacagaag gacagcgtcg cctgcgccac tccgactgca  480
gtgccactcg acagagtgag                                              500

SEQ ID NO: 62          moltype = DNA  length = 500
FEATURE                Location/Qualifiers
source                 1..500
                       mol_type = unassigned DNA
                       organism = Zea mays
SEQUENCE: 62
gctcgcgatg atggttttcg ttgacagtct tagtattact actatcttcc tcatgcatgt  60
aacgagttgc ttcgtttctc gtattatggt tatggtttcc cttggatgca tgatgaacta  120
gtgcttgcag ttgattttcc ccttattagt ttgagctgct taattcttag tagccctttt  180
tttttcttg tgcttgtcat gcacgtatgc acacacacat gagacgggca gctagcattt  240
tctgtggttc tatctcctct cggttttgtg cctgtcattt ggggcttaaa tgtatcagtt  300
gtcttttctc gtgcttggca tgcatagtat atatatgccc acatgagcaa actgctgctg  360
cttcagttcc aagtagtaca aaagattcaa attaaaattc catcgtattt aaccctagat  420
tttaattgaa tatattagat ccgcatagtt ataccaacat gactgattac acatgatacg  480
tgccctttag ttttatatca                                              500

SEQ ID NO: 63          moltype = DNA  length = 500
FEATURE                Location/Qualifiers
source                 1..500
                       mol_type = unassigned DNA
                       organism = Zea mays
SEQUENCE: 63
actttgtgag gcgaatccaa aacaaaaagg tggatgcgag aaaggcgaag tatatgtaag  60
ccggaaggcg aatttcctgg ttactgatga cctgcgtgtt cttccactct cattagcatc  120
cactgttaag attgttagtg attccaaaat ccagacctcg aatcttgtgg tcaaagaaat  180
cacattaaca aagtccaagg tatctatatc tgctacataa ctcacattat ttgcattgtg  240
ctagactacc tattcacttg gtcttgtgta actgaatctt ggaacaggtt atggagctac  300
agagggctgt cctgctgctg agtcgcaaca tactcagctc cgtgcttctg catcctaaga  360
agaacaagaa gctgcaccat taccatcgca tgtattagcc gtcgttgttg ctttactcta  420
tgattagcca caatgataac tatgtactat gtctgttttt ctgctgaatt tgtaagttat  480
cattttggcc actggtattc                                              500

SEQ ID NO: 64          moltype = DNA  length = 500
FEATURE                Location/Qualifiers
source                 1..500
                       mol_type = unassigned DNA
                       organism = Zea mays
SEQUENCE: 64
gcatgtcatg gtgtgctctg cgtgacattg acttttgggt tgcgttccca gccgtatgga  60
ctttgttaag gtttacatgc tatgtttctg ttttaatgca tgttactatc gtttagattg  120
ttatgtttta tctcatcact gttcatggtg gctacctatg gttaacggtg gcttgttcgc  180
gccttggcga cccataagtg ctgtgttttg ttgtttgttt ggtcactgtt ttttctttgc  240
gagaccagta ttaaagccag taaaatgcct tttttgtttc taggagtaca tccctaatta  300
aagccaataa atgagttact tttttttgga atgaaggacg tctttcgagt ttcgatcggt  360
agttttagtt ccaaaatctt ctgacttgag cccctctgga tgtccacgcc tactaaagct  420
ctaattatgt aaaaaaatcc tgagctcagt aacagattag gccttgaaag tgcaaaatgt  480
tcatataaat tatactgcat                                              500

SEQ ID NO: 65          moltype = DNA  length = 2000
FEATURE                Location/Qualifiers
source                 1..2000
                       mol_type = unassigned DNA
                       organism = Glycine max
SEQUENCE: 65
taattaaaaa gataatattt tatattatgt aataatatat tatttattat aaaattttca  60
taattagatt ttaattttaa tattaagtag taacaataaa tattatatta ctacttatgc  120
atatttttaa aaattagtta ctgtaaaata tatttcatga aaagtaatat tccttaatat  180
tattacagaa ttttataatt aaatattaat tttgataatt gatattaagt aataatatgt  240
catttactat acaattctga taattaattt tttattaaat aataatatta attaaatatt  300
atgaaaataa tgaaataaat atgaaatatg taattagata tcaattaatt aatactaaaa  360
```

-continued

```
tacatagata atcaaataca tttttaacta ttatttctca taaaaaatat ttaaaataat  420
aaaatgagca gatgaaaaaa ttaatgtgtt tttaatcttt tgtgtgtaat atttttaaaa  480
tattaaaata aatattttat ttattcacta ttaattattg ttcgtgttta ttaagtataa  540
tatataatta attttatgtt ttatttttga aataaaaatt atatttctat tatgaaaaca  600
aaaatataat attattgtat gtaattttga taattaaaaa ttaattttaa tatttatcct  660
aagtaatagt atactactta ttatacagtt ttaatattct aattaaatat caattttgat  720
aattttgata ttaagtagta taattaaata ttatattgtt atctacgcta atttttaaaa  780
ttacttattt taaaatatat ttcaagaaaa ataataattt aaaagtgtca attttaaaaa  840
tacgtattta aatttaaaat aattcgtaat atataataat taagaatata aattaataaa  900
ttaattatta tgtatacata tcaatgtaat ttattttaaa tttagttatt taaataaatt  960
ttgctaacag taataattaa aagtaatcat ttaaaagtga cgtgagtatt taatgaatat  1020
ttgagctttt aatatgtaat tttagttttt ttataatttc taatcaatga ttttaatttt  1080
tttttttgta attttagtc ttcttatggt aaaaatttta taattttgat caaatcctca  1140
attttacata tattttattt ctcaattaaa aattaataat tatcttgatc aatttttaca  1200
taattatttt aatatgttat taaatatttt aatttttaat tttatcaata tatatatata  1260
tatatatata tatatattat aaaatactac atacaaatat aaaattatat ttttgaatcc  1320
aactcgtaca tgatacacga gtttaaaatc tatgagatgt aatcgtttcc ttccaagtat  1380
ataggcagaa aaaacatgca ttcgtctgtt cttatactac aattgtaaat ttattgctta  1440
ttacgaagat gtcactaaaa acctcttggc taccttttca tcttccaaca acgtgcatat  1500
actactctct tgttacattt caactgcttt aacgctaagt tttctaatta atgtgtcaat  1560
aattgtttta aaactgatag gtgataatta ttctctggta atatctgatg ggtttttttt  1620
taggtatact agtatttgtt aataaaagaa gtatattgtg taagcctctg agatgtttta  1680
ttcatggtat agagcaaaaa gtgtaacaca aaatttaaat attgataaaa tcctatcctt  1740
aaaacatgaa ataaatccta aaatactcac aacaaattca taatatttta aatctaaaat  1800
aatatcctaa aaatttaaaa cagatatttt ttttaaagat aaacaaatta tttctttcta  1860
aactaaatat atgagacaaa ttctttacaa tatctactat gtagacctct atatataccc  1920
tgccctttca gtccacatta cagcacagat attttctcaa agggaaatag caccatttgg  1980
cattttacaa tttccaagct                                              2000
```

```
SEQ ID NO: 66          moltype = DNA  length = 2000
FEATURE                Location/Qualifiers
source                 1..2000
                       mol_type = unassigned DNA
                       organism = Glycine max
SEQUENCE: 66
ataaggagtg ataagctgca aaaaccaacc atgtgacatg aaagtattta cccccctagga  60
ttgaggatcc acaaaaagac acaaaagtta aactcataat taaattcaat ttcacttgtt  120
ttcacattat aattttaatc aaattattaa aattaatatt tttgtccaac atttgaatcc  180
tatatactat ctttcaattt atagctaaat tcaactcact actgatattt taattctaca  240
atcgcccacg tgcattatca cttagaatca aaacataata tatatttcaa agatttcgaa  300
ttcaatttca aatcataata tcgtaaaatt caaaaccaat ttccacggtg aacagaaacc  360
tatcttcatt tgttatcacc tatatctttc ccatttttcc attcccgaac agattcgctg  420
acgagaaagt ttctgctgta gctttaattt taatgctaat agtttggaat agaaatctct  480
gacatctcag ggagtcagaa cgtgacatat ttataggaaa tatataatct aaataaacgt  540
ttgaatttct tccaaaaata tttgaaaata tatatcagaa tattattaat gaagaaccaa  600
taaaaaattg caatttgtat atgtttaata tttaaataca ttatatttat caaataaaca  660
taaaaaaata taatactaat tatttataat aaatctttca caatcaaatt gtgtgttctt  720
tagctagcct ctatgtagta caaatgtaaa taactcatta gaaaacattt agtaaaggaa  780
aacaccgatc ttatcttcat ggaataatga atttgtttgg ttgttcattg aactgaaatg  840
ttctgctagc tccgggcgct ctttttaata ataataaaaa aagaactaaa gtattttatt  900
ttttttaatt taagattttg atgcattcac atgtgaggac aataatttat ttaatggaaa  960
agtacttgct tgatttatat catgtataac attttcatgg attaacaata attacacatc  1020
acaaacgaaa ttattttaaa atcctgtgtg gtgggaacta atgatttgat aataaaaaaa  1080
acaaaagttt ttttttttta atgaaaatac ttctttcttt actttttttt attagaatct  1140
attgtgaagt gtctcagctt tcatttttatt taattttaaa caaaacaatt actcctttcg  1200
ttatcataaa aaatactccg ttctaaaata agtgtaatgt ttaattttta tataatatta  1260
atttttcttt cagtgatact cataatatgt gtgctttaac tttttaacgt gtcgctttaa  1320
ttttttaata taatattaat agtaaggtta attttataag attattactt ttttatttat  1380
ttattattat taatttctct ttatctatgt aaaataactt acaacaacac ttaagttaaa  1440
atatgtcatg tgaaggagtg ctgccatgca cagtcattaa tacataattt ttattagtta  1500
aaagatatta aaaatacaaa attataagtg ccaaaagtga gttagaaaag tttgcctatt  1560
actaacattt tcctaatcca tgtataatcc ccatttacac cattttgtca tttctcgctg  1620
tggtaggtgt atcatttaac aatcccgcac tggactcgct gaagtatgct tttttaagga  1680
tttcttgatt ccttattggt acgcacaata aatatttctt ggagatgaaa ttctcttttt  1740
catgggacca gtctaaaaaa tcactaggta tttttttctt ctattggcat tttcttctat  1800
ggtcgaccaa cgtaaaataa aattggtctt aattttttttc cgcagcacac gtcttagtgc  1860
ctctataaat tcagcaatat gtagctgtag taatccacat aaaatccaat tcataataca  1920
ggtttaacca tttcccacta gcgatcttgt tctctaagcc taatattact cccttgatca  1980
gtctttgcat atttagaaaa                                              2000
```

```
SEQ ID NO: 67          moltype = DNA  length = 2000
FEATURE                Location/Qualifiers
source                 1..2000
                       mol_type = unassigned DNA
                       organism = Glycine max
SEQUENCE: 67
tagttggttc actaaaagaa tctattattt tatataatat tacattaatt tcttatatat  60
aaatttagat attaattcaa tatcttattc ataaaaataa atcaatatac taagaaacta  120
aatcatcatt cattgacatg attttttata ttatatttac ttattcttat ttcgttacaa  180
```

```
aattctcaat tttttatttt agattttgat tttttttctt ctaaaatccc agtttaatta  240
cttttaaagt tttattgtta tattaaaaac atatttttca tttatacatt caaaaacgtt  300
ttttcgtatt ttctattttt ctaataaatt aaagttactt atatttttga cttatttatt  360
taaattaatt ataaactatt tttttatgaa tttcaatttt ggtaatttta ttttatttaa  420
aaatgactga cgcacaaaat acatacaagt acattcttta cataacattt ctttaaatga  480
cgaacgcgtc gatttctagt cattaccctt taactaatac aaggtaaggt cgcgttaagt  540
tttcacgtaa aaaagttact atataaacac ttctctaaag acccactggc atttgtttaa  600
attaggaacc aaacacattc attttcaact catccttgag ataaaattta ctttttgaag  660
taaatattaa aaatcgtgac gatgttcaat atcattcgga aagagacata ctaatccgca  720
ttgacgcatt ttcatgccac tattttgctt tacgcatgaa acttccaaat tctccgttgg  780
tcgctttcaa ctttgcaact ttcaaaccca aatttataaa gagatcaatt ttttcttttc  840
tttttgaagg atagagagag agatcaattt ttaaatatat atagatattt tatttaattg  900
ctaaacattc attagttagt aatatgtaaa atatatttga attaaaattc ataataaata  960
aatattttat aacatataag ttatatttta aaattgtaat aaatatttat atcatgatac  1020
aaatttattt ttaactatag gtaaattctt tttgaaatat tttaaaattc aatatgaaaa  1080
taatatatta gaaaagataa aaaagattaa gaaaaatttc taaaaacatc atgattgaag  1140
aaaaactctc attaaaaatt agattctaaa aacattctca ttcaagataa ctattagtat  1200
aatttttaac ttaggaaaca ttgtttttga gaatatttct tacaaatttt ttctcatgag  1260
ggaaatgttt taatgctatc aaaataccaa ataaccctta ttaactcatt taataaaatt  1320
atataaaatt ttgaattagt ttcttactaa aagtgataaa taaataaata aatttaagaa  1380
taagaaatac taataaaaat tcttagcatg tttcttatcg ttttaagaat attattgcag  1440
aaacatcatg gaaatatttt ttagaaaatg taaaaaaaaa aaaatctaac atagagcaaa  1500
tgataaattt tgtgatgtta aaattaaata gaaatatgaa aaatcataca aacctttttg  1560
taatttttaa attcatgaaa aattttattt tataacaaaa cttatccaaa ttatagttga  1620
tcgaattaat tttaaaattt aacttaattt acgtgcaaga aaatgttata ataaattatt  1680
tatgaatgtt attatccaac tagtaatact agataatttt cattattcta taaaaaaaat  1740
ataatttgca ttaaaaataa aaataaattt cactacaatt tatttatttt gaaatttaat  1800
tctaataaac aatttaattc ttattttttta aaaaatgggt tgtcaaccgg gagagagttg  1860
gtgatttcaa tcttagtaat gacgtgggag attccattcc agtgtgtgtg ctttttctct  1920
ccctactact ataaagccat gttagtgtct gcttcaactc aagtatctct ttgtgttcat  1980
agcaattctc tattctgaag                                               2000

SEQ ID NO: 68          moltype = DNA  length = 2000
FEATURE                Location/Qualifiers
source                 1..2000
                       mol_type = unassigned DNA
                       organism = Glycine max
SEQUENCE: 68
gcattgcatt caaaatgtaa agtttacaga aatttaaaat ggttcacaaa caaacataca  60
ttctccttgt gtactcgttt ctctctgcgc tgggtacttt gagtgtataa ggatttgtat  120
aaatgaattg cgaccacgaa atctaactaa aaactgctat atatagattt tcgaaaataa  180
actgccctaa cggtcgaacg ctatcctaat gccaagtgtc ctgctacgta caccttgcat  240
gcacacataa ctgctcccta gaacggttat ccacattact cgaaatcgaa atgatttggt  300
gaagatttgt tcagaaacta cgctaagtcc agaactcttg ctgcctcgac ttcgactcgt  360
ccatacacca gttcgaattg cccaatggct cgaagtcctc tttcttgtct tagctttgta  420
cttcgtaaat acttctttga acctgggaat tccttcttaa agacttttct ctcttttcga  480
ttcgagcagg tcctgaccag actcttgctc tgtaatacgc ttcgaacctc gagacgacat  540
ccaatgcata cttagagcat attttagctc gtcgaaaata tgggccaaca gatatttaga  600
attttttttc tttcgtttaa aaataatatt taatttctct tatcttttta gttgtttaaa  660
gtggaataaa aaatggaaaa caattttggg aagaacaaaa aaagttgact ttccttcctc  720
gatcaaattg ttaaaaaata aagttttatt aaacattttt ttatttgata tgtatctctt  780
agtgttagtt agttggaaat taggttaggt agttagaact agtggtaatt agttgatgtt  840
gtaataataa catcaagact ttatattatt gagtaattaa tcttacatct tcattttgtg  900
tctcttgatt tcgatcttaa gggtgaacaa tcatcttctt ctcttataac attattgatg  960
tttgaatttt gaaccttgta aagtttgtgt ccaggtgggt acccatgctt cttgtaacaa  1020
tcatcagtat gattataaaa atcataatat gtgcaaatct tgtttccttt tactcctgaa  1080
tttcctttgt cgtaagtttc cttttctgga agcatacttc tgagaaaaac catgcttcct  1140
atagcatcta tcaatagtgt gattatcttt ccccacaatag gtacatgaag gcctagaatt  1200
caatgaattg ctgcaaattt gttttaattg tcaattcatc atcccgagtg attctcaatc  1260
ttgtgaagta atcggtaatg ctttgatcac cttgtttgat agaagtcatt tcttgctaca  1320
aatttaaaat tctcaacaga tctccttatg agtatcttaa ctttaagtcc ttccaaatgt  1380
ctctagcatt atccatctat aagatacttt gtcttatcga gggtaaaacc gagtggacaa  1440
gccaagaaac caccatattg ttacatctcc tccaagctgc atgaagagga tgaattgatg  1500
cacattttttg aattgatcca tctataaatt caattttatt tttcgcgctt aatgcagtaa  1560
gcatcgaaca attccatgag ttctagtttg tcggatcaag aatcgaagaa atcaatgcaa  1620
ttgcaagatt ttcacctgga tgaaggtagt ataggctatg gacatttagg gattggtctt  1680
gtgaagaaat ctcattggtc ataattaaga aaatgaaaaa aaagatttag gttcaagatc  1740
agggagttac gtaaaagagc actaatgcct tgataccatc ataaatattg tgcctaccat  1800
ctttgaatgt aaaattaacc aaaaaagctt gcaagagaaa ctagaaagaa aactaggaag  1860
aaatgaatga aattctatgt attgaaaatt agttctaact acaaccaatt tcaaccaact  1920
aaactaagtt ccgactaagt aacaagatcg agtatcttta atcaatttgc ccattgatta  1980
ttcttacatt ttaatttgga                                               2000

SEQ ID NO: 69          moltype = DNA  length = 2000
FEATURE                Location/Qualifiers
source                 1..2000
                       mol_type = unassigned DNA
                       organism = Glycine max
SEQUENCE: 69
```

```
acactttata cacataataa ttaatataaa tttttattta tatatagaga gctaactcaa  60
tttttaaaag tttggatgtg agtttctttc actcaaaact agacaacctt tatagtttct  120
agttttcgca tcgtcttaca gataagtaat aataataata atataaaaaa ccctcatgcc  180
tgtcgtttcg aaggtgcaac aggttcaaaa accattagtt tcaatgactt ttcacttatt  240
cagtatgtgt gaaaagtgag gagataaagg caataataca tgggactcat gcaaaataat  300
ttcactactg cattattgtc gggaagaaaa cttggaagag aagaacaaaa taaccatttg  360
tcaattttgt tttatataaa cataaaaaaa tgtcatctaa ttaatatgat tatatttttc  420
ttttaatttt tttttatcta tatatataac ctaaaattta tttatttatt ttcagttttc  480
ctacttcatt ttatattatt tcttttcctc tacttctccc atgcaagcat aatgttacgg  540
cttaatttga gaaaaagaag agagataaca ttcaaacccc agtgatctcc ccatgcggtt  600
acagtcgcac aatatatctc gctctgtgtt gaattgaaaa ggatgtgtaa ttaagggtct  660
ccacgcgtga agtaaatgaa gtagaacata tgcacaaatg ctcttagtaa ttttagggca  720
gattcctgcc ttaatttgtg gtgaccgtga ctaaaatggg aatgtcctag atacaaagtt  780
agcatgcttc ttctattgaa ttatatatac actgggtcaa tcaagaacat taatcatggt  840
acatagcatc accgtagcac atggacttta aatgaagata gatacatgta accatttcat  900
taattaattc atgtcgttaa cactcaacga aaaatagaac taaattaaag aaaatttgtt  960
gatgtgagga atgagtatga aacgtattaa gggggatggt agattaatga tgatattgac  1020
atacaggtgc ggatatgtgc ctgatagttt aatgcacaag taagaccgta ccaaatcaaa  1080
gtgcaacttg agcctttcgc tgtctagttt ctaaactact atcaagctgg attgaaaaaa  1140
tatgaatata gacaaacttg tacaacctgg tcattaaatt aaactactgt aaatgtacca  1200
aatgtaggtt ttcatattaa gagttcaata tatttatata aaacattttt acattaatct  1260
aaataagatt taattatttt atcaggttat tttattcatt aacatgctgt gacgataaaa  1320
aatttcttgt tagatgttta gaaaaatatt ttacatgcaa aattgcaaat caaacctttt  1380
tcaaattcat cgcgggaaag gaatcgatat ttctgtggac actatataca cggtatgacc  1440
attaattgga catggaccaa acaagcaata acgtcaaaat ttgtagttgt cgatgaatga  1500
atcttgcaga caaaggtgtc caaaatcatc caaagcacgg gcatatgtag ctacttaatc  1560
ttattgtggg ggggagacta gggtcccgta gaagatacct tttggggata tatagataac  1620
tttttgagag gtctggatat aatttgaagt tttaaacatc cataaattat actcttcttg  1680
tttttttgac aaacataaat tatactccaa cactatatca atactagtgt cttgatattc  1740
aaaaggtgtt cccatgattt taaatagtga tctaccatcg caatcgcaat tatgataata  1800
atatcaaagt attttgattt tccgtaatcg tacaacaatc gtaataatga ctatattaca  1860
tttttttca taatataaaa gtttctaaa tgatcaacca caagtcaatt tatgagagct  1920
agttaacgaa tatcacagcc tgtatatatt ccctatttaa acatcacatt tgttctatac  1980
acattcacct taatccgatg                                              2000

SEQ ID NO: 70          moltype = DNA  length = 500
FEATURE                Location/Qualifiers
source                 1..500
                       mol_type = unassigned DNA
                       organism = Glycine max
SEQUENCE: 70
cgggaataaa ccggaaaaaa gatgtcttgt ttagagatat ttttactatt ttactctata  60
ggctacgttt gatttccaaa gcttattact acattctact aggtgctgta aggaatagga  120
agtttattat tcactgttgt ggtctttgta tttcatgaag attagtactt tgttatttca  180
ttacctaatg aaaatatact aggtttcaat tataagatta cttttatggc tatattgttg  240
tctctttatt tcatgtttac tttgtctgta tttcacgacg tgacgaaaat aaacaataca  300
aggtttcaat cgcaaagaaa ttaaaataaa aaaataaaaa ttcaatagca aaaaatagtt  360
ctaaaatcta aatggaatgg ggcattccga gaattgaact cgggacctct cgcaccctaa  420
gcgagaatca taccactaga ccaaatgccc tttggaagtg gtttgtgaaa gttaactaat  480
ttaattagta aaatcaatgc                                              500

SEQ ID NO: 71          moltype = DNA  length = 500
FEATURE                Location/Qualifiers
source                 1..500
                       mol_type = unassigned DNA
                       organism = Glycine max
SEQUENCE: 71
ttccattaca aaaagttaag tagcaagtat tatatattat acatattgaa taattattga  60
ggctatgata gtggttcaca attatgaatt tattaattta caatatgtaa tggatggtat  120
gtatccttca tttacgataa attgttggtt tgaaaattcc ttttgtattg attctaaaga  180
ggtacgtaca atttcttttt taatcctcag ttcttttcat gattcttttt gtagcaagaa  240
aaatcacaac tcttatatca aatataggaa tgatatattt aattaactcg gaaatgtaga  300
acatgcggag aagaacatca aaacagtgga tatatacgtg tatatatata tatatatata  360
tatataagac aattccaatg taaaacaata aaaaaaatgg accaaactta actgtaaaat  420
tttatgtaca tgttttttga gttattgtcg aatcaaaatg gagttttaca ttagcaaatt  480
acgtaagagt tgtatcaaat                                              500

SEQ ID NO: 72          moltype = DNA  length = 500
FEATURE                Location/Qualifiers
source                 1..500
                       mol_type = unassigned DNA
                       organism = Glycine max
SEQUENCE: 72
tttttcttta agttgacttg acatggctga tagggctttc tcataaggaa atcctagcaa  60
aataatgccc tgcaacttat gatgttatag attgtcaatg agttgttagg caaggaatgt  120
tggatgtaaa atggttggga tagcatatat aatcccatat atatggtaca acataatcta  180
tatataaact ttattttttt acattttact atattttttt tgtccaaact ataattttgt  240
ttttcataag ctacaacata cgcatttaca gatgtaaaca ttaacattgg ctgaaaaggg  300
atgctctaca ttacgttgag atagatgaat gaatatacac aatagtatgt ctatggacta  360
```

```
tggatattca taggtcgatt agttgtgaaa aatgagacga aaaaacaaaa ttaaacaaaa  420
gaacgtaaga aaaaatgtga ttgaaataaa ttttaaatct aatataatta aatttaaatt  480
aaattttaaa tagttataat                                              500

SEQ ID NO: 73          moltype = DNA  length = 500
FEATURE                Location/Qualifiers
source                 1..500
                       mol_type = unassigned DNA
                       organism = Glycine max
SEQUENCE: 73
cgtggaggaa aaaggaattg tttggtgggg aaatgatggt gaccaatgta agcttgccaa  60
atgtccaaca gcgaaaggtg tagttactga agggtgtcct gtgttttgat ttccatttcg  120
acatcatata ttttctggtt agttaagaat taagatggtg agtgggggag taatatttct  180
gcaaatacca gttgaattag attgttttaa gcgctttaat ttggtggacc tttatgttgt  240
ggttgtgtgc aacttctcca gaacagatcg ttgttttttt ttttttttt tttatatagc  300
tagtcatttt taatttcatt ctatttcttc ttcttttttt tttaacagaa tttcgttcta  360
tttcatcatc actatcattt agaattgaca atgttttagt tgctagataa ccgcgagata  420
ttgggagttc caacatacta gtattatatt agtatcaaac tttcaagaat tataaacctt  480
ttatttccgt ttcgtgatag                                              500

SEQ ID NO: 74          moltype = DNA  length = 500
FEATURE                Location/Qualifiers
source                 1..500
                       mol_type = unassigned DNA
                       organism = Glycine max
SEQUENCE: 74
atcaatatgt atagtgacgg agacatatat catatatggt ttcatatgaa tcaagttaaa  60
aatgcacatc aactaaacaa atcttctata tggaacataa taataatttc tcaccagact  120
aacataggtt tcgatgattc cggaaataac gttgattctt tatgctccaa ttatttttat  180
tatatatata tatatatata tatatatata tatatatata tatatatatt tttttttttt  240
tttttctttt tatcacgcca gttattatat ttactttttt tttcttcttc caatccgata  300
tatacatacc attagaagat gtgaaaaatc gcctatgttt aatatatgaa aataattcta  360
attgtttatg gcatctctat tttatactta tctgaacctc ctgttgttta atactattaa  420
ttagcactca tcgtatttat catttttgt tctattttgt ctgtatccgt ttgttcactt  480
gagatgtgtg ctttttttaaa                                             500

SEQ ID NO: 75          moltype = DNA  length = 592
FEATURE                Location/Qualifiers
source                 1..592
                       mol_type = unassigned DNA
                       organism = Arabidopsis thaliana
SEQUENCE: 75
acaaagactg gtcggtcggt tttggtagac aattgaaatt agatggatgg tccggttcgg  60
tatactataa gattaaaaac agttttaaat tcagctaaac cgaactcatt tgattttatt  120
aaaccggaat catccgattc gagtttgtaa aaaataccga aattgaaaac actaaacaaa  180
aactgtatta aactgttact gaaataagag aatctcccaa ttcggtttac gtactactct  240
tcagaaatca gaaccaaaaa ttcagaaatc ggattgaacc aaacttaaat tgacggtccg  300
gttagtcttc ggctctacaa attaaaggcc caagtttctg ctttaaaaga acgaaatagt  360
taatgggctc aaaccataga ccaggtaagt catgggcttg gttagtccgg gtcaacccgg  420
tagacccgat tcctgaagaa aacctagtgg aaggtttaaa gttgtaaact ttccgaccaa  480
ataaacaaaa tcgttttcca gcttcttccg tcgccactaa accctgaggc taaacctaga  540
cgagtcaaag tgtaaaatcg ttaaacccta agagggagtg agagagagaa ga          592

SEQ ID NO: 76          moltype = DNA  length = 459
FEATURE                Location/Qualifiers
source                 1..459
                       mol_type = unassigned DNA
                       organism = Arabidopsis thaliana
SEQUENCE: 76
ttatgatttc ttcggtttca agatgatcaa atagttatag atttcatgct cacacatgct  60
cattagatgt gtacatactt tacttaccca aatctatttt ctcgcaaaga ttttgatggt  120
aaagctgatt tggttctatt gaactaaatc aaacgagttt cagactgagt gattctaatc  180
cggcccatta gcccctaaac agacccacta attacgcagc ttttaataga gtaattacac  240
ctagtttacc cactaaacca ctaagcacta attatctcac aatctaatga gcttccctcg  300
taattacttg ggctttcact ctaccattta tttgtaacag tcaagtctct actgtctcta  360
tataaactct ctaaagttaa cacacaattc tcatcacaaa caaatcaacc aaagcaactt  420
ctactctttc ttctttcgac cttatcaatc tgttgagaa                         459

SEQ ID NO: 77          moltype = DNA  length = 667
FEATURE                Location/Qualifiers
source                 1..667
                       mol_type = unassigned DNA
                       organism = Arabidopsis thaliana
SEQUENCE: 77
cagagaaact aggagacttg agaatataca ttcttgtata tttgtattcg agattgtgaa  60
aatttgacca taagtttaaa ttcttaaaaa gatatatctg atctagatga tggttataga  120
ctgtaatttt accacatgtt taatgatgga tagtgacaca catgacacat cgacaacact  180
atagcatctt atttagatta caacatgaaa tttttctgta atacatgtct ttgtacataa  240
tttaaaagta attcctaaga aatatattta tacaaggagt ttaaagaaaa catagcataa  300
```

```
agttcaatga gtagtaaaaa ccatatacag tatatagcat aaagttcaat gagtttatta  360
caaaagcatt ggttcacttt ctgtaacacg acgttaaacc ttcgtctcca ataggagcgc  420
tactgattca acatgccaat atatactaaa tacgtttcta cagtcaaatg ctttaacgtt  480
tcatgattaa gtgactattt accgtcaatc ctttcccatt cctcccacta atccaacttt  540
ttaattactc ttaaatcacc actaagcttc gaatccatcc aaaaccacaa tataaaaaca  600
gaactctcgt aactcaatca tcgcaaaaca aaacaaaaca aaacaaaaac cccaaaaaga  660
aagaata                                                            667

SEQ ID NO: 78          moltype = DNA  length = 479
FEATURE                Location/Qualifiers
source                 1..479
                       mol_type = unassigned DNA
                       organism = Arabidopsis thaliana
SEQUENCE: 78
cattatgttt gaactcttat atgggttctt cccatgttac aatacgtacc agggtgctct  60
aaaatatcca attggtcccg atctatatat gtatgtagag actcttcctt ggatagatat  120
ttggtgaatc caaaaataaa gttttacaag agatgacgaa acaaaggata gtaaaagaaa  180
tcagaatctt gattattgaa attttttaaa gacagaatca gcctttataa agaaacaata  240
ttctttattc atttccttcc aaaatctctc ttctttaaga tgatctacac aattaaatac  300
cgtcgatttc gaaaattgaa gtttaaaatc aatatgagga tttgaaataa gagcttacat  360
gcacacacac atatctctct atatataagt gagtaggttt acatggttta attttctata  420
acacgacaca cacgaaaaag agaagcaagc acaacacaat ttttttata acaactaaa   479

SEQ ID NO: 79          moltype = DNA  length = 2345
FEATURE                Location/Qualifiers
source                 1..2345
                       mol_type = unassigned DNA
                       organism = Arabidopsis thaliana
SEQUENCE: 79
ctgctgtaaa tgtgaaggtg ttgggagtaa accctcttga taccatttgc tcaaaacagt  60
ttattgcatc cctgaagagt tcattgcatc cataagcctc tataatggcg gtccatgtca  120
gagagccctt gacagcaaca gcatcgaaag agaaattagc acttctgaga tctccacatt  180
ttccatacat cttgatgatt cttgcagaaa caaatgggat cgactcaaat tcctttttca  240
gaatgtgccc atgaagctct ttccccaact ttaatgcttt gagatcactg caaacagtca  300
aaaccctacc catcgtaaca gaatctggcc tgtgttttga taacagcatc aatctgaata  360
cctcaatccc tgctcttaaa tcacaatttt ccacatagca gtcaatcata gcggtccatg  420
ctttcacatt cctttgttcc aacctgtcaa acagtctgat aggatactct ggaacaccgc  480
actttgagta catcaccatc aaggaagtga ccagggatac attcggcaag aagagattct  540
ttaaagcata acaatgaatc tcctttcctt gctttatagc cctcagctct gcgcaaacag  600
gaagaacagt agcaattgta acaacatctg gcctaaaacc ttcctgctgc atccaaacaa  660
tcgacctcaa agcttgatca aatctaccgt tggctgcgta tccagacatc aatgcagtcc  720
aagatatggc attcctctgt ttggatccat agaacacacg tctcccagaa gccatatccc  780
cacacttgca gtataaatca atcaaaccag agtgaacaaa cggctgttcc acgtaattct  840
tcgatttcaa tacatgggca tggacctcct tccccagttt cagtgcctta acatccccaa  900
gtacgggaag aatcgttgta agtataactg agtttggata tatcttttct tcactaatca  960
tcgtcctaaa cagtcccaac gcttcccact gccttttatt gtgagccaat ccagcaatca  1020
tcgccccccca aacaactata tctctctcta caatctcatc aaaaactcga cgtgcaagcc  1080
ctactttacc acacttaaaa tacatatcaa caagagaagt cttaagaaag acactattaa  1140
acaaaccatt cttaatcgca agtgcatgcg tcttcaatcc ctgtctcaaa gcagatgcac  1200
cagcaaaact cttaaacaca ttagataaac tataaacatt caaatcaaca ccaagctctc  1260
tcatttctgt aaacgtagaa agaacatctt gataccgctt cttccctgat ataacagtcc  1320
ctctaagcaa cgcattccaa gagtaaacat ttgagctagt actttcatcg aacaccttct  1380
gtgcatcttt aaccgaacca caagcagtat acatatgaac aagcttggtc cttagaaact  1440
cattactctc caacccatta atacgtatat gaacatggac ttgtttaccg tgaagcaacg  1500
acttccggcg aacacacgcc tctaaaagag cagagaaagt tgtcgcattt acaggaatcc  1560
ctctctgttc gagataatca agaatcgtga gagcgacttc gagattgttc tgcctcgcaa  1620
aaatttgaat atctctgtgg ataatgtagg ggttcttgga gtggagagga agagaagaag  1680
ggaaagcatc tctttcccta aaaggtttcg gctttttggc gggagaagtg gaaggtcgtc  1740
tagttctgct tggtctaatc ggagatttcg ccggagcgcc atctttatcg gaacgatgag  1800
gacggtggtt gagactcgtc gtcacggaga gggacgccgg gaggtctcgg attccgagag  1860
acgacactac ttccattgtg accactaacc acttgattaa gctaaaggtc gttagtattt  1920
atatgtagct ttaaactatt tttataaagt atgcaattga aattgaaagc taatatttgg  1980
gccagaaaat tgaaatatgg gcttagggcc cccaaaacaa ttgtagccca tcagttcaca  2040
cacggtttcg tttttaaaaa aagcatgtat ttagaattta ttggcttttta ttttggtggt  2100
tgcttcaatc ttcctcgttt aaaaacaatt catgtcaact tggacaagtt acaaaaaaaa  2160
cgtttcatat ttttgtcact aaaaatattc agttaaataa agtaattgac tcttcgtttt  2220
cccgacgata ctgtataaat aaacatcatg tttctacttg ttcacatatc gactctttgt  2280
ttgtccgatt ctatctctct ctttagaaac tttatctagt ctcttcgaac ttaatcttaa  2340
cgacg                                                              2345

SEQ ID NO: 80          moltype = DNA  length = 289
FEATURE                Location/Qualifiers
source                 1..289
                       mol_type = unassigned DNA
                       organism = Arabidopsis thaliana
SEQUENCE: 80
tcttgttata caatcttcaa agtttctata tttatcaagt aaccattgac tcttcgcttg  60
tatctttccg ttaagaccac ctattcaatc attctctaag ttacatgatt taagatttaa  120
gtaaaatcat taactctctg ccctctccca cttcctccac taaaaaccat ctttaatcat  180
```

```
aattaaacct caaaaatcct ttcataatca cagtattata aatagcagct cttaccaaat  240
cctctaaacc atcacacaat acaacacaaa atcttcaaaa gaaaacaca              289

SEQ ID NO: 81          moltype = DNA  length = 267
FEATURE                Location/Qualifiers
source                 1..267
                       mol_type = unassigned DNA
                       organism = Arabidopsis thaliana
SEQUENCE: 81
ttttgttgct cttgctgcat caaatacata tttaaattaa aagtaaaacc tttcgtatgc  60
attgtctgtt actcatcttc atcagaagcc ttaatcgcac catccaccac taatcattta  120
ctttcactta tccctcccca ctaataaacc ttttaattac tctttaatat ccactaacac  180
aacaaatcct tccacaaaca cactataaat accaaaccat cacaagctag tctaatcaca  240
ctaaaattcc aaacaaaaac cacacca                                      267

SEQ ID NO: 82          moltype = DNA  length = 287
FEATURE                Location/Qualifiers
source                 1..287
                       mol_type = unassigned DNA
                       organism = Arabidopsis thaliana
SEQUENCE: 82
atactaaact aaacataata atttatttat tttaatgggt ttccataaag cccaatttag  60
ttggcccaat agcttgcaaa actgggcgta acggataatt taataaagac acggtaaatg  120
cttagataga ggattagagg gtaattaaat taaccacgat cactgtgata attactacaa  180
cattaaacga caaaaaaact tttcgtctcc ctcataatct tctactatat attcgtcaca  240
tcacactcat aatctcttac aaaaaatcca taacacaaaa agaagca                287

SEQ ID NO: 83          moltype = DNA  length = 2821
FEATURE                Location/Qualifiers
source                 1..2821
                       mol_type = unassigned DNA
                       organism = Arabidopsis thaliana
SEQUENCE: 83
tgaatcatga atggtatgat cgatcttgtc ccgttgtaac cacaagcaag atcagaagcg  60
atgcatgcgt agcaaatttt aaagagagaa aaaaacaagt ttttggatgt gagtgttaaa  120
ttatttagca aatttttgta tgtaaatact actgcttgct aaacactatt ttatacctac  180
ataaccaaaa tatctttact agataattaa taataaaaaa tttattggag ctctttatgt  240
ttgacatgta agataaaata ctcatttcag aataatgttc ttatattttt ttttgttgcc  300
aaaactatca gattatgatg accaactcat tcttaaaaat tagttcttca aatgtaacag  360
ttattatcac taaaaaccta gaagacggat cctattcatt tatatacagt cagataaaga  420
gagcatctcc tgatgataaa ggtgggagtg tcattattta tattaaaaaa gtaagaataa  480
tatcatatgg aaaaaaaaat ttggtctgtt acaaaagtaa agcctatggt ttataaatcc  540
ttgacaaaga aaataaaaat aaaaaatcaa attaggaaaa acaaaaatcg gcatgatcat  600
ggctaattag gttttgatca tcttctagat tcttaatagt tttttttgct tgtagtagta  660
atgacgaaca cattttgcac actgtaactc tagaccaatg tcgtaaaata ctttacaatt  720
tgaggtaatg atacaaatat aaagattaaa gcaatgctaa tatattgaat caaagcaaat  780
attaacatta ataaaatgtt ttgaaagata attgttttga cttttgacta gtcgtaagta  840
gcaatttact agagatgagg aattgtataa gattaaggat gtatttcact atgagatttt  900
agagttagct ttgaagagtg tcaaattgga atatcatgtt ggtggaaaat tattatgctt  960
tgaaggttgg aataagcatt ggaaagccga tgatgttgag atatacattt acaatggtct  1020
cgtaatcagg tgctaaatat tgcaaggaca tgcgttgtgt aattatcatt gatttcacaa  1080
taacccatgg ggtaaatgtg gtaatttgca aaagtagtaa gggagtggaa tttggtaatt  1140
gtggatacat tgctgtcaat gttgaaataa tgctaacttt ggttggtgct gcaaaaaaaa  1200
aggtcagcca aatatgtgta gaacgaagcc gcaatatcta ctacaagatt gctactctat  1260
agatgttgaa tggggttccc aaccacttat aaaagtggat caagatcaag aaaaggagaa  1320
catgaagttt aaggtttgtg tgtgtggata ttccttcatt tgaatgtggc ttcctagatg  1380
ttgagttcat gtttttgttt tcttacatca ttaggtagca actgattgtt ttggtagctt  1440
gtttgctcat atatatcaaa attctgatag aattggaaac acatgtttgt tgttatggta  1500
ttagcatatg ttactcatta tacacacaag tacataagtt tattgtgaca aaagtgctga  1560
tattatgtga aggttatgta gagaatccgt ggagggttgg tgacgttaat gactgttgtg  1620
gatgtgttaa atctttggta atgtttcttt ccagctttaa ttacatcctc aaatgccaat  1680
gattcaatag tagtgtaatc tcctgcacaa ccgcaagaca cctgctcaaa accaaaacaa  1740
acaaaaattg ttttcgaatt gcttttaact ttggtttctc gtacaaaaaa actaatacaa  1800
aggtgcatga gtagtagtaa ctgaataaat aataagtgca aatagttgac ttaaaataag  1860
aagttgaaag agttgaatga tttcatctca ctttttacca tttgagataa ataagtttga  1920
aaattgattc aacttattca accacaaaaa ttagaaaact aaaccaatta taaaaaacga  1980
attgttcaac cctttcatct actattttgg agaggaattg attaaatgat gttcaacttt  2040
tttttcaaac tcaaaatttt cctatcattt atatatctag caattcattt gcaactgaaa  2100
tgttttttttc gtgtcaaact ctaggtttga aacccgtata catcaccaac aataactaga  2160
gtttgaaatc aaataatatt ttttcatata taaaacaatt taaaatttct tttagataat  2220
taataaaaaa tgtatgacac acagacacag ctggttgatt tgtttatttg aatttttgac  2280
taggattaag aacattaatc atcaaccgtt gattatataa gcaagttgaa gaaaaggcac  2340
ggttcagatt cacctcttct catatgatgc gttacataag atcctttccc tctttccctc  2400
attttcaggt tcagcgccat cgtcaaaaac ttttggcggt cgatcaaaaa atttcgaaat  2460
ttgaagattt cgccggcaaa tacacaaacc cgaaaatgaa taacacttca aaattttcat  2520
taccagaaga aagaaatcaa ataccttcag atctctatct tcctcattca cacaccctct  2580
ctctcttctc cttttctctc ttctcctttt ctctatctcc ctctttgttc cgttcgcatc  2640
ctctaatcat cgtcaacaag ccgacgaaga gagaaacgaa tccaaagttc gttacttgaa  2700
agctacccag aagaattcaa atctcaggta cttttcctgt ggatttgatc tgggcactgc  2760
```

```
ttattaggga tttgattgga tctacaaaat tctgccttct gggtgattca atttcacgga  2820
a                                                                  2821

SEQ ID NO: 84          moltype = DNA  length = 400
FEATURE                Location/Qualifiers
source                 1..400
                       mol_type = unassigned DNA
                       organism = Arabidopsis thaliana
SEQUENCE: 84
tttaagctta ttattatgtg tgttgcgaac tctttttaac tcttttgtta aattcttatg  60
ttttcttaac tcgtttgttc gtcaccattg ctttctcttc aaataatggc tgattttttt  120
ctataatttt ggatttgttg aatgctttct tttaaaagaa tcagattttg gacttttgac  180
caaagaaaat aataatatca gacgataaaa tagacggctc tcgataaaac taaccctaaa  240
aataaggaaa taagttcctc tttgaaccaa attttctttc tttgaccaat agatcttttt  300
gtcaacctct taaatatatt cttagtcaat cttctaataa acccattggc cattaccaaa  360
aattcctcgg aaacgctgaa taaaaaacat tctatcatct                        400

SEQ ID NO: 85          moltype = DNA  length = 386
FEATURE                Location/Qualifiers
source                 1..386
                       mol_type = unassigned DNA
                       organism = Arabidopsis thaliana
SEQUENCE: 85
gcaagcaatg tgatgacgtg ttcatctata aaactcaaag ctcgtttagt tcttttgcca  60
tgagcttttg cagattaacc ataaaatcga acctttatgt ttacaagatc cttttgtctc  120
caagtctact ggtccgttga agtttaaaga ttagatcagt agattaccct ttttgcccct  180
acgttaaagt ttgtttattt aaatacaagt ccttgtgatt tttatcactt tctcacttct  240
tcaacgacac tgattcgttt tcaaagcatt tgcgttcttg atctttttca cgagggcgat  300
ttctgaagaa cacgagaatt tgaattctgg gaaaagcttt ctcgaacttt atctgagtaa  360
attgacagag agaatcgaaa aagaaa                                       386

SEQ ID NO: 86          moltype = DNA  length = 3433
FEATURE                Location/Qualifiers
source                 1..3433
                       mol_type = unassigned DNA
                       organism = Arabidopsis thaliana
SEQUENCE: 86
gatttatact atcatgtaac tcaaatttaa atttatacta taatgtgttt cacgtttttg  60
tgttgttgac aaaacaaaat cccaaaccaa tactatgatt ttcgtagtaa aaaaagttga  120
gtctttctct ttaagaaata tgcatgtaaa aggatgtttt gatcctagca aaaagcatat  180
tacataaatt ctaggacatc ctaggattta ggaccggctc cacctcttcc aaaagtctca  240
ttgtaccttt ttcaccgcta tgatcgatta atcgttataa tattagtatt tgattttctt  300
ctattcctac tttagagttt tagataatac cttcggaaga taaaagagca aaggcaacga  360
acgtgcaaac aggttacgac agtacgttaa tgttgtctga atccttaaaa atagtaaact  420
tagcatacga agaatgcagc aaataggtac aaaaaaagta taatacgtgt ataaacatag  480
aatgtgatgt tacatacata cgtgtaaaag tttggctaca agtgtcttct acacccaacg  540
acaacacaca aaggagacaa aattgccttt tacggcagtt acgacttata cgtgtataaa  600
atggtatata cgtctatcgt tcagcttaaa aattcagatt cacaaatgat aataataata  660
gtgcagagca aatggattag atgaaactca tagaacaatt aaaagaaatg ttttgcaaga  720
aaatcactca atttttttat tataatagaa atacagagac cactaaaatt atagataaat  780
aaaactgcca tcgtgatatt cattaattct tatcagaatt aaacgaaaac aagaagtaaa  840
atatctgctg aacgaatcaa gttggctcaa atttcactaa aacatgaaaa tcaatgaaga  900
gattggagag tgttatactt atatgtctca ctctttctcg aggcaaatct ctgctcctat  960
agattcgtag gtgcctaaaa ggctcaattt gaagccatgc atgtcttttg ctttcacaat  1020
ttgtcattcc ccatgccaac ttttcacaaa tttttacagt ccatatatgt atatgcatat  1080
tgcacattta tatatctaaa gttggtggcg taacacgatg aattttaact aattgatagt  1140
cgcacaatgg catccttatg ttagtctgaa atcagtactg tatcaaattt aattctgact  1200
tttatttgac ttgtctagtt ttcagttgaa gcgaaactat aatggttaaa tgatgttttt  1260
cttatgatta tacaaaaaaa aaattcaaaa aaattcataa tgtttgataa aacgcaataa  1320
tgcaggattt gcgtttttgt ctaaaaaaaa gtaaaaactt attatgtaaa taaatgatta  1380
tggttatgtt atgaagtctt attccgttag tctgcacata tatctatccg tacaatgtga  1440
ttttttcggc gaatagttat ctaatatttt tcattctaaa acttgtatta ttatgtacaa  1500
tagttatgca atattttatt ttccctttttg atcttaaaag ttcaatgttt tgagtttttt  1560
ttttgttcca caattattga tattctacat caacatcatt attattttta ttgttgacca  1620
ataaaaataa gaaaaaaata tagttaatat tattaaacta ataaaataat aatattaaaa  1680
tgtaaaagtt atttttttaa tttgtatgaa aatttcacaa catcagactt gataaacttg  1740
atgtaataga gggaatacta aagagtcaat atgtagttag ccatgagccc atgattgtga  1800
tgtaaaaata tgtgttgaaa aatataaaac aattaaacac gagggaattc aacaattaaa  1860
gtagtatgtt tcactatgct acattacaaa ttatttagag aaaattaaat taaaataaga  1920
ggatgaggaa atgatgtgat aaaaatgttc taaagtacgt atgtaccgtg aaaagtgcaa  1980
ttatatggaa gaaaaacacc acaaacacga cactgaaacg ttgtacatac gattgcttca  2040
tctgcaagta tagaacgaat atttgtttta ttttgtctta aagtatcgat tagttccaaa  2100
aaacagcttt ctgaaaccat ttttcatttg tatggattta ttatattttg tagttttaca  2160
gatagatatc attcttaaat agttttaatt agaaaaatta tgttctatat ttcaaaatta  2220
tgttttattt tatacctata gttccaactt ccaaataaac gttttgtgcc taggttaagc  2280
atatcggtga tttgcgctca actaacgtct gctatatttg agaaacttaa atttttactg  2340
aaaaacctac gaaaaaccta cgaaaatatc tcgtacggat atgatcaata agattctatc  2400
tgaaagaaaa tgacggtcca tacttgaact cgccatttcc tcttcaacta ggaaaaaatt  2460
ggatcgacat tggatttaag aaaggaaatg aaaccacgag gcgaaagaac taagccacta  2520
```

```
gagttctcta ttttgacggt ttactaaata taatcaagag tttgtttctt tgctcgaatc  2580
ttttgaattt ttttcctgtt cgttaagaaa tcgaagagcc aagctactgg acttcatatt  2640
gtcgtgttat ataaatacaa atattataaa caaaatatga tagtactata atataagata  2700
tgtcaatttc cgaagcaaac tagatatgta ggcttctcat gacctacaaa gaacacaatc  2760
caaccagcta tcttttgccg ccctatcata tttaacgttc gtatttatcc tctctttcat  2820
ttccaaaact taatggttct tcttcattaa tacacttcaa aaaaaaaaca tccgtaatcc  2880
ccagaaagaa taagaaaaac taataaagtc acaagtcaca actaacaatt atacaccgta  2940
tctactggaa aataaagaga gagttatatc cattattcac atagaaaaaa catttttaca  3000
tgttaaagac aagtattact gtgttatctc tttttctatt tgccgcattt tgataaatta  3060
attataaaat gcaacatgct tttttttttt ttccgcgtat gtgccaatgc aacatgcttt  3120
tattaaaaaa aaaacgaata gatccaaaat gttttttttt cctttctatt tgtcttctca  3180
taaaaaagta gcctcttttt taccatctca gccgctccac gcgatgtttt cagagtctcc  3240
agcgcaaaaa acaacacgca tgtcactatc tctctcttca tttgactctg ttccaatccc  3300
tcactaactc gctatataaa tatgagagcc tccccatgaa tttcatgcat cattcaaccc  3360
ccataaccta catgcaaacc atcgtcttaa aaccctagtt ctccataaaa aaaatatcct  3420
tgaacacaaa taa                                                     3433

SEQ ID NO: 87          moltype = DNA  length = 292
FEATURE                Location/Qualifiers
source                 1..292
                       mol_type = unassigned DNA
                       organism = Arabidopsis thaliana
SEQUENCE: 87
atcttaaaac gtaaggctta agataagtag tatatggtgg atatggaacc cgcgtaatca  60
tctagaggct ctacaaatat ttattttgta tttccttctt attttgtatt tgcctacgtg  120
gcattataca acgtatttaa cttgaaacca gatttatggc ccaatgggtc gggtcgaccc  180
gaccgatttt aaactgcgct cctaactaaa aaaaagtcaa aaccctttga aaaacctaaa  240
aacgcaattt gcttcgtcgt ctctcatctc tttctctttc tccgtcgcca cc          292

SEQ ID NO: 88          moltype = DNA  length = 494
FEATURE                Location/Qualifiers
source                 1..494
                       mol_type = unassigned DNA
                       organism = Arabidopsis thaliana
SEQUENCE: 88
ttgattactg tggatctagc tagagagaag taatggcacg gacgaagaaa gctaaaaagc  60
agggagattg ttaacttacg tttttgtcct tctcttagct taaaacggtc tgataattaa  120
acttcgaatc taaacaattt aatattttac agcataatcc cagtttaact gtaatctaaa  180
caaggccaat taataaatat gcaagcccat aactacagtt tggcccatta gtttttcccc  240
gcgccaaatt tgccctagtt cctttcttct ttcccgctat ttccaaaatc tcccaaaagg  300
tcaagttcca gcaaaatgac acaatctttg taatcaacat tgttctccgt caagcttctc  360
cttcaaaatt cgtaagcttt ctgttctcta actcttttg gtttcagtat atgaatcaat  420
ccgactttgg aatctctact taaaaataaa aatcgatctt tttgctgccc agatagtgaa  480
taaccttaaa atcg                                                    494

SEQ ID NO: 89          moltype = DNA  length = 297
FEATURE                Location/Qualifiers
source                 1..297
                       mol_type = unassigned DNA
                       organism = Arabidopsis thaliana
SEQUENCE: 89
gtatttcatt gggataaatg aagcgttgtt atggatagtt ttgagttgct aaaaagccaa  60
agatctaatc gcaagtcata tagggattac atttccttgt agctcttgaa gtttttgctc  120
cctttttttgt ttgttccttg taccattttt tcttaatacg agagataaga acttatcatt  180
ttgaggctct gaagaatcaa agaggataac agttcccaat tttttcattc tctcagtaaa  240
gctttttgtt tcgttttccc aaatgttgaa gataagtata tgaaaaggca aattatt     297

SEQ ID NO: 90          moltype = DNA  length = 138
FEATURE                Location/Qualifiers
source                 1..138
                       mol_type = unassigned DNA
                       organism = Arabidopsis thaliana
SEQUENCE: 90
gtcttagtat tcatctttac actcctgcta tgttttcttt tgctaagaga attttaatct  60
ttatgtaact ggtgacgaat gcttgaaaaa tagcgtctct gttattactt ttgagaataa  120
aagatcatca ttactcac                                                138

SEQ ID NO: 91          moltype = DNA  length = 575
FEATURE                Location/Qualifiers
source                 1..575
                       mol_type = unassigned DNA
                       organism = Arabidopsis thaliana
SEQUENCE: 91
tgtatgcaaa ctccagtaat gattttgtta taatatatgg tttttaaatg atataatggc  60
atctcccttt ggatttttcc gtgtgactaa aaccgcattt ataatttata cctggacaaa  120
gaacaaaaac agtgttgcca agaaacagag catagtaaga acagagaaag tttctattca  180
agtaacttgt aaaacaagct agtagattca tgtttttgca aaaccctaga aaagtcatag  240
tttcattgct tctaaacaat taacagaaaa aaacagggaa cagaacatat agaaagaaaa  300
gacaagtaac aagtccaaca agaaaacgga ttcatgattt tgtaaccatg ctcaagaaaa  360
```

```
tctcagaatc tagacgtgat cgagactcca tggtccacct gctccgttaa aatctcagct  420
gacgactcag ggagtaaaga gttggccaca tcgatcacga accggtacct gacatcagat  480
ttagccaaac ggtccatcgc agagttgata tcactcatct ttatgagctc aatatccgaa  540
acgattttat gcttggcaca gaactcaagc atctc                             575

SEQ ID NO: 92          moltype = DNA  length = 190
FEATURE                Location/Qualifiers
source                 1..190
                       mol_type = unassigned DNA
                       organism = Arabidopsis thaliana
SEQUENCE: 92
ttgttatttc tttgactaat gtcattaatt ttctctagaa taaaacttcg aaaattgaaa  60
tgtgatgtgc acaatcattt ctgttttctt tatttggttg ataagcaaat ttggctattt  120
atgttttttt tttaacggat gcctatatat gatactgcat tgcagtgttt ttggtctttc  180
cataaaaata                                                         190

SEQ ID NO: 93          moltype = DNA  length = 267
FEATURE                Location/Qualifiers
source                 1..267
                       mol_type = unassigned DNA
                       organism = Arabidopsis thaliana
SEQUENCE: 93
gaacttttcg atagtgacgt gcatggcttg agtttgattt tctcgttttt atttatgtta  60
taattattgt gttccatcta tgaatgtaaa agatttatga aggattcgat ttttttctct  120
ttttttaaag attattataa acgtctttca taaccatctc tttattcatt atatgttcag  180
gagtgaaaaa acaaaatcta aaaaataggg ttaaatgttt gcttagcttc tctctttatg  240
tagatttgag aaccgatgaa caagaat                                      267

SEQ ID NO: 94          moltype = DNA  length = 276
FEATURE                Location/Qualifiers
source                 1..276
                       mol_type = unassigned DNA
                       organism = Arabidopsis thaliana
SEQUENCE: 94
taaatgttcc tcgctgacgt aagaagacat tagtaatggt tataatatat agctttctat  60
gaatgtatgg tgagaaaatg tctgttcact gattttgagt ttggaataaa agcatttgcg  120
tttggtttat cattgcgttt atacaaggac agagatccac tgagctggaa tagcttaaaa  180
ccattatcag aacaaaataa accatttttt gttaagaatc agagcatagt aaacaacaga  240
aacaacctaa gagaggtaac ttgtccaaga agatag                            276

SEQ ID NO: 95          moltype = DNA  length = 110
FEATURE                Location/Qualifiers
source                 1..110
                       mol_type = unassigned DNA
                       organism = Arabidopsis thaliana
SEQUENCE: 95
tagtaacttt catatcaatt aataaacgct catgtttaaa tgatcacaat ccaatgattc  60
tgcatattga gattctttaa aatcataaag agtttaaagc tgtttaggtt             110

SEQ ID NO: 96          moltype = DNA  length = 135
FEATURE                Location/Qualifiers
source                 1..135
                       mol_type = unassigned DNA
                       organism = Arabidopsis thaliana
SEQUENCE: 96
tagctttccc tttatatttt aagttaaata aaagttacca gtgaactatg tttccttttt  60
atgtgtaaca ttttctgatt tatctttgtt aaattttgtt aatcacggtc taaatcgatt  120
taaaatcgtt ttggt                                                   135

SEQ ID NO: 97          moltype = DNA  length = 248
FEATURE                Location/Qualifiers
source                 1..248
                       mol_type = unassigned DNA
                       organism = Arabidopsis thaliana
SEQUENCE: 97
catagtctca ttgttcttcg attcagtgtg ttttctttta tagttttcag ttttatctca  60
ctgtttgcat tttttacgag cctgtgtaat aggcacaatc tgttatcaat catgtaactt  120
gtttaatcaa ataaccatag agttttatgt gaaaaggtcc tttactcatt tggtgttaac  180
tctttacctc ttcaggtctt taactctgtt tatataaaac atctaatgaa caatctgtgt  240
tttgaacg                                                           248

SEQ ID NO: 98          moltype = DNA  length = 285
FEATURE                Location/Qualifiers
source                 1..285
                       mol_type = unassigned DNA
                       organism = Arabidopsis thaliana
SEQUENCE: 98
agagcattgt gttaatgata tgccattgtt gtgttttctt ctacagtttg agtttgcag   60
gaacttttct tttgtacata gccagccaaa cgtttgaatg tgttgtaata aggacttgat  120
```

-continued

```
cattttaata tgtgcaggtt ttgtctttct taacatgttg aatcgcttta tgattttacc  180
ggaacgaacc ggttgctatg gtttcggtat gatttgattt ctcgttatag gccttagtcg  240
gcccaataac gaagattctc tataaataaa tgaacataaa caagg                  285

SEQ ID NO: 99          moltype = DNA  length = 392
FEATURE                Location/Qualifiers
source                 1..392
                       mol_type = unassigned DNA
                       organism = Arabidopsis thaliana
SEQUENCE: 99
gatctatttg taccggttat caagtttttt ggatcataga aattgtatag gcttttgaca  60
ttgaaatatt ttcatagaca aaacaaagaa gcataggcaa atgtgattac actctggaac  120
aaatcttagg tttgggaaag aaattcaata acaaaacaca caaagcacaa aaagagagaa  180
tcccaattca gaaaaagagg taaaaggaaa tgagtgcgac gaacttacag ccttacaaaa  240
gtaataatca atcatctttt ctttaggctt cttcttcttc ttcgtcctcc tcgtactcct  300
cttcaccgac tgtagcatct tgatattgct gatactctgc aacaagatca ttcatgttac  360
tctctgcttc agtgaactcc atctcgtcca tt                                392

SEQ ID NO: 100         moltype = DNA  length = 297
FEATURE                Location/Qualifiers
source                 1..297
                       mol_type = unassigned DNA
                       organism = Arabidopsis thaliana
SEQUENCE: 100
cgaaggttta atgaaattat aaattttatg taatcattag ttgttttaaa aagtatttca  60
aactgtggag aaactcatga acattttgaa acgaaacgta actatatatt ttggtcgaat  120
ttaaaggtta aatcactctc attaaacaag tcaattattt caatgaattt caatttcatt  180
tattaattaa aaaaattctt ctaaaattaa atttaagtac taattaaact tggtaatgaa  240
taaacttaat tcatatagtg atacatctat aggaggccga catagacatt ctataaa     297

SEQ ID NO: 101         moltype = DNA  length = 319
FEATURE                Location/Qualifiers
source                 1..319
                       mol_type = unassigned DNA
                       organism = Arabidopsis thaliana
SEQUENCE: 101
gcaagggaag aagctaaaga agctccattt tgtttcttga ggccctgctt agtaaggaac  60
taagaataga aatgttgaag agtgtcagag gatgaatcgg ccaagttgtg aggaagtatg  120
tttccttcca tatgtatgcc taaaattttg taagagcctt aaatgagttt tgtttctttt  180
ctttgttttc aatacaatag tggatattga gctttgtata gctcatacct agatttatac  240
tatattaaga acttcttttt gtttttgccg tttgtgttct cttcattttt atgagtcaat  300
ccattgtgtt taacttcga                                               319

SEQ ID NO: 102         moltype = DNA  length = 202
FEATURE                Location/Qualifiers
source                 1..202
                       mol_type = unassigned DNA
                       organism = Arabidopsis thaliana
SEQUENCE: 102
ccttagtaag gtttataacc tgcttatttc agtcttagtt ttgatttcag tttggttcag  60
tttgtaatgt acaagtttct ctaagcttta taatctatca gtagagtctc tctatcttgt  120
tgtggtgttt cctaagaaaa ttatagcctt tgagcgagtg attgaatata tttatatggt  180
aatgaatcac accgagtcac cg                                           202
```

INCREASING GENE EDITING AND SITE-DIRECTED INTEGRATION EVENTS UTILIZING MEIOTIC AND GERMLINE PROMOTERS

This application is a divisional of U.S. application Ser. No. 17/470,784, filed Sep. 9, 2021, which claims the benefit of U.S. Provisional Patent Application No. 63/076,705, filed Sep. 10, 2020, each of which is hereby incorporated by reference in its entirety.

FIELD

The present disclosure relates to compositions and methods related to expressing guided nucleases and guide nucleic acids in egg cells and embryo tissues in plants.

REFERENCE TO AN ELECTRONIC SEQUENCE LISTING

The contents of the electronic sequence listing (777052068201SEQLIST.xml; Size: 217,655 bytes; and Date of Creation: Mar. 30, 2024) is herein incorporated by reference in its entirety.

BACKGROUND

CRISPR (Clustered Regularly Interspaced Short Palindromic Repeats) nucleases (e.g., Cas12a, CasX, Cas9) are proteins guided by guide RNAs to a target nucleic acid molecule, where the nuclease can cleave one or two strands of a target nucleic acid molecule.

SUMMARY

In one aspect, this disclosure provides a plant comprising (a) a first nucleic acid sequence encoding a guided nuclease operably linked to a heterologous egg cell-preferred or embryo tissue-preferred promoter; and (b) a second nucleic acid sequence encoding at least one guide nucleic acid operably linked to a heterologous second promoter, where the at least one guide nucleic acid is capable of forming a complex with the guided nuclease and hybridizing to a target sequence within a genome of the plant and wherein the complex induces modification of the target sequence. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line. Several embodiments relate to a seed produced by the plant. In some embodiments, the seed comprises at least one mutation in a gene of interest comprising the target sequence as compared to a seed from a control plant of the same variety that lacks the first nucleic acid sequence or second nucleic acid sequence In one aspect, this disclosure provides a plant comprising (a) a first nucleic acid sequence encoding a guided nuclease operably linked to a heterologous meiotic cell-preferred promoter; and (b) a second nucleic acid sequence encoding at least one guide nucleic acid operably linked to a heterologous second promoter, where the at least one guide nucleic acid is capable of forming a complex with the guided nuclease and hybridizing to a target sequence within a genome of the plant and wherein the complex induces modification of the target sequence. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line.

In one aspect, this disclosure provides a method of editing a genome of a plant comprising: (a) introducing to a plant cell: (i) a first nucleic acid sequence encoding a guided nuclease operably linked to a heterologous egg cell-preferred promoter; and (ii) a second nucleic acid sequence encoding at least one guide nucleic acid operably linked to a heterologous second promoter, where the at least one guide nucleic acid is capable of forming a complex with the guided nuclease and hybridizing to a target sequence within the genome; and (b) regenerating at least one plant from the plant cell of step (a), where the guided nuclease and at least one guide nucleic acid form a ribonucleoprotein within at least one egg cell of the plant, and where the ribonucleoprotein generates at least one modification within the target sequence in the at least one egg cell. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, an ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line.

In one aspect, this disclosure provides a method of editing a genome of a plant comprising: (a) introducing to a plant cell: (i) a first nucleic acid sequence encoding a guided nuclease operably linked to a heterologous meiotic cell-preferred promoter; and (ii) a second nucleic acid sequence encoding at least one guide nucleic acid operably linked to a heterologous second promoter, where the at least one guide nucleic acid is capable of forming a complex with the guided nuclease and hybridizing to a target sequence within the genome; and (b) regenerating at least one plant from the plant cell of step (a), where the guided nuclease and at least one guide nucleic acid form a ribonucleoprotein within at least one meiotic cell of the plant, and where the ribonucleoprotein generates at least one modification within the target sequence in the at least one meiotic cell. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9.

In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the meiotic cell is from a haploid inducer line.

In one aspect, this disclosure provides a method of editing a genome of a plant cell comprising: (a) crossing a first plant with a second plant, where the first plant comprises a first nucleic acid sequence encoding a guided nuclease operably linked to a heterologous embryo tissue-preferred promoter, and where the second plant comprises a second nucleic acid sequence encoding at least one guide nucleic acid operably linked to a heterologous second promoter, where the at least one guide nucleic acid is capable of forming a complex with the guided nuclease and hybridizing to a target sequence within the genome; and (b) obtaining at least one embryo from the crossing of step (a), where the guided nuclease and the at least one guide nucleic acid form a ribonucleoprotein within the at least one embryo, and where the ribonucleoprotein generates at least one modification within the target sequence in the at least one embryo. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the first plant. In some embodiments, the first plant is a hybrid inducer.

In one aspect, this disclosure provides a method of editing a genome of a plant cell comprising: (a) crossing a first plant with a second plant, where the first plant comprises a first nucleic acid sequence encoding a guided nuclease operably linked to a heterologous meiotic-cell preferred promoter, and where the second plant comprises a second nucleic acid sequence encoding at least one guide nucleic acid operably linked to a heterologous second promoter, where the at least one guide nucleic acid is capable of forming a complex with the guided nuclease and hybridizing to a target sequence within the genome; and (b) obtaining at least one embryo from the crossing of step (a), where the guided nuclease and the at least one guide nucleic acid form a ribonucleoprotein within the at least one meiotic cell, and where the ribonucleoprotein generates at least one modification within the target sequence in the at least one meiotic cell. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line.

In one aspect, this disclosure provides a method of editing a genome of a plant comprising: (a) introducing to a plant cell: (i) a first nucleic acid sequence encoding a guided nuclease operably linked to a heterologous embryo tissue-preferred promoter; and (ii) a second nucleic acid sequence encoding at least one guide nucleic acid operably linked to a heterologous second promoter, where the at least one guide nucleic acid is capable of forming a complex with the guided nuclease and hybridizing to a target sequence within the genome; (b) regenerating at least one plant from the plant cell of step (a); and (c) fertilizing the at least one plant to create at least one embryo, where the guided nuclease and at least one guide nucleic acid form a ribonucleoprotein within the at least one embryo from step (c), and where the ribonucleoprotein generates at least one modification within the target sequence in the at least one embryo. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the first plant. In some embodiments, the first plant is a hybrid inducer.

In one aspect, this disclosure provides a method of generating a site-directed integration in a plant comprising: (a) introducing to a plant cell: (i) a first nucleic acid sequence encoding a guided nuclease operably linked to a heterologous egg cell-preferred promoter; (ii) a second nucleic acid sequence encoding one or more guide nucleic acids operably linked to a heterologous second promoter, where the one or more guide nucleic acids are (A) capable of forming a complex with the guided nuclease and hybridizing to a target sequence within a genome of the plant; and (B) capable of hybridizing to a first site and a second site flanking a nucleic acid sequence encoding a gene of interest; and (iii) a third nucleic acid sequence encoding the gene of interest; and (b) regenerating at least one plant from the plant cell of step (a); where the guided nuclease and at least one guide RNA form a ribonucleoprotein within at least one egg cell of the plant, where the ribonucleoprotein generates a double-stranded break within the target sequence, the first site, and the second site, and where the gene of interest is integrated into the target site in the at least one egg cell. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, an ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line.

In one aspect, this disclosure provides a method of generating a site-directed integration in a plant comprising: (a) introducing to a plant cell: (i) a first nucleic acid sequence encoding a guided nuclease operably linked to a heterologous embryo tissue-preferred promoter; (ii) a second nucleic acid sequence encoding one or more guide nucleic acids operably linked to a heterologous second promoter, where the one or more guide nucleic acids are (A) capable of forming a complex with the guided nuclease and hybridizing to a target sequence within a genome of the plant; and (B) capable of hybridizing to a first site and a second site flanking a nucleic acid sequence encoding a gene of interest; (iii) a third nucleic acid sequence encoding the gene of interest; (b) regenerating at least one plant from the plant cell of step (a); and (c) fertilizing the at least one plant from step (b) to create at least one embryo; where the guided nuclease and at least one guide RNA form a ribonucleoprotein within at least one embryo, where the ribonucleoprotein generates a double-stranded break within the target sequence, the first site, and the second site, and where the gene of interest is integrated into the target site in the at least one embryo. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the first plant. In some embodiments, the first plant is a hybrid inducer.

In one aspect, this disclosure provides a recombinant DNA construct comprising (a) a first nucleic acid sequence encoding a guided nuclease operably linked to a heterologous egg cell-preferred promoter, meiotic cell preferred promoter or embryo tissue-preferred promoter; and (b) a second nucleic acid sequence encoding at least one guide nucleic acid operably linked to a heterologous second promoter, where the at least one guide nucleic acid is capable of hybridizing to a target sequence within a genome of a plant. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line. In some embodiments, the recombinant DNA construct is integrated into the genome of a haploid inducer line.

Several embodiments relate to a recombinant DNA construct comprising (a) a first nucleic acid sequence encoding a DNA modification enzyme operably linked to one or more one or more TALE binding sites and a minimal promoter; and (b) a second nucleic acid sequence encoding a TALE operably linked to a egg cell-preferred promoter, meiotic cell-preferred promoter or embryo tissue-preferred promoter, wherein the minimal promoter does not drive expression of the DNA modification enzyme in the absence of TALE binding to the to one or more one or more TALE binding sites. In some embodiments, the recombinant DNA construct further comprises a third nucleic acid sequence encoding a guide nucleic acid operably linked to a third promoter. In some embodiments, the DNA modification enzyme is a guided nuclease. In some embodiments, the guided nuclease is a CRISPR effector protein. In some embodiments, the first nucleic acid sequence encoding a DNA modification enzyme and the minimal promoter are operably linked 1, 2, 3, 4, 5, 6, 7, 8, 9, 10 or more TALE binding sites. In some embodiments, the CRISPR effector protein is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for expression in a plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the third promoter is a Pol III promoter. In some embodiments, the third promoter is selected from the group consisting of a tissue-preferred promoter, a tissue-specific promoter, an inducible promoter, and a constitutive promoter. In some embodiments, the third promoter is a meiotic cell-preferred, an egg cell-preferred or an embryo tissue-preferred promoter. In some embodiments, the third promoter is meiotic cell-specific, an egg cell-specific or an embryo tissue-specific promoter. In some embodiments, the third promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the third promoter comprises a nucleic acid sequence at least 90% identical to a nucleic acid sequence selected from the group consisting of SEQ ID NOs: 1-6, 21-45 and 65-88 or a functional fragment thereof. In some embodiments, the third promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the third nucleic acid sequence encoding at least one guide nucleic acid is operably linked to one or more self-cleaving ribozymes. In some embodiments, the first nucleic acid sequence, the second nucleic acid sequence, and/or the third nucleic acid sequence, are stably integrated into a genome of the plant. In some embodiments the plant is from a haploid inducer line. In some embodiments the guide nucleic acid is provided to the plant by bombardment. Several embodiments relate to a plant comprising the recombinant DNA construct. Several embodiments relate to a seed produced by a plant comprising the recombinant DNA construct. In some embodiments, the recombinant DNA construct is integrated into the genome of a haploid inducer line.

Several embodiments relate to a recombinant DNA construct comprising (a) a first nucleic acid sequence encoding at least one guide nucleic acid operably linked to one or more one or more TALE binding sites and a minimal promoter; and (b) a second nucleic acid sequence encoding a TALE operably linked to an egg cell-preferred promoter, a meiotic cell-preferred promoter or an embryo tissue-preferred promoter, wherein the minimal promoter does not drive expression of the guide nucleic acid in the absence of TALE binding to the to one or more one or more TALE binding sites. In some embodiments, the recombinant DNA construct further comprises a third nucleic acid sequence encoding a guided nuclease operably linked to a third promoter. In some embodiments, the guided nuclease is a CRISPR effector protein. In some embodiments, the first nucleic acid sequence encoding guide nucleic acid and the minimal promoter are operably linked 1, 2, 3, 4, 5, 6, 7, 8, 9, 10 or more TALE binding sites. In some embodiments, the CRISPR effector protein is selected from the group consisting of Cas9, Cas12a (e.g., LbCas12a, FnCas12a) and CasX. In some embodiments, the third nucleic acid sequence comprises a nucleic acid sequence at least 90% identical to SEQ ID NO: 7. In some embodiments, the third nucleic acid sequence is codon-optimized for expression in a plant. In some embodiments, the third nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the third promoter is selected from the group consisting of a tissue-preferred promoter, a tissue-specific promoter, an inducible promoter, and a constitutive promoter. In some embodiments, the third promoter is a meiotic cell-preferred, an egg cell-preferred or an embryo tissue-preferred promoter. In some embodiments, the third promoter is meiotic cell-specific, an egg cell-specific or an embryo tissue-specific promoter. In some embodiments, the third promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the third promoter comprises a nucleic acid sequence at least 90% identical to a nucleic acid sequence selected from the group consisting of SEQ ID NOs: 1-6, 21-45 and 65-88 or a functional fragment thereof. In some embodiments, the third promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the first nucleic acid sequence encoding the at least one guide nucleic acid is operably linked to one or more self-cleaving ribozymes. In some embodiments, the first nucleic acid sequence, the second nucleic acid sequence, and/or the third nucleic acid sequence, are stably integrated into a genome of the plant. In some embodiments the plant is from a haploid inducer line. Several embodiments relate to a plant comprising the recombinant DNA construct. Several embodiments relate to a seed produced by a plant comprising the recombinant DNA construct. In some embodiments, the recombinant DNA construct is integrated into the genome of a haploid inducer line.

Several embodiments relate to a recombinant DNA construct comprising (a) a first nucleic acid sequence encoding a guided nuclease; (b) a second nucleic acid sequence encoding a first promoter; and (c) a third nucleic acid sequence encoding DNA modification enzyme operably linked to an egg cell-preferred promoter, a meiotic cell-preferred promoter or an embryo tissue-preferred promoter, wherein the third nucleic acid is positioned between the first nucleic acid and the second nucleic acid, and wherein the third nucleic acid comprises a first target site for the DNA modification enzyme at the 5' end and a second target site for the DNA modification enzyme at the 5' end. In some embodiments, the recombinant DNA construct further comprises a fourth nucleic acid sequence encoding one or more guide nucleic acids operably linked to a third promoter. In some embodiments, the DNA modification enzyme is a recombinase. In some embodiments, the first and second target sites are Lox sites. In some embodiments, the DNA modification enzyme is an endonuclease. In some embodiments, the DNA modification enzyme is a CRISPR effector protein. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the first promoter is a meiotic cell-preferred, an egg cell-preferred or an embryo tissue-preferred promoter. In some embodiments, the first promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the first promoter comprises a nucleic acid sequence at least 90% identical to a nucleic acid sequence selected from the group consisting of SEQ ID NOs: 1-6, 21-45 and 65-88 or a functional fragment thereof. In some embodiments, the first promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments the third promoter is a Pol III promoter. Several embodiments relate to a plant comprising the recombinant DNA construct. Several embodiments relate to a seed produced by a plant comprising the recombinant DNA construct. In some embodiments the plant is from a haploid inducer line. In some embodiments, the recombinant DNA construct is integrated into the genome of a haploid inducer line.

In several embodiments, high levels of egg, embryo, and/or meiotic tissue specific expression of a DNA modification enzyme such as a guided nuclease (e.g., a CRISPR/Cas system), is achieved by providing to a plant cell: 1) an expression construct comprising a promoter as described in Table 1 operably linked to a sequence encoding a CRISPR effector protein, such as a dCas12a or dCas9 fused to a transcription activator; 2) an expression construct comprising one or more target sites operably linked to a minimal promoter and a sequence encoding the DNA modification enzyme; and 3) an expression construct encoding a guide RNA that hybridizes with the one or more target sites; and generating a plant therefrom. In some embodiments, 1, 2, 3, 4, 5, 6, 7, 8, 9, 10 or more target sites are operably linked to the minimal promoter. In some embodiments, the plant cell is from a haploid inducer line. In some embodiments, a female plant is generated that expresses high levels of the DNA modification enzyme in egg, embryo, and/or meiotic tissue. In some embodiments, the female plant is outcrossed and a population of R1 plants comprising unique edits are identified.

In several embodiments, high levels of egg, embryo, and/or meiotic tissue specific expression of a DNA modification enzyme such as a guided nuclease (e.g., a CRISPR/Cas system), is achieved by providing to a plant cell: 1) an expression construct comprising a promoter as described in Table 1 operably linked to a sequence encoding a TALE and 2) and an expression construct comprising one or more TALE binding sites (TB) operably linked to a minimal promoter and a sequence encoding the DNA modification enzyme and generating a plant therefrom. In some embodiments, an expression construct encoding one or more guide nucleic acids is further provided. In some embodiments, 1, 2, 3, 4, 5, 6, 7, 8, 9, 10 or more TBs are operably linked to the minimal promoter. In some embodiments, the plant cell is from a haploid inducer line. In some embodiments, a female plant is generated that expresses high levels of the DNA modification enzyme in egg, embryo, and/or meiotic tissue. In some embodiments, the female plant is outcrossed and a population of R1 plants comprising unique edits are identified.

Several embodiments relate to a method of generating two or more progeny plants with unique edits from a single transformed plant cell, the method comprising: (a) introducing to the plant cell: a first nucleic acid sequence encoding a guided nuclease operably linked to a heterologous meiosis-preferred promoter; and a second nucleic acid sequence encoding at least one guide nucleic acid operably linked to a heterologous second promoter, wherein the at least one guide nucleic acid is capable of hybridizing to a target sequence within the genome; and (b) regenerating a first plant from the plant cell of step (a), wherein the guided nuclease and at least one guide nucleic acid form a ribonucleoprotein within at least one meiotic cell of the first plant, and wherein the ribonucleoprotein generates at least one modification within the target sequence in the at least one meiotic cell; (c) pollinating the first plant of step (b); (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

Several embodiments relate to a method of generating two or more progeny plants with unique edits from a single transformed plant cell, the method comprising: (a) introducing to the plant cell: a first nucleic acid sequence encoding a guided nuclease operably linked to a heterologous first promoter; and a second nucleic acid sequence encoding at least one guide nucleic acid operably linked to a heterologous meiosis-preferred promoter, wherein the at least one guide nucleic acid is capable of hybridizing to a target sequence within the genome; and (b) regenerating a first plant from the plant cell of step (a), wherein the guided nuclease and at least one guide nucleic acid form a ribonucleoprotein within at least one meiotic cell of the first plant, and wherein the ribonucleoprotein generates at least one modification within the target sequence in the at least one meiotic cell; (c) pollinating the first plant of step (b); (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the first promoter is selected from the group consisting of a tissue-preferred promoter, a tissue-specific promoter, an inducible promoter, and a constitutive promoter. In some embodiments, the first promoter is a meiotic cell-preferred, an egg cell-preferred or an embryo tissue-preferred promoter. In some embodiments, the first promoter is meiotic cell-specific, an egg cell-specific or an embryo tissue-specific promoter. In some embodiments, the first promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the first promoter comprises a nucleic acid sequence at least 90% identical to a nucleic acid sequence selected from the group consisting of SEQ ID NOs: 1-6, 21-45 and 65-88 or a functional fragment thereof. In some embodiments, the first promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

A method of generating two or more progeny plants with unique edits from a single transformed plant cell, the method comprising: (a) introducing to the plant cell: a first nucleic acid sequence encoding a guided nuclease operably linked to a heterologous egg cell-preferred promoter; and a second nucleic acid sequence encoding at least one guide nucleic acid operably linked to a heterologous second promoter, wherein the at least one guide nucleic acid is capable of hybridizing to a target sequence within the genome; and (b) regenerating a first plant from the plant cell of step (a), wherein the guided nuclease and at least one guide nucleic acid form a ribonucleoprotein within at least one egg cell of the first plant, and wherein the ribonucleoprotein generates at least modification within the target sequence in the at least one egg cell; (c) pollinating the first plant of step (b); (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, an ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

A method of generating two or more progeny plants with unique edits from a single transformed plant cell, the method comprising: (a) introducing to the plant cell: a first nucleic acid sequence encoding a guided nuclease operably linked to a heterologous first promoter; and a second nucleic acid sequence encoding at least one guide nucleic acid operably linked to a heterologous egg cell-preferred promoter, wherein the at least one guide nucleic acid is capable of hybridizing to a target sequence within the genome; and (b) regenerating a first plant from the plant cell of step (a), wherein the guided nuclease and at least one guide nucleic acid form a ribonucleoprotein within at least one egg cell of the first plant, and wherein the ribonucleoprotein generates at least one modification within the target sequence in the at least one egg cell; (c) pollinating the first plant of step (b); (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the first promoter is selected from the group consisting of a tissue-preferred promoter, a tissue-specific promoter, an inducible promoter, and a constitutive promoter. In some embodiments, the first promoter is a meiotic cell-preferred, an egg cell-preferred or an embryo tissue-preferred promoter. In some embodiments, the first promoter is meiotic cell-specific, an egg cell-specific or an embryo tissue-specific promoter. In some embodiments, the first promoter is selected from the group consisting of a DSUL1 promoter, an EA1 promoter, an ES4 promoter, a DMC1 promoter, a Mps1 promoter, an Adf1 promoter and an EAL1 promoter. In some embodiments, the first promoter comprises a nucleic acid sequence at least 90% identical to a nucleic acid sequence selected from the group consisting of SEQ ID NOs: 1-6, 21-45 and 65-88 or a functional fragment thereof. In some embodiments, the first promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

A method of generating two or more progeny plants with unique edits from a single transformed plant cell, the method comprising: (a) introducing to the plant cell: a first nucleic acid sequence encoding a guided nuclease operably linked to a heterologous embryonic cell-preferred promoter; and a second nucleic acid sequence encoding at least one guide nucleic acid operably linked to a heterologous second promoter, wherein the at least one guide nucleic acid is capable of hybridizing to a target sequence within the genome; and (b) regenerating a first plant from the plant cell of step (a), (c) pollinating the first plant of step (b), wherein the guided nuclease and at least one guide nucleic acid form a ribonucleoprotein within embryonic cells, and wherein the ribonucleoprotein generates at least one modification within the target sequence in the embryonic cells; (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

A method of generating two or more progeny plants with unique edits from a single transformed plant cell, the method comprising: (a) introducing to the plant cell: a first nucleic acid sequence encoding a guided nuclease operably linked to a heterologous first promoter; and a second nucleic acid sequence encoding at least one guide nucleic acid operably linked to a heterologous embryonic cell-preferred promoter, wherein the at least one guide nucleic acid is capable of hybridizing to a target sequence within the genome; and (b) regenerating a first plant from the plant cell of step (a), (c) pollinating the first plant of step (b), wherein the guided nuclease and at least one guide nucleic acid form a ribonucleoprotein within embryonic cells, and wherein the ribonucleoprotein generates at least one modification within the target sequence in the embryonic cells; (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the first promoter is selected from the group consisting of a tissue-preferred promoter, a tissue-specific promoter, an inducible promoter, and a constitutive promoter. In some embodiments, the first promoter is a meiotic cell-preferred, an egg cell-preferred or an embryo tissue-preferred promoter. In some embodiments, the first promoter is meiotic cell-specific, an egg cell-specific or an embryo tissue-specific promoter. In some embodiments, the first promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the first promoter comprises a nucleic acid sequence at least 90% identical to a nucleic acid sequence selected from the group consisting of SEQ ID NOs: 1-6, 21-45 and 65-88 or a functional fragment thereof. In some embodiments, the first promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is out-crossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

FIGURE LEGEND

FIG. 1. Editing in reciprocal F1 plants with reproductive promoters. Transgenic R1 lines were used as either the female or male to generate reciprocal F1s. The black bars represent percent of events with an active LbCas12a when provided by the female or male parent, as indicated by new edits being present in F1 plants. The grey bars are the percent of F1 individuals containing new edits. The light grey bars are the number of unique edits found in the F1s.

Figure 2:
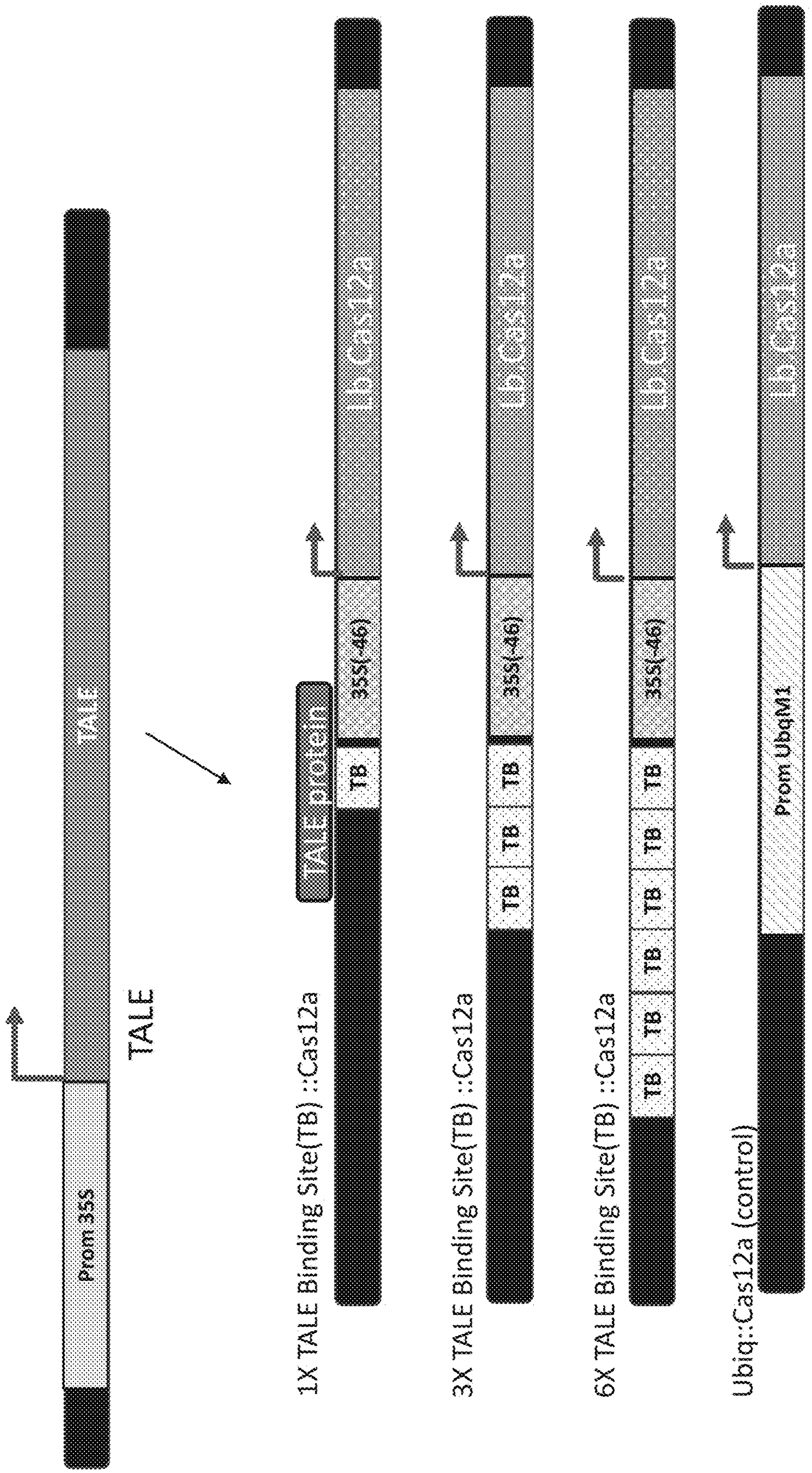

FIG. 2: Depicts a schematic illustrating vectors designed for TALE induced expression of LbCas12a. 35S(-46) is the 35S minimal promoter. TB indicates the TALE Binding site.

Figure 3:
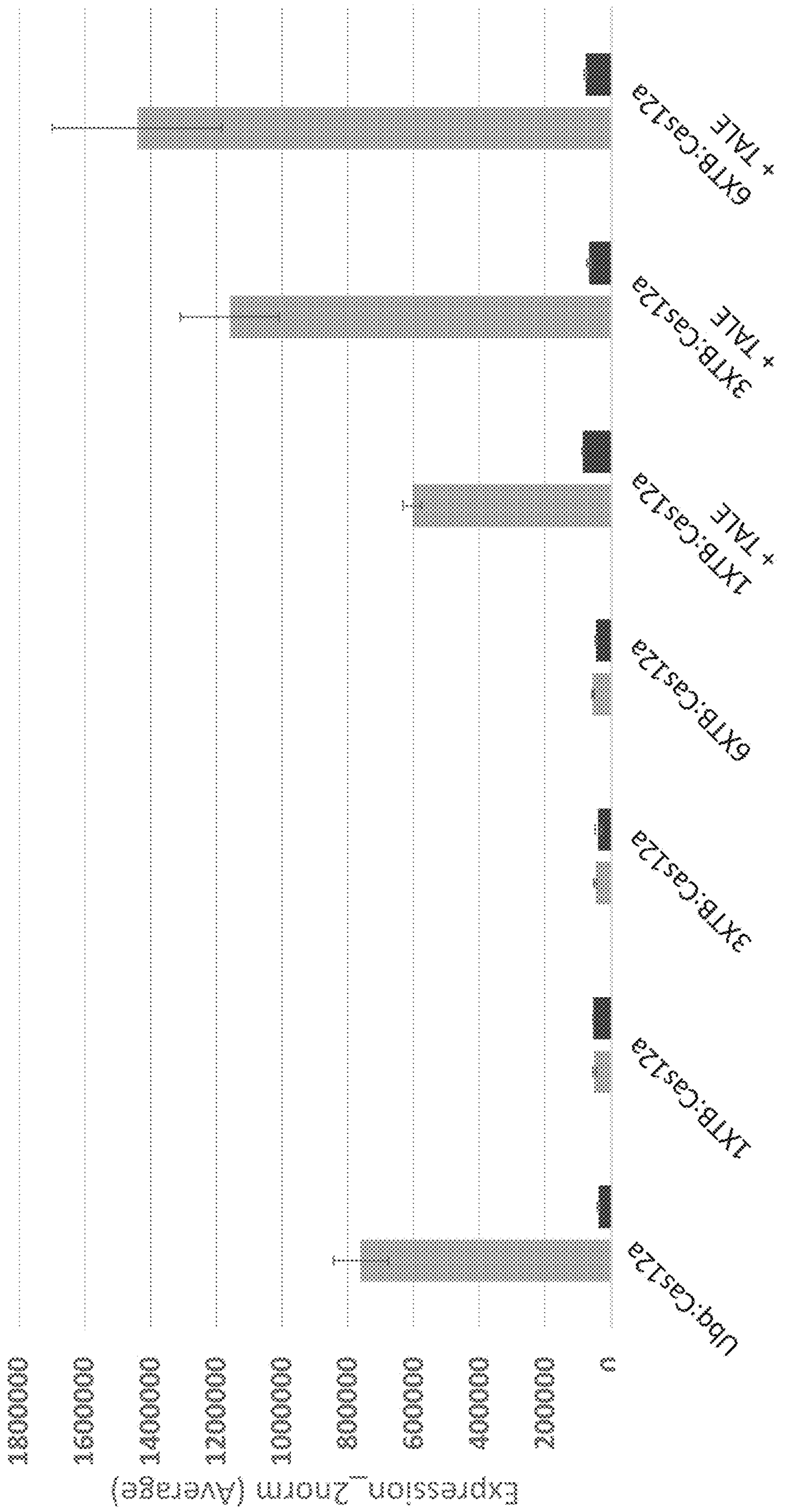

FIG. 3. RNA expression of Cas12a and TALE in corn leaf protoplasts.

Figure 4:
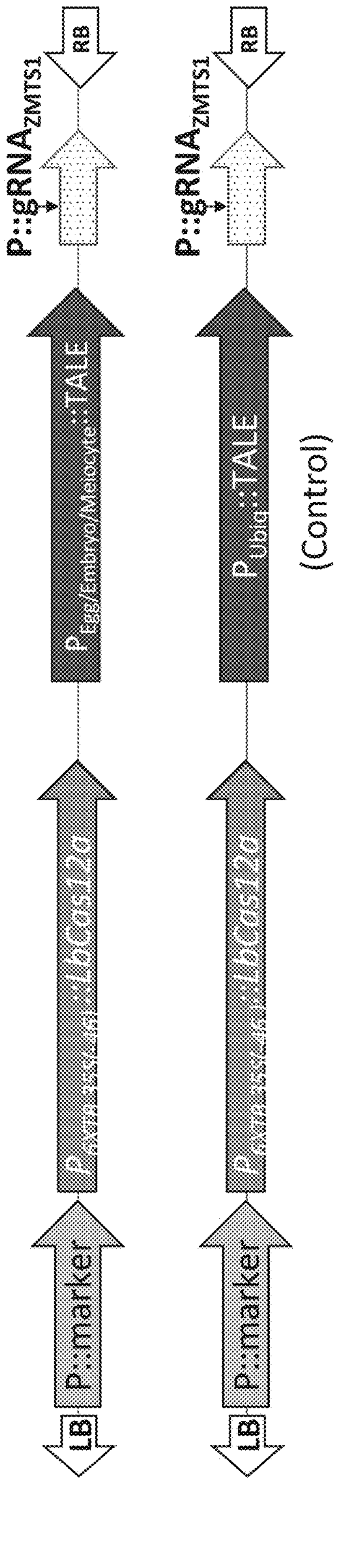

FIG. 4: Schematic illustration of T-DNA vectors designed for TALE-induced Meiocyte/Embryo/egg-cell preferred expression of LbCas12a in planta. LB indicates Left Border. RB indicates Right Border. P indicates promoter. 35S(-46) is the 35S minimal promoter. TB is the TALE Binding site.

Figure 5:
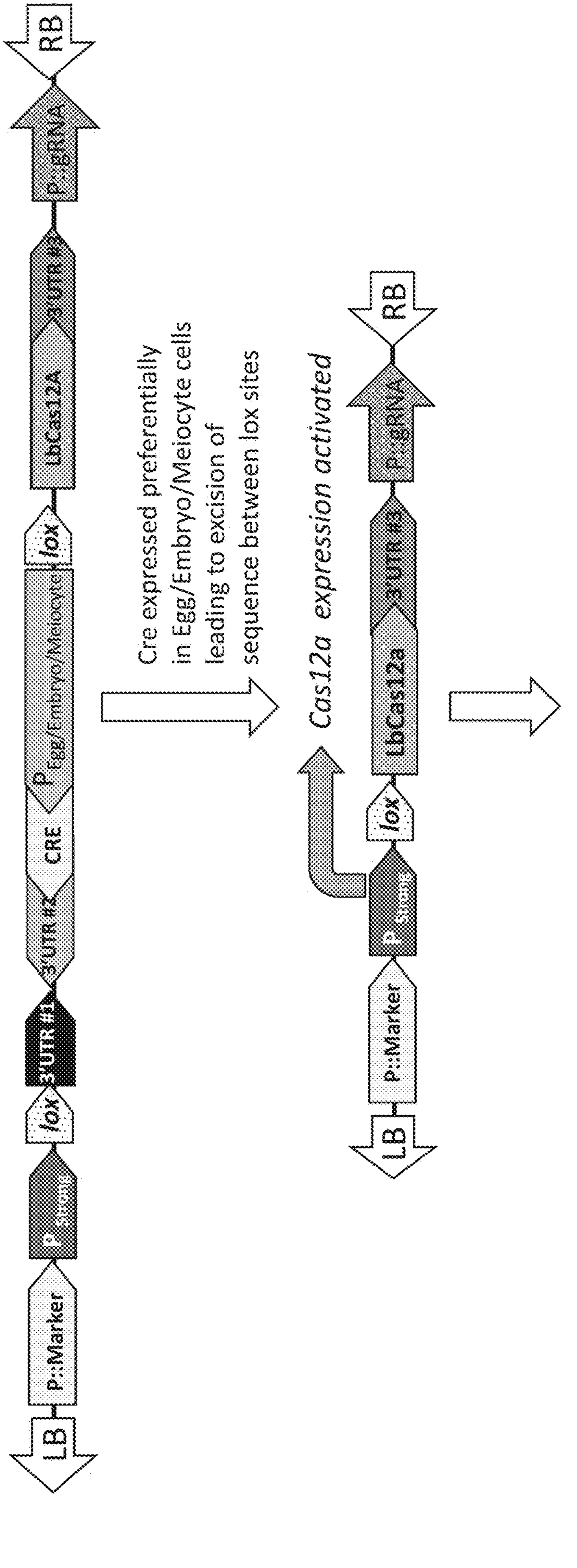

FIG. 5: Schematic illustration of T-DNA vectors designed for Meiocyte/Embryo/egg-cell preferred expression of Cas12a driven by a strong constitutive promoter. P indicates Promoter. Cre is for Cre recombinase. Arrowheads represent directionality.

DETAILED DESCRIPTION

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of this disclosure includes, unless otherwise indicated, conventional techniques of biochemistry, chemistry, molecular biology, microbiology, cell biology, plant biology, genomics, biotechnology, and genetics, which are within the skill of the art. See, for example, Green and Sambrook, Molecular Cloning: A Laboratory Manual, 4th edition (2012); Current Protocols In Molecular Biology (F. M. Ausubel, et. al. eds., (1987)); Plant Breeding Methodology (N. F. Jensen, Wiley-Interscience (1988)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture: Techniques and Experiments (Academic Press, Inc.).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc.

As used herein, terms in the singular and the singular forms "a," "an," and "the," for example, include plural referents unless the content clearly dictates otherwise.

Any composition, nucleic acid molecule, polypeptide, cell, plant, etc. provided herein is specifically envisioned for use with any method provided herein.

Several embodiments described herein relate to compositions and methods for expressing a DNA modification enzyme, for example a guided nuclease, preferentially in the egg, meiotic, and/or embryonic cells of a plant. In some embodiments, compositions and methods are provided for preferential expression of components of a CRISPR/Cas editing system in egg, meiotic, and/or embryonic cells of a plant. Several embodiments relate to compositions and methods for producing offspring with unique edits from a parent comprising an expression cassette that preferentially provides a DNA modification enzyme, for example a guided nuclease, in egg, meiotic, and/or embryonic cells. In some embodiments, a female parent plant is provided that preferentially expresses a DNA modification enzyme, for example a guided nuclease, preferentially in egg, meiotic, and/or embryonic cells. In some embodiments, a male parent plant is provided that preferentially expresses a DNA modification enzyme, for example a guided nuclease, preferentially in egg, meiotic, and/or embryonic cells. In some embodiments, a population of seeds wherein 2 or more of the seeds comprise unique edits is provided wherein the population of seeds is produced from a parent expressing a DNA modification enzyme, for example a guided nuclease, preferentially in egg, meiotic, and/or embryonic cells. Non-limiting examples of expression elements useful in the composition and methods described herein are provided in Table 1.

As used herein, an "egg cell" refers to a haploid egg cell produced by the female gametophyte of a plant. Upon fertilization by a haploid pollen cell, a diploid zygote is formed, which gives rise to an embryo. As used herein, "embryo tissue" refers to diploid tissue comprising precursor tissues for leaf, stem, and root tissue, as well as one or more cotyledons. Embryo tissue is eventually incorporated into a seed. Once the embryo begins to germinate, a seedling or plantlet is generated. As used herein, meiosis refers to a process of cell division in sexually-reproducing organisms that produces gametes. Meiosis involves two rounds of cell division that ultimately result in four haploid cells. A meiotic cell refers to a cell undergoing meiosis.

In an aspect, this disclosure provides a recombinant DNA construct comprising a first nucleic acid sequence encoding a guided nuclease capable of generating a staggered cut in a double-stranded DNA molecule operably linked to a heterologous egg cell-preferred promoter; and (b) a second nucleic acid sequence encoding at least one guide nucleic acid operably linked to a heterologous second promoter, where the at least one guide nucleic acid is capable of hybridizing to a target sequence within a genome of a plant. In an aspect, this disclosure provides a recombinant DNA construct comprising a first nucleic acid sequence encoding a guided nuclease capable of generating a staggered cut in a double-stranded DNA molecule operably linked to a heterologous embryo tissue-preferred promoter; and (b) a second nucleic acid sequence encoding at least one guide nucleic acid operably linked to a heterologous second promoter, where the at least one guide nucleic acid is capable of hybridizing to a target sequence within a genome of a plant. In an aspect, this disclosure provides a recombinant DNA construct comprising a first nucleic acid sequence encoding a guided nuclease capable of generating a staggered cut in a double-stranded DNA molecule operably linked to a heterologous meiosis-preferred promoter; and (b) a second nucleic acid sequence encoding at least one guide nucleic acid operably linked to a heterologous second promoter, where the at least one guide nucleic acid is capable of hybridizing to a target sequence within a genome of a plant cell.

In an aspect, this disclosure provides a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an egg cell-preferred promoter, where the at least one guide nucleic acid is capable of hybridizing to a target sequence within a genome of a plant. In an aspect, this disclosure provides a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an embryo tissue-preferred promoter, where the at least one guide nucleic acid is capable of hybridizing to a target sequence within a genome of a plant. In an aspect, this disclosure provides a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an meiotic-preferred promoter, where the at least one guide nucleic acid is capable of hybridizing to a target sequence within a genome of a plant cell.

In an aspect, this disclosure provides a plant comprising a recombinant DNA construct comprising a first nucleic acid sequence encoding a guided nuclease capable of generating a staggered cut in a double-stranded DNA molecule operably linked to a heterologous egg cell-preferred promoter; and (b) a second nucleic acid sequence encoding at least one guide nucleic acid operably linked to a heterologous second promoter, where the at least one guide nucleic acid is capable of hybridizing to a target sequence within a genome of the plant. In an aspect, this disclosure provides a plant comprising a recombinant DNA construct comprising a first nucleic acid sequence encoding a guided nuclease capable of generating a staggered cut in a double-stranded DNA molecule operably linked to a heterologous embryo tissue-preferred promoter; and (b) a second nucleic acid sequence encoding at least one guide nucleic acid operably linked to a heterologous second promoter, where the at least one guide nucleic acid is capable of hybridizing to a target sequence within a genome of the plant. In an aspect, this disclosure provides a plant comprising a recombinant DNA construct comprising a first nucleic acid sequence encoding a guided nuclease capable of generating a staggered cut in a double-stranded DNA molecule operably linked to a heterologous meiosis-preferred promoter; and (b) a second nucleic acid sequence encoding at least one guide nucleic acid operably linked to a heterologous second promoter, where the at least one guide nucleic acid is capable of hybridizing to a target sequence within a genome of the plant.

In an aspect, this disclosure provides a plant comprising a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an egg cell-preferred promoter, where the at least one guide nucleic acid is capable of hybridizing to a target sequence within a genome of the plant. In an aspect, this disclosure provides a plant comprising a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an embryo tissue-preferred promoter, where the at least one guide nucleic acid is capable of hybridizing to a target sequence within a genome of the plant. In an aspect, this disclosure provides a plant comprising a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an meiosis-preferred promoter, where the at least one guide nucleic acid is capable of hybridizing to a target sequence within a genome of the plant.

In an aspect, this disclosure provides a seed of any plant provided herein.

Nucleic Acids and Amino Acids

The use of the term “polynucleotide” or “nucleic acid molecule” is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise deoxyribonucleotides, ribonucleotides, or combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded.

As used herein, the term "recombinant" in reference to a nucleic acid (DNA or RNA) molecule, protein, construct, vector, etc., refers to a nucleic acid or amino acid molecule or sequence that is man-made and not normally found in nature, and/or is present in a context in which it is not normally found in nature, including a nucleic acid molecule (DNA or RNA) molecule, protein, construct, etc., comprising a combination of polynucleotide or protein sequences that would not naturally occur contiguously or in close proximity together without human intervention, and/or a polynucleotide molecule, protein, construct, etc., comprising at least two polynucleotide or protein sequences that are heterologous with respect to each other.

In one aspect, methods and compositions provided herein comprise a vector. As used herein, the term "vector" refers to a DNA molecule used as a vehicle to carry exogenous genetic material into a cell.

In an aspect, one or more polynucleotide sequences from a vector are stably integrated into a genome of a plant. In an aspect, one or more polynucleotide sequences from a vector are stably integrated into a genome of a plant cell.

In an aspect, a first nucleic acid sequence and a second nucleic acid sequence are provided in a single vector. In another aspect, a first nucleic acid sequence is provided in a first vector, and a second nucleic acid sequence is provided in a second vector.

As used herein, the term "polypeptide" refers to a chain of at least two covalently linked amino acids. Polypeptides can be encoded by polynucleotides provided herein. An example of a polypeptide is a protein. Proteins provided herein can be encoded by nucleic acid molecules provided herein.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Without being limiting, nucleic acids can be detected using hybridization. Hybridization between nucleic acids is discussed in detail in Sambrook et. al. (1989, Molecular Cloning: A Laboratory Manual, 2nd Ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

The terms "percent sequence complementarity" or "percent complementarity" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence.

Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

For optimal alignment of sequences to calculate their percent identity, various pair-wise or multiple sequence alignment algorithms and programs are known in the art, such as ClustalW or Basic Local Alignment Search Tool (BLAST®), etc., that can be used to compare the sequence identity or similarity between two or more nucleotide or protein sequences. Although other alignment and comparison methods are known in the art, the alignment and percent identity between two sequences (including the percent identity ranges described above) can be as determined by the ClustalW algorithm, see, e.g., Chenna R. et. al., "Multiple sequence alignment with the Clustal series of programs," *Nucleic Acids Research* 31: 3497-3500 (2003); Thompson J D et. al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et. al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

As used herein, a first nucleic acid molecule can "hybridize" a second nucleic acid molecule via non-covalent interactions (e.g., Watson-Crick base-pairing) in a sequence-specific, antiparallel manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymine (T), adenine (A) pairing with uracil (U), and guanine (G) pairing with cytosine (C). In addition, it is also known in the art that for hybridization between two RNA molecules (e.g., dsRNA), guanine base pairs with uracil. For example, G/U base-pairing is partially responsible for the degeneracy (i.e., redundancy) of the genetic code in the context of tRNA anti-codon base-pairing with codons in mRNA. In the context of this disclosure, a guanine of a protein-binding segment (dsRNA duplex) of a subject DNA-targeting RNA molecule is considered complementary to an uracil, and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer nucleotides) the position of mismatches becomes important (see Sambrook et. al.). Typically, the length for a hybridizable nucleic acid is at least 10 nucleotides. Illustrative minimum lengths for a hybridizable nucleic acid are: at least 15 nucleotides; at least 18 nucleotides; at least 20 nucleotides; at least 22 nucleotides; at least 25 nucleotides; and at least 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST® programs (basic local alignment search tools) and PowerBLAST programs known in the art (see Altschul et. al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Generating Edits

Several embodiments described herein relate to compositions and methods for producing heritable edits in the genome of a progeny plant by expressing a DNA modification enzyme, for example a guided nuclease, preferentially in egg, meiotic, and/or embryonic cells of a parent plant. In some embodiments, the parent plant expressing the DNA modification enzyme is female. In some embodiments, the parent plant expressing the DNA modification enzyme is male.

As used herein, the term "genome editing" or "editing" refers to any modification of a nucleotide sequence in a site-specific manner. In the present disclosure genome editing techniques include the use of DNA modification enzymes, such as endonucleases, recombinases, transposases, deaminases, methylases, helicases and any combination thereof. In an aspect, a "modification" comprises the hydrolytic deamination of cytidine or deoxycytidine to uridine or deoxyuridine, respectively. In some embodiments, a sequence-specific editing system comprises an adenine deaminase. In an aspect, a "modification" comprises the hydrolytic deamination of adenine or adenosine. In an aspect, a "modification" comprises the hydrolytic deamination of adenosine or deoxyadenosine to inosine or deoxyinosine, respectively. In an aspect, a "modification" comprises the insertion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In some embodiments, a "modification" comprises the insertion of one or more transgenes. In another aspect, a "modification" comprises the deletion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In a further aspect, a "modification" comprises the inversion of at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In still another aspect, a "modification" comprises the substitution of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In still another aspect, a "modification" comprises the duplication of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In some embodiments, a "modification" comprises the substitution of an "A" for a "C", "G" or "T" in a nucleic acid sequence. In some embodiments, a "modification" comprises the substitution of an "C" for a "A", "G" or "T" in a nucleic acid sequence. In some embodiments, a "modification" comprises the substitution of an "G" for a "A", "C" or "T" in a nucleic acid sequence. In some embodiments, a "modification" comprises the substitution of an "T" for a "A", "C" or "G" in a nucleic acid sequence. In some embodiments, a "modification" comprises the substitution of an "C" for a "U" in a nucleic acid sequence. In some embodiments, a "modification" comprises the substitution of an "G" for a "A" in a nucleic acid sequence. In some embodiments, a "modification" comprises the substitution of an "A" for a "G" in a nucleic acid sequence. In some embodiments, a "modification" comprises the substitution of an "T" for a "C" in a nucleic acid sequence.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous meiosis-preferred promoter; and (b) a second nucleic acid sequence encoding at least one guide nucleic acid operably linked to a heterologous second promoter, where the at least one guide nucleic acid is capable of hybridizing to a target sequence within the genome; and (b) regenerating at least one plant from the plant cell of step (a), where the guided nuclease and at least one guide nucleic acid form a ribonucleoprotein within at least one meiotic cell of the plant, and where the ribonucleoprotein generates at least one double-stranded break within the target sequence in the at least one meiotic cell.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to a heterologous meiosis-preferred promoter, where the at least one guide nucleic acid is capable of hybridizing to a target sequence within the genome; and (b) regenerating at least one plant from the plant cell of step (a), where the guided nuclease and at least one guide nucleic acid form a ribonucleoprotein within at least one meiotic cell of the plant, and where the ribonucleoprotein generates at least one double-stranded break within the target sequence in the at least one meiotic cell.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous egg cell-preferred promoter; and (b) a second nucleic acid sequence encoding at least one guide nucleic acid operably linked to a heterologous second promoter, where the at least one guide nucleic acid is capable of hybridizing to a target sequence within the genome; and (b) regenerating at least one plant from the plant cell of step (a), where the guided nuclease and at least one guide nucleic acid form a ribonucleoprotein within at least one egg cell of the plant, and where the ribonucleoprotein generates at least one double-stranded break within the target sequence in the at least one egg cell.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an egg cell-preferred promoter, where the at least one guide nucleic acid is capable of hybridizing to a target sequence within the genome; and (b) regenerating at least one plant from the plant cell of step (a), where the guided nuclease and at least one guide nucleic acid form a ribonucleoprotein within at least one egg cell of the plant, and where the ribonucleoprotein generates at least one double-stranded break within the target sequence in the at least one egg cell.

In an aspect, this disclosure provides a method of editing a genome of a plant cell comprising: (a) crossing a first plant with a second plant, where the first plant comprises a first nucleic acid sequence encoding a guided nuclease capable of generating a staggered cut in a double-stranded DNA molecule operably linked to a heterologous embryo tissue-preferred promoter, and where the second plant comprises a second nucleic acid sequence encoding at least one guide nucleic acid operably linked to a heterologous second promoter, wherein the at least one guide nucleic acid is capable of hybridizing to a target sequence within the genome; and (b) obtaining at least one embryo from the crossing of step (a), where the guided nuclease and the at least one guide nucleic acid form a ribonucleoprotein within the at least one embryo, and where the ribonucleoprotein generates at least one double-stranded break within the target sequence in the at least one embryo.

In an aspect, this disclosure provides a method of editing a genome of a plant cell comprising: (a) crossing a first plant with a second plant, where the first plant comprises a first nucleic acid sequence encoding a guided nuclease capable of generating a staggered cut in a double-stranded DNA molecule operably linked to a heterologous promoter, and where the second plant comprises a second nucleic acid sequence encoding at least one guide nucleic acid operably linked to an embryo tissue-preferred promoter, wherein the at least one guide nucleic acid is capable of hybridizing to a target sequence within the genome; and (b) obtaining at least one embryo from the crossing of step (a), where the guided nuclease and the at least one guide nucleic acid form a ribonucleoprotein within the at least one embryo, and where the ribonucleoprotein generates at least one double-stranded break within the target sequence in the at least one embryo.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous embryo tissue-preferred promoter; and (ii) a second nucleic acid sequence encoding at least one guide nucleic acid operably linked to a heterologous second promoter, where the at least one guide nucleic acid is capable of hybridizing to a target sequence within the genome; (b) regenerating at least one plant from the plant cell of step (a); and (c) fertilizing the at least one plant to create at least one embryo, where the guided nuclease and at least one guide nucleic acid form a ribonucleoprotein within the at least one embryo from step (c), and where the ribonucleoprotein generates at least one double-stranded break within the target sequence in the at least one embryo.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous promoter; and (ii) a second nucleic acid sequence encoding at least one guide nucleic acid operably linked to an embryo tissue-preferred promoter, where the at least one guide nucleic acid is capable of hybridizing to a target sequence within the genome; (b) regenerating at least one plant from the plant cell of step (a); and (c) fertilizing the at least one plant to create at least one embryo, where the guided nuclease and at least one guide nucleic acid form a ribonucleoprotein within the at least one embryo from step (c), and where the ribonucleoprotein generates at least one double-stranded break within the target sequence in the at least one embryo.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous meiosis-preferred promoter; and (ii) a second nucleic acid sequence encoding one or more guide nucleic acids operably linked to a heterologous second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); where the guided nuclease and at least one guide RNA form a ribonucleoprotein within at least one meiotic cell of the plant, where the ribonucleoprotein generates a double-stranded break within the target sequence, the first site, and the second site, and where the gene of interest is integrated into the target site in the at least one egg cell.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous promoter; and (ii) a second nucleic acid sequence encoding one or more guide nucleic acids operably linked to a meiosis-preferred second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); where the guided nuclease and at least one guide RNA form a ribonucleoprotein within at least one meiotic cell of the plant, where the ribonucleoprotein generates a double-stranded break within the target sequence, the first site, and the second site, and where the gene of interest is integrated into the target site in the at least one meiotic cell.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous egg cell-preferred promoter; and (ii) a second nucleic acid sequence encoding one or more guide nucleic acids operably linked to a heterologous second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); where the guided nuclease and at least one guide RNA form a ribonucleoprotein within at least one egg cell of the plant, where the ribonucleoprotein generates a double-stranded break within the target sequence, the first site, and the second site, and where the gene of interest is integrated into the target site in the at least one egg cell.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous promoter; and (ii) a second nucleic acid sequence encoding one or more guide nucleic acids operably linked to an egg cell-preferred second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); where the guided nuclease and at least one guide RNA form a ribonucleoprotein within at least one egg cell of the plant, where the ribonucleoprotein generates a double-stranded break within the target sequence, the first site, and the second site, and where the gene of interest is integrated into the target site in the at least one egg cell.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous embryo tissue-preferred promoter; (ii) a second nucleic acid sequence encoding one or more guide nucleic acids operably linked to a heterologous second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); and (c) fertilizing the at least one plant from step (b) to create at least one embryo; where the guided nuclease and at least one guide RNA form a ribonucleoprotein within at least one embryo, where the ribonucleoprotein generates a double-stranded break within the target sequence, the first site, and the second site, and where the gene of interest is integrated into the target site in the at least one embryo.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous promoter; (ii) a second nucleic acid sequence encoding one or more guide nucleic acids operably linked to an embryo tissue-preferred promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); and (c) fertilizing the at least one plant from step (b) to create at least one embryo; where the guided nuclease and at least one guide RNA form a ribonucleoprotein within at least one embryo, where the ribonucleoprotein generates a double-stranded break within the target sequence, the first site, and the second site, and where the gene of interest is integrated into the target site in the at least one embryo.

Regulatory Elements

Regulatory elements such as promoters, leaders (also known as 5' UTRs), enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are useful for modifying plant phenotypes through genetic engineering. Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), a small interfering RNA (siRNA), and the like. As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

As commonly understood in the art, the term "promoter" refers to a DNA sequence that contains an RNA polymerase binding site, transcription start site, and/or TATA box and assists or promotes the transcription and expression of an associated transcribable polynucleotide sequence and/or gene (or transgene). A promoter may be initially isolated from the 5' untranslated region (5' UTR) of a genomic copy of a gene. A promoter can be synthetically produced, varied or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, cell cycle-specific, inducible, etc.

In some embodiments, a promoter is operably linked 5' to a leader sequence. As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

Promoters that express within a specific tissue(s) of an organism, with no expression in other tissues, are referred to as "tissue-specific" promoters. Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. In another aspect, a promoter provided herein is a tissue-specific promoter. In a further aspect, a promoter provided herein is a tissue-preferred promoter. In an aspect, a tissue-preferred promoter comprises a tissue-specific promoter.

Promoters that express within a meiotic cell(s) of an organism, with no expression in non-meiotic cells, are referred to as "meiotic cell-specific" or "meiosis-specific" promoters. Promoters that drive enhanced expression in meiotic cells of an organism relative to other cells of the organism are referred to as "meiotic cell-preferred" or "meiosis-preferred" promoters. Thus, a "meiotic cell-preferred" or "meiosis-preferred" promoter causes relatively higher or preferential expression in cells of a plant undergoing meiosis, but with lower levels of expression in other cell(s) of the plant. In another aspect, a promoter provided herein is a meiosis-specific promoter. In a further aspect, a promoter provided herein is a meiosis-preferred promoter. In an aspect, a meiosis-preferred promoter comprises a meiosis-specific promoter. Promoters that express in a cell cycle dependent manner, are referred to as "cell cycle-specific" promoters. In another aspect, a promoter provided herein is a cell cycle-specific promoter. In a further aspect, a promoter provided herein is a cell cycle-preferred promoter. In an aspect, a cell cycle-preferred promoter comprises a cell cycle-specific promoter.

Determination of promoter activity can be performed using any method standard in the art. For example, without being limiting, a promoter of interest can be used to drive expression of a fluorophore or other reporting molecule, and the concentration of the expressed molecule can be used to determine promoter activity in different cell or tissue types.

Several embodiments described herein relate to expression of a DNA modification enzyme, for example a guided nuclease, preferentially in egg, meiotic, and/or embryonic cells of a plant. Nonlimiting examples of expression elements useful in the composition and methods described herein are provided in Table 1.

TABLE 1

Plant Egg, Embryo, and Meiotic Cell Promoters

| Source | Gene name/ID | Expected Expression | Promoter and leader SEQ ID NO: | 3'UTR SEQ ID NO: |
|---|---|---|---|---|
| Corn | ZmDSUL1 | Embryo | 1 | — |
| Corn | ZmEA1 | Egg/Embryo | 2 | — |
| Corn | ZmES4 | Egg/Embryo | 3 | — |
| Corn | ZmDMC1 | Meiocyte | 4 | — |
| Corn | ZmMps1 | Meiocyte | 5 | — |
| Corn | ZmAdf1 | Meiocyte | 6 | — |
| Corn | GRMZM2G141762 | Ovary (including Egg) | 21 | — |
| Corn | A1ZM025370 | Egg | 22 | — |
| Corn | GRMZM2G119150 | Ovary (including Egg) | 23 | — |
| Corn | Zm.AC185611 | Egg and zygote | 24 | 46 |
| Corn | GRMZM2G025133 | Zygote and egg | 25 | 47 |
| Corn | GRMZM2G103251 | Zygote | 26 | 48 |
| Corn | P-Zm.EAL1:1 GRMZM2G456746 | Egg | 27 | — |
| Corn | P-ZmES2/3 GRMZM2G128301 | Egg and zygote | 28 | — |
| Corn | GRMZM2G466856 | Egg and Embryo | 29 | 49 |
| Corn | GRMZM2G075386 | Egg and Embryo | 30 | 50 |
| Corn | GRMZM2G466848 | Egg and Embryo | 31 | 51 |
| Corn | GRMZM2G047842 | Egg and Embryo | 32 | 52 |
| Corn | GRMZM2G025720 | Egg and Embryo | 33 | 53 |
| Corn | GRMZM2G083190 | Egg and Embryo | 34 | 54 |
| Corn | GRMZM2G536120 | Egg and Embryo | 35 | 55 |
| Corn | GRMZM2G125162 | Egg and Embryo | 36 | 56 |
| Corn | AC211413.4_FG001 | Egg and Embryo | 37 | 57 |
| Corn | GRMZM2G457612 | Egg and Embryo | 38 | — |
| Corn | GRMZM2G328205 | Embryo | 39 | 58 |
| Corn | GRMZM2G337139 | Embryo | 40 | 59 |
| Corn | AC215302.3_FG001 | Egg specific | 41 | 60 |
| Corn | GRMZM2G417287 | Egg specific | 42 | 61 |
| Corn | GRMZM2G103251 | Egg and Embryo | 43 | 62 |
| Corn | GRMZM2G035685 | Egg and Embryo | 44 | 63 |
| Corn | GRMZM2G150827 | Egg and Embryo | 45 | 64 |
| Soy | Glyma.05G128300 | Ovule | 65 | 70 |
| Soy | Glyma.03G037900 | Ovule | 66 | 71 |
| Soy | Glyma.04G248800 | Ovule | 67 | 72 |
| Soy | Glyma.04G090700 | Ovule | 68 | 73 |
| Soy | Glyma.07G050200 | Ovule | 69 | 74 |
| Arabidopsis | Yao AT4G05410 | Egg | 75 | 89 |
| Arabidopsis | EC1.1 AT1G76750 | Egg | 76 | 90 |
| Arabidopsis | DD45 AT2G21740 | Egg | 77 | 91 |
| Arabidopsis | DD33 AT2G20070 | Egg | 78 | 92 |
| Arabidopsis | AtP5p AT1G71470 | Egg | 79 | 93 |
| Arabidopsis | EC1.3 AT2G21750 | Egg | 80 | 94 |
| Arabidopsis | EC1.4 AT4G39340 | Egg | 81 | 95 |
| Arabidopsis | EC1.5 AT5G64720 | Egg | 82 | 96 |
| Arabidopsis | CDC45 AT3G25100 | Meiotic | 83 | 97 |
| Arabidopsis | MGE1p AT4G40020 | Meiotic | 84 | 98 |
| Arabidopsis | MGE2p AT4G20900 | Meiotic | 85 | 99 |
| Arabidopsis | WOX2 AT5G59340 | Early embryo | 86 | 100 |
| Arabidopsis | F17L21.26 AT1G27470 | Early embryo | 87 | 101 |
| Arabidopsis | POLA3 AT5G41880 | Early embryo | 88 (Promoter + 5'UTR intron + leader) | 102 |

In one embodiment, fragments of a promoter sequence disclosed in Table 1 are provided. Promoter fragments may comprise egg, embryo, and/or meiotic expression activity, as described above, and may be useful alone or in combination with other promoters and promoter fragments, such as in constructing chimeric promoters, or in combination with other expression elements and expression element fragments. In some embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. In some embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, at least about 1000, at least about 1050, at least about 1100, or at least about 1150 contiguous nucleotides, of a DNA sequence comprising a TATA box and having at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to SEQ ID NO. 1-6, 21-45, 65-69 or 75-88, having promoter activity as disclosed herein. Methods for producing such fragments from a starting promoter molecule are well known in the art.

In an aspect, a meiosis cell-preferred or meiosis-preferred promoter comprises a DMC1 promoter. In an aspect, a meiotic cell-preferred or meiosis-preferred promoter comprises an Mps1 promoter. In an aspect, a meiotic cell-preferred or meiosis-preferred promoter comprises an Adf1 promoter. In an aspect, a meiotic cell-preferred or meiosis-preferred promoter comprises a promoter selected from the group consisting of a DMC1 promoter, a Mps1 promoter, and an Adf1 promoter.

In an aspect, an expression element described in Table 1 is operably linked to a nucleic acid encoding a DNA modification enzyme, such as a guided nuclease. In an aspect, an expression element described in Table 1 is operably linked to a nucleic acid encoding a Cas9 nuclease. In an aspect, an expression element described in Table 1 is operably linked to a nucleic acid encoding a Cas12a nuclease. In an aspect, an expression element described in Table 1 is operably linked to a nucleic acid encoding a CasX nuclease. In an aspect, an expression element described in Table 1 is operably linked to a nucleic acid encoding a guide nucleic acid. In an aspect, an expression element described in Table 1 is operably linked to a nucleic acid encoding a guide RNA. In an aspect, an expression element described in Table 1 is operably linked to a nucleic acid encoding a single-guide RNA. In some embodiments, the guide RNA acid is flanked by self-cleaving ribozymes. In an aspect, an expression element described in Table 1 is operably linked to a nucleic acid encoding a recombinase (e.g., Cre recombinase). In an aspect, an expression element described in Table 1 is operably linked to a nucleic acid encoding a TALE.

In an aspect, a DMC1 promoter is operably linked to a nucleic acid encoding a guided nuclease. In an aspect, a DMC1 promoter is operably linked to a nucleic acid encoding a Cas9 nuclease. In an aspect, a DMC1 promoter is operably linked to a nucleic acid encoding a Cas12a nuclease. In an aspect, a DMC1 promoter is operably linked to a nucleic acid encoding a CasX nuclease. In an aspect, a DMC1 promoter is operably linked to a nucleic acid encoding a guide nucleic acid. In an aspect, a DMC1 promoter is operably linked to a nucleic acid encoding a guide RNA. In an aspect, a DMC1 promoter is operably linked to a nucleic acid encoding a single-guide RNA. In some embodiments, the guide RNA acid is flanked by self-cleaving ribozymes. In an aspect, a DMC1 promoter is operably linked to a nucleic acid encoding a recombinase (e.g., Cre recombinase). In an aspect, a DMC1 promoter is operably linked to a nucleic acid encoding a TALE.

In an aspect, a Mps1 promoter is operably linked to a nucleic acid encoding a guided nuclease. In an aspect, a Mps1 promoter is operably linked to a nucleic acid encoding a Cas9 nuclease. In an aspect, a Mps1 promoter is operably linked to a nucleic acid encoding a Cas12a nuclease. In an aspect, a Mps1 promoter is operably linked to a nucleic acid encoding a CasX nuclease. In an aspect, a Mps1 promoter is operably linked to a nucleic acid encoding a guide nucleic acid. In an aspect, a Mps1 promoter is operably linked to a nucleic acid encoding a guide RNA. In an aspect, a Mps1 promoter is operably linked to a nucleic acid encoding a single-guide RNA. In some embodiments, the guide RNA acid is flanked by self-cleaving ribozymes. In an aspect, a Mps1 promoter is operably linked to a nucleic acid encoding a recombinase (e.g., Cre recombinase). In an aspect, a Mps1 promoter is operably linked to a nucleic acid encoding a TALE.

In an aspect, an Adf1 promoter is operably linked to a nucleic acid encoding a guided nuclease. In an aspect, an Adf1 promoter is operably linked to a nucleic acid encoding a Cas9 nuclease. In an aspect, an Adf1 promoter is operably linked to a nucleic acid encoding a Cas12a nuclease. In an aspect, an Adf1 promoter is operably linked to a nucleic acid encoding a CasX nuclease. In an aspect, an Adf1 promoter is operably linked to a nucleic acid encoding a guide nucleic acid. In an aspect, an Adf1 promoter is operably linked to a nucleic acid encoding a guide RNA. In an aspect, an Adf1 promoter is operably linked to a nucleic acid encoding a single-guide RNA. In some embodiments, the guide RNA acid is flanked by self-cleaving ribozymes. In an aspect, an Adf1 promoter is operably linked to a nucleic acid encoding a recombinase (e.g., Cre recombinase). In an aspect, an Adf1 promoter is operably linked to a nucleic acid encoding a TALE.

In an aspect, a DMC1 promoter comprises a nucleic acid sequence at least 80% identical to SEQ ID NO: 4, or a functional fragment thereof. In an aspect, a DMC1 promoter comprises a nucleic acid sequence at least 85% identical to SEQ ID NO: 4, or a functional fragment thereof. In an aspect, a DMC1 promoter comprises a nucleic acid sequence at least 90% identical to SEQ ID NO: 4, or a functional fragment thereof. In an aspect, a DMC1 promoter comprises a nucleic acid sequence at least 95% identical to SEQ ID NO: 4, or a functional fragment thereof. In an aspect, a DMC1 promoter comprises a nucleic acid sequence at least 96% identical to SEQ ID NO: 4, or a functional fragment thereof. In an aspect, a DMC1 promoter comprises a nucleic acid sequence at least 97% identical to SEQ ID NO: 4, or a functional fragment thereof. In an aspect, a DMC1 promoter comprises a nucleic acid sequence at least 98% identical to SEQ ID NO: 4, or a functional fragment thereof. In an aspect, a DMC1 promoter comprises a nucleic acid sequence at least 99% identical to SEQ ID NO: 4, or a functional fragment thereof. In an aspect, a DMC1 promoter comprises a nucleic acid sequence 100% identical to SEQ ID NO: 4, or a functional fragment thereof.

In an aspect, a Mps1 promoter comprises a nucleic acid sequence at least 80% identical to SEQ ID NO: 5, or a functional fragment thereof. In an aspect, a Mps1 promoter comprises a nucleic acid sequence at least 85% identical to SEQ ID NO: 5, or a functional fragment thereof. In an aspect, a Mps1 promoter comprises a nucleic acid sequence at least 90% identical to SEQ ID NO: 5, or a functional fragment thereof. In an aspect, a Mps1 promoter comprises a nucleic acid sequence at least 95% identical to SEQ ID NO: 5, or a functional fragment thereof. In an aspect, a Mps1 promoter comprises a nucleic acid sequence at least 96% identical to SEQ ID NO: 5, or a functional fragment thereof. In an aspect, a Mps1 promoter comprises a nucleic acid sequence at least 97% identical to SEQ ID NO: 5, or a functional fragment thereof. In an aspect, a Mps1 promoter comprises a nucleic acid sequence at least 98% identical to SEQ ID NO: 5, or a functional fragment thereof. In an aspect, a Mps1 promoter comprises a nucleic acid sequence at least 99% identical to SEQ ID NO:5, or a functional fragment thereof. In an aspect, a Mps1 promoter comprises a nucleic acid sequence 100% identical to SEQ ID NO: 5, or a functional fragment thereof.

In an aspect, an Adf1 promoter comprises a nucleic acid sequence at least 80% identical to SEQ ID NO: 6, or a functional fragment thereof. In an aspect, an Adf1 promoter comprises a nucleic acid sequence at least 85% identical to SEQ ID NO: 6, or a functional fragment thereof. In an aspect, an Adf1 promoter comprises a nucleic acid sequence at least 90% identical to SEQ ID NO: 6, or a functional fragment thereof. In an aspect, an Adf1 promoter comprises a nucleic acid sequence at least 95% identical to SEQ ID NO: 6, or a functional fragment thereof. In an aspect, an Adf1 promoter comprises a nucleic acid sequence at least 96% identical to SEQ ID NO: 6, or a functional fragment thereof. In an aspect, an Adf1 promoter comprises a nucleic acid sequence at least 97% identical to SEQ ID NO: 6, or a functional fragment thereof. In an aspect, an Adf1 promoter comprises a nucleic acid sequence at least 98% identical to SEQ ID NO: 6, or a functional fragment thereof. In an aspect, an Adf1 promoter comprises a nucleic acid sequence at least 99% identical to SEQ ID NO: 6, or a functional fragment thereof. In an aspect, an Adf1 promoter comprises a nucleic acid sequence 100% identical to SEQ ID NO: 6, or a functional fragment thereof.

In an aspect, a meiocyte-preferred promoter comprises a nucleic acid sequence at least 80% identical to a nucleic acid sequence selected from the group consisting of SEQ ID NOs: 4-6, 83-85 or a functional fragment thereof. In an aspect, a meiocyte-preferred promoter comprises a nucleic acid sequence at least 85% identical to a nucleic acid sequence selected from the group consisting of SEQ ID NOs: 4-6, 83-85 or a functional fragment thereof. In an aspect, a meiocyte-preferred promoter comprises a nucleic acid sequence at least 90% identical to a nucleic acid sequence selected from the group consisting of SEQ ID NOs: 4-6, 83-85 or a functional fragment thereof. In an aspect, a meiocyte-preferred promoter comprises a nucleic acid sequence at least 95% identical to a nucleic acid sequence selected from the group consisting of SEQ ID NOs: 4-6, 83-85 or a functional fragment thereof. In an aspect, a meiocyte-preferred promoter comprises a nucleic acid sequence at least 96% identical to a nucleic acid sequence selected from the group consisting of SEQ ID NOs: 4-6, 83-85 or a functional fragment thereof. In an aspect, a meiocyte-preferred promoter comprises a nucleic acid sequence at least 97% identical to a nucleic acid sequence selected from the group consisting of SEQ ID NOs: 4-6, 83-85 or a functional fragment thereof. In an aspect, a meiocyte-preferred promoter comprises a nucleic acid sequence at least 98% identical to a nucleic acid sequence selected from the group consisting of SEQ ID NOs: 4-6, 83-85 or a functional fragment thereof. In an aspect, a meiocyte-preferred promoter comprises a nucleic acid sequence at least 99% identical to a nucleic acid sequence selected from the group consisting of SEQ ID NOs: 4-6, 83-85 or a functional fragment thereof. In an aspect, a meiocyte-preferred promoter comprises a nucleic acid sequence 100% identical to a nucleic acid sequence selected from the group consisting of SEQ ID NOs: 4-6, 83-85 or a functional fragment thereof.

As used herein, an "egg cell-preferred promoter" refers to a promoter that exhibits higher or preferential expression in an egg cell as compared to other cell or tissue types of the plant. Egg cell-preferred promoters can exhibit expression in nearby cells such as, without being limiting, synergids, antipodal cells, central cells, integument cells, stigma cells, and style cells. An egg cell-preferred promoter can also exhibit expression in other ovary cells, for example the ovule. An egg cell-preferred promoter can also exhibit expression in other plant tissues, such as, without being limiting, pollen cells, root cells, embryo cells, stem cells, meristem cells, floral cells, and leaf cells, as long as the egg cell-preferred promoter exhibits higher or preferential expression in an egg cell.

As used herein, an "egg cell-specific promoter" refers to a promoter that exhibits expression exclusively in an egg cell. In an aspect, an egg cell-preferred promoter comprises an egg cell-specific promoter.

As used herein, an "ovule tissue preferred promoter" refers to a promoter that exhibits higher or preferential expression in at least one or all of the ovule tissue as compared to other cell or tissue types of the plant. In seed plants, the ovule is the structure that gives rise to and contains the female reproductive cells. As used herein, the ovule is initially composed of unreduced tissue that gives rise to the haploid tissue of the female gametophyte. The female gametophyte further develops into the "mature egg sac", comprised of four unique cell types: one egg cell, a central cell, two synergids and three or more antipodal cells. As used herein, the ovule preferred promoter can exhibit expression in pre or post pollinated ovule. An ovule preferred promoter can also exhibit expression in other ovary cells.

As used herein, an "ovule tissue-specific promoter" refers to a promoter that exhibits expression exclusively in ovule. In an aspect, an ovule tissue-preferred promoter comprises an ovule tissue-specific promoter.

As used herein, an "embryo tissue-preferred promoter" refers to a promoter that exhibits higher or preferential expression in embryo tissue as compared to other cell or tissue types of the plant. Embryo tissue-preferred promoters can exhibit expression in nearby cells such as, without being limiting, endosperm cells, cotyledon cells, and seed coat cells. An embryo tissue-preferred promoter can also exhibit expression in other plant tissues, such as, without being limiting, pollen cells, root cells, egg cells, stem cells, meristem cells, floral cells, and leaf cells, as long as the embryo tissue-preferred promoter exhibits higher or preferential expression in embryo tissue.

As used herein, an "embryo tissue-specific promoter" refers to a promoter that exhibits expression exclusively in embryo tissue. In an aspect, an embryo tissue-preferred promoter comprises an embryo tissue-specific promoter.

As used herein, an "zygote cell-preferred promoter" refers to a promoter that exhibits higher or preferential expression in zygotes as compared to other cell or tissue types of the plant. Upon fertilization of an egg cell by a haploid pollen cell, a diploid zygote is formed, which gives rise to an embryo. A zygote cell-preferred promoter can also exhibit expression in other plant cells, such as, without being limiting, pollen cells, egg cells, stem cells, meristem cells, endosperm cells, cotyledon cells, floral cells, leaf cells and embryo tissue as long as the zygote tissue-preferred promoter exhibits higher or preferential expression in the zygote.

As used herein, an "zygote cell-specific promoter" refers to a promoter that exhibits expression exclusively in the zygote. In an aspect, a zygote cell-preferred promoter comprises a zygote cell-specific promoter.

It will be appreciated that the same promoter can be both egg cell-preferred, zygote cell-preferred and embryo-tissue preferred, as a fertilized egg upon pollination will develop into a zygote which will give rise to embryo tissue.

In an aspect, an embryo tissue-preferred or embryo tissue-specific promoter comprises a DSUL1 promoter. In an aspect, an egg cell-preferred or embryo tissue-preferred promoter comprises an EA1 promoter. In an aspect, an egg cell-preferred or embryo tissue-preferred promoter comprises an ES4 promoter. In an aspect, an egg cell-preferred or embryo tissue-preferred promoter comprises an EAL1 promoter. In an aspect, an egg cell-preferred or embryo tissue-preferred promoter comprises a promoter selected from the group consisting of a DSUL1 promoter, an EA1 promoter, an ES4 promoter, and an EAL1 promoter.

In an aspect, a DSUL1 promoter is operably linked to a nucleic acid encoding a guided nuclease. In an aspect, a DSUL1 promoter is operably linked to a nucleic acid encoding a Cas9 nuclease. In an aspect, a DSUL1 promoter is operably linked to a nucleic acid encoding a Cas12a nuclease. In an aspect, a DSUL1 promoter is operably linked to a nucleic acid encoding a CasX nuclease. In an aspect, a DSUL1 promoter is operably linked to a nucleic acid encoding a guide nucleic acid. In an aspect, a DSUL1 promoter is operably linked to a nucleic acid encoding a guide RNA. In an aspect, a DSUL1 promoter is operably linked to a nucleic acid encoding a single-guide RNA. In some embodiments, the guide RNA acid is flanked by self-cleaving ribozymes. In an aspect, a DSUL1 promoter is operably linked to a nucleic acid encoding a recombinase (e.g., Cre recombinase). In an aspect, a DSUL1 promoter is operably linked to a nucleic acid encoding a TALE.

In an aspect, an EA1 promoter is operably linked to a nucleic acid encoding a guided nuclease. In an aspect, an EA1 promoter is operably linked to a nucleic acid encoding a Cas9 nuclease. In an aspect, an EA1 promoter is operably linked to a nucleic acid encoding a Cas12a nuclease. In an aspect, an EA1 promoter is operably linked to a nucleic acid encoding a CasX nuclease. In an aspect, an EA1 promoter is operably linked to a nucleic acid encoding a guide nucleic acid. In an aspect, an EA1 promoter is operably linked to a nucleic acid encoding a guide RNA. In an aspect, an EA1 promoter is operably linked to a nucleic acid encoding a single-guide RNA. In some embodiments, the guide RNA acid is flanked by self-cleaving ribozymes. In an aspect, an EA1 promoter is operably linked to a nucleic acid encoding a recombinase (e.g., Cre recombinase). In an aspect, an EA1 promoter is operably linked to a nucleic acid encoding a TALE.

In an aspect, an ES4 promoter is operably linked to a nucleic acid encoding a guided nuclease. In an aspect, an ES4 promoter is operably linked to a nucleic acid encoding a Cas9 nuclease. In an aspect, an ES4 promoter is operably linked to a nucleic acid encoding a Cas12a nuclease. In an aspect, an ES4 promoter is operably linked to a nucleic acid encoding a CasX nuclease. In an aspect, an ES4 promoter is operably linked to a nucleic acid encoding a guide nucleic acid. In an aspect, an ES4 promoter is operably linked to a nucleic acid encoding a guide RNA. In an aspect, an ES4 promoter is operably linked to a nucleic acid encoding a single-guide RNA. In some embodiments, the guide RNA acid is flanked by self-cleaving ribozymes. In an aspect, an ES4 promoter is operably linked to a nucleic acid encoding a recombinase (e.g., Cre recombinase). In an aspect, an ES4 promoter is operably linked to a nucleic acid encoding a TALE.

In an aspect, an EAL1 promoter is operably linked to a nucleic acid encoding a guided nuclease. In an aspect, an EAL1 promoter is operably linked to a nucleic acid encoding a Cas9 nuclease. In an aspect, an EAL1 promoter is operably linked to a nucleic acid encoding a Cas12a nuclease. In an aspect, an EAL1 promoter is operably linked to a nucleic acid encoding a CasX nuclease. In an aspect, an EAL1 promoter is operably linked to a nucleic acid encoding a guide nucleic acid. In an aspect, an EAL1 promoter is operably linked to a nucleic acid encoding a guide RNA. In an aspect, an EAL1 promoter is operably linked to a nucleic acid encoding a single-guide RNA. In some embodiments, the guide RNA acid is flanked by self-cleaving ribozymes. In an aspect, an EAL1 promoter is operably linked to a nucleic acid encoding a recombinase (e.g., Cre recombinase). In an aspect, an EAL1 promoter is operably linked to a nucleic acid encoding a TALE.

In an aspect, a DSUL1 promoter comprises a nucleic acid sequence at least 80% identical to SEQ ID NO: 1, or a functional fragment thereof. In an aspect, a DSUL1 promoter comprises a nucleic acid sequence at least 85% identical to SEQ ID NO: 1, or a functional fragment thereof. In an aspect, a DSUL1 promoter comprises a nucleic acid sequence at least 90% identical to SEQ ID NO: 1, or a functional fragment thereof. In an aspect, a DSUL1 promoter comprises a nucleic acid sequence at least 95% identical to SEQ ID NO: 1, or a functional fragment thereof. In an aspect, a DSUL1 promoter comprises a nucleic acid sequence at least 96% identical to SEQ ID NO: 1, or a functional fragment thereof. In an aspect, a DSUL1 promoter comprises a nucleic acid sequence at least 97% identical to SEQ ID NO: 1, or a functional fragment thereof. In an aspect, a DSUL1 promoter comprises a nucleic acid sequence at least 98% identical to SEQ ID NO: 1, or a functional fragment thereof. In an aspect, a DSUL1 promoter comprises a nucleic acid sequence at least 99% identical to SEQ ID NO: 1, or a functional fragment thereof. In an aspect, a DSUL1 promoter comprises a nucleic acid sequence 100% identical to SEQ ID NO: 1, or a functional fragment thereof.

In an aspect, an EA1 promoter comprises a nucleic acid sequence at least 80% identical to SEQ ID NO: 2, or a functional fragment thereof. In an aspect, an EA1 promoter comprises a nucleic acid sequence at least 85% identical to SEQ ID NO: 2, or a functional fragment thereof. In an aspect, an EA1 promoter comprises a nucleic acid sequence at least 90% identical to SEQ ID NO: 2, or a functional fragment thereof. In an aspect, an EA1 promoter comprises a nucleic acid sequence at least 95% identical to SEQ ID NO: 2, or a functional fragment thereof. In an aspect, an EA1 promoter comprises a nucleic acid sequence at least 96% identical to SEQ ID NO: 2, or a functional fragment thereof. In an aspect, an EA1 promoter comprises a nucleic acid sequence at least 97% identical to SEQ ID NO: 2, or a functional fragment thereof. In an aspect, an EA1 promoter comprises a nucleic acid sequence at least 98% identical to SEQ ID NO: 2, or a functional fragment thereof. In an aspect, an EA1 promoter comprises a nucleic acid sequence at least 99% identical to SEQ ID NO: 2, or a functional fragment thereof. In an aspect, an EA1 promoter comprises a nucleic acid sequence 100% identical to SEQ ID NO: 2, or a functional fragment thereof.

In an aspect, an ES4 promoter comprises a nucleic acid sequence at least 80% identical to SEQ ID NO: 3, or a functional fragment thereof. In an aspect, an ES4 promoter comprises a nucleic acid sequence at least 85% identical to SEQ ID NO: 3, or a functional fragment thereof. In an aspect, an ES4 promoter comprises a nucleic acid sequence at least 90% identical to SEQ ID NO: 3, or a functional fragment thereof. In an aspect, an ES4 promoter comprises a nucleic acid sequence at least 95% identical to SEQ ID NO: 3, or a functional fragment thereof. In an aspect, an ES4 promoter comprises a nucleic acid sequence at least 96% identical to SEQ ID NO: 3, or a functional fragment thereof. In an aspect, an ES4 promoter comprises a nucleic acid sequence at least 97% identical to SEQ ID NO: 3, or a functional fragment thereof. In an aspect, an ES4 promoter comprises a nucleic acid sequence at least 98% identical to SEQ ID NO: 3, or a functional fragment thereof. In an aspect, an ES4 promoter comprises a nucleic acid sequence at least 99% identical to SEQ ID NO: 3, or a functional fragment thereof. In an aspect, an ES4 promoter comprises a nucleic acid sequence 100% identical to SEQ ID NO: 3, or a functional fragment thereof.

In an aspect, an egg cell-preferred promoter, ovule tissue-preferred promoter, zygote cell-preferred or an embryo tissue-preferred promoter comprises a nucleic acid sequence at least 80% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 85% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 90% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 95% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 96% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 97% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 98% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 99% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence 100% identical to a nucleic acid sequence selected from the group consisting of SEQ ID NOs: 1-3, 21-45, 65-69, 75-82, 86-88 or a functional fragment thereof.

It is appreciated in the art that a fragment of a promoter sequence can function to drive transcription of an operably linked nucleic acid molecule. For example, without being limiting, if a 1000 bp promoter is truncated to 500 bp, and the 500 bp fragment is capable of driving transcription, the 500 bp fragment is referred to as a "functional fragment."

In an aspect, an egg cell-preferred promoter is operably linked to a nucleic acid sequence encoding a DNA modification enzyme, such as a guided nuclease. In an aspect, an egg cell-preferred promoter is operably linked to a nucleic acid sequence encoding a Cas9 nuclease. In an aspect, an egg cell-preferred promoter is operably linked to a nucleic acid sequence encoding a Cas12a nuclease. In an aspect, an egg cell-preferred promoter is operably linked to a nucleic acid sequence encoding a CasX nuclease. In an aspect, an egg cell-preferred promoter is operably linked to a nucleic acid sequence encoding a guide nucleic acid. In an aspect, an egg cell-preferred promoter is operably linked to a nucleic acid sequence encoding a guide RNA. In an aspect, an egg cell-preferred promoter is operably linked to a nucleic acid sequence encoding a single-guide RNA. In some embodiments, the guide RNA acid is flanked by self-cleaving ribozymes. In an aspect, an egg cell-preferred promoter is operably linked to a nucleic acid sequence encoding a recombinase (e.g., Cre recombinase). In an aspect, an egg cell-preferred promoter is operably linked to a nucleic acid sequence encoding a TALE.

In an aspect, an egg cell-specific promoter is operably linked to a nucleic acid sequence encoding a DNA modification enzyme, such as a guided nuclease. In an aspect, an egg cell-specific promoter is operably linked to a nucleic acid sequence encoding a Cas9 nuclease. In an aspect, an egg cell-specific promoter is operably linked to a nucleic acid sequence encoding a Cas12a nuclease. In an aspect, an egg cell-specific promoter is operably linked to a nucleic acid sequence encoding a CasX nuclease. In an aspect, an egg cell-specific promoter is operably linked to a nucleic acid sequence encoding a guide nucleic acid. In an aspect, an egg cell-specific promoter is operably linked to a nucleic acid sequence encoding a guide RNA. In an aspect, an egg cell-specific promoter is operably linked to a nucleic acid sequence encoding a single-guide RNA. In some embodiments, the guide RNA acid is flanked by self-cleaving ribozymes. In an aspect, an egg cell-specific promoter is operably linked to a nucleic acid sequence encoding a recombinase (e.g., Cre recombinase). In an aspect, an egg cell-specific promoter is operably linked to a nucleic acid sequence encoding a TALE.

In an aspect, an embryo tissue-preferred promoter is operably linked to a nucleic acid sequence encoding a DNA modification enzyme, such as a guided nuclease. In an aspect, an embryo tissue-preferred promoter is operably linked to a nucleic acid sequence encoding a Cas9 nuclease. In an aspect, an embryo tissue-preferred promoter is operably linked to a nucleic acid sequence encoding a Cas12a nuclease. In an aspect, an embryo tissue-preferred promoter is operably linked to a nucleic acid sequence encoding a CasX nuclease. In an aspect, an embryo tissue-preferred promoter is operably linked to a nucleic acid sequence encoding a guide nucleic acid. In an aspect, an embryo tissue-preferred promoter is operably linked to a nucleic acid sequence encoding a guide RNA. In an aspect, an embryo tissue-preferred promoter is operably linked to a nucleic acid sequence encoding a single-guide RNA. In some embodiments, the guide RNA acid is flanked by self-cleaving ribozymes. In an aspect, an embryo tissue-preferred promoter is operably linked to a nucleic acid sequence encoding a recombinase (e.g., Cre recombinase). In an aspect, an embryo tissue-preferred promoter is operably linked to a nucleic acid sequence encoding a TALE.

In an aspect, an embryo tissue-specific promoter is operably linked to a nucleic acid sequence encoding a DNA modification enzyme, such as a guided nuclease. In an aspect, an embryo tissue-specific promoter is operably linked to a nucleic acid sequence encoding a Cas9 nuclease. In an aspect, an embryo tissue-specific promoter is operably linked to a nucleic acid sequence encoding a Cas12a nuclease. In an aspect, an embryo tissue-specific promoter is operably linked to a nucleic acid sequence encoding a CasX nuclease. In an aspect, an embryo tissue-specific promoter is operably linked to a nucleic acid sequence encoding a guide nucleic acid. In an aspect, an embryo tissue-specific promoter is operably linked to a nucleic acid sequence encoding a guide RNA. In an aspect, an embryo tissue-specific promoter is operably linked to a nucleic acid sequence encoding a single-guide RNA. In some embodiments, the guide RNA acid is flanked by self-cleaving ribozymes. In an aspect, an embryo tissue-specific promoter is operably linked to a nucleic acid sequence encoding a recombinase (e.g., Cre recombinase). In an aspect, an embryo tissue-specific promoter is operably linked to a nucleic acid sequence encoding a TALE.

Several embodiments described herein relate to methods and compositions for providing egg, embryo, and/or meiotic plant tissue preferred or specific expression of a DNA modification enzyme, such as a guided nuclease (e.g., a CRISPR/Cas system), from a constitutive promoter. In some embodiments, a transcribable polynucleotide encoding a DNA modification enzyme, such as a guided nuclease (e.g., a CRISPR/Cas system) is operably linked to a constitutive promoter by excision of a intervening polynucleotide sequence preferentially or specifically in egg, embryo, and/or meiotic plant tissue. In some embodiments, the intervening sequence is excised by a recombinase that is preferentially or selectively expressed in egg, embryo, and/or meiotic plant tissue. In some embodiments, the intervening sequence is excised by Cre-mediated excision of an intervening Cre expression cassette, where Cre is preferentially or selectively expressed in egg, embryo, and/or meiotic plant tissue.

Promoters that drive expression in all or most tissues of the plant are referred to as "constitutive" promoters. Promoters that drive expression during certain periods or stages of development are referred to as "developmental" promoters. An "inducible" promoter is a promoter that initiates transcription in response to an environmental stimulus such as heat, cold, drought, light, or other stimuli, such as wounding or chemical application. A promoter can also be classified in terms of its origin, such as being heterologous, homologous, chimeric, synthetic, etc.

As used herein, the term "heterologous" in reference to a promoter is a promoter sequence having a different origin relative to its associated transcribable DNA sequence, coding sequence or gene (or transgene), and/or not naturally occurring in the plant species to be transformed. The term "heterologous" can refer more broadly to a combination of two or more DNA molecules or sequences, such as a promoter and an associated transcribable DNA sequence, coding sequence or gene, when such a combination is man-made and not normally found in nature.

In an aspect, a promoter provided herein is a constitutive promoter. In still another aspect, a promoter provided herein is an inducible promoter. In an aspect, a promoter provided herein is selected from the group consisting of a constitutive promoter, a tissue-specific promoter, a tissue-preferred promoter, and an inducible promoter.

RNA polymerase III (Pol III) promoters can be used to drive the expression of non-protein coding RNA molecules, such as guide RNAs. In an aspect, a promoter provided herein is a Pol III promoter. In another aspect, a Pol III promoter provided herein is operably linked to a nucleic acid molecule encoding a non-protein coding RNA. In yet another aspect, a Pol III promoter provided herein is operably linked to a nucleic acid molecule encoding a guide nucleic acid. In still another aspect, a Pol III promoter provided herein is operably linked to a nucleic acid molecule encoding a single-guide RNA. In a further aspect, a Pol III promoter provided herein is operably linked to a nucleic acid molecule encoding a CRISPR RNA (crRNA). In another aspect, a Pol III promoter provided herein is operably linked to a nucleic acid molecule encoding a tracer RNA (tracrRNA). In some embodiments, a nucleic acid molecule encoding a non-protein coding RNA (e.g., a gRNA, a single-guide RNA, a crRNA, a tracrRNA, etc.) is operably linked to a Pol III promoter by excision of a intervening polynucleotide sequence preferentially or specifically in egg, embryo, and/or meiotic plant tissue. In some embodiments, the intervening sequence is excised by a recombinase that is preferentially or selectively expressed in egg, embryo, and/or meiotic plant tissue. In some embodiments, the intervening sequence is excised by Cre-mediated excision of an intervening Cre expression cassette, where Cre is preferentially or selectively expressed in egg, embryo, and/or meiotic plant tissue.

Non-limiting examples of Pol III promoters include a U6 promoter, an H1 promoter, a 5S promoter, an Adenovirus 2 (Ad2) VAI promoter, a tRNA promoter, and a 7SK promoter. See, for example, Schramm and Hernandez, 2002, *Genes & Development,* 16:2593-2620, which is incorporated by reference herein in its entirety. In an aspect, a Pol III promoter provided herein is selected from the group consisting of a U6 promoter, an H1 promoter, a 5S promoter, an Adenovirus 2 (Ad2) VAI promoter, a tRNA promoter, and a 7SK promoter. In another aspect, a guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a single-guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a CRISPR RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a tracer RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter.

In an aspect, a promoter provided herein is a Dahlia Mosaic Virus (DaMV) promoter. In another aspect, a promoter provided herein is a U6 promoter. In another aspect, a promoter provided herein is an actin promoter. In an aspect, a promoter provided herein is a Cauliflower Mosaic Virus (CaMV) 35S promoter. In an aspect, a promoter provided herein is a ubiquitin promoter.

In an aspect, a constitutive promoter is selected from the group consisting of a CaMV 35S promoter, an actin promoter, and a ubiquitin promoter.

Examples describing a promoter that can be used herein include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use are a nopaline synthase (NOS) promoter (Ebert et. al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et. al., *Plant Molecular Biology* (1987) 9: 315-324), the CaMV 35S promoter (Odell et. al., *Nature* (1985) 313: 810-812), the figwort mosaic virus 35S-promoter (U.S. Pat. Nos. 6,051,753; 5,378,619), the sucrose synthase promoter (Yang and Russell, *Proceedings of the National Academy of Sciences, USA* (1990) 87: 4144-4148), the R gene complex promoter (Chandler et. al., *Plant Cell* (1989) 1: 1175-1183), and the chlorophyll a/b binding protein gene promoter, PC1SV (U.S. Pat. No. 5,850,019), and AGRtu.nos (GenBank Accession V00087; Depicker et. al., *Journal of Molecular and Applied Genetics* (1982) 1: 561-573; Bevan et. al., 1983) promoters.

Promoter hybrids can also be used and constructed to enhance transcriptional activity (see U.S. Pat. No. 5,106,739), or to combine desired transcriptional activity, inducibility and tissue specificity or developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure.

In an aspect, a constitutive promoter is operably linked to a nucleic acid sequence encoding a guided nuclease by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a Cas9 nuclease by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a Cas12a nuclease by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a CasX nuclease by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a guide nucleic acid by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a guide RNA by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a single-guide RNA by Cre-mediated excision of an intervening Cre expression cassette, where Cre is preferentially or selectively expressed in egg, embryo, and/or meiotic plant tissue.

In an aspect, an inducible promoter is operably linked to a nucleic acid sequence encoding a guided nuclease. In an aspect, an inducible promoter is operably linked to a nucleic acid sequence encoding a Cas9 nuclease. In an aspect, an inducible promoter is operably linked to a nucleic acid sequence encoding a Cas12a nuclease. In an aspect, an inducible promoter is operably linked to a nucleic acid sequence encoding a CasX nuclease. In an aspect, an inducible promoter is operably linked to a nucleic acid sequence encoding a guide nucleic acid. In an aspect, an inducible promoter is operably linked to a nucleic acid sequence encoding a guide RNA. In an aspect, an inducible promoter is operably linked to a nucleic acid sequence encoding a single-guide RNA. In some embodiments, the guide RNA acid is flanked by self-cleaving ribozymes. In an aspect, an inducible promoter is operably linked to a nucleic acid sequence encoding a recombinase (e.g., Cre recombinase). In an aspect, an inducible promoter is operably linked to a nucleic acid sequence encoding a TALE.

In an aspect, a developmental promoter is operably linked to a nucleic acid sequence encoding a guided nuclease. In an aspect, a developmental promoter is operably linked to a nucleic acid sequence encoding a Cas9 nuclease. In an aspect, a developmental promoter is operably linked to a nucleic acid sequence encoding a Cas12a nuclease. In an aspect, a developmental promoter is operably linked to a nucleic acid sequence encoding a CasX nuclease. In an aspect, a developmental promoter is operably linked to a nucleic acid sequence encoding a guide nucleic acid. In an aspect, a developmental promoter is operably linked to a nucleic acid sequence encoding a guide RNA. In an aspect, a developmental promoter is operably linked to a nucleic acid sequence encoding a single-guide RNA. In some embodiments, the guide RNA acid is flanked by self-cleaving ribozymes. In an aspect, a developmental promoter is operably linked to a nucleic acid sequence encoding a recombinase (e.g., Cre recombinase). In an aspect, a developmental promoter is operably linked to a nucleic acid sequence encoding a TALE.

As used herein the term "leader" refers to a nucleotide segment between the transcription start site (TSS) and protein coding sequence start site of a gene. It is isolated from the untranslated 5' region of the genomic copy of a gene. Leaders can be used as 5' regulatory elements to regulate the expression of operably linked transcribable polynucleotide molecules. The leader molecule can be used with a heterologous promoter or with its native promoter.

As used herein, the term "3' transcription termination molecule" or "3' UTR" refers to a DNA sequence that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et. al., Proc. Natl. Acad. Sci. USA, 80:4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806). 3' UTRs typically find beneficial use for the recombinant expression of specific genes. 3'UTRs can be used as 3'regulatory elements to regulate the expression of operably linked transcribable polynucleotide molecules. 3'UTRs can be used as 3' regulatory elements to regulate the tissue/cell preferred expression of operably linked transcribable polynucleotide molecules. 3' UTRs can be used with a heterologous promoter or with its native promoter. Non-limiting examples of 3' UTRs useful in practicing the various embodiments described here include SEQ ID NOs 46-64, 70-74, 89-102

DNA Modification Enzymes

Several embodiments relate to compositions and methods for preferential or specific expression of one or more components of a genome editing system in egg, embryo, and/or meiotic plant tissue. Several embodiments relate to a gene regulatory element as described in Table 1 operably linked to a heterologous transcribable DNA molecule encoding one or more components of a genome editing system. Genome editing systems may be used to introduce one or more insertions, deletions, substitutions, base modifications, translocations, or inversions to a genome of a host cell. In some embodiments, a gene regulatory element as described in Table 1 is operably linked to a heterologous transcribable DNA molecule encoding a sequence-specific DNA modification enzyme, such as a CRISPR-Cas effector protein, a zinc finger protein, or a transcription activator (TAL) protein. In some embodiments, the sequence-specific DNA modification enzyme maybe a fusion protein. In some embodiments, the sequence-specific DNA modification enzyme maybe a guided nuclease.

Guided nucleases are nucleases that form a complex (e.g., a ribonucleoprotein) with a guide nucleic acid molecule (e.g., a guide RNA), which then guides the complex to a target site within a target sequence. One non-limiting example of guided nucleases are CRISPR nucleases.

CRISPR (Clustered Regularly Interspaced Short Palindromic Repeats) nucleases (e.g., Cas9, CasX, Cas12a (also referred to as Cpf1), CasY) are proteins found in bacteria that are guided by guide RNAs ("gRNAs") to a target nucleic acid molecule, where the endonuclease can then cleave one or two strands the target nucleic acid molecule. Although the origins of CRISPR nucleases are bacterial, many CRISPR nucleases have been shown to function in eukaryotic cells.

While not being limited by any particular scientific theory, a CRISPR nuclease forms a complex with a guide RNA (gRNA), which hybridizes with a complementary target site, thereby guiding the CRISPR nuclease to the target site. In class II CRISPR-Cas systems, CRISPR arrays, including spacers, are transcribed during encounters with recognized invasive DNA and are processed into small interfering CRISPR RNAs (crRNAs). The crRNA comprises a repeat sequence and a spacer sequence which is complementary to a specific protospacer sequence in an invading pathogen. The spacer sequence can be designed to be complementary to target sequences in a eukaryotic genome.

In some embodiments, a gene regulatory element as described herein is operably linked to a heterologous transcribable DNA molecule encoding a CRISPR-Cas effector protein. In some embodiments, the CRISPR-Cas effector protein is selected from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. Examples of CRISPR-Cas effector proteins include, but are not limited to, Cas9, C2c1, C2c3, C2c4, C2c5, C2c8, C2c9, C2c10, Cas12a (also referred to as Cpf1), Cas12b, Cas12c, Cas12d, Cas12e, Cas12h, Cas12i, Cas12g, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), Csf5, Cas14a, Cas14b, and Cas14c effector protein. In some embodiments, a gene regulatory element as described herein is operably linked to a CRISPR-Cas effector protein comprising a mutation in its nuclease active site (e.g., RuvC, HNH, and/or NUC domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation. In some embodiments, a gene regulatory element as described herein is operably linked to a CRISPR-Cas effector protein having a mutation in its nuclease active site to generate a nickase activity operably linked to a reverse transcriptase enzyme.

CRISPR effector proteins associate with their respective crRNAs in their active forms. CasX, similar to the class II endonuclease Cas9, requires another non-coding RNA component, referred to as a trans-activating crRNA (tracrRNA), to have functional activity. Nucleic acid molecules provided herein can combine a crRNA and a tracrRNA into one nucleic acid molecule in what is herein referred to as a "single guide RNA" (sgRNA). Cas12a does not require a tracrRNA to be guided to a target site; a crRNA alone is sufficient for Cas12a. The gRNA guides the active CRISPR nuclease complex to a target site, where the CRISPR nuclease can cleave the target site.

When a CRISPR effector protein and a guide RNA form a complex, the whole system is called a "ribonucleoprotein." Ribonucleoproteins provided herein can also comprise additional nucleic acids or proteins.

In an aspect, a CRISPR effector protein and a guide nucleic acid form a ribonucleoprotein in an egg cell. In another aspect, a CRISPR effector protein and a guide nucleic acid form a ribonucleoprotein in embryo tissue. In an aspect, a Cas9 nuclease and a guide nucleic acid form a ribonucleoprotein in an egg cell. In another aspect, a Cas9 nuclease and a guide nucleic acid form a ribonucleoprotein in embryo tissue. In an aspect, a Cas12a nuclease and a guide nucleic acid form a ribonucleoprotein in an egg cell. In another aspect, a Cas12a nuclease and a guide nucleic acid form a ribonucleoprotein in embryo tissue. In an aspect, a CasX nuclease and a guide nucleic acid form a ribonucleoprotein in an egg cell. In another aspect, a CasX nuclease and a guide nucleic acid form a ribonucleoprotein in embryo tissue. In an aspect, a CRISPR effector protein and a guide RNA form a ribonucleoprotein in an egg cell. In another aspect, a CRISPR effector protein and a guide RNA form a ribonucleoprotein in embryo tissue. In an aspect, a Cas9 nuclease and a guide RNA form a ribonucleoprotein in an egg cell. In another aspect, a Cas9 nuclease and a guide RNA form a ribonucleoprotein in embryo tissue. In an aspect, a Cas12a nuclease and a guide RNA form a ribonucleoprotein in an egg cell. In another aspect, a Cas12a nuclease and a guide RNA form a ribonucleoprotein in embryo tissue. In an aspect, a CasX nuclease and a guide RNA form a ribonucleoprotein in an egg cell. In another aspect, a CasX nuclease and a guide RNA form a ribonucleoprotein in embryo tissue. In an aspect, a guided nuclease and a single-guide RNA form a ribonucleoprotein in an egg cell. In another aspect, a guided nuclease and a single-guide RNA form a ribonucleoprotein in embryo tissue. In another aspect, a CasX nuclease and a single-guide RNA form a ribonucleoprotein in embryo tissue. In another aspect, a Cas9 nuclease and a single-guide RNA form a ribonucleoprotein in embryo tissue.

In an aspect, a ribonucleoprotein generates at least one double-stranded break within a target site in an egg cell. In an aspect, a ribonucleoprotein generates at least one double-stranded break within a target site in embryo tissue. In an aspect, a ribonucleoprotein generates at least one single-stranded break within a target site in an egg cell. In an aspect, a ribonucleoprotein generates at least one single-stranded break within a target site in embryo tissue.

A prerequisite for cleavage of the target site by a CRISPR ribonucleoprotein is the presence of a conserved Protospacer Adjacent Motif (PAM) near the target site. Depending on the CRISPR nuclease, cleavage can occur within a certain number of nucleotides (e.g., between 18-23 nucleotides for Cas12a) from the PAM site. PAM sites are only required for type I and type II CRISPR associated proteins, and different CRISPR endonucleases recognize different PAM sites. Without being limiting, Cas12a can recognize at least the following PAM sites: TTTN, and YTN; and CasX can recognize at least the following PAM sites: TTCN, TTCA, and TTC (where T is thymine; C is cytosine; A is adenine; Y is thymine or cytosine; and N is thymine, cytosine, guanine, or adenine).

Cas12a is an RNA-guided nuclease of a class II, type V CRISPR/Cas system. Cas12a nucleases generate staggered cuts when cleaving a double-stranded DNA molecule. Staggered cuts of double-stranded DNA produce a single-stranded DNA overhang of at least one nucleotide. This is in contrast to a blunt-end cut (such as those generated by Cas9), which does not produce a single-stranded DNA overhang when cutting double-stranded DNA.

In an aspect, a Cas12a nuclease provided herein is a Lachnospiraceae bacterium Cas12a (LbCas12a) nuclease. In another aspect, a Cas12a nuclease provided herein is a *Francisella novicida* Cas12a (FnCas12a) nuclease. In an aspect, a Cas12a nuclease is selected from the group consisting of LbCas12a and FnCas12a.

In an aspect, a Cas12a nuclease, or a nucleic acid encoding a Cas12a nuclease, is derived from a bacteria genus selected from the group consisting of *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium, Acidaminococcus, Peregrinibacteria, Butyrivibrio, Parcubacteria, Smithella, Candidatus, Moraxella*, and *Leptospira*.

In an aspect, a Cas12a nuclease is encoded by a polynucleotide comprising a sequence at least 80% identical to a polynucleotide selected from the group consisting of SEQ ID NO: 7. In another aspect, a Cas12a nuclease is encoded by a polynucleotide comprising a sequence at least 85% identical to a polynucleotide selected from the group consisting of SEQ ID NO: 7. In another aspect, a Cas12a nuclease is encoded by a polynucleotide comprising a sequence at least 90% identical to a polynucleotide selected from the group consisting of SEQ ID NO: 7. In another aspect, a Cas12a nuclease is encoded by a polynucleotide comprising a sequence at least 95% identical to a polynucleotide selected from the group consisting of SEQ ID NO: 7. In another aspect, a Cas12a nuclease is encoded by a polynucleotide comprising a sequence at least 96% identical to a polynucleotide selected from the group consisting of SEQ ID NO: 7. In another aspect, a Cas12a nuclease is encoded by a polynucleotide comprising a sequence at least 97% identical to a polynucleotide selected from the group consisting of SEQ ID NO: 7. In another aspect, a Cas12a nuclease is encoded by a polynucleotide comprising a sequence at least 98% identical to a polynucleotide selected from the group consisting of SEQ ID NO: 7. In another aspect, a Cas12a nuclease is encoded by a polynucleotide comprising a sequence at least 99% identical to a polynucleotide selected from the group consisting of SEQ ID NO: 7. In another aspect, a Cas12a nuclease is encoded by a polynucleotide comprising a sequence 100% identical to a polynucleotide selected from the group consisting of SEQ ID NO: 7.

CasX is a type of class II CRISPR-Cas nuclease that has been identified in the bacterial phyla Deltaproteobacteria and Planctomycetes. Similar to Cas12a, CasX nucleases generate staggered cuts when cleaving a double-stranded DNA molecule. However, unlike Cas12a, CasX nucleases require a crRNA and a tracrRNA, or a single-guide RNA, in order to target and cleave a target nucleic acid.

In an aspect, a CasX nuclease provided herein is a CasX nuclease from the phylum Deltaproteobacteria. In another aspect, a CasX nuclease provided herein is a CasX nuclease from the phylum Planctomycetes. Without being limiting, additional suitable CasX nucleases are those set forth in WO 2019/084148, which is incorporated by reference herein in its entirety.

In an aspect, a guided nuclease capable of generating a staggered cut in a double-stranded DNA molecule is selected from the group consisting of Cas12a and CasX. In an aspect, a guided nuclease is selected from the group consisting of Cas12a and CasX.

In an aspect, a guided nuclease is a RNA-guided nuclease. In another aspect, a guided nuclease is a CRISPR nuclease. In another aspect, a guided nuclease is a Cas12a nuclease. In another aspect, a guided nuclease is a CasX nuclease.

As used herein, a "nuclear localization signal" (NLS) refers to an amino acid sequence that "tags" a protein for import into the nucleus of a cell. In an aspect, a nucleic acid molecule provided herein encodes a nuclear localization signal. In another aspect, a nucleic acid molecule provided herein encodes two or more nuclear localization signals.

In an aspect, a CRISPR effector protein provided herein comprises a nuclear localization signal. In an aspect, a Cas9 effector protein provided herein comprises a nuclear localization signal. In an aspect, a nuclear localization signal is positioned on the N-terminal end of a Cas12a nuclease. In a further aspect, a nuclear localization signal is positioned on the C-terminal end of a Cas9 effector protein. In yet another aspect, a nuclear localization signal is positioned on both the N-terminal end and the C-terminal end of a Cas9 effector protein.

In an aspect, a Cas12a effector protein provided herein comprises a nuclear localization signal. In an aspect, a nuclear localization signal is positioned on the N-terminal end of a Cas12a effector protein. In a further aspect, a nuclear localization signal is positioned on the C-terminal end of a Cas12a effector protein. In yet another aspect, a nuclear localization signal is positioned on both the N-terminal end and the C-terminal end of a Cas12a effector protein.

In an aspect, a CasX effector protein provided herein comprises a nuclear localization signal. In an aspect, a nuclear localization signal is positioned on the N-terminal end of a CasX effector protein. In a further aspect, a nuclear localization signal is positioned on the C-terminal end of a CasX effector protein. In yet another aspect, a nuclear localization signal is positioned on both the N-terminal end and the C-terminal end of a CasX effector protein.

In an aspect, a ribonucleoprotein comprises at least one nuclear localization signal. In another aspect, a ribonucleoprotein comprises at least two nuclear localization signals. In an aspect, a nuclear localization signal provided herein is encoded by SEQ ID NO: 8 or 9.

Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www[dot]kazusa[dot] or[dot]jp[forwards slash]codon and these tables can be adapted in a number of ways. See Nakamura et. al., 2000, *Nucl. Acids Res.* 28:292. Computer algorithms for codon optimizing a particular sequence for expression in a particular plant cell are also available, such as Gene Forge (Aptagen; Jacobus, PA), are also available.

As used herein, "codon optimization" refers to a process of modifying a nucleic acid sequence for enhanced expression in a plant cell of interest by replacing at least one codon (e.g., at least 1, 2, 3, 4, 5, 10, 15, 20, 25, 50, or more codons) of a sequence with codons that are more frequently or most frequently used in the genes of the plant cell while maintaining the original amino acid sequence (e.g., introducing silent mutations).

In an aspect, one or more codons (e.g., 1, 2, 3, 4, 5, 10, 15, 20, 25, 50, or more, or all codons) in a sequence encoding a guided nuclease correspond to the most frequently used codon for a particular amino acid. In another aspect, one or more codons (e.g., 1, 2, 3, 4, 5, 10, 15, 20, 25, 50, or more, or all codons) in a sequence encoding a Cas9 effector protein, a Cas12a effector protein or a CasX effector protein correspond to the most frequently used codon for a particular amino acid. As to codon usage in plants, reference is made to Campbell and Gowri, 1990, *Plant Physiol.*, 92: 1-11; and Murray et. al., 1989, *Nucleic Acids Res.*, 17:477-98, each of which is incorporated herein by reference in their entireties.

In an aspect, a nucleic acid molecule encodes a guided nuclease that is codon optimized for a plant. In an aspect, a nucleic acid molecule encodes a Cas9 effector protein that is codon optimized for a plant. In an aspect, a nucleic acid molecule encodes a Cas12a effector protein that is codon optimized for a plant. In an aspect, a nucleic acid molecule encodes a CasX effector protein that is codon optimized for a plant.

In another aspect, a nucleic acid molecule provided herein encodes a guided nuclease that is codon optimized for a plant cell. In another aspect, a nucleic acid molecule provided herein encodes a guided nuclease that is codon optimized for a monocotyledonous plant species. In another aspect, a nucleic acid molecule provided herein encodes a guided nuclease that is codon optimized for a dicotyledonous plant species. In a further aspect, a nucleic acid molecule provided herein encodes a guided nuclease that is codon optimized for a gymnosperm plant species. In a further aspect, a nucleic acid molecule provided herein encodes a guided nuclease that is codon optimized for an angiosperm plant species. In a further aspect, a nucleic acid molecule provided herein encodes a guided nuclease that is codon optimized for a corn cell. In a further aspect, a nucleic acid molecule provided herein encodes a guided nuclease that is codon optimized for a soybean cell. In a further aspect, a nucleic acid molecule provided herein encodes a guided nuclease that is codon optimized for a rice cell. In a further aspect, a nucleic acid molecule provided herein encodes a guided nuclease that is codon optimized for a wheat cell. In a further aspect, a nucleic acid molecule provided herein encodes a guided nuclease that is codon optimized for a cotton cell. In a further aspect, a nucleic acid molecule provided herein encodes a guided nuclease that is codon optimized for a sorghum cell. In a further aspect, a nucleic acid molecule provided herein encodes a guided nuclease that is codon optimized for an alfalfa cell. In a further aspect, a nucleic acid molecule provided herein encodes a guided nuclease that is codon optimized for a sugarcane cell. In a further aspect, a nucleic acid molecule provided herein encodes a guided nuclease that is codon optimized for an *Arabidopsis* cell. In a further aspect, a nucleic acid molecule provided herein encodes a guided nuclease that is codon optimized for a tomato cell. In a further aspect, a nucleic acid molecule provided herein encodes a guided nuclease that is codon optimized for a cucumber cell. In a further aspect, a nucleic acid molecule provided herein encodes a guided nuclease that is codon optimized for a potato cell. In a further aspect, a nucleic acid molecule provided herein encodes a guided nuclease that is codon optimized for an onion cell.

In another aspect, a nucleic acid molecule provided herein encodes a Cas12a effector protein that is codon optimized for a plant cell. In another aspect, a nucleic acid molecule provided herein encodes a Cas12a effector protein that is codon optimized for a monocotyledonous plant species. In another aspect, a nucleic acid molecule provided herein encodes a Cas12a effector protein that is codon optimized for a dicotyledonous plant species. In a further aspect, a nucleic acid molecule provided herein encodes a Cas12a effector protein that is codon optimized for a gymnosperm plant species. In a further aspect, a nucleic acid molecule provided herein encodes a Cas12a effector protein that is codon optimized for an angiosperm plant species. In a further aspect, a nucleic acid molecule provided herein encodes a Cas12a effector protein that is codon optimized for a corn cell. In a further aspect, a nucleic acid molecule provided herein encodes a Cas12a effector protein that is codon optimized for a soybean cell. In a further aspect, a nucleic acid molecule provided herein encodes a Cas12a effector protein that is codon optimized for a rice cell. In a further aspect, a nucleic acid molecule provided herein encodes a Cas12a effector protein that is codon optimized for a wheat cell. In a further aspect, a nucleic acid molecule provided herein encodes a Cas12a effector protein that is codon optimized for a cotton cell. In a further aspect, a nucleic acid molecule provided herein encodes a Cas12a effector protein that is codon optimized for a sorghum cell. In a further aspect, a nucleic acid molecule provided herein encodes a Cas12a effector protein that is codon optimized for an alfalfa cell. In a further aspect, a nucleic acid molecule provided herein encodes a Cas12a effector protein that is codon optimized for a sugar cane cell. In a further aspect, a nucleic acid molecule provided herein encodes a Cas12a effector protein that is codon optimized for an *Arabidopsis* cell. In a further aspect, a nucleic acid molecule provided herein encodes a Cas12a effector protein that is codon optimized for a tomato cell. In a further aspect, a nucleic acid molecule provided herein encodes a Cas12a effector protein that is codon optimized for a cucumber cell. In a further aspect, a nucleic acid molecule provided herein encodes a Cas12a effector protein that is codon optimized for a potato cell. In a further aspect, a nucleic acid molecule provided herein encodes a Cas12a effector protein that is codon optimized for an onion cell.

In another aspect, a nucleic acid molecule provided herein encodes a CasX effector protein that is codon optimized for a plant cell. In another aspect, a nucleic acid molecule provided herein encodes a CasX effector protein that is codon optimized for a monocotyledonous plant species. In another aspect, a nucleic acid molecule provided herein encodes a CasX effector protein that is codon optimized for a dicotyledonous plant species. In a further aspect, a nucleic acid molecule provided herein encodes a CasX effector protein that is codon optimized for a gymnosperm plant species. In a further aspect, a nucleic acid molecule provided herein encodes a CasX effector protein that is codon optimized for an angiosperm plant species. In a further aspect, a nucleic acid molecule provided herein encodes a CasX effector protein that is codon optimized for a corn cell. In a further aspect, a nucleic acid molecule provided herein encodes a CasX effector protein that is codon optimized for a soybean cell. In a further aspect, a nucleic acid molecule provided herein encodes a CasX effector protein that is codon optimized for a rice cell. In a further aspect, a nucleic acid molecule provided herein encodes a CasX effector protein that is codon optimized for a wheat cell. In a further aspect, a nucleic acid molecule provided herein encodes a CasX effector protein that is codon optimized for a cotton cell. In a further aspect, a nucleic acid molecule provided herein encodes a CasX effector protein that is codon optimized for a sorghum cell. In a further aspect, a nucleic acid molecule provided herein encodes a CasX effector protein that is codon optimized for an alfalfa cell. In a further aspect, a nucleic acid molecule provided herein encodes a CasX effector protein that is codon optimized for a sugar cane cell. In a further aspect, a nucleic acid molecule provided herein encodes a CasX effector protein that is codon optimized for an *Arabidopsis* cell. In a further aspect, a nucleic acid molecule provided herein encodes a CasX effector protein that is codon optimized for a tomato cell. In a further aspect, a nucleic acid molecule provided herein encodes a CasX effector protein that is codon optimized for a cucumber cell. In a further aspect, a nucleic acid molecule provided herein encodes a CasX effector protein that is codon optimized for a potato cell. In a further aspect, a nucleic acid molecule provided herein encodes a CasX effector protein that is codon optimized for an onion cell.

Guide Nucleic Acids

As used herein, a "guide nucleic acid" refers to a nucleic acid that forms a ribonucleoprotein (e.g., a complex) with a CRISPR effector protein (e.g., without being limiting, Cas9, Cas12a, CasX) and then guides the ribonucleoprotein to a specific sequence in a target nucleic acid molecule, where the guide nucleic acid and the target nucleic acid molecule share complementary sequences. In an aspect, a ribonucleoprotein provided herein comprises at least one guide nucleic acid.

In an aspect, a guide nucleic acid comprises DNA. In another aspect, a guide nucleic acid comprises RNA. In an aspect, a guide nucleic acid comprises DNA, RNA, or a combination thereof. In an aspect, a guide nucleic acid is single-stranded. In another aspect, a guide nucleic acid is at least partially double-stranded.

When a guide nucleic acid comprises RNA, it can be referred to as a "guide RNA." In another aspect, a guide nucleic acid comprises DNA and RNA. In another aspect, a guide RNA is single-stranded. In another aspect, a guide RNA is double-stranded. In a further aspect, a guide RNA is partially double-stranded.

In an aspect, a guide nucleic acid comprises a guide RNA. In another aspect, a guide nucleic acid comprises at least one guide RNA. In another aspect, a guide nucleic acid comprises at least two guide RNAs. In another aspect, a guide nucleic acid comprises at least three guide RNAs. In another aspect, a guide nucleic acid comprises at least five guide RNAs. In another aspect, a guide nucleic acid comprises at least ten guide RNAs.

In another aspect, a guide nucleic acid comprises at least 10 nucleotides. In another aspect, a guide nucleic acid comprises at least 11 nucleotides. In another aspect, a guide nucleic acid comprises at least 12 nucleotides. In another aspect, a guide nucleic acid comprises at least 13 nucleotides. In another aspect, a guide nucleic acid comprises at least 14 nucleotides. In another aspect, a guide nucleic acid comprises at least 15 nucleotides. In another aspect, a guide nucleic acid comprises at least 16 nucleotides. In another aspect, a guide nucleic acid comprises at least 17 nucleotides. In another aspect, a guide nucleic acid comprises at least 18 nucleotides. In another aspect, a guide nucleic acid comprises at least 19 nucleotides. In another aspect, a guide nucleic acid comprises at least 20 nucleotides. In another aspect, a guide nucleic acid comprises at least 21 nucleotides. In another aspect, a guide nucleic acid comprises at least 22 nucleotides. In another aspect, a guide nucleic acid comprises at least 23 nucleotides. In another aspect, a guide nucleic acid comprises at least 24 nucleotides. In another aspect, a guide nucleic acid comprises at least 25 nucleotides. In another aspect, a guide nucleic acid comprises at least 26 nucleotides. In another aspect, a guide nucleic acid comprises at least 27 nucleotides. In another aspect, a guide nucleic acid comprises at least 28 nucleotides. In another aspect, a guide nucleic acid comprises at least 30 nucleotides. In another aspect, a guide nucleic acid comprises at least 35 nucleotides. In another aspect, a guide nucleic acid comprises at least 40 nucleotides. In another aspect, a guide nucleic acid comprises at least 45 nucleotides. In another aspect, a guide nucleic acid comprises at least 50 nucleotides.

In another aspect, a guide nucleic acid comprises between 10 nucleotides and 50 nucleotides. In another aspect, a guide nucleic acid comprises between 10 nucleotides and 40 nucleotides. In another aspect, a guide nucleic acid comprises between 10 nucleotides and 30 nucleotides. In another aspect, a guide nucleic acid comprises between 10 nucleotides and 20 nucleotides. In another aspect, a guide nucleic acid comprises between 16 nucleotides and 28 nucleotides. In another aspect, a guide nucleic acid comprises between 16 nucleotides and 25 nucleotides. In another aspect, a guide nucleic acid comprises between 16 nucleotides and 20 nucleotides.

In an aspect, a guide nucleic acid comprises at least 70% sequence complementarity to a target site. In an aspect, a guide nucleic acid comprises at least 75% sequence complementarity to a target site. In an aspect, a guide nucleic acid comprises at least 80% sequence complementarity to a target site. In an aspect, a guide nucleic acid comprises at least 85% sequence complementarity to a target site. In an aspect, a guide nucleic acid comprises at least 90% sequence complementarity to a target site. In an aspect, a guide nucleic acid comprises at least 91% sequence complementarity to a target site. In an aspect, a guide nucleic acid comprises at least 92% sequence complementarity to a target site. In an aspect, a guide nucleic acid comprises at least 93% sequence complementarity to a target site. In an aspect, a guide nucleic acid comprises at least 94% sequence complementarity to a target site. In an aspect, a guide nucleic acid comprises at least 95% sequence complementarity to a target site. In an aspect, a guide nucleic acid comprises at least 96% sequence complementarity to a target site. In an aspect, a guide nucleic acid comprises at least 97% sequence complementarity to a target site. In an aspect, a guide nucleic acid comprises at least 98% sequence complementarity to a target site. In an aspect, a guide nucleic acid comprises at least 99% sequence complementarity to a target site. In an aspect, a guide nucleic acid comprises 100% sequence complementarity to a target site. In another aspect, a guide nucleic acid comprises between 70% and 100% sequence complementarity to a target site. In another aspect, a guide nucleic acid comprises between 80% and 100% sequence complementarity to a target site. In another aspect, a guide nucleic acid comprises between 90% and 100% sequence complementarity to a target site. In an aspect, a guide nucleic acid is capable of hybridizing to a target site.

As noted above, some guided nucleases, such as CasX and Cas9, require another non-coding RNA component, referred to as a trans-activating crRNA (tracrRNA), to have functional activity. Guide nucleic acid molecules provided herein can combine a crRNA and a tracrRNA into one nucleic acid molecule in what is herein referred to as a "single guide RNA" (sgRNA). The gRNA guides the active CasX complex to a target site within a target sequence, where CasX can cleave the target site. In other embodiments, the crRNA and tracrRNA are provided as separate nucleic acid molecules. In an aspect, a guide nucleic acid comprises a crRNA. In another aspect, a guide nucleic acid comprises a tracrRNA. In a further aspect, a guide nucleic acid comprises a sgRNA.

Target Sites

As used herein, a "target sequence" refers to a selected sequence or region of a DNA molecule in which a modification (e.g., cleavage, deamination, site-directed integration) is desired. A target sequence comprises a target site.

As used herein, a "target site" refers to the portion of a target sequence that is modified (e.g., cleaved) by a CRISPR effector protein. In contrast to a non-target nucleic acid (e.g., non-target ssDNA) or non-target region, a target site comprises significant complementarity to a guide nucleic acid or a guide RNA.

In an aspect, a target site is 100% complementary to a guide nucleic acid. In another aspect, a target site is 99% complementary to a guide nucleic acid. In another aspect, a target site is 98% complementary to a guide nucleic acid. In another aspect, a target site is 97% complementary to a guide nucleic acid. In another aspect, a target site is 96% complementary to a guide nucleic acid. In another aspect, a target site is 95% complementary to a guide nucleic acid. In another aspect, a target site is 94% complementary to a guide nucleic acid. In another aspect, a target site is 93% complementary to a guide nucleic acid. In another aspect, a target site is 92% complementary to a guide nucleic acid. In another aspect, a target site is 91% complementary to a guide nucleic acid. In another aspect, a target site is 90% complementary to a guide nucleic acid. In another aspect, a target site is 85% complementary to a guide nucleic acid. In another aspect, a target site is 80% complementary to a guide nucleic acid.

In an aspect, a target site comprises at least one PAM site. In an aspect, a target site is adjacent to a nucleic acid sequence that comprises at least one PAM site. In another aspect, a target site is within 5 nucleotides of at least one PAM site. In a further aspect, a target site is within 10 nucleotides of at least one PAM site. In another aspect, a target site is within 15 nucleotides of at least one PAM site. In another aspect, a target site is within 20 nucleotides of at least one PAM site. In another aspect, a target site is within 25 nucleotides of at least one PAM site. In another aspect, a target site is within 30 nucleotides of at least one PAM site.

In an aspect, a target site is positioned within genic DNA. In another aspect, a target site is positioned within a gene. In another aspect, a target site is positioned within a gene of interest. In another aspect, a target site is positioned within an exon of a gene. In another aspect, a target site is positioned within an intron of a gene. In another aspect, a target site is positioned within 5'-UTR of a gene. In another aspect, a target site is positioned within a 3'-UTR of a gene. In another aspect, a target site is positioned within intergenic DNA.

In an aspect, a target DNA molecule is single-stranded. In another aspect, a target DNA molecule is double-stranded.

In an aspect, a target sequence comprises genomic DNA. In an aspect, a target sequence is positioned within a nuclear genome. In an aspect, a target sequence comprises chromosomal DNA. In an aspect, a target sequence comprises plasmid DNA. In an aspect, a target sequence is positioned within a plasmid. In an aspect, a target sequence comprises mitochondrial DNA. In an aspect, a target sequence is positioned within a mitochondrial genome. In an aspect, a target sequence comprises plastid DNA. In an aspect, a target sequence is positioned within a plastid genome. In an aspect, a target sequence comprises chloroplast DNA. In an aspect, a target sequence is positioned within a chloroplast genome. In an aspect, a target sequence is positioned within a genome selected from the group consisting of a nuclear genome, a mitochondrial genome, and a plastid genome.

In an aspect, a target sequence comprises genic DNA. As used herein, "genic DNA" refers to DNA that encodes one or more genes. In another aspect, a target sequence comprises intergenic DNA. In contrast to genic DNA, "intergenic DNA" comprises noncoding DNA, and lacks DNA encoding a gene. In an aspect, intergenic DNA is positioned between two genes.

In an aspect, a target sequence encodes a gene. As used herein, a "gene" refers to a polynucleotide that can produce a functional unit (e.g., without being limiting, for example, a protein, or a non-coding RNA molecule). A gene can comprise a promoter, an enhancer sequence, a leader sequence, a transcriptional start site, a transcriptional stop site, a polyadenylation site, one or more exons, one or more introns, a 5'-UTR, a 3'-UTR, or any combination thereof. A “gene sequence” can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a gene encodes a non-protein-coding RNA molecule or a precursor thereof. In another aspect, a gene encodes a protein. In some embodiments, the target sequence is selected from the group consisting of: a promoter, an enhancer sequence, a leader sequence, a transcriptional start site, a transcriptional stop site, a polyadenylation site, an exon, an intron, a splice site, a 5'-UTR, a 3'-UTR, a protein coding sequence, a non-protein-coding sequence, a miRNA, a pre-miRNA and a miRNA binding site.

Non-limiting examples of a non-protein-coding RNA molecule include a microRNA (miRNA), a miRNA precursor (pre-miRNA), a small interfering RNA (siRNA), a small RNA (18 to 26 nucleotides in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single guide RNA (sgRNA). In an aspect, a non-protein-coding RNA molecule comprises a miRNA. In an aspect, a non-protein-coding RNA molecule comprises a siRNA. In an aspect, a non-protein-coding RNA molecule comprises a ta-siRNA. In an aspect, a non-protein-coding RNA molecule is selected from the group consisting of a miRNA, a siRNA, and a ta-siRNA.

As used herein, a “gene of interest” refers to a polynucleotide sequence encoding a protein or a non-protein-coding RNA molecule that is to be integrated into a target sequence, or, alternatively, an endogenous polynucleotide sequence encoding a protein or a non-protein-coding RNA molecule that is to be edited by a ribonucleoprotein. In an aspect, a gene of interest encodes a protein. In another aspect, a gene of interest encodes a non-protein-coding RNA molecule. In an aspect, a gene of interest is exogenous to a targeted DNA molecule. In an aspect, a gene of interest replaces an endogenous gene in a targeted DNA molecule.

Mutations

In an aspect, a ribonucleoprotein or method provided herein generates at least one mutation in a target sequence of an egg, embryo, and/or meiotic cell.

In an aspect, a seed produced from a plant provided herein comprises at least one mutation in a gene of interest comprising a target site as compared to a seed of a control plant of the same line or variety that lacks a first nucleic acid sequence encoding a guided nuclease operably linked to an egg cell-preferred promoter or a second nucleic acid encoding at least one guide nucleic acid operably linked to a heterologous second promoter. In an aspect, a seed produced from a plant provided herein comprises at least one mutation in a gene of interest comprising a target site as compared to a seed of a control plant of the same line or variety that lacks a first nucleic acid sequence encoding a guided nuclease operably linked to an embryo tissue-preferred promoter or a second nucleic acid encoding at least one guide nucleic acid operably linked to a heterologous second promoter.

In an aspect, a seed produced from a plant provided herein comprises at least one mutation in a gene of interest comprising a target site as compared to a seed of a control plant of the same line or variety that lacks a first nucleic acid sequence encoding a guided nuclease operably linked to a heterologous promoter or a second nucleic acid encoding at least one guide nucleic acid operably linked to an egg cell-preferred promoter. In an aspect, a seed produced from a plant provided herein comprises at least one mutation in a gene of interest comprising a target site as compared to a seed of a control plant of the same line or variety that lacks a first nucleic acid sequence encoding a guided nuclease operably linked to a heterologous promoter or a second nucleic acid encoding at least one guide nucleic acid operably linked to an embryo tissue-preferred promoter.

As used herein, a “mutation” refers to a non-naturally occurring alteration to a nucleic acid or amino acid sequence as compared to a naturally occurring reference nucleic acid or amino acid sequence from the same organism. It will be appreciated that, when identifying a mutation, the reference sequence should be from the same nucleic acid (e.g, gene, non-coding RNA) or amino acid (e.g, protein). In determining if a difference between two sequences comprises a mutation, it will be appreciated in the art that the comparison should not be made between homologous sequences of two different species or between homologous sequences of two different varieties of a single species. Rather, the comparison should be made between the edited (e.g., mutated) sequence and the endogenous, non-edited (e.g., “wildtype”) sequence of the same organism.

Several types of mutations are known in the art. In an aspect, a mutation comprises an insertion. An “insertion” refers to the addition of one or more nucleotides or amino acids to a given polynucleotide or amino acid sequence, respectively, as compared to an endogenous reference polynucleotide or amino acid sequence. In another aspect, a mutation comprises a deletion. A “deletion” refers to the removal of one or more nucleotides or amino acids to a given polynucleotide or amino acid sequence, respectively, as compared to an endogenous reference polynucleotide or amino acid sequence. In another aspect, a mutation comprises a substitution. A “substitution” refers to the replacement of one or more nucleotides or amino acids to a given polynucleotide or amino acid sequence, respectively, as compared to an endogenous reference polynucleotide or amino acid sequence. In another aspect, a mutation comprises an inversion. An “inversion” refers to when a segment of a polynucleotide or amino acid sequence is reversed end-to-end. In an aspect, a mutation provided herein comprises a mutation selected from the group consisting of an insertion, a deletion, a substitution, and an inversion.

In an aspect, a plant or seed comprises at least one mutation in a gene of interest, where the at least one mutation results in the deletion of one or more amino acids from a protein encoded by the gene of interest as compared to a wildtype protein.

In an aspect, a plant or seed comprises at least one mutation in a gene of interest, where the at least one mutation results in the substitution of one or more amino acids within a protein encoded by the gene of interest as compared to a wildtype protein.

In an aspect, a plant or seed comprises at least one mutation in a gene of interest, where the at least one mutation results in the insertion of one or more amino acids within a protein encoded by the gene of interest as compared to a wildtype protein.

Mutations in coding regions of genes (e.g., exonic mutations) can result in a truncated protein or polypeptide when a mutated messenger RNA (mRNA) is translated into a protein or polypeptide. In an aspect, this disclosure provides a mutation that results in the truncation of a protein or polypeptide. As used herein, a "truncated" protein or polypeptide comprises at least one fewer amino acid as compared to an endogenous control protein or polypeptide. For example, if endogenous Protein A comprises 100 amino acids, a truncated version of Protein A can comprise between 1 and 99 amino acids.

Without being limited by any scientific theory, one way to cause a protein or polypeptide truncation is by the introduction of a premature stop codon in an mRNA transcript of an endogenous gene. In an aspect, this disclosure provides a mutation that results in a premature stop codon in an mRNA transcript of an endogenous gene. As used herein, a "stop codon" refers to a nucleotide triplet within an mRNA transcript that signals a termination of protein translation. A "premature stop codon" refers to a stop codon positioned earlier (e.g., on the 5'-side) than the normal stop codon position in an endogenous mRNA transcript. Without being limiting, several stop codons are known in the art, including "UAG," "UAA," "UGA," "TAG," "TAA," and "TGA."

In an aspect, a seed or plant comprises at least one mutation, where the at least one mutation results in the introduction of a premature stop codon in a messenger RNA encoded by the gene of interest as compared to a wildtype messenger RNA.

In an aspect, a mutation provided herein comprises a null mutation. As used herein, a "null mutation" refers to a mutation that confers a complete loss-of-function for a protein encoded by a gene comprising the mutation, or, alternatively, a mutation that confers a complete loss-of-function for a small RNA encoded by a genomic locus. A null mutation can cause lack of mRNA transcript production, a lack of small RNA transcript production, a lack of protein function, or a combination thereof.

A mutation provided herein can be positioned in any part of an endogenous gene. In an aspect, a mutation provided herein is positioned within an exon of an endogenous gene. In another aspect, a mutation provided herein is positioned within an intron of an endogenous gene. In a further aspect, a mutation provided herein is positioned within a 5'-untranslated region of an endogenous gene. In still another aspect, a mutation provided herein is positioned within a 3'-untranslated region of an endogenous gene. In yet another aspect, a mutation provided herein is positioned within a promoter of an endogenous gene.

In an aspect, a mutation is positioned at a splice site within a gene. A mutation at a splice site can interfere with the splicing of exons during mRNA processing. If one or more nucleotides are inserted, deleted, or substituted at a splice site, splicing can be perturbed. Perturbed splicing can result in unspliced introns, missing exons, or both, from a mature mRNA sequence. Typically, although not always, a "GU" sequence is required at the 5' end of an intron and a "AG" sequence is required at the 3' end of an intron for proper splicing. If either of these splice sites are mutated, splicing perturbations can occur.

In an aspect, a seed or plant comprises at least one mutation, where the at least one mutation comprises the deletion of one or more splice sites from a gene of interest. In another aspect, a seed or plant comprises at least one mutation, where the at least one mutation is positioned within one or more splice sites from a gene of interest.

In an aspect, a mutation comprises a site-directed integration. In an aspect, a site-directed integration comprises the insertion of all or part of a desired sequence into a target sequence.

As used herein, "site-directed integration" refers to all, or a portion, of a desired sequence (e.g., an exogenous gene, an edited endogenous gene) being inserted or integrated at a desired site or locus within the plant genome (e.g., target sequence). As used herein, a "desired sequence" refers to a DNA molecule comprising a nucleic acid sequence that is to be integrated into a genome of a plant or plant cell. The desired sequence can comprise a transgene or construct. In an aspect, a nucleic acid molecule comprising a desired sequence comprises one or two homology arms flanking the desired sequence to promote the targeted insertion event through homologous recombination and/or homology-directed repair.

In an aspect, a method provided herein comprises site-directed integration of a desired sequence into a target sequence.

Any site or locus within the genome of a plant can be chosen for site-directed integration of a transgene or construct of the present disclosure. In an aspect, a target sequence is positioned within a B, or supernumerary, chromosome.

For site-directed integration, a double-strand break (DSB) or nick may first be made at a target sequence via a guided nuclease or ribonucleoprotein provided herein. In the presence of a desired sequence, the DSB or nick can then be repaired by homologous recombination (HR) between the homology arm(s) of the desired sequence and the target sequence, or by non-homologous end joining (NHEJ), resulting in site-directed integration of all or part of the desired sequence into the target sequence to create the targeted insertion event at the site of the DSB or nick.

In an aspect, site-directed integration comprises the use of NHEJ repair mechanisms endogenous to a cell. In another aspect, site-directed integration comprises the use of HR repair mechanisms endogenous to a cell.

In an aspect, repair of a double-stranded break generates at least one mutation in a gene of interest as compared to a control plant of the same line or variety.

In an aspect, a mutation comprises the integration of at least 5 contiguous nucleotides of a desired sequence into a target sequence. In an aspect, a mutation comprises the integration of at least 10 contiguous nucleotides of a desired sequence molecule into a target sequence. In an aspect, a mutation comprises the integration of at least 15 contiguous nucleotides of a desired sequence into a target sequence. In an aspect, a mutation comprises the integration of at least 20 contiguous nucleotides of a desired sequence into a target sequence. In an aspect, a mutation comprises the integration of at least 25 contiguous nucleotides of a desired sequence into a target sequence. In an aspect, a mutation comprises the integration of at least 50 contiguous nucleotides of a desired sequence into a target sequence. In an aspect, a mutation comprises the integration of at least 100 contiguous nucleotides of a desired sequence into a target sequence. In an aspect, a mutation comprises the integration of at least 250 contiguous nucleotides of a desired sequence into a target sequence. In an aspect, a mutation comprises the integration of at least 500 contiguous nucleotides of a desired sequence into a target sequence. In an aspect, a mutation comprises the integration of at least 1000 contiguous nucleotides of a desired sequence into a target sequence. In an aspect, a mutation comprises the integration of at least 2000 contiguous nucleotides of a desired sequence into a target sequence.

In an aspect, a mutation comprises the integration of between 5 contiguous nucleotides and 3500 contiguous nucleotides of a desired sequence into a target sequence. In an aspect, a mutation comprises the integration of between 5 contiguous nucleotides and 2500 contiguous nucleotides of a desired sequence into a target sequence. In an aspect, a mutation comprises the integration of between 5 contiguous nucleotides and 1500 contiguous nucleotides of a desired sequence into a target sequence. In an aspect, a mutation comprises the integration of between 5 contiguous nucleotides and 750 contiguous nucleotides of a desired sequence into a target sequence. In an aspect, a mutation comprises the integration of between 5 contiguous nucleotides and 500 contiguous nucleotides of a desired sequence into a target sequence. In an aspect, a mutation comprises the integration of between 5 contiguous nucleotides and 250 contiguous nucleotides of a desired sequence into a target sequence. In an aspect, a mutation comprises the integration of between 5 contiguous nucleotides and 150 contiguous nucleotides of a desired sequence into a target sequence. In an aspect, a mutation comprises the integration of between 25 contiguous nucleotides and 2500 contiguous nucleotides of a desired sequence into a target sequence. In an aspect, a mutation comprises the integration of between 25 contiguous nucleotides and 1500 contiguous nucleotides of a desired sequence into a target sequence. In an aspect, a mutation comprises the integration of between 25 contiguous nucleotides and 750 contiguous nucleotides of a desired sequence into a target sequence. In an aspect, a mutation comprises the integration of between 50 contiguous nucleotides and 2500 contiguous nucleotides of a desired sequence into a target sequence. In an aspect, a mutation comprises the integration of between 50 contiguous nucleotides and 1500 contiguous nucleotides of a desired sequence into a target sequence. In an aspect, a mutation comprises the integration of between 50 contiguous nucleotides and 750 contiguous nucleotides of a desired sequence into a target sequence. In an aspect, a mutation comprises the integration of between 100 contiguous nucleotides and 2500 contiguous nucleotides of a desired sequence into a target Sequence. In an aspect, a mutation comprises the integration of between 100 contiguous nucleotides and 1500 contiguous nucleotides of a desired sequence into a target Sequence. In an aspect, a mutation comprises the integration of between 100 contiguous nucleotides and 750 contiguous nucleotides of a desired sequence into a target Sequence.

In an aspect, a method provided herein comprises detecting an edit or a mutation in a target sequence. The screening and selection of mutagenized or edited plants or plant cells can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the above-referenced techniques are known in the art.

Recombinases

Several embodiments described herein relate to methods and compositions for preferably or specifically inducing site-specific recombination in egg, embryo, and/or meiotic plant tissue. Several embodiments described herein relate to methods and compositions for providing egg, embryo, and/or meiotic plant tissue preferred or specific expression of a recombinase. Several embodiments described herein relate to methods and compositions for preferably or specifically expressing a DNA modification enzyme, such as a guided nuclease (e.g., a CRISPR/Cas system), in egg, embryo, and/or meiotic plant tissue by inducing site-specific recombination to operably linking a polynucleotide encoding a DNA modification enzyme to a constitutive promoter. In some embodiments, a transcribable polynucleotide encoding a DNA modification enzyme, such as a guided nuclease (e.g., a CRISPR/Cas system) is operably linked to a constitutive promoter by recombinase-mediated excision of a intervening polynucleotide sequence preferentially or specifically in egg, embryo, and/or meiotic plant tissue.

Site-specific recombination occurs when DNA strand exchange takes place between DNA segments possessing at least some sequence homology with each other. Site-specific recombinases are able to recognize and bind to "recombination sites," which are short, specific DNA sequences which are cleaved by the recombinase, allowing the exchange of DNA strands, which is followed by strand repair. Typically, each recombinase protein binds to a specific, and unique, recombination site. As used herein, a "recombinase" refers to an enzyme that is capable of catalyzing site-specific recombination events within DNA. Recombinases are capable of excising DNA, inserting DNA, inverting DNA, translocating DNA, and/or exchanging DNA.

In an aspect, this disclosure provides methods and compositions for specifically or preferentially providing a recombinase in egg, embryo, and/or meiotic plant tissue. In an aspect, this disclosure provides a nucleic acid sequence encoding a recombinase operably linked to a promoter as described in Table 1. In an aspect, a recombinant nucleic acid construct comprises a sequence encoding at least one recombinase operably linked to a promoter as described in Table 1. In an aspect, a recombinant nucleic acid construct comprising a sequence encoding at least one recombinase operably linked to a promoter as described in Table 1 is provided to a plant cell in combination with a recombinant nucleic acid construct comprising a polynucleotide encoding a DNA modification enzyme, an intervening sequence flanked by recombination sites, and a constitutive promoter, wherein excision of the intervening sequence operably links polynucleotide encoding a DNA modification enzyme to the constitutive promoter preferentially in egg, embryo, and/or meiotic tissue.

In an aspect, a recombinase is a tyrosine recombinase. In an aspect, a tyrosine recombinase is selected from the group consisting of a Cre recombinase and a Flp recombinase.

In an aspect, a recombinase is Cre recombinase. Cre-lox is a site-specific recombination system derived from the bacteriophage P1. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete.

In an aspect, a recombinase is Flippase (Flp). The Flp-FRT site-specific recombination system comes from the 2p plasmid from the baker's yeast *Saccharomyces cerevisiae* and is similar to the Cre-lox system. Flp is capable of inducing recombination between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites.

In an aspect, a recombination site is a lox site. In an aspect, a lox site is selected from the group consisting of a loxP site, a lox 2272 site, a loxN site, a lox 511 site, a lox 5171 site, a lox71 site, a lox66 site, a loxLTR site, an M2 site, an M3 site, an M7 site, and an M11 site. In an aspect, a recombination site is an FRT site.

TALE

Several embodiments provided herein relate to the use of TALE activators to preferentially express a DNA modification enzyme, such as a guided nuclease (e.g., a CRISPR/Cas system), in egg, embryo, and/or meiotic plant tissue. In several embodiments, high levels of egg, embryo, and/or meiotic tissue specific expression of a DNA modification enzyme such as a guided nuclease (e.g., a CRISPR/Cas system), by providing to a plant cell: 1) an expression construct comprising a promoter as described in Table 1 operably linked to a sequence encoding a TALE and 2) and an expression construct comprising one or more TALE binding sites (TB) operably linked to a minimal promoter and a sequence encoding the DNA modification enzyme and generating a plant therefrom. In some embodiments, an expression construct encoding one or more guide nucleic acids is further provided. In some embodiments, levels of egg, embryo, and/or meiotic tissue specific expression of a DNA modification enzyme can be modulated by altering the number of TBs.

As used herein, "TALE protein" refers to a transcription activator-like effector (TALE) protein or a homolog thereof. TALE proteins were originally identified as a virulence factor from the phytopathogenic bacterial genera *Xanthomonas* or *Ralstonia*. These proteins are secreted by the phytopathogenic bacteria to alter transcription of host genes in plant cells. TALE proteins bind DNA in the nucleus, via a domain of DNA-binding repeats, where they act as transcriptional activators thereby contributing to virulence. The TALE moves to the nucleus, where it recognizes and binds to a specific DNA sequence in the regulatory region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs. As used herein, a "TALE binding site" (TBS) refers to a specific DNA sequence that is recognized and bound by the "TALE DNA-binding domain" of the TALE protein.

Plants

Any plant or plant cell can be used with the methods and compositions provided herein. In an aspect, a plant is selected from the group consisting of a corn plant, a rice plant, a sorghum plant, a wheat plant, an alfalfa plant, a barley plant, a millet plant, a rye plant, a sugarcane plant, a cotton plant, a soybean plant, a canola plant, a tomato plant, an onion plant, a cucumber plant, an *Arabidopsis* plant, and a potato plant. In an aspect, a plant is an angiosperm. In an aspect, a plant is a gymnosperm. In an aspect, a plant is a monocotyledonous plant. In an aspect, a plant is a dicotyledonous plant. In an aspect, a plant is a plant of a family selected from the group consisting of Alliaceae, Anacardiaceae, Apiaceae, Arecaceae, Asteraceae, Brassicaceae, Caesalpiniaceae, Cucurbitaceae, Ericaceae, Fabaceae, Juglandaceae, Malvaceae, Mimosaceae, Moraceae, Musaceae, Orchidaceae, Papilionaceae, Pinaceae, Poaceae, Rosaceae, Rutaceae, Rubiaceae, and Solanaceae.

In an aspect, a plant cell is selected from the group consisting of a corn cell, a rice cell, a sorghum cell, a wheat cell, an alfalfa cell, a barley cell, a millet cell, a rye cell, a sugarcane cell, a cotton cell, a soybean cell, a canola cell, a tomato cell, an onion cell, a cucumber cell, an *Arabidopsis* cell, and a potato cell. In an aspect, a plant cell is an angiosperm plant cell. In an aspect, a plant cell is a gymnosperm plant cell. In an aspect, a plant cell is a monocotyledonous plant cell. In an aspect, a plant cell is a dicotyledonous plant cell. In an aspect, a plant cell is a plant cell of a family selected from the group consisting of Alliaceae, Anacardiaceae, Apiaceae, Arecaceae, Asteraceae, Brassicaceae, Caesalpiniaceae, Cucurbitaceae, Ericaceae, Fabaceae, Juglandaceae, Malvaceae, Mimosaceae, Moraceae, Musaceae, Orchidaceae, Papilionaceae, Pinaceae, Poaceae, Rosaceae, Rutaceae, Rubiaceae, and Solanaceae.

As used herein, a "variety" refers to a group of plants within a species (e.g., without being limiting *Zea mays*) that share certain genetic traits that separate them from other possible varieties within that species. Varieties can be inbreds or hybrids, though commercial plants are often hybrids to take advantage of hybrid vigor. Individuals within a hybrid cultivar are homogeneous, nearly genetically identical, with most loci in the heterozygous state.

As used herein, the term "inbred" means a line that has been bred for genetic homogeneity. In an aspect, a seed provided herein is an inbred seed. In an aspect, a plant provided herein is an inbred plant.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines. In an aspect, a seed provided herein is a hybrid seed. In an aspect, a plant provided herein is a hybrid plant.

Transformation

Methods can involve transient transformation or stable integration of any nucleic acid molecule into any plant or plant cell provided herein.

As used herein, "stable integration" or "stably integrated" refers to a transfer of DNA into genomic DNA of a targeted cell or plant that allows the targeted cell or plant to pass the transferred DNA to the next generation of the transformed organism. Stable transformation requires the integration of transferred DNA within the reproductive cell(s) of the transformed organism. As used herein, "transiently transformed" or "transient transformation" refers to a transfer of DNA into a cell that is not transferred to the next generation of the transformed organism. In a transient transformation the transformed DNA does not typically integrate into the transformed cell's genomic DNA. In one aspect, a method stably transforms a plant cell or plant with one or more nucleic acid molecules provided herein. In another aspect, a method transiently transforms a plant cell or plant with one or more nucleic acid molecules provided herein.

In an aspect, a nucleic acid molecule encoding a guided nuclease is stably integrated into a genome of a plant. In an aspect, a nucleic acid molecule encoding a Cas12a nuclease is stably integrated into a genome of a plant. In an aspect, a nucleic acid molecule encoding a CasX nuclease is stably integrated into a genome of a plant. In an aspect, a nucleic acid molecule encoding a guide nucleic acid is stably integrated into a genome of a plant. In an aspect, a nucleic acid molecule encoding a guide RNA is stably integrated into a genome of a plant. In an aspect, a nucleic acid molecule encoding a single-guide RNA is stably integrated into a genome of a plant.

Numerous methods for transforming cells with a recombinant nucleic acid molecule or construct are known in the art, which can be used according to methods of the present application. Any suitable method or technique for transformation of a cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants.

In an aspect, a method comprises providing a cell with a nucleic acid molecule via *Agrobacterium*-mediated transformation. In an aspect, a method comprises providing a cell with a nucleic acid molecule via polyethylene glycol-mediated transformation. In an aspect, a method comprises providing a cell with a nucleic acid molecule via biolistic transformation. In an aspect, a method comprises providing a cell with a nucleic acid molecule via liposome-mediated transfection. In an aspect, a method comprises providing a cell with a nucleic acid molecule via viral transduction. In an aspect, a method comprises providing a cell with a nucleic acid molecule via use of one or more delivery particles. In an aspect, a method comprises providing a cell with a nucleic acid molecule via microinjection. In an aspect, a method comprises providing a cell with a nucleic acid molecule via electroporation.

In an aspect, a nucleic acid molecule is provided to a cell via a method selected from the group consisting of *Agrobacterium*-mediated transformation, polyethylene glycol-mediated transformation, biolistic transformation, liposome-mediated transfection, viral transduction, the use of one or more delivery particles, microinjection, and electroporation.

Other methods for transformation, such as vacuum infiltration, pressure, sonication, and silicon carbide fiber agitation, are also known in the art and envisioned for use with any method provided herein.

Methods of transforming cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

Delivery vehicles, vectors, particles, nanoparticles, formulations and components thereof for expression of one or more elements of a nucleic acid molecule are as used in WO 2014/093622. In an aspect, a method of providing a nucleic acid molecule or a protein to a cell comprises delivery via a delivery particle. In an aspect, a method of providing a nucleic acid molecule to a plant cell or plant comprises delivery via a delivery vesicle. In an aspect, a delivery vesicle is selected from the group consisting of an exosome and a liposome. In an aspect, a method of providing a nucleic acid molecule to a plant cell or plant comprises delivery via a viral vector. In an aspect, a viral vector is selected from the group consisting of an adenovirus vector, a lentivirus vector, and an adeno-associated viral vector. In another aspect, a method providing a nucleic acid molecule to a plant cell or plant comprises delivery via a nanoparticle. In an aspect, a method providing a nucleic acid molecule to a plant cell or plant comprises microinjection. In an aspect, a method providing a nucleic acid molecule to a plant cell or plant comprises polycations. In an aspect, a method providing a nucleic acid molecule to a plant cell or plant comprises a cationic oligopeptide.

In an aspect, a delivery particle is selected from the group consisting of an exosome, an adenovirus vector, a lentivirus vector, an adeno-associated viral vector, a nanoparticle, a polycation, and a cationic oligopeptide. In an aspect, a method provided herein comprises the use of one or more delivery particles. In another aspect, a method provided herein comprises the use of two or more delivery particles. In another aspect, a method provided herein comprises the use of three or more delivery particles.

Suitable agents to facilitate transfer of nucleic acids into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning includes (a) surfactants, (b) organic solvents, aqueous solutions, or aqueous mixtures of organic solvents, (c) oxidizing agents, (e) acids, (f) bases, (g) oils, (h) enzymes, or combinations thereof.

Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e. g., plant-sourced oils, crop oils (such as those listed in the 9$^{th}$ Compendium of Herbicide Adjuvants, publicly available on line at www(dot) herbicide(dot)adjuvants(dot)com) can be used, e. g., paraffinic oils, polyol fatty acid esters, or oils with short-chain molecules modified with amides or polyamines such as polyethyleneimine or N-pyrrolidine.

Examples of useful surfactants include sodium or lithium salts of fatty acids (such as tallow or tallowamines or phospholipids) and organosilicone surfactants. Other useful surfactants include organosilicone surfactants including nonionic organosilicone surfactants, e. g., trisiloxane ethoxylate surfactants or a silicone polyether copolymer such as a copolymer of polyalkylene oxide modified heptamethyl trisiloxane and allyloxypolypropylene glycol methylether (commercially available as Silwet® L-77).

Useful physical agents can include (a) abrasives such as carborundum, corundum, sand, calcite, pumice, garnet, and the like, (b) nanoparticles such as carbon nanotubes or (c) a physical force. Carbon nanotubes are disclosed by Kam et. al. (2004) Am. Chem. Soc, 126 (22):6850-6851, Liu et. al. (2009) Nano Lett, 9(3): 1007-1010, and Khodakovskaya et. al. (2009) ACS Nano, 3(10):3221-3227. Physical force agents can include heating, chilling, the application of positive pressure, or ultrasound treatment. Embodiments of the method can optionally include an incubation step, a neutralization step (e.g., to neutralize an acid, base, or oxidizing agent, or to inactivate an enzyme), a rinsing step, or combinations thereof. The methods of the invention can further include the application of other agents which will have enhanced effect due to the silencing of certain genes. For example, when a polynucleotide is designed to regulate genes that provide herbicide resistance, the subsequent application of the herbicide can have a dramatic effect on herbicide efficacy.

Agents for laboratory conditioning of a plant cell to permeation by polynucleotides include, e.g., application of a chemical agent, enzymatic treatment, heating or chilling, treatment with positive or negative pressure, or ultrasound treatment. Agents for conditioning plants in a field include chemical agents such as surfactants and salts.

In an aspect, a transformed or transfected cell is a plant cell. Recipient plant cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a guard cell, a trichome cell, a root hair cell, a storage root cell, or a tuber cell. In another aspect, this disclosure provides a protoplast. In another aspect, this disclosure provides a plant callus cell. Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference. Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In one aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction. In one aspect, this disclosure provides a non-reproductive plant cell.

Use of Haploids/Haploid Induction Lines

Several embodiments relate to the use of the methods and compositions as described herein in combination with haploid induction techniques. As used herein, a "haploid" cell or nucleus comprises a single set of unpaired chromosomes (x). In contrast, a "diploid" cell or nucleus comprises two complete sets of chromosomes (2x) that are capable of homologous pairing. As used herein, a "haploid plant" describes a sporophyte comprising a plurality of cells comprising a haploid nuclear genome. A haploid plant provided herein can be a maternal haploid plant, meaning it has lost its paternal nuclear genome while retaining its maternal nuclear genome. Alternatively, a haploid plant provided herein can be a paternal haploid plant, meaning it has lost its maternal nuclear genome while retaining its paternal nuclear genome. Typically, maternal mitochondria and plastid (e.g., chloroplast) genomes are retained in both maternal and paternal haploid plants.

In some embodiments, a 'doubled haploid (DH)' method is used to rapidly produce homozygous plants. Progenies of DH plants are genetically homogeneous material, allowing breeders to evaluate their traits of interest on genetically fixed material at an early stage of the breeding cycle, thus increasing breeding efficiency (see Gilles L M et. al. Curr Biol. 2017 Oct. 23; 27(20):R1095-R1097. The DH technology relies on two main steps: (1) a haploid induction system to generate haploid embryos or plantlets, and (2) a chromosome doubling step to restore diploidy of these plantlets.

"Haploid induction (HI)" is a phenomena in some plants characterized by loss of the parental inducer chromosomes during embryo development. As used herein, a "haploid induction (HI) plant" is a plant capable of inducing haploidization in a progeny plant by eliminating one set of chromosomes. Maternal haploid induction is triggered by the pollinator (male) parent. Paternal haploid induction is triggered by the female parent.

Haploid inducer lines are routinely used in plant breeding especially for maize. A number of known haploid-inducing maize lines exist including but not limited to: stock 6, MHI (Moldovian Haploid Inducer), indeterminate gametophyte (ig 1) mutation, KEMS, RWK, ZEM, ZMS, KMS. Haploid inducer lines have also been created in *Arabidopsis thaliana*, *Brassica juncea* and maize by the use of engineered centromeric histone 3 (CENH3) variants (See Ravi and Chan. 2010. Nature. 464:615-6190). In some aspects, the haploid induction lines described here include the Maize Stock 6 line, maize plants harboring mutations in the ig-1 locus, MHI inducer lines, KEMS inducer lines, RWK inducer lines, ZEM inducer lines, ZMS inducer lines, KMS inducer lines. In some aspects the Haploid inducer line comprises a modified MATRILINEAL/NOT LIKE DAD/ZmPHOSPHOLIPASE-A1 (MATL/NLD/ZmPLA1) gene. In some aspects, the haploid inducer line described herein comprises a modified CEN H3 variant.

The benefits offered by haploid induction systems to crop breeding programs are diverse, as DH technology can be used in conjunction with several different molecular techniques to overcome various constraints to crop improvement. One example is the use of haploid induction systems to expand the application of genome editing technologies to crops. The genome editing component (for e.g., the guided nuclease) could be introduced into the Haploid Inducer line which is then crossed to a non-inducer maize line. The haploid progeny is then screened for nuclease-induced mutations and genome doubling is subsequently induced to produce diploid, editing component-free, genome-edited cultivars. This methodology has been described in detail in US20190169596 (Application U.S. Ser. No. 16/275,200) and is incorporated herein by reference in its entirety.

The present disclosure will now be described with reference to the following examples. It should be appreciated that these examples are not intended to limit the scope of the claims to the present disclosure; but are rather intended to be examples of certain embodiments. Any variations in the exemplified methods that occur to the skilled artisan are intended to fall within the scope of the present disclosure.

EXAMPLES

Example 1. Expression of Cas12a in Meiotic Egg Cells or Embryo Tissue to Generate Germinal Mutations or Targeted Integration of Template DNA Several *Agrobacterium* T-DNA vectors were generated to preferentially express Cas12a in corn egg cells and/or corn embryo cells undergoing meiosis (meiocytes). See Table 2.

TABLE 2

Cassettes designed to express Cas12a preferentially, or solely, in corn egg cells and/or corn embryo cells and/or cells undergoing meiosis.

| Construct | Promoter::LbCas12a | Expression | Promoter SEQ ID NO. |
|---|---|---|---|
| 1 | ZmDSUL1::LbCas12a | Embryo | 1 |
| 2 | ZmEA1::LbCas12a | Egg/Embryo | 2 |
| 3 | ZmES4::LbCas12a | Egg/Embryo | 3 |
| 4 | ZmDMC1::LbCas12a | Meiocyte | 4 |
| 5 | ZmMps1::LbCas12a | Meiocyte | 5 |
| 6 | ZmAdf1::LbCas12a | Meiocyte | 6 |

The plant codon optimized LbCas12a sequence (SEQ ID NO: 7) in these cassettes was flanked by NLS sequences at the 5' and 3' ends (SEQ ID:8 and SEQ ID:9) and operably linked to a transcription terminator sequence from a rice Lipid transfer protein (LTP) gene (described in US20200080096 as SEQ ID NO:8). Each vector also contained an expression cassette encoding a Cas12a gRNA targeting a unique corn genomic site (ZmTS1) under the control of the Pol III ZmU6 promoter (SEQ ID NO: 10); an expression cassette flanked by ZmTS1 target sites, where the cassette comprised a constitutive promoter operably linked to a Gene of Interest (GOI); and an expression cassette for a selectable marker conferring resistance to the herbicide glyphosate. Corn 01DKD2 cultivar embryos were transformed with the vectors described above by *agrobacterium*-mediated transformation and R0 plants were regenerated from the transformed corn cells. DNA was extracted from leaf samples from 59-153 R0 seedlings generated from each construct. The genomic target site was sequenced and analyzed for the presence of targeted mutations. A Taqman based assay was also performed to identify the copy number of the Cas12a carrying construct. For all reproductive promoters except ZmDSUL, no mutations were detected at ZmTS1 site in the R0 generation. The ZmDSUL:LbCas12a (Construct 1), showed about a 32% target site mutation rate in the R0 seedlings (See Table 3). Lack of mutations at the ZmTS1 target site in the newly transformed (or R0) plants is expected where LbCas12a expression is confined to the reproductive tissue.

20 R0 lines from each transformed construct were grown to maturity and at least one ear from each transformed corn plant was self-pollinated. 10 R1 lines were selected and up to 16 seedlings per line were germinated, screened for mutations in ZmTS1 and the mutation rates (cutting rates) were calculated. Taqman assays were also performed to determine the presence and copy number of the LbCas12a expression cassette. The overall target site mutation rate among all lines generated from Constructs 2-5 ranged from about a 1.1% to 14%. The average mutation rates are shown in Table 3. 4 R1 seedlings expressing ZmDSUL::LbCas12a (Construct 1) were tested and no mutations were observed. Co-expression of Cas12a and its cognitive gRNA in cells undergoing meiosis are expected to generate a double stranded break at the ZmTS1 target site and subsequent imperfect DNA repair generates unique mutations in egg cells and embryos created by the pollination.

TABLE 3

Average mutation rates observed at ZmTS1 target site in R0 and R1 plants

| | Promoter | | | | | |
|---|---|---|---|---|---|---|
| Construct | ZmDMC1 4 | ZmMps1 5 | ZmAdf1 6 | ZmES4 3 | ZmEA1 2 | DSUL1 1 |
| Expression | Meiotic | Meiotic | Meiotic | Egg/ Embryo | Egg/ Embryo | Embryo |
| R0 Events tested | 153 | 110 | 153 | 81 | 115 | 59 |
| R0 Cutting Rate (Avg.) | 0% | 0% | 0% | 0% | 0% | 32% |
| R1 Cutting (Avg.) | 7.69% | 2.67% | 1.10% | 14.04% | 3.60% | 0.00% |

Mutation rates in R1 plants generated from individual R0 lines can vary as shown in Tables 4-8. For example, in the highest cutting promoter, ZmES4, some lines with single copy Cpf1 cassette showed 0% mutation rate, while another line showed about an 11% mutation rate. The highest mutation rate observed was 46%, which originated from an R0 line that had two copies of ZmES4:LbCas12a. In the ZmES4:Cas12a plants, consistently among all lines tested, R0 lines with 2 copies of Cas12a had a higher target mutation rate than one copy R0 lines (see Table 7).

TABLE 4

Mutation rates in R1 seedlings from pZmDMC1::LbCas12a transformed Corn plants.

| R0 Event | Number of R1 plants | Number Cas12a+ plants | Number Cas12a+ Mutation+ | % mutations in Cas12a+ plants | Cas12a Copy number |
|---|---|---|---|---|---|
| ZM_S22307337 | 13 | 10 | 0 | 0.00% | 1 |
| ZM_S22307366 | 12 | 8 | 0 | 0.00% | 1 |
| ZM_S22307385 | 15 | 11 | 0 | 0.00% | 1 |
| ZM_S22307402 | 16 | 14 | 0 | 0.00% | 1 |
| ZM_S22307410 | 16 | 14 | 3 | 21.43% | 1 |

TABLE 4-continued

Mutation rates in R1 seedlings from pZmDMC1::LbCas12a transformed Corn plants.

| R0 Event | Number of R1 plants | Number Cas12a+ plants | Number Cas12a+ Mutation+ | % mutations in Cas12a+ plants | Cas12a Copy number |
|---|---|---|---|---|---|
| ZM_S22307411 | 16 | 13 | 1 | 7.69% | 1 |
| ZM_S22307475 | 14 | 11 | 1 | 9.09% | 1 |
| ZM_S22307488 | 12 | 11 | 1 | 9.09% | 1 |
| ZM_S22307495 | 15 | 12 | 1 | 8.33% | 2 |

TABLE 5

Mutation rates in R1 seedlings from pZmMPS4::LbCas12a transformed Corn plants.

| R0 Event | Number of R1 plants | Number Cas12a+ plants | Number Cas12a+ Mutation+ | % Mutant in Cas12a+ plants | Cas12a copy number |
|---|---|---|---|---|---|
| ZM_S22324677 | 15 | 12 | 1 | 8.33% | 2 |
| ZM_S22324740 | 16 | 12 | 0 | 0.00% | 1 |
| ZM_S22324702 | 13 | 8 | 0 | 0.00% | 1 |
| ZM_S22324681 | 16 | 9 | 0 | 0.00% | 1 |
| ZM_S22324728 | 16 | 14 | 0 | 0.00% | 2 |
| ZM_S22324698 | 15 | 11 | 0 | 0.00% | 1 |
| ZM_S22324652 | 14 | 10 | 1 | 10.00% | 2 |
| ZM_S22324654 | 16 | 9 | 1 | 11.11% | 1 |
| ZM_S22324675 | 15 | 14 | 1 | 7.14% | 1 |
| ZM_S22324723 | 13 | 10 | 0 | 0.00% | 1 |

TABLE 6

Mutation rates in R1 seedlings from pZmAdf1::LbCas12a transformed Corn plants.

| R0 Event | Number of R1 plants | Number Cas12a+ plants | Number Cas12a+ Mutation+ | % mutant in Cas12a+ plants | Cas12a copy number |
|---|---|---|---|---|---|
| ZM_S22309320 | 16 | 12 | 1 | 8.33% | 2 |
| ZM_S22309333 | 11 | 8 | 0 | 0.00% | 1 |
| ZM_S22309363 | 14 | 9 | 0 | 0.00% | 1 |
| ZM_S22309387 | 16 | 13 | 0 | 0.00% | 1 |
| ZM_S22309393 | 15 | 9 | 0 | 0.00% | 1 |
| ZM_S22309410 | 14 | 9 | 0 | 0.00% | 1 |
| ZM_S22309419 | 12 | 10 | 0 | 0.00% | 1 |
| ZM_S22309422 | 14 | 10 | 0 | 0.00% | 1 |
| ZM_S22309465 | 14 | 11 | 0 | 0.00% | 1 |

TABLE 7

Mutation rates in R1 seedlings from pZmES4::LbCas12a transformed Corn plants.

| R0 Event | Number of R1 plants | Number Cas12a+ plants | Number Cas12a + Mutation+ | % mutant in Cas12a+ plants | LbCas12a Copy Number |
|---|---|---|---|---|---|
| ZM_S22321323 | 16 | 13 | 6 | 46.15% | 2 |
| ZM_S22321283 | 15 | 9 | 0 | 0.00% | 1 |
| ZM_S22321299 | 15 | 11 | 4 | 36.36% | 2 |
| ZM_S22321291 | 15 | 8 | 1 | 12.50% | 2 |
| ZM_S22321261 | 15 | 11 | 0 | 0.00% | 1 |
| ZM_S22321307 | 13 | 12 | 3 | 25.00% | 2 |
| ZM_S22321298 | 16 | 12 | 1 | 8.33% | 1 |
| ZM_S22321335 | 13 | 9 | 3 | 33.33% | 2 |
| ZM_S22321326 | 10 | 9 | 1 | 11.11% | 1 |
| ZM_S22321262 | 14 | 13 | 1 | 7.69% | 1 |

TABLE 8

Mutation rates in R1 seedlings from pZmEA1::LbCas12a transformed Corn plants.

| R0 Event | Number of R1 plants | Number Cas12+a plants | Number Cas12a+ Mutation+ | % Mutations in Cas12a+ plants | Cas12a copy number |
|---|---|---|---|---|---|
| ZM_S22317328 | 12 | 9 | 1 | 11.11% | 1 |
| ZM_S22317003 | 14 | 10 | 1 | 10.00% | 1 |
| ZM_S22317338 | 14 | 10 | 2 | 20.00% | 1 |
| ZM_S22317300 | 15 | 10 | 0 | 0.00% | 1 |
| ZM_S22317305 | 13 | 9 | 0 | 0.00% | 1 |
| ZM_S22316987 | 16 | 12 | 1 | 8.33% | 1 |
| ZM_S22317322 | 15 | 10 | 0 | 0.00% | 1 |
| ZM_S22317345 | 16 | 11 | 0 | 0.00% | 1 |
| ZM_S22316989 | 13 | 11 | 0 | 0.00% | 1 |
| ZM_S22317296 | 10 | 8 | 0 | 0.00% | 1 |

TABLE 9

Mutation rates in R1 seedlings from pZmEDSUL1::LbCas12a transformed Corn plants.

| R0 Event | Number of R1 plants | Number Cas12a+ plants | Number Cas12a+ Mutation+ | % mutations in Cas12a+ plants | Cas12a copy number |
|---|---|---|---|---|---|
| ZM_S22307430 | 13 | 10 | 0 | 0.00% | 1 |
| ZM_S22307433 | 12 | 8 | 0 | 0.00% | 1 |
| ZM_S22307451 | 14 | 10 | 0 | 0.00% | 1 |
| ZM_S22307456 | 15 | 7 | 0 | 0.00% | 1 |

To increase confidence in the targeted mutation rate, three R0 lines were selected from ZmES4:LbCas12a transformants. For the selected lines, 152, 112, and 86 R1 seedlings were screened. The mutation rates were 74.2%, 49.4%, and 8.3%, respectively. The lines with 74.2% and 49.4% observed mutation rates were R1 seeds from a R0 line that had 2 copies of ZmES4:Cas12a.

Unique targeted mutations in R1 plants: Two R0 lines (ZM_S22321326 and ZM_S22321323) from ZmES4::LbCas12a, which is expected to selectively express LbCas12a in egg and synergid cells, were analyzed to assess the types of mutations created. Five mutant plants were produced from the ZM_S22321326 line. The sequencing results from the ZmTS1 gRNA target loci indicated that all five plants had unique mutations at the target site. 49 mutant seedlings were analyzed from the ZM_S22321323 R0 line which had two copies of ZmES4:LbCas12a. Out of 49 mutant seedlings, 56 target site mutations were identified. This suggests that some plants contained heterologous mutations. The 49 plants had a total of 23 unique mutations.

TABLE 10

Type and number of unique mutations observed in R1 plants from ZmES4::LbCas12a R0 ZM_S22321326 event.

| | ZM_S22321326 | |
|---|---|---|
| Mutation | Mutation Type | # of Mutations |
| 1 | 1 bp deletion at nucleotide 16 of the target site | 1 |
| 2 | 9 bp deletion at nucleotide 16 of the target site | 1 |
| 3 | 8 bp deletion at nucleotide 17 of the target site | 1 |
| 4 | 7 bp deletion at nucleotide 15 of the target site | 1 |
| 5 | 2 bp deletion at nucleotide 23 of the target site | 1 |
| | Total | 5 |

TABLE 11

Type and number of unique mutations observed in R1 plants from ZmES4::LbCas12a R0 ZM_S22321323 event.

| | ZM_S22321323 | |
|---|---|---|
| Mutation | Mutation Type | # of Mutations |
| 1 | 8 bp deletion at nucleotide 17 of the target site | 9 |
| 2 | 10 bp deletion at nucleotide 15 of the target site | 6 |
| 3 | 7 bp deletion at nucleotide 15 of the target site | 4 |
| 4 | 2 bp deletion at nucleotide 15 of the target site | 2 |
| 5 | 12 bp deletion at nucleotide 16 of the target site | 1 |
| 6 | 35 bp deletion at nucleotide 2 of the target site | 2 |
| 7 | 240 bp deletion at nucleotide 15 of the target site | 1 |
| 8 | 229 bp deletion at nucleotide 15 of the target site | 2 |
| 9 | 9 bp deletion at nucleotide 16 of the target site | 10 |
| 10 | 7 bp deletion at nucleotide 20 of the target site | 1 |
| 11 | 13 bp deletion at nucleotide 15 of the target site | 2 |
| 12 | 10 bp deletion at nucleotide 13 of the target site | 2 |
| 13 | 1nucletide substitution at position 15 of the target site and a 12 bp deletion starting at position 16 of the target site | 1 |
| 14 | 14 bp deletion at nucleotide 14 of the target site | 2 |
| 15 | 10 bp deletion at nucleotide 16 of the target site | 1 |
| 16 | 11 bp deletion at nucleotide 10 of the target site | 1 |
| 17 | 1 bp deletion at nucleotide 1 of the target site | 1 |
| 18 | 6 bp deletion at nucleotide 15 of the target site | 1 |
| 19 | 17 bp deletion at nucleotide 13 of the target site | 1 |
| 20 | 13 bp deletion at nucleotide 15 of the target site | 3 |
| 21 | 1 nucleotide substitution at position 8 of the target site | 1 |
| 22 | 8 bp deletion at nucleotide 14 of the target site | 1 |
| 23 | 8 bp deletion at nucleotide 18 of the target site | 1 |
| | Total | 56 |

Testing for Site Directed Integration of Template DNA in Plants Expressing Cas12a.

In addition to the Cas12a and gRNA expression cassette, each vector also contained an expression cassette for a gene of interest (GOI) that was flanked by the ZmTS1 gRNA target sequences. Expression of Cas12a in reproductive tissues is expected to create double stranded breaks on both sides of the GOI cassette releasing it from the T-DNA. This released DNA could serve as a donor for targeted insertion at the genomic ZmTS1 target site. When the CRISPR-Cpf1 complex cuts the target site within the genome, the non-homologous end joining (NHEJ) DNA repair pathway could insert the donor GOI cassette into the genomic target site. This form of SDI is also known as trans-fragment targeting (TFT). To test for SDI by TFT, flank PCR assays similar to those described in WO2019084148 were used to identify putative targeted insertions. Primers were designed to PCR amplify the expected insertion flanking sequence. Four separate PCR reactions were carried out: a left flank PCR and a right flank PCR for potential inserts that were positioned in the sense orientation, and a left flank PCR and a right flank PCR for inserts that were positioned in the antisense direction. In the initial screen of R0 lines, two plants showed flank positive PCRs. Both were identified in ZmES4:LbCas12a line and both produced only one flank PCR product. While one flank positive plant was in a line with an established mutation rate (11.11%), the other flank positive plant was in a line that had 0% mutation rate.

Taken together, the data shows that reproductive editing can be achieved when LbCas12a is expressed under the control of the promoter DMC1, Mps1 or Adf1 that preferentially or solely express in cells undergoing meiosis. Reproductive editing can also be achieved when LbCas12a is expressed by the Egg or Embryo expressing promoters like ZmES4 and ZmEA1. Additionally, the data demonstrates that a single R0 plant can produce many R1 offspring each with unique target site edits. This suggests that these promoters can be used to drive the expression of nucleases so as to increase the frequency of unique edits produced per transformed plants.

Germinal Mutations are Heritable to the F1 Generation

Two R1 individuals from the ZmES4::LbCas12a R0 event ZM_S22321323 were grown to maturity and cross pollinated with a wild type 01DKD2 tester. R1 plant-1 comprised a 7 bp deletion at nucleotide 15 of the target site (see mutation 3 in Table 11) and R1 plant-2 comprised a 9 bp deletion at nucleotide 16 of the target site (see mutation 9 in Table 11). 32 seedlings for each of the F1 lines were planted and screened for inheritance of mutations in ZmTS1 target site. 11 of the 32 F1 seedlings from Plant-1 cross germinated and 6 of them inherited the R1 event specific mutation. 5 of the 32 seedlings from plant-2 cross germinated and 3 of them inherited the R1 event specific mutation.

Example 2. Expression of Cas12a in Cells Undergoing Meiosis to Generate Germinal Mutations Several constructs are generated to preferentially express Cas12a in corn cells undergoing meiosis, in corn egg cells and/or corn embryos. See Table 12.

TABLE 12

Cassettes designed to express Cas12a preferentially, or solely, in cells undergoing meiosis, corn egg cells and/or in corn embryos.

| Construct | Promoter::LbCas12a | Expression | Promoter SEQ ID NO. |
|---|---|---|---|
| 7 (Control) | ZmUbqM1::LbCas12a | Constitutive | 11 |
| 8 | ZmDSUL1::LbCas12a | Embryo | 1 |
| 9 | ZmEA1::LbCas12a | Egg/Embryo | 2 |
| 10 | ZmES4::LbCas12a | Egg/Embryo | 3 |
| 11 | ZmDMC1::LbCas12a | Meiotic | 4 |
| 12 | ZmMps1::LbCas12a | Meiotic | 5 |
| 13 | ZmAdf1::LbCas12a | Meiotic | 6 |

The plant codon optimized LbCas12a sequence (SEQ ID NO: 7) in the expression cassettes described in Table 12 is flanked by NLS sequences at the 5' and 3' ends (SEQ ID:8 and SEQ ID:9). Each construct described in Table 12 is introduced simultaneously with a construct ("gRNA construct") encoding a gRNA complementary to a target site under the control of the Pol III ZmU6 promoter (SEQ ID NO: 10) into corn cells using biolistic transformation methods routinely used in the art. Alternatively, the constructs described in Table 12 can be transformed either biolistically or through an *Agrobacterium* T-DNA vector into cells containing a gRNA construct. The resulting transformed corn cells comprise one of constructs 7-13, as well as the gRNA construct. Corn plants are regenerated from the transformed corn cells and grown to maturity. At least one ear from each transformed corn plant is pollinated. Seed resulting from the pollination is screened for mutations in the target site and the number and types of mutations produced using constructs 8-13 is compared to the transformed corn plants produced using construct 7. Co-expression of Cas12a from constructs 8-13 and its cognitive guide RNA from the gRNA construct is expected to result in double stranded breaks in the genomic DNA at the target site, with subsequent DNA repair generating one or more unique mutations.

Example 3. Expression of gRNA in Egg or Embryo Tissue with a Constitutively-Expressed Cas12a to Generate Germinal Mutations Several constructs are generated to preferentially express a guide RNA (gRNA) complementary to a target site under the control of a Pol II promoter in meiotic cells, corn egg cells and/or corn embryos. See Table 3. Following transcription, Pol-II products are rapidly modified with a 5' cap and poly-A tail and exported from the nucleus. These modifications and altered localization could prevent efficient use of gRNA. To optimize the gRNA availability and performance, self-cleaving ribozymes are incorporated into the gRNA cassette design. It has been reported that self-cleaving ribozymes facilitate cleavage/processing of the gRNA transcript from Pol II expressed transcripts to produce the precise guide molecule (see Wang et. al., 2018, J. of Integrative Plant Biol, 60:8, 626-631).

TABLE 13

Constructs designed to express a gRNA preferentially, or solely, in corn egg cells and/or corn embryos.

| Construct | Promoter::gRNA | Promoter SEQ ID NO. |
|---|---|---|
| 14 (Control) | ZmUbqM1::ribozyme-gRNA-ribozyme | 11 |
| 15 | ZmDSUL1::ribozyme-gRNA-ribozyme | 1 |
| 16 | ZmEA1::ribozyme-gRNA-ribozyme | 2 |
| 17 | ZmES4::ribozyme-gRNA-ribozyme | 3 |
| 18 | ZmDMC1::ribozyme-gRNA-ribozyme | 4 |
| 19 | ZmMps1::ribozyme-gRNA-ribozyme | 5 |
| 20 | ZmAdf1::ribozyme-gRNA-ribozyme | 6 |

The constructs described in Table 13 are stably introduced into corn cells using transformation methods routinely used in the art. Additionally, a construct ("Cas12a construct") comprising a plant codon optimized nucleic acid sequence encoding a Cas12a protein (SEQ ID NO: 1) flanked by NLS sequences at the 5' and 3' ends (SEQ ID:2 and SEQ ID:3) and under the control of a ubiquitous ZmUbgM1 promoter (SEQ ID NO: 11) is co-introduced with each construct provided in Table 13. The resulting transformed corn cells comprise one of constructs 14-20, as well as the Cas12a construct. Corn plants are regenerated from the transformed corn cells and grown to maturity. At least one ear from each transformed corn plant is pollinated. Seed resulting from the pollination is screened for mutations in the target site, and the number and type of mutations produced using constructs 15-20 is compared to the transformed corn plants produced using construct 14. Selective expression of gRNA is expected to generate one or more unique mutations in each meiotic cell, egg cell, or in each embryo created by the pollination.

Example 4. Expression of Cas12a and gRNA as a Single Transcript in Cells Undergoing Meiosis, Egg Cells or Embryo Tissue to Generate Germinal Mutations Several constructs are generated to preferentially express LbCas12a and a guide RNA (gRNA) complementary to a target site as a single transcript in cells undergoing meiosis, corn egg cells and/or corn embryos. See Table 14.

TABLE 14

Constructs designed to express a LbCas12a and a gRNA flanked by self-cleaving ribozymes in a single transcript in meiotic cells, corn egg cells and/or corn embryos.

| Construct | Promoter::gRNA | Promoter SEQ ID NO. |
|---|---|---|
| 21 (Control) | ZmUbqM1::LbCas12a-ribozyme-gRNA-ribozyme | 11 |
| 22 | ZmDSUL1::LbCas12a-ribozyme-gRNA-ribozyme | 1 |
| 23 | ZmEA1::LbCas12a-ribozyme-gRNA-ribozyme | 2 |
| 24 | ZmES4::LbCas12a-ribozyme-gRNA-ribozyme | 3 |
| 25 | ZmDMC1::LbCas12a-ribozyme-gRNA-ribozyme | 4 |
| 26 | ZmMps1::LbCas12a-ribozyme-gRNA-ribozyme | 5 |
| 27 | ZmAdf1::LbCas12a-ribozyme-gRNA-ribozyme | 6 |

Each construct described in Table 14 is stably introduced into corn cells using biolistic transformation methods or *agrobacterium* transformation methods routinely used in the art. The resulting transformed corn cells comprise one of constructs 21-27. Corn plants are regenerated from the transformed corn cells and grown to maturity. At least one ear from each transformed corn plant is pollinated. The LbCas12a and gRNA are transcribed as part of a single transcript in cells where the promoter expresses. Subsequently, ribozyme mediated cleavage occurs releasing the gRNA segments. LbCas12a protein transcribed from the transcript forms ribonucleoproteins (RNPs) with the gRNAs. The RNPs will generate a double-stranded break at the target site and subsequent repair will generate one or more unique mutations in each meiotic cell, egg cell, or in each embryo created by the pollination. Seed resulting from the pollination is screened for mutations in the target site and the number and type of mutations produced using constructs 22-27 is compared to the transformed corn plants produced using construct 21.

Example 5. Generating Mutations Via Crossing

Transgenic corn plants comprising one of Constructs 8-13 (see Example 2, Table 2) are generated and grown to flowering stage. An additional transgenic corn plant comprising the gRNA construct of Example 2 is also generated and grown to flowering stage. The corn plants comprising one of Constructs 8-13 are crossed with the corn pant comprising the gRNA construct, generating progeny corn plants comprising Cas12a and the gRNA being expressed in the resulting embryos.

Alternatively, transgenic corn plants comprising one of Constructs 15-20 (see Example 3, Table 13) are generated and grown to flowering stage. An additional transgenic corn plant comprising the Cas12a construct of Example 3 is also generated and grown to flowering stage. The corn plants comprising one of Constructs 15-20 are crossed with the corn pant comprising the Cas12a construct, generating progeny corn plants comprising Cas12a and the gRNA being expressed in the resulting embryos.

Co-expression of Cas12a and the gRNA generate a double-stranded break within the target site, thereby generating a unique mutation in each cell where the both components of the CRISPR system are expressed. Resulting embryos, or plants arising from the resulting embryos, are screened to identify mutations in the target site.

Example 6. Expression of Cas12a During Meiosis, in Egg Cells or Embryo Tissue of Reciprocal F1s to Generate Different Germinal Mutations R1 seeds containing T-DNA vectors that preferentially express Cas12a in corn meiotic tissue, egg and/or corn embryo cells as described in Example 1 were planted. See Table 15 for a list of constructs.

TABLE 15

Cassettes to express Cas12a preferentially, or solely, in corn zygotes or embryos.

| Construct | Promoter::LbCas12a::terminator (3'UTR) | Promoter SEQ ID NO. |
|---|---|---|
| 6 | ZmAdf1::LbCas12a::OsLTP$_{Term}$ | 6 |
| 5 | ZmMps1::LbCas12a::OsLTP$_{Term}$ | 5 |
| 4 | ZmDMC1::LbCas12a::OsLTP$_{Term}$ | 4 |
| 3 | ZmES4::LbCas12a::OsLTP$_{Term}$ | 3 |

R1 individuals from each transformed construct representing 4-10 independent events per construct were grown to maturity and reciprocal crosses were attempted with all individuals. F1 seeds were recovered from 6-29 crosses per direction per construct. Up to 72 seedlings from each F1 ear were germinated, screened for mutations in the ZmTS1 target site and the mutation rates (cutting rates) were calculated. See Table 16.

TABLE 16

Total events and samples screened in F1 reciprocal cross progeny

| Promoter driving Cas12a | Event parent | Total events | Total F1 samples |
|---|---|---|---|
| ZmAdf1 | female | 14 | 508 |
| | Male | 10 | 85 |
| ZmDMC1 | female | 6 | 94 |
| | Male | 4 | 21 |
| ZmMps1 | female | 6 | 169 |
| | Male | 5 | 43 |

TABLE 16-continued

Total events and samples screened in F1 reciprocal cross progeny

| Promoter driving Cas12a | Event parent | Total events | Total F1 samples |
|---|---|---|---|
| ZmES4 | female | 8 | 652 |
| | Male | 7 | 194 |

Taqman assays were performed to determine the copy number of the LbCas12a expression cassette. The overall target site mutation rate among all F1s ranged from 0 to 14%, and showed directional expression (FIG. 1 and Table 16).

F1 mutation rate was compared to the mutation rate from the event parent (R1) in order to determine how many new edits (present in F1 and not in the R1 parent) were generated. These data are summarized in FIG. 1. The ZmES4: LbCas12a construct showed the highest rate of cutting from the female (average of 12% of samples containing new edits). ZmDMC1:LbCas12a showed the highest rate of cutting from the male (average of 14% of samples containing new edits).

ZmES4:LbCas12a not only produced a high percentage of F1 plants with new edits when carried by the female parent, it also produced a high number of unique edits in the F1 plants (FIG. 1, Table 17). When carried by the female parent, ZmES4:LbCas12a produced 39 different mutation types as detected in F1 plants. The other promoters tested produced a maximum of 4 unique edits types in 1 progeny (see FIG. 1).

The new edits observed in the ZmES4:LbCas12a F1 plants were highly abundant. Sequencing of the target site showed 40%-100% of the sequencing reads containing the mutant alleles, indicating these edits are made early in embryo/zygote development and are thus fixed in the plant (Table 17). Edits that become fixed in the plant will be present in that plant's germline and thus inherited in its progeny.

ZmES4 retains high embryo/zygote expression generation after generation, and many independent events show functional activity of LbCas12a. Nearly every edited plant in each event contains a unique edit (Table 17). Moreover, all but one ZmES4 event tested produced new edits, with mutation rates per event of up to 20% (Table 17).

TABLE 17

ZmES4::LbCas12a editing summary in F1s by event.

| Event | Event parent | Total Samples (Cas12a+) | Total samples with edits* | Total samples with new** edits | Total samples with new heritable edits$ | % samples with edits | % samples with new edits | % samples with new heritable edits | Different edits& in total edited samples | Different new edits | Different heritable edits |
|---|---|---|---|---|---|---|---|---|---|---|---|
| ZM_S22 | female | 55 | 26 | 11 | 11 | 47.27 | 20.00 | 20.00 | 12 | 9 | 9 |
| 321294 | male | 12 | 0 | 0 | 0 | 0.00 | 0.00 | 0.00 | 0 | 0 | 0 |
| ZM_S22 | female | 16 | 6 | 0 | 0 | 37.50 | 0.00 | 0.00 | 1 | 0 | 0 |
| 321298 | male | 0 | 0 | 0 | 0 | 0.00 | 0.00 | 0.00 | 0 | 0 | 0 |
| ZM_S22 | female | 39 | 26 | 4 | 4 | 66.67 | 10.26 | 10.26 | 10 | 4 | 4 |
| 321299 | male | 13 | 4 | 0 | 0 | 30.77 | 0.00 | 0.00 | 1 | 0 | 0 |
| ZM_S22 | female | 162 | 100 | 25 | 25 | 61.73 | 15.43 | 15.43 | 20 | 16 | 16 |
| 321304 | male | 38 | 7 | 0 | 0 | 18.42 | 0.00 | 0.00 | 2 | 0 | 0 |
| ZM_S22 | female | 72 | 29 | 2 | 2 | 40.28 | 2.78 | 2.78 | 4 | 2 | 2 |
| 321307 | male | 27 | 2 | 0 | 0 | 7.41 | 0.00 | 0.00 | 1 | 0 | 0 |
| ZM_S22 | female | 182 | 114 | 24 | 24 | 62.64 | 13.19 | 13.19 | 22 | 15 | 15 |
| 321323 | male | 70 | 36 | 6 | 6 | 51.43 | 8.57 | 8.57 | 6 | 1 | 1 |

TABLE 17-continued

ZmES4::LbCas12a editing summary in F1s by event.

| Event | Event parent | Total Samples (Cas12a+) | Total samples with edits* | Total samples with new** edits | Total samples with new heritable edits$^{\$}$ | % samples with edits | % samples with new edits | % samples with new heritable edits | Different edits$^{\&}$ in total edited samples | Different new edits | Different heritable edits |
|---|---|---|---|---|---|---|---|---|---|---|---|
| ZM_S22 | female | 92 | 63 | 17 | 17 | 68.48 | 18.48 | 18.48 | 19 | 14 | 14 |
| 321324 | male | 4 | 0 | 0 | 0 | 0.00 | 0.00 | 0.00 | 0 | 0 | 0 |
| ZM_S22 | female | 34 | 2 | 2 | 2 | 5.88 | 5.88 | 5.88 | 2 | 2 | 2 |
| 321326 | male | 30 | 0 | 0 | 0 | 0.00 | 0.00 | 0.00 | 0 | 0 | 0 |

*Total samples with edits includes samples with both new edits and edits that were inherited.

**New edits are defined as an edit found in the F1 that was not detected in the R1 parent.

$^{\$}$Heritable edits are defined as edits that detected by sequencing with at least 40% of total sequencing reads from a sa,ple mapping to the edit.

$^{\&}$Different edits refers to the number of unique edits identified.

Example 7. Expression of Cas12a in Corn Egg Cells, Meiotic Cells or Embryos to Enable Editing from a Haploid Induction Line to a Target Genome Vectors are generated to preferentially express Cas12a in zygote, embryo, egg and/or meiotic cells of a haploid induction (HI) line, which generates haploids when crossed to another line. Non-limiting examples of promoters and regulatory sequences useful to drive expression embryo, egg and/or meiotic cells are provided in Table 1. An expression cassette is provided in which a plant codon optimized LbCas12a sequence is flanked by NLS sequences at the 5' and 3' ends and operably linked to a promoter as described in Table 1. Each vector may also contain an expression cassette encoding one or more Cas12a gRNAs targeting unique corn genomic target sites; and, optionally, an expression cassette encoding a selectable marker conferring resistance to the herbicide glyphosate. The vector may either be transformed directly into the haploid induction line, or events containing the vector may be generated in a different germplasm, which is then crossed into the haploid induction line. The resulting "editing inducer" will contain the haploid induction trait as well as the expression cassette encoding Cas12a and, optionally, a gRNA directed to the target site. In some embodiments, the gRNA could be delivered to the haploid induction line or WT germplasm separately from the cassette expressing Cas12a.

Editing induced by a DNA modification enzyme, such as a guided nuclease (e.g., a CRISPR/Cas system,) expressed from the haploid inducer genome is limited by the efficiency of editing that can occur in the short period after fertilization but before elimination of the genome contributed by the haploid inducer. In systems where haploid induction is contributed by the female parent, having strong expression of the genome editing components from the maternal genome just before or shortly after fertilization is a desired characteristic. Thus, identifying and using promoters that express at high levels in the maternal tissue (e.g., in egg and embryo tissue), such as the ZmES4 promoter (see Example 6) is highly desired.

An inducer line carrying an event comprising the expression construct(s) described above (editing inducer) is crossed as a female to a male wild type germplasm. After pollen from the male wild type parent contacts the female haploid inducer parent, there will be a period of time (shortly before/during, and/or after fertilization) during which the editing machinery (e.g., a CRISPR/Cas system) expressed from the inducer parent will contact the genome inherited from the male parent, and induce a modification. In certain embodiments, genome editing occurs while the progeny of the induction cross is in the zygote phase of its life cycle. In certain embodiments, genome editing requires a longer period of time, potentially spanning several rounds of mitotic divisions in the tissues of the progeny plant.

Following the editing of the wild type genome, the inducer genome and the expression cassettes encoding the editing machinery (e.g., Cas12a and gRNA), will be lost from the cells in a certain frequency of progeny via one of the mechanisms of genome elimination that is characteristic of maternal haploid induction lines, thus yielding a corresponding frequency of haploid progeny plants containing edits in the male genome but no expression cassettes encoding the editing machinery. Haploid progeny can be identified using any method known in the art including sequencing of genomic DNA, genotyping with molecular markers, and phenotyping with plant or seed markers. The haploid progeny can be screened for editing at the target site(s) by any method known in the art, including sequencing of the target site. Edited haploids are selected and then doubled using any method known in the art, such as colchine treatment. The doubled haploid is homozygous for the edited allele and can be utilized in a breeding pipeline.

A single editing inducer line could be used to create a wide variety of unique edits across multiple germplasms, alleviating germplasm dependent transformation constraints. Further, an inducer line expressing the editing machinery (e.g., Cas12a and gRNA) in the egg, embryo, and/or meiotic tissue can produce a wide array of unique edits, eliminating the need to create multiple transgenic events to identify a particular edit or generate a range of edited alleles.

Example 8: TALE Activators can Drive Robust LbCas12a Expression in Corn Protoplasts This example describes the use of TALEs to induce robust and specific expression of a transcribable polynucleotide in egg, embryo, and/or meiotic plant cells.

Transcription Activator-Like Effectors (TALEs) are transcription factors that comprise a C terminal activation domain and can activate/increase the expression of an operably linked transcribable polynucleotide once TALEs bind to the TALE binding site at or near the promoter. To test if a TALE could boost expression of Cas12a, several cassettes were designed that employed the minimal 35S(-46) promoter operably linked to a *Zea mays* DNAK intron and placed upstream of a polynucleotide sequence encoding Cas12a (See FIG. 2). The minimal 35S(-46) promoter has the TATA box, but lacks the transcription factor binding sites that will induce gene expression. Three expression constructs were generated, each comprising the 35S(-46):Lb.Cas12a cassette with one to six TALE protein binding sites (TB) (SEQ ID NO 15) placed upstream of the minimal 35S(-46) promoter (see Table 7). As a control, a polynucleotide sequence encoding LbCas12a was operably linked to the constitutive Ubiquitin promoter. Finally, a separate expression construct comprising a polynucleotide sequence (SEQ ID NO 16) encoding the TALE protein with the C terminal activation domain (SEQ ID NO 17) operably linked to the full 35S promoter was also generated.

TABLE 18

Cassettes designed to express Cas12a preferentially, or solely, in the presence of TALE activator protein.

| Construct | Cassette | Details | Regulatory Seq |
|---|---|---|---|
| 28 | 1XTB:35S(−46): LbCas12a | At most one TALE protein will bind upstream of the 35S(−46): Lb.Cas12a | 12 |
| 29 | 3XTB:35S(−46): LbCas12a | At most three TALE proteins will bind upstream of the 35S(−46): Lb.Cas12a | 13 |
| 30 | 6XTB:35S(−46): LbCas12a | At most six TALE proteins will bind upstream of the 35S(−46): Lb.Cas12a | 14 |
| 31 (control) | Ubiquitin: LbCas12a | TALE proteins are not expected to bind/drive the expression of the Ubiquitin promoter | 11 |

TB = Tale Binding site.

The constructs described in Table 18 were transfected into corn leaf protoplasts with and without the TALE expressing construct. After 18-24 hours, RNA was isolated and the expression of Cas12a and TALE was quantified using TaqMan assays (See FIG. 3).

The data showed that the 1 XTB:Cas12a, 3XTB:Cas12a and 6XTB:Cas12a constructs did not express well as the Ubq:Cas12a control in the absence of TALE expression (see FIG. 3). However, in the presence of TALE expression, high expression of Cas12a was observed, and expression increased with the number of TALE binding sites. The 3XTB:Cas12a and 6XTB:Cas12a constructs showed higher Cas12a expression than the Ubq:Cas12a control (see FIG. 3). This data suggests that not only can a TALE protein induce high expression of a gene operably linked to a TALE binding site, but that expression can be modulated depending on how many of the TALE binding sites are included.

Example 9: TALE Induced Meiocyte/Embryo/Egg-Cell Preferred Expression of LbCas12a A potential downside of tissue/cell preferred promoters is that they tend to not be robustly expressed. This example describes constructs that have been generated to overcome this limitation and induce robust expression of a transcribable polynucleotide, such as Cas12a, in a tissue/cell preferred manner.

Several constructs are generated for robust, TALE-induced Cas12a expression preferentially in egg, embryo and/or meiotic cells. Constructs are generated comprising a plant codon optimized LbCas12a coding sequence flanked by NLS sequences at the 5' and 3' ends and operably linked to the OsLTP transcription terminator sequence and the minimal 35S(-46) promoter with 1, 3, or 6 TALE binding sites. Expression constructs are also generated comprising a TALE coding sequence (SEQ ID NO 16) operably linked to a promoter that preferentially or solely expresses in egg, embryo and/or meiotic cells. Non-limiting examples of promoters and regulatory sequences to drive preferential egg, embryo and/or meiotic cell expression are provided in Table 1. An expression cassette comprising a TALE coding sequence operably linked to a constitutive Ubiquitin promoter is generated as a control. Corn 01DKD2 cultivar embryos are transformed with a vector(s) comprising the expression cassettes as described above and an expression cassette encoding a Cas12a gRNA complementary to a unique corn genomic target site (ZmTS1) under the control of a plant Pol III promoter and an expression cassette for a selectable marker conferring resistance to the herbicide glyphosate by *agrobacterium*-mediated transformation and R0 plants are generated from the transformed corn cells. Several R0 lines from each transformed construct are grown to maturity and at least one ear from each transformed corn plant are pollinated. Several R1 lines are selected, seedlings are germinated and screened for LbCas12a induced edits in the target site and the editing rates are calculated. It is anticipated that when plants comprising the Cas12a, gRNA and TALE expression vectors described above reach the reproductive stage, TALE expressed preferentially in the meiocytes, egg cells, and/or embryo cells will bind to TALE protein binding sites upstream of the 35S(-46):Lb.Cas12a and induce robust expression preferentially in meiocytes, egg cells, and/or embryo cells. The R1 plants generated from the transformed R0 lines are expected to exhibit a significant number of unique mutations at the ZmTS1 target site.

Example 10: Tissue Preferred High Expression of CRISPR/Cas12a Editing System Components This example describes the design of a vector to enable Meiocyte/Embryo/egg-cell preferred expression of Cas12a that is driven by a strong constitutive promoter.

A recombinant *Agrobacterium* T-DNA construct is produced that comprises in 5' to 3' order, a left Border (LB) sequence; a selectable marker cassette in forward orientation; a sequence encoding a strong expression promoter in forward orientation; a first lox site, a first 3'UTR (UnTranslated Region) in forward orientation; a CRE recombinase cassette comprising a second 3'UTR in reverse orientation, a sequence encoding the CRE recombinase in reverse orientation operably linked to a promoter that preferentially or solely expresses in meiocytes, egg cells, and/or embryo cells; a second lox site in the same orientation as the first; a sequence encoding a plant codon optimized LbCas12a nuclease in forward orientation and operably linked to a third 3'UTR also in the forward orientation; and optionally an LbCas12a guide RNA expression cassette. The recombinant T-DNA construct is illustrated in FIG. 5. Non limiting examples of a strong promoters include: the 35S promoter from Cauliflower mosaic virus (SEQ ID NO:18), a promoter from Citrus Yellow mosaic virus (SEQ ID NO:19), Ubiquitin promoter from *Sorghum bicolor* (SEQ ID NO 20), and *Zea mays* Ubiquitin promoter (SEQ ID NO:11).

The vector described above comprises an expression cassette comprising a sequence encoding CRISPR/Cas editing system components and a constitutive, strong/high-expressing promoter that is interrupted by an expression cassette that preferentially expresses Cre recombinase in egg cells and/or embryo cells and/or cells undergoing meiosis. The Cre expression cassette is flanked by lox sites in the same orientation, such that preferential expression of Cre in egg, embryo and/or meiotic cells will cause excision of the sequence between the lox sites and operably linking the sequence encoding CRISPR/Cas editing system components with the constitutive, strong/high-expressing promoter. The excised sequence includes the Cre expression cassette and the first 3'UTR sequence that is intended to terminate any unintended transcription that might be initiated by the constitutive, strong/high-expressing promoter.

The vector is introduced to plant cells via *Agrobacterium*-mediated transformation. Once Cre recombinase is expressed in egg, embryo and/or meiotic cells, it mediates the excision of the sequence between the lox sites enabling high expression of Cas12a only in the tissue where Cre is expressed.

The invention claimed is:

1. A recombinant DNA construct comprising (a) a first nucleic acid sequence encoding a CRISPR effector protein operably linked to 1, 2, 3, 4, 5, 6, 7, 8, 9, or 10 transcription activator-like effector (TALE) binding sites and a minimal promoter; and (b) a second nucleic acid sequence encoding a TALE operably linked to an egg cell-preferred promoter, wherein the egg cell-preferred promoter is an ES4 promoter that comprises a nucleic acid sequence having at least 90% identity to the sequence of SEQ ID NO: 3, wherein the minimal promoter does not drive expression of the CRISPR effector protein in the absence of TALE binding to one or more of the TALE binding sites.

2. The recombinant DNA construct of claim 1, further comprising a third nucleic acid sequence encoding a guide nucleic acid operably linked to a third promoter.

3. The recombinant DNA construct of claim 1, wherein the CRISPR effector protein is selected from the group consisting of Cas9, Cas12a, Cas12b and CasX.

4. The recombinant DNA construct of claim 1, wherein the minimal promoter is a 35S(-46) promoter.

5. A plant comprising in its genome the recombinant DNA construct of claim 1.

* * * * *